United States Patent
Subramanian et al.

(10) Patent No.: US 12,018,087 B2
(45) Date of Patent: *Jun. 25, 2024

(54) MUSCLE-TARGETING COMPLEXES COMPRISING AN ANTI-TRANSFERRIN RECEPTOR ANTIBODY LINKED TO AN OLIGONUCLEOTIDE AND METHODS OF DELIVERING OLIGONUCLEOTIDE TO A SUBJECT

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US); Cody A. Desjardins, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/468,580

(22) Filed: Sep. 15, 2023

(65) Prior Publication Data

US 2024/0067744 A1 Feb. 29, 2024

Related U.S. Application Data

(63) Continuation-in-part of application No. 18/184,741, filed on Mar. 16, 2023, now Pat. No. 11,795,233, which is a continuation of application No. 17/936,483, filed on Sep. 29, 2022, now Pat. No. 11,787,869, which is a continuation of application No. 17/846,738, filed on Jun. 22, 2022, now Pat. No. 11,518,816, which is a continuation of application No. 17/671,707, filed on Feb. 15, 2022, now Pat. No. 11,390,682, which is a continuation of application No. 17/400,295, filed on Aug. 12, 2021, now Pat. No. 11,286,305, which is a continuation of application No. 17/205,123, filed on Mar. 18, 2021, now Pat. No. 11,111,309, which is a continuation of application No. 17/264,948, filed as application No. PCT/US2019/044990 on Aug. 2, 2019, now abandoned, application No. 18/468,580, filed on Sep. 15, 2023 is a continuation-in-part of application No. 17/264,905, filed as application No. PCT/US2019/044987 on Aug. 2, 2019, now abandoned, application No. 18/468,580, filed on Sep. 15, 2023 is a continuation-in-part of application No. 17/265,016, filed as application No. PCT/US2019/044960 on Aug. 2, 2019, now abandoned, application No. 18/468,580, filed on Sep. 15, 2023 is a continuation-in-part of application No. 17/264,998, filed as application No. PCT/US2019/044982 on Aug. 2, 2019, now abandoned, application No. 18/468,580, filed on Sep. 15, 2023 is a continuation-in-part of application No. 17/265,044, filed as application No. PCT/US2019/044955 on Aug. 2, 2019, now abandoned, application No. 18/468,580, filed on Sep. 15, 2023 is a continuation-in-part of application No.

(Continued)

(51) Int. Cl.
*C07K 16/28* (2006.01)
*A61K 47/68* (2017.01)
*A61P 21/00* (2006.01)
*C12N 15/113* (2010.01)

(52) U.S. Cl.
CPC ...... *C07K 16/2881* (2013.01); *A61K 47/6807* (2017.08); *A61K 47/6849* (2017.08); *A61K 47/6889* (2017.08); *A61P 21/00* (2018.01); *C12N 15/113* (2013.01); *C07K 2317/55* (2013.01); *C07K 2317/92* (2013.01)

(58) Field of Classification Search
CPC ............ C07K 16/2881; C07K 2317/55; C07K 2317/92; C12N 15/113
See application file for complete search history.

(56) References Cited

U.S. PATENT DOCUMENTS 2,631,173 A   3/1953  Hillyer et al.
6,214,345 B1  4/2001  Firestone et al.
(Continued)

FOREIGN PATENT DOCUMENTS

CN   103443125 A   12/2013
CN   103732259 A    4/2014
(Continued)

OTHER PUBLICATIONS

[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.

(Continued)

*Primary Examiner* — Robert S Landsman
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits expression or activity of DUX4. In some embodiments, the molecular payload is an oligonucleotide, such as an antisense oligonucleotide or RNAi oligonucleotide.

27 Claims, 6 Drawing Sheets

Specification includes a Sequence Listing.

Related U.S. Application Data

17/265,024, filed as application No. PCT/US2019/044949 on Aug. 2, 2019, now abandoned, application No. 18/468,580, filed on Sep. 15, 2023 is a continuation-in-part of application No. 17/265,019, filed as application No. PCT/US2019/044959 on Aug. 2, 2019, now abandoned, application No. 18/468,580, filed on Sep. 15, 2023 is a continuation-in-part of application No. 17/264,972, filed as application No. PCT/US2019/044961 on Aug. 2, 2019, now abandoned.

(60) Provisional application No. 62/713,933, filed on Aug. 2, 2018, provisional application No. 62/859,672, filed on Jun. 10, 2019, provisional application No. 62/858,888, filed on Jun. 7, 2019, provisional application No. 62/855,761, filed on May 31, 2019, provisional application No. 62/779,161, filed on Dec. 13, 2018, provisional application No. 62/713,914, filed on Aug. 2, 2018, provisional application No. 62/713,959, filed on Aug. 2, 2018, provisional application No. 62/859,694, filed on Jun. 10, 2019, provisional application No. 62/858,925, filed on Jun. 7, 2019, provisional application No. 62/855,781, filed on May 31, 2019, provisional application No. 62/779,173, filed on Dec. 13, 2018, provisional application No. 62/714,010, filed on Aug. 2, 2018, provisional application No. 62/714,025, filed on Aug. 2, 2018, provisional application No. 62/855,766, filed on May 31, 2019, provisional application No. 62/714,031, filed on Aug. 2, 2018, provisional application No. 62/714,035, filed on Aug. 2, 2018, provisional application No. 62/714,034, filed on Aug. 2, 2018.

(56) References Cited

U.S. PATENT DOCUMENTS

| | | |
|---|---|---|
| 7,015,315 B1 | 3/2006 | Cook et al. |
| 7,064,142 B2 | 6/2006 | Sato et al. |
| 7,265,131 B2 | 9/2007 | Johnson et al. |
| 7,575,886 B2 | 8/2009 | Venkataraman et al. |
| 8,580,756 B2 | 11/2013 | Hansen et al. |
| 8,846,639 B2 | 9/2014 | Swayze et al. |
| 8,859,629 B2 | 10/2014 | van Delft et al. |
| 8,952,147 B2 | 2/2015 | Bouchard et al. |
| 9,045,754 B2 | 6/2015 | Bhanot et al. |
| 9,222,940 B2 | 12/2015 | van Delft et al. |
| 9,260,371 B2 | 2/2016 | Bertozzi et al. |
| 9,428,534 B2 | 8/2016 | Christensen et al. |
| 9,504,758 B2 | 11/2016 | van Delft et al. |
| 9,550,834 B2 | 1/2017 | Shirai et al. |
| 9,550,988 B2 | 1/2017 | Swayze |
| 9,610,362 B2 | 4/2017 | Armstrong |
| 9,617,540 B2 | 4/2017 | Bhanot et al. |
| 9,695,418 B2 | 7/2017 | Seth et al. |
| 9,708,406 B2 | 7/2017 | Zhang et al. |
| 9,708,614 B2 | 7/2017 | Christensen et al. |
| 9,765,338 B2 | 9/2017 | Bennett et al. |
| 10,131,682 B2 | 11/2018 | Zhao |
| 10,238,753 B2 | 3/2019 | Armstrong |
| 10,239,807 B2 | 3/2019 | van Delft et al. |
| 10,266,502 B2 | 4/2019 | van Delft et al. |
| 10,434,111 B2 | 10/2019 | Bertozzi et al. |
| 10,493,092 B2 | 12/2019 | Swayze |
| 10,550,188 B2 | 2/2020 | Geall et al. |
| 10,881,743 B2 | 1/2021 | Geall et al. |
| 11,111,309 B2 | 9/2021 | Subramanian et al. |
| 11,168,141 B2 | 11/2021 | Subramanian et al. |
| 11,230,605 B2 | 1/2022 | Launay et al. |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 11,497,815 B2 | 11/2022 | Subramanian et al. |
| 11,518,816 B2 | 12/2022 | Subramanian et al. |
| 11,633,496 B2 | 4/2023 | Subramanian et al. |
| 11,633,498 B2 | 4/2023 | Subramanian et al. |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,759,525 B1 | 9/2023 | Subramanian et al. |
| 11,771,776 B2 | 10/2023 | Subramanian et al. |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 11,911,484 B2 | 2/2024 | Subramanian et al. |
| 2004/0063654 A1 | 4/2004 | Davis et al. |
| 2004/0191243 A1 | 9/2004 | Chen et al. |
| 2005/0084906 A1 | 4/2005 | Goetsch et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2011/0009471 A1 | 1/2011 | Kaneko et al. |
| 2011/0256157 A1 | 10/2011 | Howard et al. |
| 2012/0122801 A1 | 5/2012 | Platenburg |
| 2012/0201809 A1 | 8/2012 | Bhat et al. |
| 2012/0225013 A1 | 9/2012 | Dennis et al. |
| 2013/0028891 A1 | 1/2013 | Penichet et al. |
| 2013/0066063 A1 | 3/2013 | Berry et al. |
| 2013/0137763 A1 | 5/2013 | van Delft et al. |
| 2013/0177579 A1 | 7/2013 | Lin et al. |
| 2013/0237585 A1 | 9/2013 | Bennett et al. |
| 2014/0193436 A1 | 7/2014 | Prudent |
| 2014/0323552 A1 | 10/2014 | Burghes et al. |
| 2015/0064181 A1 | 3/2015 | Armstrong |
| 2015/0225722 A1 | 8/2015 | Ozsolak |
| 2015/0258210 A1 | 9/2015 | van Delft et al. |
| 2016/0015828 A1 | 1/2016 | Torgov et al. |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0250347 A1 | 9/2016 | van Delft et al. |
| 2016/0272973 A1 | 9/2016 | Shehadeh |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2017/0342169 A1 | 11/2017 | Akamatsu et al. |
| 2017/0348416 A1 | 12/2017 | Hasler et al. |
| 2018/0002433 A1 | 1/2018 | Zhang et al. |
| 2018/0021449 A1 | 1/2018 | Armstrong |
| 2018/0134797 A1 | 5/2018 | Zhang et al. |
| 2018/0369400 A1 | 12/2018 | Levin et al. |
| 2019/0000986 A1 | 1/2019 | Levin et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0153083 A1 | 5/2019 | Juste et al. |
| 2019/0211362 A1 | 7/2019 | Lundberg et al. |
| 2019/0240346 A1 | 8/2019 | Sugo et al. |
| 2019/0298847 A1 | 10/2019 | Geall et al. |
| 2019/0336615 A1 | 11/2019 | Thompson et al. |
| 2020/0046742 A1 | 2/2020 | Bertozzi et al. |
| 2020/0048174 A1 | 2/2020 | van Delft et al. |
| 2020/0123267 A1 | 4/2020 | Zhang et al. |
| 2020/0282074 A1 | 9/2020 | Levin et al. |
| 2020/0325237 A1 | 10/2020 | Darimont et al. |
| 2021/0038739 A1 | 2/2021 | Takahashi et al. |
| 2021/0130486 A1 | 5/2021 | Darimont et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |

(56) References Cited

U.S. PATENT DOCUMENTS

| | | |
|---|---|---|
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016950 A1 | 1/2024 | Weeden et al. |
| 2024/0016952 A1 | 1/2024 | Subramanian et al. |
| 2024/0066139 A1 | 2/2024 | Subramanian et al. |
| 2024/0066140 A1 | 2/2024 | Subramanian et al. |
| 2024/0067743 A1 | 2/2024 | Subramanian et al. |
| 2024/0067744 A1 | 2/2024 | Subramanian et al. |

FOREIGN PATENT DOCUMENTS

| | | |
|---|---|---|
| EP | 2149605 A2 | 2/2010 |
| EP | 2410053 A1 | 1/2012 |
| EP | 2410054 A1 | 1/2012 |
| EP | 3031920 A1 | 6/2016 |
| EP | 3067421 A1 | 9/2016 |
| EP | 2623609 B1 | 1/2017 |
| EP | 3202905 A1 | 8/2017 |
| EP | 2922818 B1 | 9/2018 |
| EP | 3473270 A1 | 4/2019 |
| EP | 3489360 A2 | 5/2019 |
| EP | 3 560 958 A1 | 10/2019 |
| IL | 54795 A | 10/1980 |
| JP | 2002-253259 A | 9/2002 |
| JP | 2013-538560 A | 1/2012 |
| JP | 2016-528258 A | 9/2016 |
| WO | WO 1989/007970 A1 | 9/1989 |
| WO | WO 1991/004753 A1 | 4/1991 |
| WO | WO 2003/059951 A2 | 7/2003 |
| WO | WO 2004/069991 A2 | 8/2004 |
| WO | WO 2005/023825 A2 | 3/2005 |
| WO | WO 2006/022688 A1 | 3/2006 |
| WO | WO 2007/089612 A2 | 8/2007 |
| WO | WO 2008/018795 A1 | 2/2008 |
| WO | WO 2008/049085 A1 | 4/2008 |
| WO | WO 2009/144481 A2 | 12/2009 |
| WO | WO 2010/048586 A1 | 4/2010 |
| WO | WO 2011/136645 A1 | 11/2011 |
| WO | WO 2012/012443 A2 | 1/2012 |
| WO | WO 2012/012467 A2 | 1/2012 |
| WO | WO 2012/075037 A1 | 6/2012 |
| WO | WO 2012/144906 A1 | 10/2012 |
| WO | WO 2013/085550 A2 | 6/2013 |
| WO | WO 2013/126746 A2 | 8/2013 |
| WO | WO 2013/138662 A1 | 9/2013 |
| WO | WO 2013/162363 A1 | 10/2013 |
| WO | WO 2014/065661 A1 | 5/2014 |
| WO | WO 2015/021457 A2 | 2/2015 |
| WO | WO 2015/023937 A1 | 2/2015 |
| WO | WO 2015/042581 A1 | 3/2015 |
| WO | WO 2015/179741 A1 | 11/2015 |
| WO | WO 2016/081643 A1 | 5/2016 |
| WO | WO 2016/081670 A2 | 5/2016 |
| WO | WO 2016/187425 A1 | 11/2016 |
| WO | WO 2017/100467 A2 | 6/2017 |
| WO | WO 2017/106643 A1 | 6/2017 |
| WO | WO 2017/143156 A1 | 8/2017 |
| WO | WO 2017/173408 A1 | 10/2017 |
| WO | WO 2017/192679 A1 | 11/2017 |
| WO | WO 2017/205191 A1 | 11/2017 |
| WO | WO 2017/221883 A1 | 12/2017 |
| WO | WO 2018/129384 A1 | 7/2018 |
| WO | WO 2018/226861 A1 | 12/2018 |
| WO | WO 2019/060775 A1 | 3/2019 |
| WO | WO 2019/071028 A1 | 4/2019 |
| WO | WO 2019/113393 A1 | 6/2019 |
| WO | WO 2019/136180 A2 | 7/2019 |
| WO | WO 2019/151539 A1 | 8/2019 |
| WO | WO 2019/157224 A1 | 8/2019 |
| WO | WO 2019/215175 A1 | 11/2019 |
| WO | WO 2019/229658 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/163817 A1 | 8/2020 |
| WO | WO 2020/247738 A1 | 12/2020 |
| WO | WO 2020/247782 A1 | 12/2020 |
| WO | WO 2020/247818 A1 | 12/2020 |
| WO | WO 2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |

(56) References Cited

FOREIGN PATENT DOCUMENTS

| | | |
|---|---|---|
| WO | WO 2022/026152 A1 | 2/2022 |
| WO | WO 2022/051665 A1 | 3/2022 |
| WO | WO 2022/056266 A2 | 3/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |
| WO | WO 2023/044398 A1 | 3/2023 |
| WO | WO 2023/077120 A1 | 5/2023 |
| WO | WO 2023/086864 A1 | 5/2023 |
| WO | WO 2023/201318 A1 | 10/2023 |
| WO | WO 2023/201324 A1 | 10/2023 |
| WO | WO 2023/201332 A1 | 10/2023 |
| WO | WO 2024/011135 A1 | 1/2024 |
| WO | WO 2024/011150 A1 | 1/2024 |

OTHER PUBLICATIONS

[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.

[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.

[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.

[No Author Listed], Baliforsen—Ionis Pharmaceuticals Drug Profile. Springer Nature Switzerland AG. Nov. 15, 2016. 9 pages.

[No Author Listed], Building the world's leading muscle disease company. Dyne Company Overview. Jun. 2021. 42 pages.

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.

[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:~:text=Cayman's Transferrin Receptor%2FCD71 Extracellular,molecular weight of 103.6 kDa (Year: 2021). 3 pages.

Agard et al., A Comparative Study of Bioorthogonal Reactions with Azides. ACS Chem. Biol. 2006;1(10):644-8. Epub Oct. 20, 2006.

Agard et al., A Strain-Promoted [3 + 2] Azide-Alkyne Cycloaddition for Covalent Modification of Biomolecules in Living Systems. J. Am. Chem. Soc. Nov. 2004;126(46):15046- 7.

Anciaux et al., Transition-metal-catalyzed reactions of diazo compounds. 1. Cyclopropanation of double bonds. The Journal of Organic Chemistry. Feb. 1980;45(4):695-702.

Antony-Mayer et al., Bicyclo[6.1.0]nonynes. Chemische Berichte. Nov. 1988;121(11):2013-8.

Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.

Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.

Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.

Ast et al., Estergruppenhaltige Polyalkenylene durch Olefin-Metathese. Die Makromolekulare Chemie. May 1976;177(5):1349-55.

Barfield et al., A Novel HER2-targeted Antibody-drug Conjugate Offers the Possibility of Clinical Dosing at Trastuzumab-equivalent Exposure Levels. Mol Cancer Ther. Sep. 2020;19(9):1866-1874. doi: 10.1158/1535-7163.MCT-20-0190. Epub Jul. 10, 2020.

Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.

Baskin et al., Copper-free click chemistry for dynamic in vivo imaging. PNAS. Oct. 2007;104(43):16793-7.

Behlke, Chemical modification of siRNAs for in vivo use. Oligonucleotides. Dec. 2008;18(4):305-19.

Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.

Beskrovnaya, Forcetm platform delivers exon skipping PMO, leads to durable increases in dystrophin protein in mdx mice and is well tolerated NHPs. Presented at Muscle Study Group Annual Scientific Meeting. Oct. 1, 2021. 29 pages.

Bien-Ly et al., Transferrin receptor (TfR) trafficking determines brain uptake of TfR antibody affinity variants. J Exp Med. Feb. 10, 2014;211(2):233-44. Epub Jan. 27, 2014.

Black, 9.13.4.1.1.3.2 Variation 2: C-Alkylation (and Arylation) by Carbenes and Free Radicals. Science of Synthesis. 2001;9:514.

Buntz et al., Quantitative fluorescence imaging determines the absolute number of locked nucleic acid oligonucleotides needed for suppression of target gene expression. Nucleic Acids Res. Jan. 25, 2019;47(2):953-969. doi: 10.1093/nar/gky1158.

Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.

Candelaria et al., Antibodies Targeting the Transferrin Receptor 1 (TfR1) as Direct Anti-cancer Agents. Front Immunol. Mar. 17, 2021;12:607692.

Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.

Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Cho et al., Myotonic dystrophy: emerging mechanisms for DM1 and DM2. Biochim Biophys Acta. Feb. 2007;1772(2):195-204. Epub Jun. 20, 2006.

Chothia et al., Canonical structures for the hypervariable regions of immunoglobulins. J Mol Biol. Aug. 20, 1987;196(4):901-17. doi: 10.1016/0022-2836(87)90412-8.

Clark et al., Increased brain uptake of targeted nanoparticles by adding an acid-cleavable linkage between transferrin and the nanoparticle core. PNAS. Oct. 2015;112(40):12486-91.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., Antisense research and applications. 1993. p. 15-35.

Crooke et al., Kinetic characteristics of Escherichia coli RNase H1: cleavage of various antisense oligonucleotide-RNA duplexes. Biochem J. Dec. 1, 1995;312(Pt 2):599-608. doi: 10.1042/bj3120599.

(56) References Cited

OTHER PUBLICATIONS

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.
Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.
Curtius, Ueber die Einwirkung von salpetriger Säure auf salzsauren Glycocolläther. Berichte der deutschen chemischen Gesellschaft. Jul.-Dec. 1883;16(2):2230-1.
Danis et al., Potential therapeutic application of antisense oligonucleotides in the treatment of ocular diseases. Expert Opin Pharmacother. Feb. 2001;2(2):277-91.
Darimont et al., A novel antibody-oligonucleotide conjugate (AOC) platform enables efficient regulation of muscle targets in mice. Abstract. 8-05. J. Cach Sarcopen Musc. 2017; 8:1065-66.
Davis et al., Improved targeting of miRNA with antisense oligonucleotides. Nucleic Acids Res. May 11, 2006;34(8):2294-304. doi: 10.1093/nar/gkl183. Print 2006.
Debets et al., Bioorthogonal labelling of biomolecules: new functional handles and ligation methods. Org Biomol Chem. Oct. 14, 2013;11(38):6439-55. Epub Aug. 23, 2013.
Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.
Desjardins et al., Building a FORCETM platform-based DMD franchise for the treatment of individuals with mutations amenable to exon skipping. Neuromusc Dis. Oct. 2022; 32: S101-2. Abstract.
Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.
Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.
Desjardins et al., ForceTM platform achieves robust exon skipping, restores dystrophin at the sarcolemma and halts progression of fibrosis in the severe D2-$^{mdx}$ model of DMD. Abstract. Mar. 2023. 1 page.
Desjardins et al., ForceTM platform achieves robust exon skipping, restores dystrophin at the sarcolemma and halts progression of fibrosis in the severe D2-$^{mdx}$ model of DMD. Poster. Presented at The Muscular Dystrophy Association Clinical and Scientific Conference. Mar. 19-22, 2023. 1 page.
Dommerholt et al., Readily accessible bicyclononynes for bioorthogonal labeling and three-dimensional imaging of living cells. Angew Chem Int Ed. Dec. 3, 2010;49(49):9422-5.
Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.
Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.
Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.
Elangkovan et al., Gene Therapy for Duchenne Muscular Dystrophy. J Neuromuscul Dis. 2021;8(s2):S303-S316.
Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.
Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.
Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.
Furling et al., Abstract R.P.1.01 Therapeutic RNA strategies for myotonic dystrophy with CTG repeats. Neuromuscular Disorders. 2004;14:585. 2 pages total.
Furling et al., Viral vector producing antisense RNA restores myotonic dystrophy myoblast functions. Gene Ther. May 2003;10(9):795-802.
Gagnon et al., RNAi factors are present and active in human cell nuclei. Cell Rep. Jan. 16, 2014;6(1):211-21. Epub Jan. 2, 2014.
Galderisi et al., Myotonic dystrophy: antisense oligonucleotide inhibition of DMPK gene expression in vitro. Biochem Biophys Res Commun. Apr. 25, 1996;221(3):750-4.
Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.
Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.
Giles et al., Enhanced RNase H activity with methylphosphonodiester/phosphodiester chimeric antisense oligodeoxynucleotides. Anticancer Drug Des. Feb. 1992;7(1):37-48.
Girones et al. Comparison of the kinetics of cycling of the transferrin receptor in the presence or absence of bound diferric transferrin. Biochem J. Nov. 15, 1989;264(1):35-46.
Gong et al., Simple Method to Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.
Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.
Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.
Iwaki et al., Preparation of Chiral Stationary Phase via Activated Carbamate Intermediate for Liquid Chromatographic Optical Resolution. Chromatographia. Oct. 1987;23:727-30.
Jain et al., Current ADC Linker Chemistry. Pharm Res. Nov. 2015;32(11):3526-40. Epub Mar. 11, 2015.
Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.
Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.
Jepsen et al., Locked nucleic acid: a potent nucleic acid analog in therapeutics and biotechnology. Oligonucleotides. 2004;14(2):130-46. doi: 10.1089/1545457041526317.
Juliano, The delivery of therapeutic oligonucleotides. Nucleic Acids Res. Aug. 19, 2016;44(14):6518-48. doi: 10.1093/nar/gkw236. Epub Apr. 15, 2016.
Kher et al., Antisense Oligonucleotides and RNA Interference. Challenges in Delivery of Therapeutic Genomics and Proteomics. Aug. 2011:325-86.

(56) References Cited

OTHER PUBLICATIONS

Kline et al., Methods to Make Homogenous Antibody Drug Conjugates. Pharm Res. Nov. 2015;32(11):3480-93. Epub Dec. 16, 2014.

Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

Kurreck et al., Design of antisense oligonucleotides stabilized by locked nucleic acids. Nucleic Acids Res. May 1, 2002;30(9):1911-8. doi: 10.1093/nar/30.9.1911.

Kurreck, Antisense technologies. Improvement through novel chemical modifications. Eur J Biochem. Apr. 2003;270(8):1628-44.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Langlois et al., Abstract 831—Ribozyme and Antisense RNA-Based Gene Therapies for Myotonic Dystrophy. Molecular Therapy. May 2003;7(5, Part 2):S320.

Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.

Langlois et al., Hammerhead ribozyme-mediated destruction of nuclear foci in myotonic dystrophy myoblasts. Mol Ther. May 2003;7(5 Pt 1):670-80.

Lawrence et al., Crystal structure of the ectodomain of human transferrin receptor. Science. Oct. 22, 1999;286(5440):779-82. doi: 10.1126/science.286.5440.779.

Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Liang et al., RNase H1-Dependent Antisense Oligonucleotides are Robustly Active in Directing RNA Cleavage in Both the Cytoplasm and the Nucleus. Mol Ther. Sep. 6, 2017;25(9):2075-2092. Epub Jun. 27, 2017.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.

Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mignon, Update on Ionis-DMPKRX Program. 2018 MDF Annual Conference. Nashville, TN. Sep. 14-15, 2018:22 pages.

Mojsov et al., A Quantitative Evaluation of Methods for Coupling Asparagine. The Journal of Organic Chemistry. Feb. 1980;45(4):555-60.

Monia et al., Evaluation of 2'-modified oligonucleotides containing 2'-deoxy gaps as antisense inhibitors of gene expression. J Biol Chem. Jul. 5, 1993;268(19):14514-22.

Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.

Mulders et al., Molecular therapy in myotonic dystrophy: focus on RNA gain-of-function. Human Molecular Genetics. 2010;19(1):R90-7. Epub Apr. 20, 2010.

Mulders et al., Triplet-repeat oligonucleotide-mediated reversal of RNA toxicity in myotonic dystrophy. PNAS. Aug. 18, 2009;106(33):13915-20. Supporting information included. 13 pages.

Naylor et al., DELIVER, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.

Naylor et al., DELIVER, a randomized, double-blind, placebo controlled, multiple ascending dose study of DYNE-251 in boys with DMD amenable to Exon 51 skipping. Abstract. Mar. 2023. 1 page.

Overby et al., RNA-mediated therapies in myotonic dystrophy. Drug Discov Today. Dec. 2018;23(12):2013-2022. Epub Aug. 4, 2018.

Padlan et al., A possible procedure for reducing the immunogenicity of antibody variable domains while preserving their ligand-binding properties. Molecular Immunology. Apr.-May 1991;28(4-5):489-98.

Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.

Panowski et al., Site-specific antibody drug conjugates for cancer therapy. MAbs. Jan.-Feb. 2014;6(1):34-45.

Picariello et al., Dyne-101 achieves durable knockdown of toxic human nuclear *DMPK* RNA and correction of splicing in the hTfR1/DMSXL mouse model of DM1. Presented at The Muscular Dystrophy Association Clinical and Scientific Conference. Mar. 13-16, 2022. 1 page.

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.

Qian et al., Targeted drug delivery via the transferrin receptor-mediated endocytosis pathway. Pharmacol Rev. Dec. 2002;54(4):561-87. doi: 10.1124/pr.54.4.561.

(56) References Cited

OTHER PUBLICATIONS

Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.

Roberts et al., Advances in oligonucleotide drug delivery. Nat Rev Drug Discov. Oct. 2020;19(10):673-694. doi: 10.1038/s41573-020-0075-7. Epub Aug. 11, 2020.

Roberts et al., The Halogenation of Ethylenes. J. Am. Chem. Soc. May 1937;59(5):947-8.

Sahenk et al., The muscular dystrophies: distinct pathogenic mechanisms invite novel therapeutic approaches. Curr Rheumatol Rep. Jun. 2011;13(3):199-207.

Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.

Scanlon, Anti-genes: siRNA, ribozymes and antisense. Curr Pharm Biotechnol. Oct. 2004;5(5):415-20.

Scherr et al., Detection of antisense and ribozyme accessible sites on native mRNAs: application to NCOA3 mRNA. Mol Ther. Nov. 2001;4(5):454-60.

Schnyder et al., Targeting of skeletal muscle in vitro using biotinylated immunoliposomes. Biochem J. Jan. 1, 2004;377(Pt 1):61-7. doi: 10.1042/BJ20031034.

Setten et al., The current state and future directions of RNAi-based therapeutics. Nat Rev Drug Discov. Jun. 2019;18(6):421-446. doi: 10.1038/s41573-019-0017-4.

Shen et al., Chemistry, mechanism and clinical status of antisense oligonucleotides and duplex RNAs. Nucleic Acids Res. Feb. 28, 2018;46(4):1584-1600.

Singh et al., Catalytic Enantioselective Cyclopropanation of Olefins Using Carbenoid Chemistry. Synthesis. Feb. 1997;137-49.

Stein, The experimental use of antisense oligonucleotides: a guide for the perplexed. J Clin Invest. Sep. 2001;108(5):641-4.

Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.

Strop et al., Location matters: site of conjugation modulates stability and pharmacokinetics of antibody drug conjugates. Chem Biol. Feb. 21, 2013;20(2):161-7.

Subramanian et al., Abstract 1074. Targeted delivery of oligonucleotide therapeutics to muscle demonstrates potential to treat duchenne muscular dystrophy. Abstract. Mol Ther. 28(4S1): 465. (2020) 1 page.

Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.

Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.

Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.

Swayze et al., The medicinal chemistry of oligonucleotides. In: Antisense Drug Technology, Second Edition. 2007. Crooke, Ed. Chapter 6: 143-182.

Thomas et al., Myotonic Dystrophy and Developmental Regulation of RNA Processing. Comprehensive Physiology. Apr. 2018;8(2):509-53. Epub Mar. 25, 2018.

Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.

Tron et al., Click chemistry reactions in medicinal chemistry: applications of the 1,3-dipolar cycloaddition between azides and alkynes. Med Res Rev. Mar. 2008;28(2):278-308.

Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.

Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.

Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.

Wagner et al., Transferrin-polycation conjugates as carriers for DNA uptake into cells. Proc Natl Acad Sci U S A. May 1990;87(9):3410-4. doi: 10.1073/pnas.87.9.3410.

Walder et al., Role of RNase H in hybrid-arrested translation by antisense oligonucleotides. Proc. Natl. Acad. Sci. Jul. 1988;85:5011-5.

Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.

Walles et al., ADME and Safety Aspects of Non-cleavable Linkers in Drug Discovery and Development. Curr Top Med Chem. 2017;17(32):3463-3475. doi: 10.2174/1568026618666180118153502.

Wheeler et al., Reversal of RNA dominance by displacement of protein sequestered on triplet repeat RNA. Science. Jul. 17, 2009;325(5938):336-9.

Wheeler et al., Targeting nuclear RNA for in vivo correction of myotonic dystrophy. Nature. Aug. 2, 2012;488(7409):111-5. doi: 10.1038/nature11362.

Wheeler, Myotonic dystrophy: therapeutic strategies for the future. Neurotherapeutics. Oct. 2008;5(4):592-600.

Wilton et al., Exon skipping and Duchenne muscular dystrophy: hope, hype and how feasible? Neurol India. Jul.-Sep. 2008;56(3):254-62. doi: 10.4103/0028-3886.43443.

Wolf et al., ACHIEVE trial, a randomized, placebo-controlled, multiple ascending dose study of Dyne-101 in individuals with myotonic dystrophy Type 1 (DM1). Abstract. Mar. 2023. 1 page.

Wolf et al., ACHIEVE trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.

Wu et al., Determination of the role of the human RNase H1 in the pharmacology of DNA-like antisense drugs. J Biol Chem. Apr. 23, 2004;279(17):17181-9. Epub Feb. 11, 2004.

Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.

Yao et al., Targeted Delivery of ASOs Demonstrates Potential to Treat Duchenne Muscular Dystrophy. Poster. Presented at ASGCT; May 12, 2020. 1 page.

Ye et al., Generation and functional characterization of the anti-transferrin receptor single-chain antibody-GAL4 (TfRscFv-GAL4) fusion protein. BMC Biotechnol. Nov. 28, 2012;12:91.

Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.

Zanotti et al., Abstract 17. Repeat dosing with DYNE-101 is Well Tolerated and Leads to a Sustained Reduction of *DMPK* RNA expression in key muscles for DM1 pathology in hTfR1/DMSXL mice and NHPs. Abstract. Mol Ther. Apr. 2022; 30(4S1): 9.

Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.

Zanotti et al., Abstract 82. The ForceTM platform delivers oligonucleotides to the brain in a DM1 mouse model and in NHPs. Mol Ther. Apr. 2023; 31(4S1): 44.

Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.

(56) References Cited

OTHER PUBLICATIONS

Zanotti et al., DYNE-101 achieves durable knockdown of toxic human nuclear *DMPK* RNA and correction of splicing in the hTfR1/DMSXL mouse model of DM1. Abstract. Mar. 2022. 1 page.

Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.

Zanotti, Repeat dosing with DYNE-101 is Well Tolerated and Leads to a Sustained Reduction of *DMPK* RNA expression in key muscles for DM1 pathology in hTfR1/DMSXL mice and NHPs. Presented at American Society of Gene & Cell Therapy Conference. May 16, 2022. 15 pages.

Zanotti, The Force™ platform delivers oligonucleotides to the brain in a DM1 mouse model and in NHPs. Presented at American Society of Gene & Cell Therapy Conference. May 17, 2023. 16 pages.

Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.

Altshuler et al., Generation of recombinant antibodies and means for increasing their affinity. Biochemistry (Mosc). Dec. 2010;75(13):1584-605. With English translation.

Brown et al., Tolerance of single, but not multiple, amino acid replacements in antibody VH CDR 2: a means of minimizing B cell wastage from somatic hypermutation? J Immunol. May 1, 1996;156(9):3285-91.

Gray et al., Combinatorial peptide libraries: mining for cell-binding peptides. Chem Rev. Jan. 22, 2014;114(2):1020-81.

Samoylova et al., Elucidation of muscle-binding peptides by phage display screening. Muscle Nerve. Apr. 1999;22(4):460-6.

Schneider et al., Structural features of the cell surface receptor for transferrin that is recognized by the monoclonal antibody OKT9. J Biol Chem. Jul. 25, 1982;257(14):8516-22.

MUSCLE-TARGETING COMPLEXES COMPRISING AN ANTI-TRANSFERRIN RECEPTOR ANTIBODY LINKED TO AN OLIGONUCLEOTIDE AND METHODS OF DELIVERING OLIGONUCLEOTIDE TO A SUBJECT

RELATED APPLICATIONS

This application is a continuation-in-part of U.S. application Ser. No. 18/184,741, entitled "MUSCLE-TARGETING COMPLEX COMPRISING AN ANTI-TRANSFERRIN RECEPTOR ANTIBODY LINKED TO AN OLIGONUCLEOTIDE", filed Mar. 16, 2023, now U.S. Pat. No. 11,795,233, which is a continuation of U.S. application Ser. No. 17/936,483, entitled "METHODS OF USING MUSCLE TARGETING COMPLEXES TO DELIVER AN OLIGONUCLEOTIDE TO A SUBJECT HAVING FACIOSCAPULOHUMERAL MUSCULAR DYSTROPHY OR A DISEASE ASSOCIATED WITH MUSCLE WEAKNESS", filed Sep. 29, 2022, now U.S. Pat. No. 11,787,169, which is a continuation of U.S. application Ser. No. 17/846,738, entitled "METHODS OF DELIVERING AN OLIGONUCLEOTIDE TO A SUBJECT HAVING FACIOSCAPULOHUMERAL MUSCULAR DYSTROPHY", filed Jun. 22, 2022, now U.S. Pat. No. 11,518,816, which is a continuation of U.S. application Ser. No. 17/671,707, entitled "METHODS OF INTRAVENOUSLY DELIVERING ANTI-TRANSFERRIN ANTIBODY/OLIGONUCLEOTIDE COMPLEXES TO SUBJECTS HAVING MUSCULAR DYSTROPHY," filed Feb. 15, 2022, now U.S. Pat. No. 11,390,682, which is a continuation of U.S. application Ser. No. 17/400,295, filed Aug. 12, 2021, entitled "COMPLEX COMPRISING ANTI-TRANSFERRIN RECEPTOR ANTIBODY COVALENTLY LINKED TO AN OLIGONUCLEOTIDE THAT TARGETS DUX4 RNA," now U.S. Pat. No. 11,286,305, which is a continuation of U.S. application Ser. No. 17/205,123, entitled "A METHOD FOR REDUCING EXPRESSION OF DUX4 IN A MUSCLE CELL BY ADMINISTERING AN ANTI-TRANSFERRIN RECEPTOR ANTIBODY LINKED TO AN OLIGONUCLEOTIDE TARGETING DUX4," filed Mar. 18, 2021, now U.S. Pat. No. 11,111,309, which is a continuation of U.S. application Ser. No. 17/264,948, now abandoned, entitled "MUSCLE TARGETING COMPLEXES AND USES THEREOF FOR TREATING FACIOSCAPULOHUMERAL MUSCULAR DYSTROPHY," filed Feb. 1, 2021, which is a national stage filing under 35 U.S.C. § 371 of International Application No. PCT/US2019/044990, entitled "MUSCLE TARGETING COMPLEXES AND USES THEREOF FOR TREATING FACIOSCAPULOHUMERAL MUSCULAR DYSTROPHY," filed Aug. 2, 2019, which claims the benefit of the filing date of U.S. Provisional Application No. 62/713,933, entitled "MUSCLE TARGETING COMPLEXES AND USES THEREOF FOR TREATING FACIOSCAPULOHUMERAL MUSCULAR DYSTROPHY", filed Aug. 2, 2018. This application is a continuation-in-part of U.S. application Ser. No. 17/264,905, filed Feb. 1, 2021, now abandoned, entitled "MUSCLE TARGETING COMPLEXES AND USES THEREOF FOR TREATING MYOTONIC DYSTROPHY", which is a national stage filing under 35 U.S.C. § 371 of International Patent Application No. PCT/US2019/044987, filed Aug. 2, 2019, entitled "MUSCLE TARGETING COMPLEXES AND USES THEREOF FOR TREATING MYOTONIC DYSTROPHY", which claims the benefit of the filing date of U.S. Provisional Application No. 62/859,672, filed Jun. 10, 2019, entitled "MUSCLE TARGETING COMPLEXES AND USES THEREOF FOR TREATING MYOTONIC DYSTROPHY", of U.S. Provisional Application No. 62/858,888, filed Jun. 7, 2019, entitled "MUSCLE TARGETING COMPLEXES AND USES THEREOF FOR TREATING MYOTONIC DYSTROPHY", of U.S. Provisional Application No. 62/855,761, filed May 31, 2019, entitled "MUSCLE TARGETING COMPLEXES AND USES THEREOF FOR TREATING MYOTONIC DYSTROPHY", of U.S. Provisional Application No. 62/779,161, filed Dec. 13, 2018, entitled "MUSCLE TARGETING COMPLEXES AND USES THEREOF FOR TREATING MYOTONIC DYSTROPHY", and of U.S. Provisional Application No. 62/713,914, filed Aug. 2, 2018, entitled "MUSCLE TARGETING COMPLEXES AND USES THEREOF FOR TREATING MYOTONIC DYSTROPHY". This application is a continuation-in-part of U.S. application Ser. No. 17/265,016, filed Feb. 1, 2021, now abandoned, entitled "MUSCLE TARGETING COMPLEXES AND USES THEREOF FOR TREATING POMPE DISEASE", which is a national stage filing under 35 U.S.C. § 371 of International Patent Application No. PCT/US2019/044960, filed Aug. 2, 2019, entitled "MUSCLE TARGETING COMPLEXES AND USES THEREOF FOR TREATING POMPE DISEASE", which claims the benefit of the filing date of U.S. Provisional Application No. 62/713,959, filed Aug. 2, 2018, entitled "MUSCLE TARGETING COMPLEXES AND USES THEREOF FOR TREATING POMPE DISEASE". This application is a continuation-in-part of U.S. application Ser. No. 17/264,998, filed Feb. 1, 2021, now abandoned, entitled "MUSCLE-TARGETING COMPLEXES AND USES THEREOF", which is a national stage filing under 35 U.S.C. § 371 of International Patent Application No. PCT/US2019/044982, filed Aug. 2, 2019, entitled "MUSCLE-TARGETING COMPLEXES AND USES THEREOF", which claims the benefit of the filing date of U.S. Provisional Application No. 62/859,694, filed Jun. 10, 2019, entitled "MUSCLE-TARGETING COMPLEXES AND USES THEREOF", of U.S. Provisional Application No. 62/858,925, filed Jun. 7, 2019, entitled "MUSCLE-TARGETING COMPLEXES AND USES THEREOF", of U.S. Provisional Application No. 62/855,781, filed May 31, 2019, entitled "MUSCLE-TARGETING COMPLEXES AND USES THEREOF", of U.S. Provisional Application No. 62/779,173, filed Dec. 13, 2018, entitled "MUSCLE-TARGETING COMPLEXES AND USES THEREOF" and of U.S. Provisional Application No. 62/714,010, filed Aug. 2, 2018, entitled "MUSCLE-TARGETING COMPLEXES AND USES THEREOF". This application is a continuation-in-part of U.S. application Ser. No. 17/265,044, filed Feb. 1, 2021, now abandoned, entitled "MUSCLE-TARGETING COMPLEXES AND USES THEREOF IN TREATING MUSCLE ATROPHY", which is a national stage filing under 35 U.S.C. § 371 of International Patent Application No. PCT/US2019/044955, filed Aug. 2, 2019, entitled "MUSCLE-TARGETING COMPLEXES AND USES THEREOF IN TREATING MUSCLE ATROPHY", which claims the benefit of the filing date of U.S. Provisional Application No. 62/714,025, filed Aug. 2, 2018, entitled "MUSCLE-TARGETING COMPLEXES FOR TREATING MUSCLE ATROPHY". This application is a continuation-in-part of U.S. application Ser. No. 17/265,024, filed Feb. 1, 2021, now abandoned, entitled "MUSCLE TARGETING COMPLEXES AND USES THEREOF FOR TREATING DYSTROPHINOPATHIES", which is a national stage filing under 35 U.S.C. § 371 of International Patent Application No. PCT/US2019/044949, filed Aug. 2, 2019, entitled "MUSCLE TARGETING COMPLEXES AND USES THEREOF FOR TREATING DYSTROPHINOPATHIES", which claims the benefit of the filing date of U.S. Provisional Application No. 62/855,766, filed May 31, 2019, entitled "MUSCLE TARGETING COMPLEXES AND USES THEREOF FOR TREATING DYSTROPHINOPATHIES" and of U.S. Provisional Application No. 62/714,031, filed Aug. 2, 2018, entitled "MUSCLE TARGETING COMPLEXES AND USES THEREOF FOR TREATING DYSTROPHINOPATHIES". This application is a continuation-in-part of U.S. application Ser. No. 17/265,019, filed Feb. 1, 2021, now abandoned, entitled "MUSCLE TARGETING COMPLEXES AND USES THEREOF FOR TREATING FRIEDREICH'S ATAXIA", which is a national stage filing under 35 U.S.C. § 371 of International Patent Application No. PCT/US2019/044959, filed Aug. 2, 2019, entitled "MUSCLE TARGETING COMPLEXES AND USES THEREOF FOR TREATING FRIEDREICH'S ATAXIA", which claims the benefit of the filing date of U.S. Provisional Application No. 62/714,035, filed Aug. 2, 2018, entitled "MUSCLE TARGETING COMPLEXES AND USES THEREOF FOR TREATING FRIEDREICH'S ATAXIA". This application is a continuation-in-part of U.S. application Ser. No. 17/264,972, filed Feb. 1, 2021, now abandoned, entitled "MUSCLE TARGETING COMPLEXES AND USES THEREOF FOR TREATING HYPERTROPHIC CARDIOMYOPATHY", which is a national stage filing under 35 U.S.C. § 371 of International Patent Application No. PCT/US2019/044961, filed Aug. 2, 2019, entitled "MUSCLE TARGETING COMPLEXES AND USES THEREOF FOR TREATING HYPERTROPHIC CARDIOMYOPATHY", which claims the benefit of the filing date of U.S. Provisional Application No. 62/714,034, filed Aug. 2, 2018, entitled "MUSCLE TARGETING COMPLEXES AND USES THEREOF FOR TREATING HYPERTROPHIC CARDIOMYOPATHY." The contents of each of the above-mentioned applications are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO AN ELECTRONIC SEQUENCE LISTING

The contents of the electronic sequence listing (D082470001US09-SEQ-ZJG.xml; Size: 931,455 bytes; and Date of Creation: Sep. 12, 2023) is herein incorporated by reference in its entirety.

BACKGROUND OF INVENTION

Muscular dystrophies (MDs) are a group of diseases characterized by the progressive weakness and loss of muscle mass. These diseases are caused by mutations in genes which encode proteins needed to form healthy muscle tissue. Facioscapulohumeral muscular dystrophy (FSHD) is a dominantly inherited type of MD which primarily affects muscles of the face, shoulder blades, and upper arms. Other symptoms of FSHD include abdominal muscle weakness, retinal abnormalities, hearing loss, and joint pain and inflammation. FSHD is the most prevalent of the nine types of MD affecting both adults and children, with a worldwide incidence of about 1 in 8,300 people. FSHD is caused by aberrant production of double homeobox 4 (DUX4), a protein whose function is unknown. The DUX4 gene, which encodes the DUX4 protein, is located in the D4Z4 repeat region on chromosome 4 and is typically expressed only in fetal development, after which it is repressed by hypermethylation of the D4Z4 repeats which surround and compact the DUX4 gene. Two types of FSHD, Type 1 and Type 2 have been described. Type 1, which accounts for about 95% of cases, is associated with deletions of D4Z4 repeats on chromosome 4. Unaffected individuals generally have more than 10 repeats arrayed in the subtelomeric region of chromosome 4, whereas the most common form of FSHD (FSHD1) is caused by a contraction of the array to fewer than 10 repeats, associated with decreased epigenetic repression and variegated expression of DUX4 in skeletal muscle. Type 2 FSHD, which accounts for about 5% of cases, is associated with mutations of the SMCHD1 gene on chromosome 18. Besides supportive care and treatments to address the symptoms of the disease, there are no effective therapies for FSHD.

SUMMARY OF INVENTION

According to some aspects, the disclosure provides complexes that target muscle cells for purposes of delivering molecular payloads to those cells. In some embodiments, complexes provided herein are particularly useful for delivering molecular payloads that inhibit the expression or activity of DUX4, e.g., in a subject having or suspected of having Facioscapulohumeral muscular dystrophy (FSHD). Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can inhibit DUX4 gene expression in the muscle cells. In some embodiments, the oligonucleotides are released by endosomal cleavage of covalent linkers connecting oligonucleotides and muscle-targeting agents of the complexes.

Some aspects of the disclosure comprise a complex comprising a muscle-targeting agent covalently linked to a molecular payload configured for inhibiting expression or activity of DUX4, wherein the muscle-targeting agent specifically binds to an internalizing cell surface receptor on muscle cells.

In some embodiments, the muscle-targeting agent is a muscle-targeting antibody. In some embodiments, a muscle-targeting antibody is an antibody that specifically binds to an extracellular epitope of a transferrin receptor (e.g., an epitope of the apical domain of the transferrin receptor). A muscle-targeting antibody may specifically binds to an epitope of a sequence in the range of C89 to F760 of SEQ ID NO: 1-3. In some embodiments, the equilibrium dissociation constant (Kd) of binding of a muscle-targeting antibody to a transferrin receptor is in a range from $10^{-11}$ M to $10^{-6}$ M.

In some embodiments, a muscle-targeting antibody of a complex competes for specific binding to an epitope of a transferrin receptor with an antibody listed in Table 1 (e.g., competes for specific binding to an epitope of a transferrin receptor with an Kd of less than or equal to $10^{-6}$ M, e.g., in a range of $10^{-11}$ M to $10^{-6}$ M).

In some embodiments, a muscle-targeting antibody of a complex does not specifically bind to the transferrin binding site of a transferrin receptor and/or does not inhibit binding of transferrin to a transferrin receptor. In some embodiments, a muscle-targeting antibody of a complex is cross-reactive with extracellular epitopes of two or more of a human, non-human primate and rodent transferrin receptor. In some embodiments, a muscle-targeting antibody of a complex is configured to promote transferrin receptor mediated internalization of the molecular payload into a muscle cell.

A muscle-targeting antibody (e.g., muscle-targeting antibody is an antibody that specifically binds to an extracellular epitope of a transferrin receptor) is a chimeric antibody, wherein optionally the chimeric antibody is a humanized monoclonal antibody. A muscle-targeting antibody may be in the form of a ScFv, Fab fragment, Fab' fragment, F(ab')$_2$ fragment, or Fv fragment.

In some embodiments, a molecular payload of a complex is an oligonucleotide (e.g., an oligonucleotide that targets DUX4). In some embodiments, an oligonucleotide comprises at least 15 consecutive nucleotides of SEQ ID NO: 45. In some embodiments, an oligonucleotide comprises SEQ ID NO: 45. In some embodiments, an oligonucleotide comprises a sequence that is complementary to at least 15 consecutive nucleotides of SEQ ID NO: 46.

In some embodiments, an oligonucleotide comprises a region of complementarity to a DUX4 gene. In some embodiments, an oligonucleotide comprises an antisense strand that hybridizes, in a cell, with a wild-type DUX4 mRNA transcript encoded by the allele. In some embodiments, an oligonucleotide comprises an antisense strand that hybridizes, in a cell, with a mutant DUX4 mRNA transcript encoded by the allele. An oligonucleotide may comprise a strand complementary to the coding sequence of DUX4.

In some embodiments, an oligonucleotide comprises a strand complementary to the non-coding sequence of DUX4. In some embodiments, an oligonucleotide may comprise a strand complementary to a 5' or 3' UTR sequence of DUX4. In some embodiments, an oligonucleotide mediates epigenetic silencing of DUX4.

An oligonucleotide of the disclosure may comprise at least one modified internucleotide linkage (e.g., a phosphorothioate linkage). In some embodiments, an oligonucleotide comprises phosphorothioate linkages in the Rp stereochemical conformation and in the Sp stereochemical conformation. In some embodiments, an oligonucleotide comprises phosphorothioate linkages that are all in the Rp stereochemical conformation. In other embodiments, an oligonucleotide comprises phosphorothioate linkages that are all in the Sp stereochemical conformation.

An oligonucleotide of the disclosure may comprise one or more modified nucleotides (e.g., 2'-modified nucleotides). In some embodiments, a modified nucleotide is a 2'-O-methyl, 2'-fluoro (2'-F), 2'-O-methoxyethyl (2'-MOE), or 2', 4'-bridged nucleotide. In some embodiments, a modified nucleotides is a bridged nucleotide (e.g., selected from: 2',4'-constrained 2'-O-ethyl (cEt) and locked nucleic acid (LNA) nucleotides).

In some embodiments, an oligonucleotide is a gapmer oligonucleotide that directs RNAse H-mediated cleavage of the DUX4 mRNA transcript in a cell. A gapmer oligonucleotide may comprise a central portion of 5 to 15 deoxyribonucleotides flanked by wings of 2 to 8 modified nucleotides (e.g., 2'-modified nucleotides).

In some embodiments, an oligonucleotide is a mixmer oligonucleotide (e.g., a mixmer oligonucleotide inhibits translation of a DUX4 mRNA transcript). A mixmer oligonucleotide may comprise two or more different 2' modified nucleotides.

In some embodiments, an oligonucleotide is an RNAi oligonucleotide that promotes RNAi-mediated cleavage of the DUX4 mRNA transcript. An RNAi oligonucleotide may be a double-stranded oligonucleotide of 19 to 25 nucleotides in length. In some embodiments, an RNAi oligonucleotide comprises at least one 2' modified nucleotide.

In some embodiments, an oligonucleotide comprises a guide sequence for a genome editing nuclease.

In some embodiments, an oligonucleotide is a phosphorodiamidite morpholino oligomer (PMO).

In other embodiments, a molecular payload is a polypeptide (e.g., a polypeptide that inhibits DUX4 expression). In some embodiments, a molecular payload is a polypeptide that binds to a DUX4 enhancer sequence, thereby blocking recruitment of one or more activators of DUX4 expression.

In some embodiments, a muscle-targeting agent is covalently linked to a molecular payload via a cleavable linker (e.g., a protease-sensitive linker, pH-sensitive linker, or glutathione-sensitive linker). A protease-sensitive linker may comprise a sequence cleavable by a lysosomal protease and/or an endosomal protease. In some embodiments, a protease-sensitive linker comprises a valine-citrulline dipeptide sequence. A pH-sensitive linker may be cleaved at a pH in a range of 4 to 6.

In some embodiments, a muscle-targeting agent is covalently linked to a molecular payload via a non-cleavable linker (e.g., an alkane linker).

In some embodiments, a muscle-targeting antibody comprises a non-natural amino acid to which an oligonucleotide can be covalently linked. In some embodiments, a muscle-targeting antibody is covalently linked to an oligonucleotide via conjugation to a lysine residue or a cysteine residue of the antibody. In some embodiments, an oligonucleotide is conjugated to a cysteine residue of the antibody via a maleimide-containing linker, optionally wherein the maleimide-containing linker comprises a maleimidocaproyl or maleimidomethyl cyclohexane-1-carboxylate group.

In some embodiments, a muscle-targeting antibody is a glycosylated antibody that comprises at least one sugar moiety to which a oligonucleotide is covalently linked. In some embodiments, a glycosylated antibody that comprises at least one sugar moiety that is a branched mannose. In some embodiments, a muscle-targeting antibody is a glycosylated antibody that comprises one to four sugar moieties each of which is covalently linked to a separate oligonucleotide. In some embodiments, a muscle-targeting antibody is a fully-glycosylated antibody or a partially-glycosylated antibody. A partially-glycosylated antibody may be produced via chemical or enzymatic means. In some embodiments, a partially-glycosylated antibody is produced in a cell that is deficient for an enzyme in the N- or O-glycosylation pathway.

Some aspects of the disclosure comprise a method of delivering an molecular payload to a cell expressing transferrin receptor, the method comprising contacting the cell with a complex comprising a muscle-targeting agent covalently linked to a molecular payload configured for inhibiting expression or activity of DUX4.

Some aspects of the disclosure comprise a method of inhibiting expression or activity of DUX4 in a cell, the method comprising contacting the cell with a complex comprising a muscle-targeting agent covalently linked to a molecular payload configured for inhibiting expression or activity of DUX4 in an amount effective for promoting internalization of the molecular payload to the cell. In some embodiments, the cell is in vitro. In some embodiments, the cell is in a subject. In some embodiments, the subject is a human.

Some aspects of the disclosure comprise a method of treating a subject having one or more deletions of a D4Z4 repeat in chromosome 4 that is associated with facioscapulohumeral muscular dystrophy, the method comprising administering to the subject an effective amount of a complex comprising a muscle-targeting agent covalently linked to a molecular payload configured for inhibiting expression or activity of DUX4. In some embodiments, the subject has 10 or fewer D4Z4 repeats (e.g., the subject has 9, 8, 7, 6, 5, 4, 3, 2, or 1 D4Z4 repeats). In some embodiments, the subject has no D4Z4 repeats.

DETAILED DESCRIPTION OF INVENTION

Figure 1:
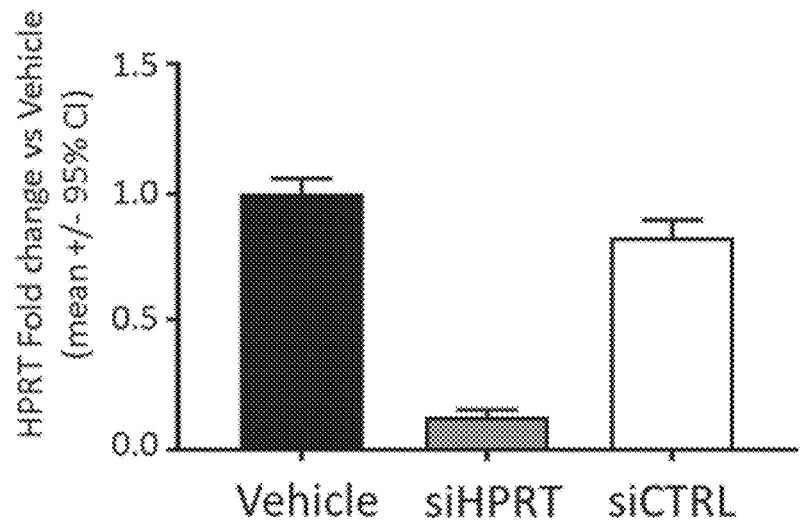
FIG. 1 depicts a non-limiting schematic showing the effect of transfecting cells with an siRNA.
Figure 2:
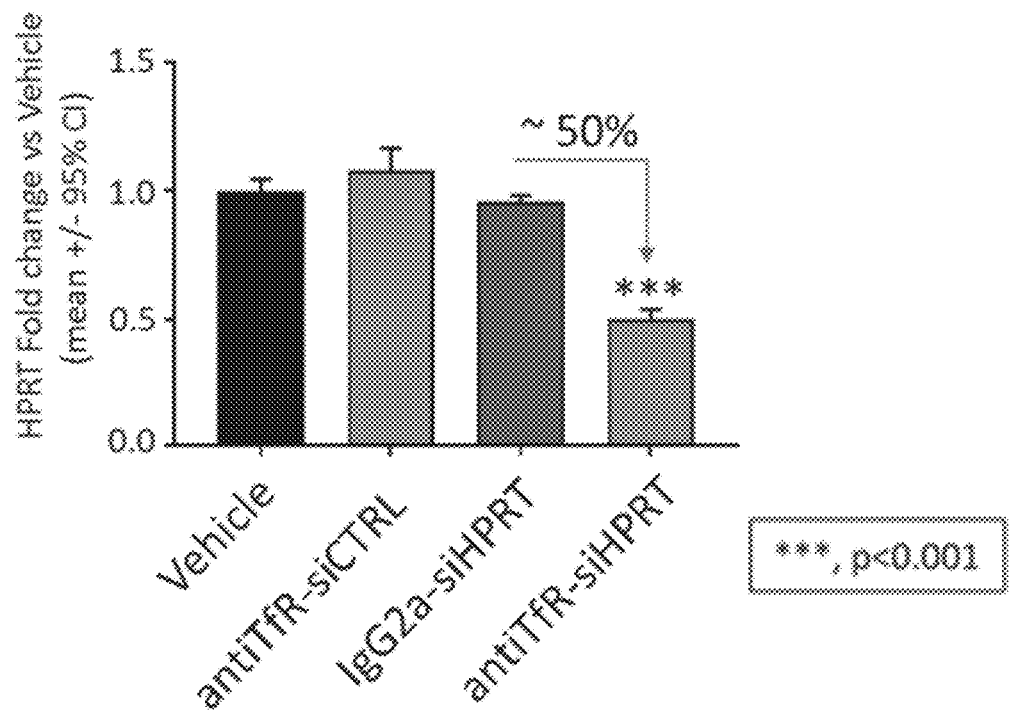
FIG. 2 depicts a non-limiting schematic showing the activity of a muscle targeting complex comprising an siRNA.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that inhibit the expression or activity of target genes in muscle cells, e.g., in a subject having or suspected of having a rare muscle disease. For example, in some embodiments, complexes are provided for targeting a DUX4 to treat subjects having FSHD. In some embodiments, complexes provided herein comprise oligonucleotides that inhibit expression of DUX4 in a subject that has one or more D4Z4 repeat deletions on chromosome 4. In some embodiments, complexes provided herein comprise molecular payloads such as guide molecules (e.g., guide RNAs) that are capable of targeting nucleic acid programmable nucleases (e.g., Cas9) to a DUX4 gene in order to inactivate the gene in muscle cells, for example, by removing a portion of the DUX4 gene, or by introducing an inactivating mutation or stop codon into the DUX4 gene. In some embodiments, such nucleic programmable nucleases could be used to inactivate DUX4 that is aberrantly expressed in muscle cells.

Further aspects of the disclosure, including a description of defined terms, are provided below.

I. Definitions

Administering: As used herein, the terms "administering" or "administration" means to provide a complex to a subject in a manner that is physiologically and/or pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha ($\alpha$), delta ($\Delta$), epsilon ($\epsilon$), gamma ($\gamma$) or mu ($\mu$) heavy chain. In some embodiments, the heavy chain of an antibody described herein can comprise a human alpha ($\alpha$), delta ($\Delta$), epsilon ($\epsilon$), gamma ($\gamma$) or mu ($\mu$) heavy chain. In a particular embodiment, an antibody described herein comprises a human gamma 1 CH1, CH2, and/or CH3 domain. In some embodiments, the amino acid sequence of the VH domain comprises the amino acid sequence of a human gamma ($\gamma$) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferring receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

DUX4: As used herein, the term "DUX4" refers to a gene that encodes double homeobox 4, a protein which is generally expressed during fetal development and in the testes of adult males. In some embodiments, DUX4 may be a human (Gene ID: 100288687), non-human primate (e.g., Gene ID: 750891, Gene ID: 100405864), or rodent gene (e.g., Gene ID: 306226). In humans, expression of the DUX4 gene outside of fetal development and the testes is associated with facioscapulohumeral muscular dystrophy. In addition, multiple human transcript variants (e.g., as annotated under GenBank RefSeq Accession Numbers: NM_001293798.2, NM_001306068.2 (SEQ ID NO: 52), NM_001363820.1) have been characterized that encode different protein isoforms.

Facioscapulohumeral muscular dystrophy (FSHD): As used herein, the term "facioscapulohumeral muscular dystrophy (FSHD)" refers to a genetic disease caused by mutations in the DUX4 gene or SMCHD1 gene that is characterized by muscle mass loss and muscle atrophy, primarily in the muscles of the face, shoulder blades, and upper arms. Two types of the disease, Type 1 and Type 2, have been described. Type I is associated with deletions in D4Z4 repeat regions on chromosome 4 which contain the DUX4 gene. Type 2 is associated with mutations in the SMCHD1 gene. Both Type 1 and Type 2 FSHD are characterized by aberrant production of the DUX4 protein after fetal development outside of the testes. Facioscapulohumeral dystrophy, the genetic basis for the disease, and related symptoms are described in the art (see, e.g. Campbell, A. E., et al., "Facioscapulohumeral dystrophy: Activatin an early embryonic transcriptional program in human skeletal muscle" Human Mol Genet. (2018); and Tawil, R. "Facioscapulohumeral muscular dystrophy" Handbook Clin. Neurol. (2018), 148:541-548.) FSHD Type 1 is associated with Online Mendelian Inheritance in Man (OMIM) Entry #158900. FSHD Type 2 is associated with OMIM Entry #158901.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having FSHD.

Transferrin receptor: As used herein, the term, "transferrin receptor" (also known as TFRC, CD71, p90, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

II. Complexes

Provided herein are complexes that comprise a targeting agent, e.g. an antibody, covalently linked to a molecular payload. In some embodiments, a complex comprises a muscle-targeting antibody covalently linked to a oligonucleotide. A complex may comprise an antibody that specifically binds a single antigenic site or that binds to at least two antigenic sites that may exist on the same or different antigens.

A complex may be used to modulate the activity or function of at least one gene, protein, and/or nucleic acid. In some embodiments, the molecular payload present with a complex is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a DUX4 in muscle cells.

In some embodiments, a complex comprises a muscle-targeting agent, e.g. an anti-transferrin receptor antibody, covalently linked to a molecular payload, e.g. an antisense oligonucleotide that targets a DUX4.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" *Nature* 1988; 333:861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" *J Biol Chem* 1996; 271: 15160-5; and Weisbart R. H. et al., "Cell type specific targeted intracellular delivery into muscle of a monoclonal antibody that binds myosin IIb" *Mol Immunol.* 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to as an anti-transferrin receptor antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or derivatized using several known methodologies, e.g. library design using phage display. Exemplary methodologies have been characterized in the art and are incorporated by reference (Díez, P. et al. "High-throughput phage-display screening in array format", Enzyme and microbial technology, 2015, 79, 34-41.; Christoph M. H. and Stanley, J. R. "Antibody Phage Display: Technique and Applications" J Invest Dermatol. 2014, 134:2.; Engleman, Edgar (Ed.) "Human Hybridomas and Monoclonal Antibodies." 1985, Springer.). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522.; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052.).

Any appropriate anti-transferrin receptor antibodies may be used in the complexes disclosed herein. Examples of anti-transferrin receptor antibodies, including associated references and binding epitopes, are listed in Table 1. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 1.

TABLE 1

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |
| (From Genentech) Clones 7A4, 8A2, 15D2, 10D11, 7B10, | WO 2016/081643, filed May 26, 2016, entitled "ANTI-TRANSFERRIN RECEPTOR ANTIBODIES AND METHODS OF USE" U.S. Pat. No. 9,708,406, filed | Apical domain and non-apical regions |

TABLE 1-continued

List of anti-transferrin receptor antibody clones, including associated references and binding epitope information.

| Antibody Clone Name | Reference(s) | Epitope/Notes |
|---|---|---|
| 15G11, 16G5, 13C3, 16G4, 16F6, 7G7, 4C2, 1B12, and 13D4 (From Armagen) | May 20, 2014, "Anti-transferrin receptor antibodies and methods of use" | |
| 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. Pat. App. 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A *Streptococcus* invasion. Cellular microbiology. 16: 1806-21. | |
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 (From INSERM) | Commercially available anti-transferrin receptor antibodies. | Novus Biologicals 8100 Southpark Way, A-8 Littleton CO 80120 |
| BA120g | U.S. Pat. App. 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I.S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K.C. et al. "Transferrin receptors in human tissues: their distribution and possible clinical relevance." J Clin Pathol. 1983 May; 36(5):539-45. | |

In some embodiments, the muscle-targeting agent is an anti-transferrin receptor antibody. In some embodiment, an anti-transferrin receptor antibody specifically binds to a transferrin protein having an amino acid sequence as disclosed herein. In some embodiments, an anti-transferrin receptor antibody may specifically bind to any extracellular epitope of a transferrin receptor or an epitope that becomes exposed to an antibody, including the apical domain, the transferrin binding domain, and the protease-like domain. In some embodiments, an anti-transferrin receptor antibody binds to an amino acid segment of a human or non-human primate transferrin receptor, as provided in SEQ ID Nos. 1-3 in the range of amino acids C89 to F760. In some embodiments, an anti-transferrin receptor antibody specifically binds with binding affinity of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. Anti-transferrin receptor antibodies used herein may be capable of competing for binding with other anti-transferrin receptor antibodies, e.g. OKT9, 8D3, that bind to transferrin receptor with $10^{-3}$ M, $10^{-4}$ M, $10^{-5}$ M, $10^{-6}$ M, $10^{-7}$ M, or less.

An example human transferrin receptor amino acid sequence, corresponding to NCBI sequence NP_003225.2 (transferrin receptor protein 1 isoform 1, *Homo sapiens*) is as follows:

(SEQ ID NO: 1)
MMDQARSAFSNLFGGEPLSYTRFSLARQVDGDNSHVEMKLAVDEEENADN
NTKANVTKPKRCSGSICYGTIAVIVFFLIGFMIGYLGYCKGVEPKTECER
LAGTESPVREEPGEDFPAARRLYWDDLKRKLSEKLDSTDFTGTIKLLNEN
SYVPREAGSQKDENLALYVENQFREFKLSKVWRDQHFVKIQVKDSAQNSV
IIVDKNGRLVYLVENPGGYVAYSKAATVTGKLVHANFGTKKDFEDLYTPV
NGSIVIVRAGKITFAEKVANAESLNAIGVLIYMDQTKFPIVNAELSFFGH
AHLGTGDPYTPGFPSFNHTQFPPSRSSGLPNIPVQTISRAAAEKLFGNME
GDCPSDWKTDSTCRMVTSESKNVKLTVSNVLKEIKILNIFGVIKGFVEPD
HYVVVGAQRDAWGPGAAKSGVGTALLLKLAQMFSDMVLKDGFQPSRSIIF
ASWSAGDFGSVGATEWLEGYLSSLHLKAFTYINLDKAVLGTSNFKVSASP
LLYTLIEKTMQNVKHPVTGQFLYQDSNWASKVEKLTLDNAAFPFLAYSGI
PAVSFCFCEDTDYPYLGTTMDTYKELIERIPELNKVARAAAEVAGQFVIK
LTHDVELNLDYERYNSQLLSFVRDLNQYRADIKEMGLSLOWLYSARGDFF
RATSRLTTDFGNAEKTDRFVMKKLNDRVMRVEYHFLSPYVSPKESPFRHV
FWGSGSHTLPALLENLKLRKQNNGAFNETLFRNQLALATWTIQGAANALS
GDVWDIDNEF

An example non-human primate transferrin receptor amino acid sequence, corresponding to NCBI sequence NP_001244232.1 (transferrin receptor protein 1, *Macaca mulatta*) is as follows:

(SEQ ID NO: 2)
MMDQARSAFSNLFGGEPLSYTRFSLARQVDGDNSHVEMKLGVDEEENTDN
NTKPNGTKPKRCGGNICYGTIAVIIFFLIGFMIGYLGYCKGVEPKTECER
LAGTESPAREEPEEDFPAAPRLYWDDLKRKLSEKLDTTDFTSTIKLLNEN
LYVPREAGSQKDENLALYIENQFREFKLSKVWRDQHFVKIQVKDSAQNSV
IIVDKNGGLVYLVENPGGYVAYSKAATVTGKLVHANFGTKKDFEDLDSPV
NGSIVIVRAGKITFAEKVANAESLNAIGVLIYMDQTKFPIVKADLSFFGH
AHLGTGDPYTPGFPSFNHTQFPPSQSSGLPNIPVQTISRAAAEKLFGNME
GDCPSDWKTDSTCKMVTSENKSVKLTVSNVLKETKILNIFGVIKGFVEPD
HYVVVGAQRDAWGPGAAKSSVGTALLLKLAQMFSDMVLKDGFQPSRSIIF
ASWSAGDFGSVGATEWLEGYLSSLHLKAFTYINLDKAVLGTSNFKVSASP
LLYTLIEKTMQDVKHPVTGRSLYQDSNWASKVEKLTLDNAAFPFLAYSGI
PAVSFCFCEDTDYPYLGTTMDTYKELVERIPELNKVARAAAEVAGQFVIK
LTHDTELNLDYERYNSQLLLFLRDLNQYRADVKEMGLSLOWLYSARGDFF
RATSRLTTDFRNAEKRDKFVMKKLNDRVMRVEYYFLSPYVSPKESPFRHV
FWGSGSHTLSALLESLKLRRQNNSAFNETLFRNQLALATWTIQGAANALS
GDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 3)
MMDQARSAFSNLFGGEPLSYTRFSLARQVDGDNSHVEMKLGVDEEENTDN
NTKANGTKPKRCGGNICYGTIAVIIFFLIGFMIGYLGYCKGVEPKTECER
LAGTESPAREEPEEDFPAAPRLYWDDLKRKLSEKLDTTDFTSTIKLLNEN
LYVPREAGSQKDENLALYIENQFREFKLSKVWRDQHFVKIQVKDSAQNSV
IIVDKNGGLVYLVENPGGYVAYSKAATVTGKLVHANFGTKKDFEDLDSPV
NGSIVIVRAGKITFAEKVANAESLNAIGVLIYMDQTKFPIVKADLSFFGH
AHLGTGDPYTPGFPSFNHTQFPPSQSSGLPNIPVQTISRAAAEKLFGNME
GDCPSDWKTDSTCKMVTSENKSVKLTVSNVLKETKILNIFGVIKGFVEPD
HYVVVGAQRDAWGPGAAKSSVGTALLLKLAQMFSDMVLKDGFQPSRSIIF
ASWSAGDFGSVGATEWLEGYLSSLHLKAFTYINLDKAVLGTSNFKVSASP
LLYTLIEKTMQDVKHPVTGRSLYQDSNWASKVEKLTLDNAAFPFLAYSGI
PAVSFCFCEDTDYPYLGTTMDTYKELVERIPELNKVARAAAEVAGQFVIK
LTHDTELNLDYERYNSQLLLFLRDLNQYRADVKEMGLSLOWLYSARGDFF
RATSRLTTDFRNAEKRDKFVMKKLNDRVMRVEYYFLSPYVSPKESPFRHV
FWGSGSHTLSALLESLKLRRQNNSAFNETLFRNQLALATWTIQGAANALS
GDVWDIDNEF

An example mouse transferrin receptor amino acid sequence, corresponding to NCBI sequence NP_001344227.1 (transferrin receptor protein 1, *Mus musculus*) is as follows:

(SEQ ID NO: 4)
MMDQARSAFSNLFGGEPLSYTRFSLARQVDGDNSHVEMKLAADEEENADN
NMKASVRKPKRFNGRLCFAAIALVIFFLIGFMSGYLGYCKRVEQKEECVK
LAETEETDKSETMETEDVPTSSRLYWADLKTLLSEKLNSIEFADTIKQLS
QNTYTPREAGSQKDESLAYYIENQFHEFKFSKVWRDEHYVKIQVKSSIGQ
NMVTIVQSNGNLDPVESPEGYVAFSKPTEVSGKLVHANFGTKKDFEELSY
SVNGSLVIVRAGEITFAEKVANAQSFNAIGVLIYMDKNKFPVVEADLALF
GHAHLGTGDPYTPGFPSFNHTQFPPSQSSGLPNIPVQTISRAAAEKLFGK
MEGSCPARWNIDSSCKLELSQNQNVKLIVKNVLKERRILNIFGVIKGYEE
PDRYVVVGAQRDALGAGVAAKSSVGTGLLLKLAQVFSDMISKDGFRPSRS
IIFASWTAGDFGAVGATEWLEGYLSSLHLKAFTYINLDKVVLGTSNFKVS
ASPLLYTLMGKIMQDVKHPVDGKSLYRDSNWISKVEKLSFDNAAYPFLAY
SGIPAVSFCFCEDADYPLGTRLDTYEALTQKVPQLNOMVRTAAEVAGQL
IIKLTHDVELNLDYEMYNSKLLSFMKDLNQFKTDIRDMGLSLOWLYSARG
DYFRATSRLTTDFHNAEKTNRFVMREINDRIMKVEYHFLSPYVSPRESPF

-continued
RHIFWGSGSHTLSALVENLKLRQKNITAFNETLFRNQLALATWTIQGVAN

ALSGDIWNIDNEF

In some embodiments, an anti-transferrin receptor antibody binds to an amino acid segment of the receptor as follows: FVKIQVKDSAQNSVIIVDKNGRLVYLVENPG-GYVAYSKAATVTGKLVHANFGTKKDFE DLYTPVNG-SIVIVRAGKITFAEKVANAESLN-AIGVLIYMDQTKFPIVNAELSFFGHAHLG TGDPYTPGFPSFNHTQFPPSRSSGLPNIPVQTIS-RAAAEKLFGNMEGDCPSDWKTDSTCR MVTS-ESKNVKLTVSNVLKE (SEQ ID NO: 5) and does not inhibit the binding interactions between transferrin receptors and transferrin and/or human hemochromatosis protein (also known as HFE).

Appropriate methodologies may be used to obtain and/or produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988.).

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

Some aspects of the disclosure provide proteins that bind to transferrin receptor (e.g., an extracellular portion of the transferrin receptor). In some embodiments, transferrin receptor antibodies provided herein bind specifically to transferrin receptor (e.g., human transferrin receptor). Transferrin receptors are internalizing cell surface receptors that transport transferrin across the cellular membrane and participate in the regulation and homeostasis of intracellular iron levels. In some embodiments, transferrin receptor antibodies provided herein bind specifically to transferrin receptor from human, non-human primates, mouse, rat, etc. In some embodiments, transferrin receptor antibodies provided herein bind to human transferrin receptor. In some embodiments, transferrin receptor antibodies provided herein specifically bind to human transferrin receptor. In some embodiments, transferrin receptor antibodies provided herein bind to an apical domain of human transferrin receptor. In some embodiments, transferrin receptor antibodies provided herein specifically bind to an apical domain of human transferrin receptor.

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 1. In some embodiments, transferrin receptor antibodies include the CDR-H1, CDR-H2, and CDR-H3 as provided for any one of the anti-transferrin receptor antibodies selected from Table 1. In some embodiments, anti-transferrin receptor antibodies include the CDR-L1, CDR-L2, and CDR-L3 as provided for any one of the anti-transferrin receptor antibodies selected from Table 1. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 1. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 1. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or light chain CDR3s of any one of the anti-transferrin receptor antibodies selected from Table 1.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/or CDR-L3 sequences from one of the anti-transferrin receptor antibodies selected from Table 1. In some embodiments, the position of one or more CDRs along the VH (e.g., CDR-H1, CDR-H2, or CDR-H3) and/or VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or CDR-H3 described herein may be one, two, three, four, five or more amino acids shorter than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or CDR-H3 described herein may be one, two, three, four, five or more amino acids longer than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 1. For example, the antibodies may include one or more CDR sequence(s) from any of the anti-transferrin receptor antibodies selected from Table 1 containing up to 5, 4, 3, 2, or 1 amino acid residue variations as compared to the corresponding CDR region in any one of the CDRs provided herein (e.g., CDRs from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 1. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 1.

In some embodiments, anti-transferrin receptor antibodies of the disclosure include any antibody that includes a heavy chain variable domain and/or a light chain variable domain of any anti-transferrin receptor antibody, such as any one of the anti-transferrin receptor antibodies selected from Table 1. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 1.

Aspects of the disclosure provide anti-transferrin receptor antibodies having a heavy chain variable (VH) and/or a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 1. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 1.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 1. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 1. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 1. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 1. In some embodiments, the light chain variable framework region that is derived from said amino acid sequence consists of said amino acid sequence but for the presence of up to 10 amino acid substitutions, deletions, and/or insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 1. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 1. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 1. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 1.

In some embodiments, the anti-transferrin receptor antibody is any anti-transferrin receptor antibody, such as any one of the anti-transferrin receptor antibodies selected from Table 1.

In some embodiments, an anti-transferrin receptor antibody comprises a VL domain comprising the amino acid sequence of any anti-transferrin receptor antibody, such as any one of the anti-transferrin receptor antibodies selected from Table 1, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, the muscle-targeting agent is a transferrin receptor antibody (e.g., the antibody and variants thereof as described in International Application Publication WO 2016/081643, incorporated herein by reference).

The heavy chain and light chain CDRs of the antibody according to different definition systems are provided in Table 1.1. The different definition systems, e.g., the Kabat definition, the Chothia definition, and/or the contact definition have been described. See, e.g., (e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273: 927-948; and Almagro, J. Mol. Recognit. 17:132-143 (2004). See also hgmp.mrc.ac.uk and bioinforg.uk/abs).

TABLE 1.1

Heavy chain and light chain CDRs of a mouse transferrin receptor antibody

| CDRs | Kabat | Chothia | Contact |
|---|---|---|---|
| CDR-H1 | SYWMH (SEQ ID NO: 17) | GYTFTSY (SEQ ID NO: 23) | TSYWMH (SEQ ID NO: 25) |
| CDR-H2 | EINPTNGRTNYIEKFKS (SEQ ID NO: 18) | NPTNGR (SEQ ID NO: 24) | WIGEINPTNGRTN (SEQ ID NO: 26) |
| CDR-H3 | GTRAYHY (SEQ ID NO: 19) | GTRAYHY (SEQ ID NO: 19) | ARGTRA (SEQ ID NO: 27) |
| CDR-L1 | RASDNLYSNLA (SEQ ID NO: 20) | RASDNLYSNLA (SEQ ID NO: 20) | YSNLAWY (SEQ ID NO: 28) |
| CDR-L2 | DATNLAD (SEQ ID NO: 21) | DATNLAD (SEQ ID NO: 21) | LLVYDATNLA (SEQ ID NO: 29) |
| CDR-L3 | QHFWGTPLT (SEQ ID NO: 22) | QHFWGTPLT (SEQ ID NO: 22) | QHFWGTPL (SEQ ID NO: 30) |

The heavy chain variable domain (VH) and light chain variable domain sequences are also provided:

VH
(SEQ ID NO: 33)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSS

VL
(SEQ ID NO: 34)
DIQMTQSPASLSVSVGETVTITCRASDNLYSNLAWYQQKQGKSPQLLVYD

ATNLADGVPSRFSGSGSGTQYSLKINSLQSEDFGTYYCQHFWGTPLTFGA

GTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 1.1. Alternatively or in addition, the transferrin receptor antibody of the present disclosure comprises a CDR-L1, a CDR-L2, and a CDR-L3 that are the same as the CDR-L1, CDR-L2, and CDR-L3 shown in Table 1.1.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 1.1. "Collectively" means that the total number of amino acid variations in all of the three heavy chain CDRs is within the defined range. Alternatively or in addition, the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 1.1.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 1.1. Alternatively or in addition, the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 1.1.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 1.1. In some embodiments, the transferrin receptor antibody of the present disclosure comprises a CDR-L3 containing one amino acid variation as compared with the CDR-L3 as shown in Table 1.1. In some embodiments, the transferrin receptor antibody of the present disclosure comprises a CDR-L3 of QHFAGTPLT (SEQ ID NO: 31 according to the Kabat and Chothia definition system) or QHFAGTPL (SEQ ID NO: 32 according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 1.1, and comprises a CDR-L3 of QHFAGTPLT (SEQ ID NO: 31 according to the Kabat and Chothia definition system) or QHFAGTPL (SEQ ID NO: 32 according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 1.1. Alternatively or in addition, the transferrin receptor antibody of the present disclosure comprises light chain CDRs that collectively are at least 80% (e.g., 80%, 85%, 90%, 95%, or 98%) identical to the light chain CDRs as shown in Table 1.1.

In some embodiments, the transferrin receptor antibody of the present disclosure comprises a VH comprising the amino acid sequence of SEQ ID NO: 33. Alternatively or in addition, the transferrin receptor antibody of the present disclosure comprises a VL comprising the amino acid sequence of SEQ ID NO: 34.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 33. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 34.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 33. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 34.

In some embodiments, the transferrin receptor antibody of the present disclosure is a humanized antibody (e.g., a humanized variant of an antibody). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 1.1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1.1) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 34, and/or one or more amino acid substitutions at positions 1, 5, 7, 11, 12, 20, 38, 40, 44, 66, 75, 81, 83, 87, and 108 as compared with the VH as set forth in SEQ ID NO: 33. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 34, and/or amino acid substitutions at all of positions 1, 5, 7, 11, 12, 20, 38, 40, 44, 66, 75, 81, 83, 87, and 108 as compared with the VH as set forth in SEQ ID NO: 33.

In some embodiments, the transferrin receptor antibody of the present disclosure is a humanized antibody and contains the residues at positions 43 and 48 of the VL as set forth in SEQ ID NO: 34. Alternatively or in addition, the transferrin receptor antibody of the present disclosure is a humanized antibody and contains the residues at positions 48, 67, 69, 71, and 73 of the VH as set forth in SEQ ID NO: 33.

The VH and VL amino acid sequences of an example humanized antibody that may be used in accordance with the present disclosure are provided:

Humanized VH (SEQ ID NO: 35)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSS

Humanized VL (SEQ ID NO: 36)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELK

In some embodiments, the transferrin receptor antibody of the present disclosure comprises a VH comprising the amino acid sequence of SEQ ID NO: 35. Alternatively or in addition, the transferrin receptor antibody of the present disclosure comprises a VL comprising the amino acid sequence of SEQ ID NO: 36.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 35. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 36.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 35. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 36.

In some embodiments, the transferrin receptor antibody of the present disclosure is a humanized variant comprising amino acid substitutions at one or more of positions 43 and 48 as compared with the VL as set forth in SEQ ID NO: 34, and/or amino acid substitutions at one or more of positions 48, 67, 69, 71, and 73 as compared with the VH as set forth in SEQ ID NO: 33. In some embodiments, the transferrin receptor antibody of the present disclosure is a humanized variant comprising a S43A and/or a V48L mutation as compared with the VL as set forth in SEQ ID NO: 34, and/or one or more of A67V, L69I, V71R, and K73T mutations as compared with the VH as set forth in SEQ ID NO: 33

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 34, and/or amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 33.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An exemplary human IgG1 constant region is given below:

(SEQ ID NO: 37)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

(SEQ ID NO: 38)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCP

Other antibody heavy and light chain constant regions are well known in the art, e.g., those provided in the IMGT database (imgt.org) or at vbase2.org/vbstat.php., both of which are incorporated by reference herein.

Exemplary heavy chain and light chain amino acid sequences of the transferrin receptor antibodies described are provided below:

```
Heavy Chain (VH + human IgG1 constant region)
                                    (SEQ ID NO: 39)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (VL + kappa light chain)
                                    (SEQ ID NO: 40)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain (humanized VH + human IgG1 constant
region)
                                    (SEQ ID NO: 41)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (humanized VL + kappa light chain)
                                    (SEQ ID NO: 42)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELKASTKGPSVFPLAPSSKSTSGGTAALGCLVKDYFPEPVTVSWNS

GALTSGVHTFPAVLQSSGLYSLSSVVTVPSSSLGTQTYICNVNHKPSNTK

VDKKVEPKSCDKTHTCP
```

In some embodiments, the transferrin receptor antibody described herein comprises a heavy chain comprising an amino acid sequence that is at least 80% (e.g., 80%, 85%, 90%, 95%, or 98%) identical to SEQ ID NO: 39. Alternatively or in addition, the transferrin receptor antibody described herein comprises a light chain comprising an amino acid sequence that is at least 80% (e.g., 80%, 85%, 90%, 95%, or 98%) identical to SEQ ID NO: 40. In some embodiments, the transferrin receptor antibody described herein comprises a heavy chain comprising the amino acid sequence of SEQ ID NO: 39. Alternatively or in addition, the transferrin receptor antibody described herein comprises a light chain comprising the amino acid sequence of SEQ ID NO: 40.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 40.

In some embodiments, the transferrin receptor antibody described herein comprises a heavy chain comprising an amino acid sequence that is at least 80% (e.g., 80%, 85%, 90%, 95%, or 98%) identical to SEQ ID NO: 41. Alternatively or in addition, the transferrin receptor antibody described herein comprises a light chain comprising an amino acid sequence that is at least 80% (e.g., 80%, 85%, 90%, 95%, or 98%) identical to SEQ ID NO: 42. In some embodiments, the transferrin receptor antibody described herein comprises a heavy chain comprising the amino acid sequence of SEQ ID NO: 41. Alternatively or in addition, the transferrin receptor antibody described herein comprises a light chain comprising the amino acid sequence of SEQ ID NO: 42.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain of humanized antibody as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 40.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Exemplary FABs amino acid sequences of the transferrin receptor antibodies described herein are provided below:

```
Heavy Chain FAB (VH + a portion of human IgG1
constant region)
                                    (SEQ ID NO: 43)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain FAB (humanized VH + a portion of human
IgG1 constant region)
                                    (SEQ ID NO: 44)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT
```

-continued

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 39).

b. Other Muscle-Targeting Antibodies

In some embodiments, the muscle-targeting antibody is an antibody that specifically binds hemojuvelin, caveolin-3, Duchenne muscular dystrophy peptide, myosin IIb, or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109:6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cγ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" Biochim Biophys Acta 2008, 1786: 126-38; Jarver P., et al., "In vivo biodistribution and efficacy of peptide mediated delivery" Trends Pharmacol Sci 2010; 31:528-35; Samoylova T. I., et al., "Elucidation of muscle-binding peptides by phage display screening" Muscle Nerve 1999; 22:460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." Biomol Eng 2002; 18:269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 6) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 6). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." *Int J Pharm* 2002; 231:177-84; the entire contents of which are hereby incorporated by reference. Here, a 12 amino acid peptide having the sequence SKTFNTHPQSTP (SEQ ID NO: 7) was identified and this muscle-targeting peptide showed improved binding to C2C12 cells relative to the ASSLNIA (SEQ ID NO: 6) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" *J Virol* 2005; 79:13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEHKEEELI (SEQ ID NO: 8) appeared most frequently. Accordingly, in some embodiments, the muscle-targeting agent comprises the amino acid sequence TARGEHKEEELI (SEQ ID NO: 8).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cal, D. "BDNF-mediated enhancement of inflammation and injury in the aging heart." Physiol Genomics. 2006, 24:3, 191-7.; Zhang, L. "Molecular profiling of heart endothelial cells." Circulation, 2005, 112:11, 1601-11.; McGuire, M. J. et al. "In vitro selection of a peptide with high selectivity for cardiomyocytes in vivo." J Mol Biol. 2004, 342:1, 171-82.). Exemplary muscle-targeting peptides comprise an amino acid sequence of the following group: CQAQGQLVC (SEQ ID NO: 9), CSERSMNFC (SEQ ID NO: 10), CPKTRRVPC (SEQ ID NO: 11), WLSEAGPVVTVRALRGTGSW (SEQ ID NO: 12), ASSLNIA (SEQ ID NO: 6), CMQHSMRVC (SEQ ID NO: 13), and DDTRHWG (SEQ ID NO: 14). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147.).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20.; Germer, K. et al. "RNA aptamers and their therapeutic and diagnostic applications." Int. J. Biochem. Mol. Biol. 2013; 4:27-40.). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214.; Thiel, W. H. et al. "Smooth Muscle Cell-targeted RNA Aptamer Inhibits Neointimal Formation." Mol Ther. 2016, 24:4, 779-87.). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a DUX4. Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to cause degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Any suitable oligonucleotide may be used as a molecular payload, as described herein. Examples of oligonucleotides useful for targeting DUX4 are provided in U.S. Pat. No. 9,988,628, published on Feb. 2, 2017, entitled "AGENTS USEFUL IN TREATING FACIOSCAPULOHUMERAL MUSCULAR DYSTROPHY"; U.S. Pat. No. 9,469,851, published Oct. 30, 2014, entitled "RECOMBINANT VIRUS PRODUCTS AND METHODS FOR INHIBITING EXPRESSION OF DUX4"; US Patent Application Publication 20120225034, published on Sep. 6, 2012, entitled "AGENTS USEFUL IN TREATING FACIOSCAPULOHUMERAL MUSCULAR DYSTROPHY"; PCT Patent Application Publication Number WO 2013/120038, published on Aug. 15, 2013, entitled "MORPHOLINO TARGETING DUX4 FOR TREATING FSHD"; Chen et al., "Morpholino-mediated Knockdown of DUX4 Toward Facioscapulohumeral Muscular Dystrophy Therapeutics," Molecular Therapy, 2016, 24:8, 1405-1411.; and Ansseau et al., "Antisense Oligonucleotides Used to Target the DUX4 mRNA as Therapeutic Approaches in Facioscapulohumeral Muscular Dystrophy (FSHD)," Genes, 2017, 8, 93; the contents of each of which are incorporated herein in their entireties. In some embodiments, the oligonucleotide is an antisense oligonucleotide, a morpholino, a siRNA, a shRNA, or another nucleotide which hybridizes with the target DUX4 gene or mRNA.

In some embodiments, oligonucleotides may have a region of complementarity to a sequence as set forth as: Human DUX4, corresponding to NCBI sequence NM_001293798.1 (SEQ ID NO: 15) as below and/or Mouse DUX4, corresponding to NCBI sequence NM_001081954.1 (SEQ ID NO: 16), as below. In some embodiments, the oligonucleotide may have a region of complementarity to a hypomethylated, contracted D4Z4 repeat, as in Daxinger, et al., "Genetic and Epigenetic Contributors to FSHD," published in Curr Opin Genet Dev in 2015, Lim J-W, et al., DICER/AGO-dependent epigenetic silencing of D4Z4 repeats enhanced by exogenous siRNA suggests mechanisms and therapies for FSHD Hum Mol Genet. 2015 September 1; 24(17):4817-4828, the contents of each of which are incorporated in their entireties.

In some embodiments, oligonucleotides may have a region of complementarity to a sequence set forth as follows, which is an example human DUX4 gene sequence (NM_001293798.1) (SEQ ID NO: 15):

ATGGCCCTCCCGACACCCTCGGACAGCACCCTCCCCGCGGAAGCCCGGGG

ACGAGGACGGCGACGGAGACTCGTTTGGACCCCGAGCCAAAGCGAGGCCC

TGCGAGCCTGCTTTGAGCGGAACCCGTACCCGGGCATCGCCACCAGAGAA

CGGCTGGCCCAGGCCATCGGCATTCCGGAGCCCAGGGTCCAGATTTGGTT

TCAGAATGAGAGGTCACGCCAGCTGAGGCAGCACCGGCGGGAATCTCGGC

CCTGGCCCGGGAGACGCGGCCCGCCAGAAGGCCGGCGAAAGCGGACCGCC

GTCACCGGATCCCAGACCGCCCTGCTCCTCCGAGCCTTTGAGAAGGATCG

CTTTCCAGGCATCGCCGCCCGGGAGGAGCTGGCCAGAGAGACGGGCCTCC

CGGAGTCCAGGATTCAGATCTGGTTTCAGAATCGAAGGGCCAGGCACCCG

GGACAGGGTGGCAGGGCGCCCGCGCAGGCAGGCGGCCTGTGCAGCGCGGC

CCCCGGCGGGGGTCACCCTGCTCCCTCGTGGGTCGCCTTCGCCCACACCG

GCGCGTGGGGAACGGGGCTTCCCGCACCCCACGTGCCCTGCGCGCCTGGG

GCTCTCCCACAGGGGGCTTTCGTGAGCCAGGCAGCGAGGGCCGCCCCCGC

-continued
GCTGCAGCCCAGCCAGGCCGCGCCGGCAGAGGGGATCTCCCAACCTGCCC

CGGCGCGCGGGGATTTCGCCTACGCCGCCCCGGCTCCTCCGGACGGGGCG

CTCTCCCACCCTCAGGCTCCTCGGTGGCCTCCGCACCCGGGCAAAAGCCG

GGAGGACCGGGACCCGCAGCGCGACGGCCTGCCGGGCCCCTGCGCGGTGG

CACAGCCTGGGCCCGCTCAAGCGGGGCCGCAGGGCCAAGGGGTGCTTGCG

CCACCCACGTCCCAGGGGAGTCCGTGGTGGGGCTGGGGCCGGGGTCCCCA

GGTCGCCGGGCGGCGTGGGAACCCCAAGCCGGGGCAGCTCCACCTCCCC

AGCCCGCGCCCCCGGACGCCTCCGCCTCCGCGCGGCAGGGGCAGATGCAA

GGCATCCCGGCGCCCTCCCAGGCGCTCCAGGAGCCGGCGCCCTGGTCTGC

ACTCCCCTGCGGCCTGCTGCTGGATGAGCTCCTGGCGAGCCCGGAGTTTC

TGCAGCAGGCGCAACCTCTCCTAGAAACGGAGGCCCCGGGGGAGCTGGAG

GCCTCGGAAGAGGCCGCCTCGCTGGAAGCACCCCTCAGCGAGGAAGAATA

CCGGGCTCTGCTGGAGGAGCTTTAG

In some embodiments, oligonucleotides may have a region of complementarity to a sequence set forth as follows, which is an example mouse DUX4 gene sequence (SEQ ID NO: 16) (NM_001081954.1):

ATGGCAGAAGCTGGCAGCCCTGTTGGTGGCAGTGGTGTGGCACGGGAATC

CCGGCGGCGCAGGAAGACGGTTTGGCAGGCCTGGCAAGAGCAGGCCCTGC

TATCAACTTTCAAGAAGAAGAGATACCTGAGCTTCAAGGAGAGGAAGGAG

CTGGCCAAGCGAATGGGGGTCTCAGATTGCCGCATCCGCGTGTGGTTTCA

GAACCGCAGGAATCGCAGTGGAGAGGAGGGGCATGCCTCAAAGAGGTCCA

TCAGAGGCTCCAGGCGGCTAGCCTCGCCACAGCTCCAGGAAGAGCTTGGA

TCCAGGCCACAGGGTAGAGGCATGCGCTCATCTGGCAGAAGGCCTCGCAC

TCGACTCACCTCGCTACAGCTCAGGATCCTAGGGCAAGCCTTTGAGAGGA

ACCCACGACCAGGCTTTGCTACCAGGGAGGAGCTGGCGCGTGACACAGGG

TTGCCCGAGGACACGATCCACATATGGTTTCAAAACCGAAGAGCTCGGCG

GCGCCACAGGAGGGGCAGGCCCACAGCTCAAGATCAAGACTTGCTGGCGT

CACAAGGGTCGGATGGGGCCCCTGCAGGTCCGGAAGGCAGAGAGCGTGAA

GGTGCCCAGGAGAACTTGTTGCCACAGGAAGAAGCAGGAAGTACGGGCAT

GGATACCTCGAGCCCTAGCGACTTGCCCTCCTTCTGCGGAGAGTCCCAGC

CTTTCCAAGTGGCACAGCCCCGTGGAGCAGGCCAACAAGAGGCCCCCACT

CGAGCAGGCAACGCAGGCTCTCTGGAACCCCTCCTTGATCAGCTGCTGGA

TGAAGTCCAAGTAGAAGAGCCTGCTCCAGCCCCTCTGAATTTGGATGGAG

ACCCTGGTGGCAGGGTGCATGAAGGTTCCCAGGAGAGCTTTTGGCCACAG

GAAGAAGCAGGAAGTACAGGCATGGATACTTCTAGCCCCAGCGACTCAAA

CTCCTTCTGCAGAGAGTCCCAGCCTTCCCAAGTGGCACAGCCCTGTGGAG

CGGGCCAAGAAGATGCCCGCACTCAAGCAGACAGCACAGGCCCTCTGGAA

CTCCTCCTCCTTGATCAACTGCTGGACGAAGTCCAAAAGGAAGAGCATGT

GCCAGTCCCACTGGATTGGGGTAGAAATCCTGGCAGCAGGGAGCATGAAG

GTTCCCAGGACAGCTTACTGCCCCTGGAGGAAGCAGTAAATTCGGGCATG

```
                                                    -continued
GATACCTCGATCCCTAGCATCTGGCCAACCTTCTGCAGAGAATCCCAGCC

TCCCCAAGTGGCACAGCCCTCTGGACCAGGCCAAGCACAGGCCCCCACTC

AAGGTGGGAACACGGACCCCCTGGAGCTCTTCCTCTATCAACTGTTGGAT

GAAGTCCAAGTAGAAGAGCATGCTCCAGCCCCTCTGAATTGGGATGTAGA

TCCTGGTGGCAGGGTGCATGAAGGTTCGTGGGAGAGCTTTTGGCCACAGG

AAGAAGCAGGAAGTACAGGCCTGGATACTTCAAGCCCCAGCGACTCAAAC

TCCTTCTTCAGAGAGTCCAAGCCTTCCCAAGTGGCACAGCGCCGTGGAGC

GGGCCAAGAAGATGCCCGCACTCAAGCAGACAGCACAGGCCCTCTGGAAC

TCCTCCTCTTTGATCAACTGCTGGACGAAGTCCAAAAGGAAGAGCATGTG

CCAGCCCCACTGGATTGGGGTAGAAATCCTGGCAGCATGGAGCATGAAGG

TTCCCAGGACAGCTTACTGCCCCTGGAGGAAGCAGCAAATTCGGGCAGGG

ATACCTCGATCCCTAGCATCTGGCCAGCCTTCTGCAGAAAATCCCAGCCT

CCCCAAGTGGCACAGCCCTCTGGACCAGGCCAAGCACAGGCCCCCATTCA

AGGTGGGAACACGGACCCCCTGGAGCTCTTCCTTGATCAACTGCTGACCG

AAGTCCAACTTGAGGAGCAGGGGCCTGCCCCTGTGAATGTGGAGGAAACA

TGGGAGCAAATGGACACAACACCTATCTGCCTCTCACTTCAGAAGAATAT

CAGACTCTTCTAGATATGCTCTGA.
```

In some embodiments, an oligonucleotide may have a region of complementarity to DUX4 gene sequences of multiple species, e.g., selected from human, mouse and non-human species.

In some embodiments, an oligonucleotide that targets DUX4 is a FM10 sequence. In some embodiments, an oligonucleotide that targets DUX4 is a phosphorodiamidate morpholino version of a FM10 sequence. In some embodiments, an oligonucleotide that targets DUX4 comprises the sequence GGGCATTTTAATATATCTCTGAACT (SEQ ID NO: 45). In some embodiments, an oligonucleotide that targets DUX4 comprises a sequence that is complementary to at least 15 consecutive nucleotides of

```
                                               (SEQ ID NO: 46)
AGTTCAGAGATATATTAAAATGCCC.
```

In some embodiments, muscle specific E3 ubiquitin ligases are overexpressed in FSHD and function in muscle atrophy (see, e.g., Vanderplanck, C. et al. "The FSHD Atrophic Myotube Phenotype Is Caused by DUX4 Expression" PLoS One 6,10:e26820, 2011). In some embodiments, downregulation of these ligases presents a viable therapeutic strategy. In some embodiments, an oligonucleotide may target, e.g., inhibit the expression of, a muscle specific E3 ubiquitin ligase implicated in FSHD, such as MuRF1 (also known as TRIM63) and MAFbx (also known as Fbx032). In some embodiments, an oligonucleotide may have a region of complementarity to at least one MuRF1 gene sequence, e.g. human MuRF1 (NCBI Gene ID 84676). In some embodiments, an oligonucleotide may have a region of complementarity to at least one MAFbx gene sequence, e.g. human MAFbx (NCBI Gene ID 114907).

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In a some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

b. Oligonucleotide Modifications:

The oligonucleotides described herein may be modified, e.g., comprise a modified sugar moiety, a modified internucleoside linkage, a modified nucleotide and/or combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleotides

In some embodiments, an oligonucleotide include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, an oligonucleotide can include at least one 2'-O-methyl-modified nucleotide, and in some embodiments, all of the nucleotides include a 2'-O-methyl modification. In some embodiments, an oligonucleotide comprises modified nucleotides in which the ribose ring comprises a bridge moiety connecting two atoms in the ring, e.g., connecting the 2'-O atom to the 4'-C atom. In some embodiments, the oligonucleotides are "locked," e.g., comprise modified nucleotides in which the ribose ring is "locked" by a methylene bridge connecting the 2'-O atom and the 4'-C atom. Examples of LNAs are described in International Patent Application Publication WO/2008/043753, published on Apr. 17, 2008, and entitled "RNA Antagonist Compounds For The Modulation Of PCSK9", the contents of which are incorporated herein by reference in its entirety.

Other modifications that may be used in the oligonucleotides disclosed herein include ethylene-bridged nucleic acids (ENAs). ENAs include, but are not limited to, 2'-O,4'-C-ethylene-bridged nucleic acids. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties.

In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. In some embodiments, the oligonucleotide comprises a modified nucleotide disclosed in one of the following United States Patent or Patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-Modified Bicyclic Nucleic Acid Analogs"; U.S. Pat. No. 7,569,686, issued on Aug. 4, 2009, and entitled "Compounds And Methods For Synthesis Of Bicyclic Nucleic Acid Analogs"; U.S. Pat. No. 7,335,765, issued on Feb. 26, 2008, and entitled "Novel Nucleoside And Oligonucleotide Analogues"; U.S. Pat. No. 7,314,923, issued on Jan. 1, 2008, and entitled "Novel Nucleoside And Oligonucleotide Analogues"; U.S. Pat. No. 7,816,333, issued on Oct. 19, 2010, and entitled "Oligonucleotide Analogues And Methods Utilizing The Same" and US Publication Number 2011/0009471 now U.S. Pat. No. 8,957,201, issued on Feb. 17, 2015, and entitled "Oligonucleotide Analogues And Methods Utilizing The Same", the entire contents of each of which are incorporated herein by reference for all purposes.

In some embodiments, the oligonucleotide comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA.

In some embodiments, the oligonucleotide may have at least one modified nucleotide that results in an increase in Tm of the oligonucleotide in a range of 1° C., 2° C., 3° C., 4° C., or 5° C. compared with an oligonucleotide that does not have the at least one modified nucleotide. The oligonucleotide may have a plurality of modified nucleotides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleotide.

The oligonucleotide may comprise alternating nucleotides of different kinds. For example, an oligonucleotide may comprise alternating deoxyribonucleotides or ribonucleotides and 2'-fluoro-deoxyribonucleotides. An oligonucleotide may comprise alternating deoxyribonucleotides or ribonucleotides and 2'-O-methyl nucleotides. An oligonucleotide may comprise alternating 2'-fluoro nucleotides and 2'-O-methyl nucleotides. An oligonucleotide may comprise alternating bridged nucleotides and 2'-fluoro or 2'-O-methyl nucleotides.

d. Internucleotide Linkages/Backbones

In some embodiments, oligonucleotide may contain a phosphorothioate or other modified internucleotide linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleotide linkages at the first, second, and/or third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177, 196; 5,188,897; 5,264,423; 5,276,019; 5,278,302; 5,286, 717; 5,321,131; 5,399,676; 5,405,939; 5,453,496; 5,455, 233; 5,466,677; 5,476,925; 5,519,126; 5,536,821; 5,541, 306; 5,550,111; 5,563, 253; 5,571,799; 5,587,361; and 5,625,050.

In some embodiments, oligonucleotides may have heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides are adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides are provided that comprise nucleoside units that are joined together by either substantially all Sp or substantially all Rp phosphorothioate intersugar linkages. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, the oligonucleotide is a gapmer. A gapmer oligonucleotide generally has the formula 5'-X—Y—Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., one to six modified nucleotides. Examples of modified nucleotides include, but are not limited to, 2' MOE or 2'OMe or Locked Nucleic Acid bases (LNA). The flanking sequences X and Z may be of one to twenty nucleotides, one to eight nucleotides or one to five nucleotides in length, in some embodiments. The flanking sequences X and Z may be of similar length or of dissimilar lengths. The gap-segment Y may be a nucleotide sequence of five to twenty nucleotides, size to twelve nucleotides or six to ten nucleotides in length, in some embodiments.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

i. Mixmers

In some embodiments, an oligonucleotide described herein may be a mixmer or comprise a mixmer sequence pattern. In general, mixmers are oligonucleotides that comprise both naturally and non-naturally occurring nucleotides or comprise two different types of non-naturally occurring nucleotides typically in an alternating pattern. Mixmers generally have higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Such oligonucleotides that are incapable of recruiting RNAse H have been described, for example, see WO2007/112754 or WO2007/112753.

In some embodiments, the mixmer comprises or consists of a repeating pattern of nucleotide analogues and naturally occurring nucleotides, or one type of nucleotide analogue and a second type of nucleotide analogue. However, a mixmer need not comprise a repeating pattern and may instead comprise any arrangement of modified nucleotides and naturally occurring nucleotides or any arrangement of one type of modified nucleotide and a second type of modified nucleotide. The repeating pattern, may, for instance be every second or every third nucleotide is a modified nucleotide, such as LNA, and the remaining nucleotides are naturally occurring nucleotides, such as DNA, or are a 2' substituted nucleotide analogue such as 2'MOE or 2' fluoro analogues, or any other modified nucleotide described herein. It is recognized that the repeating pattern of modified nucleotide, such as LNA units, may be combined with modified nucleotide at fixed positions—e.g. at the 5' or 3' termini.

In some embodiments, a mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive modified nucleotide, such as at least two consecutive LNAs. In some embodiments, the mixmer comprises at least a region consisting of at least three consecutive modified nucleotide units, such as at least three consecutive LNAs.

In some embodiments, the mixmer does not comprise a region of more than 7, more than 6, more than 5, more than 4, more than 3, or more than 2 consecutive nucleotide analogues, such as LNAs. In some embodiments, LNA units may be replaced with other nucleotide analogues, such as those referred to herein.

Mixmers may be designed to comprise a mixture of affinity enhancing modified nucleotides, such as in non-limiting example LNA nucleotides and 2'-O-methyl nucleotides. In some embodiments, a mixmer comprises modified internucleoside linkages (e.g., phosphorothioate internucleoside linkages or other linkages) between at least two, at least three, at least four, at least five or more nucleotides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleotides. For example, in some embodiments, a mixmer may comprise morpholino nucleotides mixed (e.g., in an alternating manner) with one or more other nucleotides (e.g., DNA, RNA nucleotides) or modified nucleotides (e.g., LNA, 2'-O-Methyl nucleotides).

In some embodiments, mixmers are useful for splice correcting or exon skipping, for example, as reported in Touznik A., et al., LNA/DNA mixmer-based antisense oligonucleotides correct alternative splicing of the SMN2 gene and restore SMN protein expression in type 1 SMA fibroblasts Scientific Reports, volume 7, Article number: 3672 (2017), Chen S. et al., Synthesis of a Morpholino Nucleic Acid (MNA)-Uridine Phosphoramidite, and Exon Skipping Using MNA/2'-O-Methyl Mixmer Antisense Oligonucleotide, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule.

k. microRNA (miRNAs)

In some embodiments, an oligonucleotide may be a microRNA (miRNA). MicroRNAs (referred to as "miR-NAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3',5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from Streptococcus pyogenes (see, e.g., "Complete genome sequence of an M1 strain of Streptococcus pyogenes." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via a oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled Methods of delivering multiple targeting oligonucleotides to a cell using cleavable linkers, which was published on Nov. 5, 2015; US Patent Application Number 2015/0247141 A1, entitled Multimeric Oligonucleotide Compounds, which was published on Sep. 3, 2015, US Patent Application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules:

Any suitable small molecule may be used as a molecular payload, as described herein. In some embodiments, the small molecule is as described in US Patent Application Publication 20170340606, published on Nov. 30, 2017, entitled "METHODS OF TREATING MUSCULAR DYSTROPHY" or as described in US Patent Application Publication 20180050043, published on Feb. 22, 2018, entitled "INHIBITION OF DUX4 EXPRESSION USING BROMODOMAIN AND EXTRA-TERMINAL DOMAIN PROTEIN INHIBITORS (BETi). Further examples of small molecule payloads are provided in Bosnakovski, D., et al., High-throughput screening identifies inhibitors of DUX4-induced myoblast toxicity, Skelet Muscle, February 2014, and Choi. S., et al., "Transcriptional Inhibitors Identified in a 160,000-Compound Small-Molecule DUX4 Viability Screen," Journal of Biomolecular Screening, 2016. For example, in some embodiments, the small molecule is a transcriptional inhibitor, such as SHC351, SHC540, SHC572. In some embodiments, the small molecule is STR00316 increases production or activity of another protein, such as integrin. In some embodiments, the small molecule is a bromodomain inhibitor (BETi), such as JQ1, PF1-1, I-BET-762, I-BET-151, RVX-208, or CPI-0610.

iii. Peptides

Any suitable peptide or protein may be used as a molecular payload, as described herein. In some embodiments, a protein is an enzyme. These peptides or proteins may be produced, synthesized, and/or derivatized using several methodologies, e.g. phage displayed peptide libraries, one-bead one-compound peptide libraries, or positional scanning synthetic peptide combinatorial libraries. In some embodiments, the peptide or protein may bind a DME1 or DME2 enhancer to inhibit DUX4 expression, e.g., by blocking binding of an activator.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5' methyl cap. In some embodiments, a mRNA may comprise a polyA tail, optionally of up to 160 nucleotides in length. In some embodiments, the gene expression construct may be expressed, e.g., overexpressed, within the nucleus of a muscle cell. In some embodiments, the gene expression construct encodes a oligonucleotide (e.g., an shRNA targeting DUX4) or a protein that downregulates the expression of DUX4 (e.g., a peptide or protein that binds to DME1 or DME2 enhancer to inhibit DUX4 expression, e.g., by blocking binding of an activator). In some embodiments, the gene expression construct encodes a oligonucleotide (e.g., an shRNA targeting MuRF1 or MAFbx) that downregulates the expression of MuRF1 or MAFbx, respectively. In some embodiments, the gene expression constructs encodes a protein that comprises at least one zinc finger. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "CLOSED-ENDED LINEAR DUPLEX DNA FOR NON-VIRAL GENE TRANSFER"; U.S. Pat. No. 8,853,377B2, issued on Oct. 7, 2014, entitled, "MRNA FOR USE IN TREATMENT OF HUMAN GENETIC DISEASES"; and U.S. Pat. No. 8,822,663B2, issued on Sep. 2, 2014, ENGINEERED NUCLEIC ACIDS AND METHODS OF USE THEREOF," the contents of each of which are incorporated herein by reference in their entireties.

C. Linkers

Complexes described herein generally comprise a linker that connects a muscle-targeting agent to a molecular payload. A linker comprises at least one covalent bond. In some embodiments, a linker may be a single bond, e.g., a disulfide bond or disulfide bridge, that connects a muscle-targeting agent to a molecular payload. However, in some embodiments, a linker may connect a muscle-targeting agent to a molecular payload through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the muscle-targeting agent or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493.; Jain, N. et al. "Current ADC Linker Chemistry" Pharm Res. 2015, 32:11, 3526-3540.; McCombs, J. R. and Owen, S. C. "Antibody Drug Conjugates: Design and Selection of Linker, Payload and Conjugation Chemistry" AAPS J. 2015, 17:2, 339-351.).

A precursor to a linker typically will contain two different reactive species that allow for attachment to both the muscle-targeting agent and a molecular payload. In some embodiments, the two different reactive species may be a nucleophile and/or an electrophile. In some embodiments, a linker is connected to a muscle-targeting agent via conjugation to a lysine residue or a cysteine residue of the muscle-targeting agent. In some embodiments, a linker is connected to a cysteine residue of a muscle-targeting agent via a maleimide-containing linker, wherein optionally the maleimide-containing linker comprises a maleimidocaproyl or maleimidomethyl cyclohexane-1-carboxylate group. In some embodiments, a linker is connected to a cysteine residue of a muscle-targeting agent or thiol functionalized molecular payload via a 3-arylpropionitrile functional group. In some embodiments, a linker is connected to a muscle-targeting agent and/or a molecular payload via an amide bond, a hydrazide, a triazole, a thioether or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by an disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

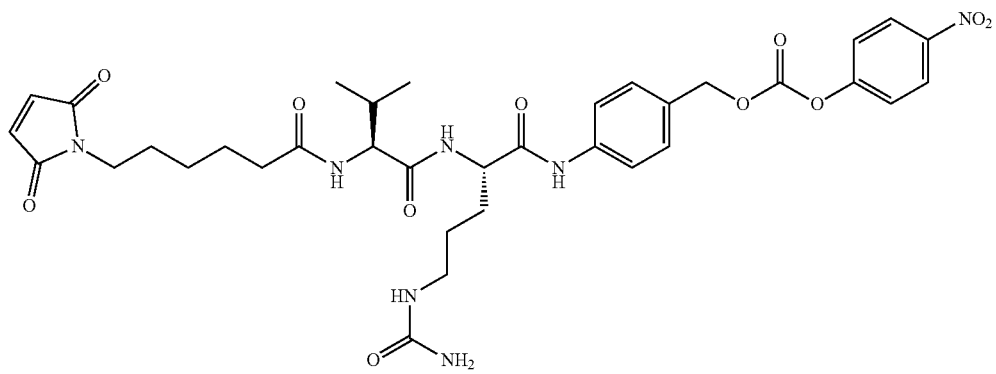 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of:

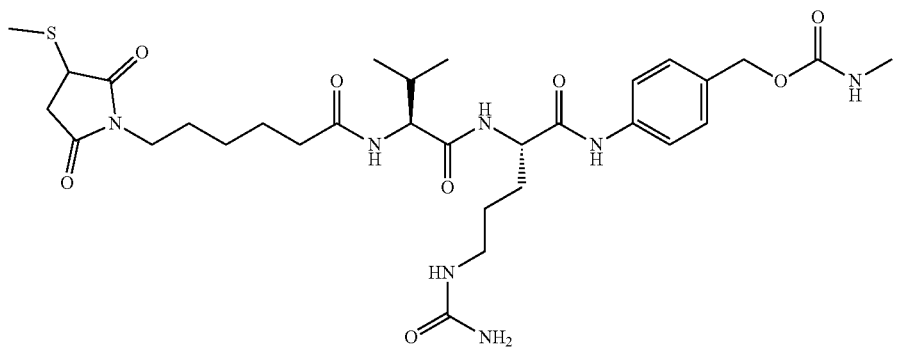

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or an alkoxy-amine linker. In some embodiments, sortase-mediated ligation will be utilized to covalently link a muscle-targeting agent comprising a LPXT sequence to a molecular payload comprising a $(G)_n$ sequence (see, e.g. Proft T. Sortase-mediated protein ligation: an emerging biotechnology tool for protein modification and immobilization. Biotechnol Lett. 2010, 32(1):1-10.).

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S; an optionally substituted heterocyclylene further comprising at least one heteroatom selected from N, O, and S; an imino, an optionally substituted nitrogen species, an optionally substituted oxygen species O, an optionally substituted sulfur species, or a poly(alkylene oxide), e.g. polyethylene oxide or polypropylene oxide.

iii. Linker Conjugation

In some embodiments, a linker is connected to a muscle-targeting agent and/or molecular payload via a phosphate, thioether, ether, carbon-carbon, or amide bond. In some embodiments, a linker is connected to an oligonucleotide through a phosphate or phosphorothioate group, e.g. a terminal phosphate of an oligonucleotide backbone. In some embodiments, a linker is connected to an muscle-targeting agent, e.g. an antibody, through a lysine or cysteine residue present on the muscle-targeting agent In some embodiments, a linker is connected to a muscle-targeting agent and/or molecular payload by a cycloaddition reaction between an azide and an alkyne to form a triazole, wherein the azide and the alkyne may be located on the muscle-targeting agent, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "Fused Cyclooctyne Compounds And Their Use In Metal-free Click Reactions". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase". In some embodiments, a cycloaddition reaction between an azide and an alkyne to form a triazole, wherein the azide and the alkyne may be located on the muscle-targeting agent, molecular payload, or the linker is as described in International Patent Application Publication WO2014065661, published on May 1, 2014, entitled, "Modified antibody, antibody-conjugate and process for the preparation thereof"; or International Patent Application Publication WO2016170186, published on Oct. 27, 2016, entitled, "Process For The Modification Of A Glycoprotein Using A Glycosyltransferase That Is Or Is Derived From A β(1,4)-N-Acetylgalactosaminyltransferase".

In some embodiments, a linker further comprises a spacer, e.g., a polyethylene glycol spacer or an acyl/carbomoyl sulfamide spacer, e.g., a HydraSpace™ spacer. In some embodiments, a spacer is as described in Verkade, J. M. M. et al., "*A Polar Sulfamide Spacer Significantly Enhances the Manufacturability, Stability, and Therapeutic Index of Antibody-Drug Conjugates*", Antibodies, 2018, 7, 12.

In some embodiments, a linker is connected to a muscle-targeting agent and/or molecular payload by the Diels-Alder reaction between a dienophile and a diene/hetero-diene, wherein the dienophile and the diene/hetero-diene may be located on the muscle-targeting agent, molecular payload, or the linker. In some embodiments a linker is connected to a muscle-targeting agent and/or molecular payload by other pericyclic reactions, e.g. ene reaction. In some embodiments, a linker is connected to a muscle-targeting agent and/or molecular payload by an amide, thioamide, or sulfonamide bond reaction. In some embodiments, a linker is connected to a muscle-targeting agent and/or molecular payload by a condensation reaction to form an oxime, hydrazone, or semicarbazide group existing between the linker and the muscle-targeting agent and/or molecular payload.

In some embodiments, a linker is connected to a muscle-targeting agent and/or molecular payload by a conjugate addition reactions between a nucleophile, e.g. an amine or a hydroxyl group, and an electrophile, e.g. a carboxylic acid or an aldehyde. In some embodiments, a nucleophile may exist on a linker and an electrophile may exist on a muscle-targeting agent or molecular payload prior to a reaction between a linker and a muscle-targeting agent or molecular payload. In some embodiments, an electrophile may exist on a linker and a nucleophile may exist on a muscle-targeting agent or molecular payload prior to a reaction between a linker and a muscle-targeting agent or molecular payload. In some embodiments, an electrophile may be an azide, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

D. Examples of Antibody-Molecular Payload Complexes

Other aspects of the present disclosure provide complexes comprising any one the muscle targeting agent (e.g., a transferrin receptor antibodies) described herein covalently linked to any of the molecular payloads (e.g., an oligonucleotide) described herein. In some embodiments, the muscle targeting agent (e.g., a transferrin receptor antibody) is covalently linked to a molecular payload (e.g., an oligonucleotide) via a linker. Any of the linkers described herein may be used. In some embodiments, the linker is linked to the 5' end, the 3' end, or internally of the oligonucleotide. In some embodiments, the linker is linked to the antibody via a thiol-reactive linkage (e.g., via a cysteine in the antibody).

An exemplary structure of a complex comprising a transferrin receptor antibody covalently linked to an oligonucleotide via a Val-cit linker is provided below:

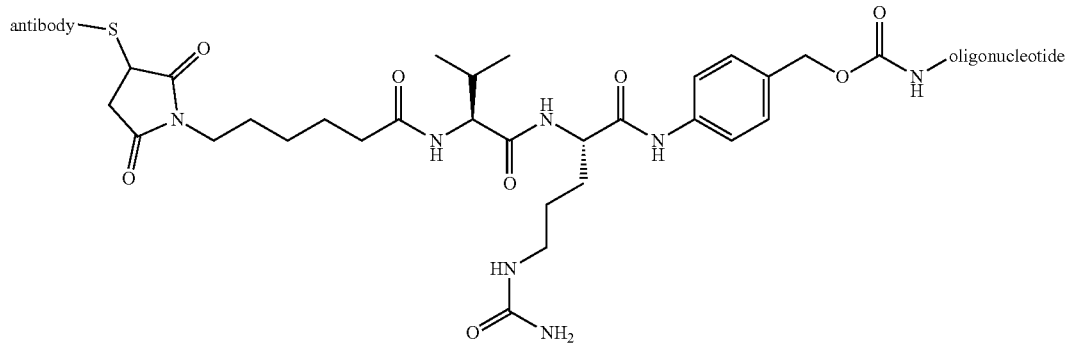

wherein the linker is linked to the 5' end, the 3' end, or internally of the oligonucleotide, and wherein the linker is linked to the antibody via a thiol-reactive linkage (e.g., via a cysteine in the antibody).

It should be appreciated that antibodies can be linked to oligonucleotides with different stochiometries, a property that may be referred to as a drug to antibody ratios (DAR) with the "drug" being the oligonucleotide. In some embodiments, one oligonucleotide is linked to an antibody (DAR=1). In some embodiments, two oligonucleotides are linked to an antibody (DAR=2). In some embodiments, three oligonucleotides are linked to an antibody (DAR=3). In some embodiments, four oligonucleotides are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating oligonucleotides to different sites on an antibody and/or by conjugating multimers to one or more sites on antibody. For example, a DAR of 2 may be achieved by conjugating a single oligonucleotide to two different sites on an antibody or by conjugating a dimer oligonucleotide to a single site of an antibody.

In some embodiments, the complex described herein comprises a transferrin receptor antibody (e.g., an antibody or any variant thereof as described herein) covalently linked to an oligonucleotide. In some embodiments, the complex described herein comprises a transferrin receptor antibody (e.g., an antibody or any variant thereof as described herein) covalently linked to an oligonucleotide via a linker (e.g., a Val-cit linker). In some embodiments, the linker (e.g., a Val-cit linker) is linked to the 5' end, the 3' end, or internally of the oligonucleotide. In some embodiments, the linker (e.g., a Val-cit linker) is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide, wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide, wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide, wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide, wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a linker (e.g., a Val-cit linker), wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a Val-cit linker, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1, and wherein the complex comprises the structure of:

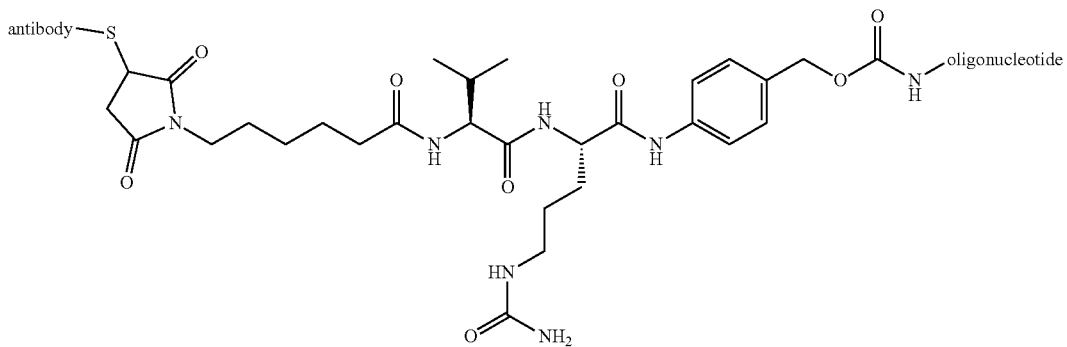

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 33 and a VL having the amino acid sequence of SEQ ID NO: 34, and wherein the complex comprises the structure of:

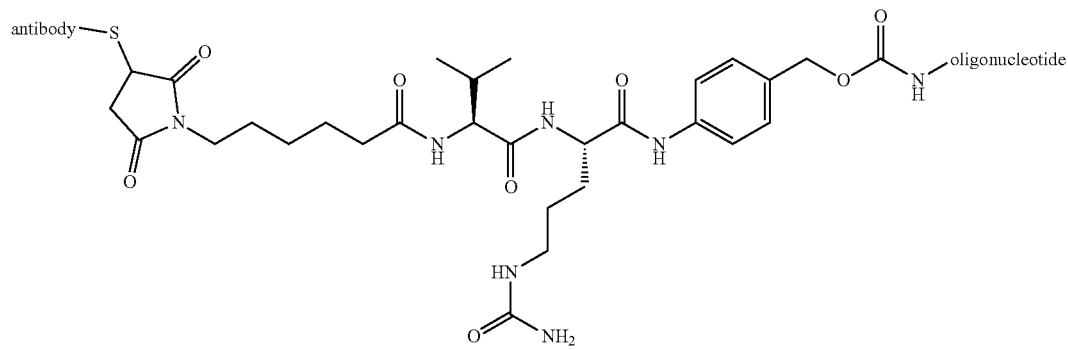

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 35 and a VL having the amino acid sequence of SEQ ID NO: 36, and wherein the complex comprises the structure of:

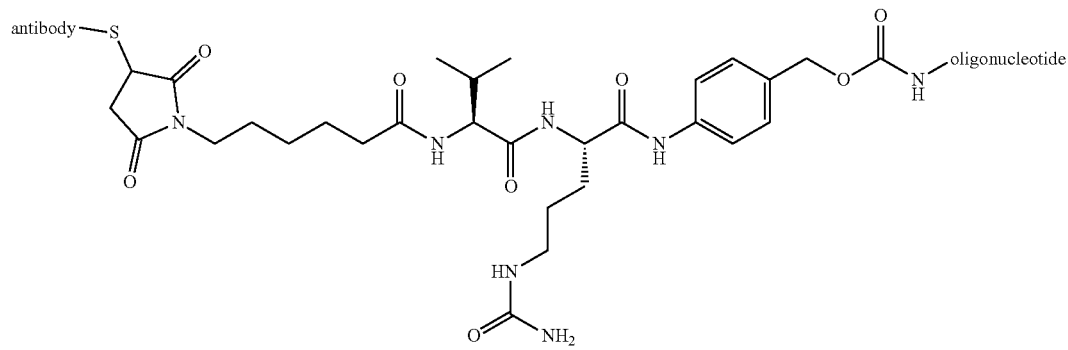

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

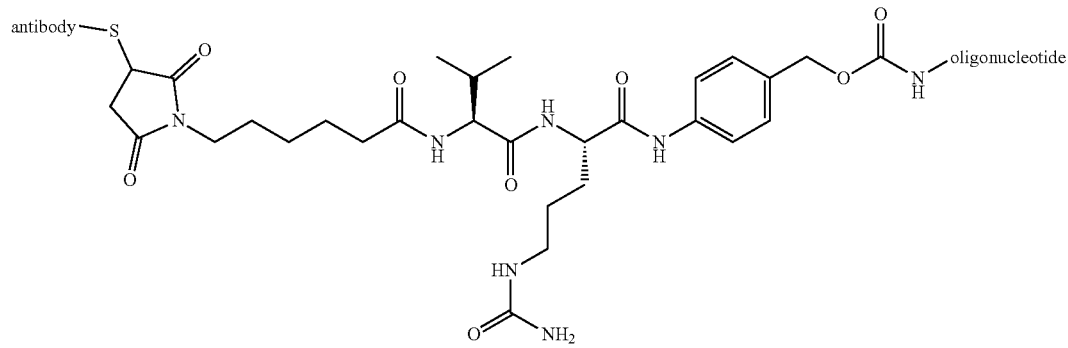

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 39 and a light chain having the amino acid sequence of SEQ ID NO: 40, and wherein the complex comprises the structure of:

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 41 and a light chain having the amino acid sequence of SEQ ID NO: 42, and wherein the complex comprises the structure of:

THEREOF FOR TREATING HYPERTROPHIC CARDIOMYOPATHY"; the entire contents of each of which are incorporated herein by reference.

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes

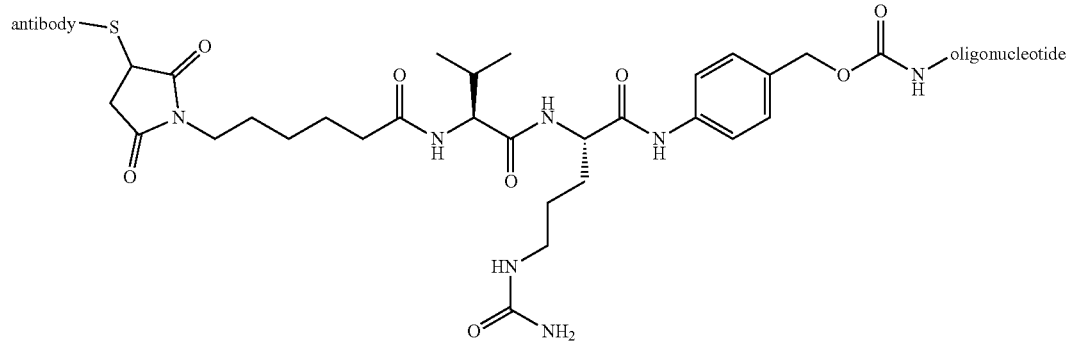

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

Further examples of complexes and molecular payloads (e.g., oligonucleotides useful for targeting muscle genes) are provided in US Patent Application Publication US20210308272, published on Oct. 7, 2021, entitled, "MUSCLE TARGETING COMPLEXES AND USES THEREOF FOR TREATING MYOTONIC DYSTROPHY"; US Patent Application Publication US20210317226, published on Oct. 14, 2021, entitled, "MUSCLE TARGETING COMPLEXES AND USES THEREOF FOR TREATING POMPE DISEASE"; US Patent Application Publication US20210308274, published on Oct. 7, 2021, 2020, entitled, "MUSCLE TARGETING COMPLEXES AND USES THEREOF FOR TREATING FRIEDREICH'S ATAXIA"; US Patent Application Publication US20210261680, published on Aug. 26, 2021, entitled, "MUSCLE-TARGETING COMPLEXES AND USES THEREOF"; US Patent Application Publication US20220378934, published on Dec. 1, 2022, entitled, "MUSCLE-TARGETING COMPLEXES AND USES THEREOF IN TREATING MUSCLE ATROPHY"; US Patent Application Publication US20210308273, published on Oct. 7, 2021, entitled, "MUSCLE TARGETING COMPLEXES AND USES THEREOF FOR TREATING DYSTROPHINOPATHIES"; US Patent Application Publication US20210324101, published on Oct. 21, 2021, entitled, "MUSCLE TARGETING COMPLEXES AND USES are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the a complexes in a required amount in a selected solvent with one or a combination of ingredients enumerated above, as required, followed by filtered sterilization.

In some embodiments, a composition may contain at least about 0.1% of the a complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently to a molecular payload as described herein are effective in treating FSHD. In some embodiments, complexes are effective in treating Type I FSHD. In some embodiments, complexes are effective in treating Type II FSHD. In some embodiments, FSHD is associated with deletions in D4Z4 repeat regions on chromosome 4 which contain the DUX4 gene. In some embodiments, FSHD is associated with mutations in the SMCHD1 gene.

In some embodiments, a subject may be a human subject, a non-human primate subject, a rodent subject, or any suitable mammalian subject. In some embodiments, a subject may have myotonic dystrophy. In some embodiments, a subject has elevated expression of the DUX4 gene outside of fetal development and the testes. In some embodiments, the subject has facioscapulohumeral muscular dystrophy of Type I or Type II. In some embodiments, the subject having FSHD has mutations in the SMCHD1 gene. In some embodiments, the subject having FSHD has deletion mutations in D4Z4 repeat regions on chromosome 4.

An aspect of the disclosure includes a methods involving administering to a subject an effective amount of a complex as described herein. In some embodiments, an effective amount of a pharmaceutical composition that comprises a complex comprising a muscle-targeting agent covalently to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment The efficacy of treatment may be assessed using any suitable methods. In some embodiments, the efficacy of treatment may be assessed by evaluation of observation of symptoms associated with FSHD including muscle mass loss and muscle atrophy, primarily in the muscles of the face, shoulder blades, and upper arms.

In some embodiments, a pharmaceutical composition that comprises a complex comprising a muscle-targeting agent covalently to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, or 6 months.

In some embodiments, a pharmaceutical composition may comprises more than one complex comprising a muscle-targeting agent covalently to a molecular payload. In some embodiments, a pharmaceutical composition may further comprise any other suitable therapeutic agent for treatment of a subject, e.g. a human subject having FSHD. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting Gene Expression with Transfected Antisense Oligonucleotides A siRNA that targets hypoxanthine phosphoribosyltransferase (HPRT) was tested in vitro for its ability to reduce expression levels of HPRT in an immortalized cell line. Briefly, Hepa 1-6 cells were transfected with either a control siRNA (siCTRL; 100 nM) or the siRNA that targets HPRT (siHPRT; 100 nM), formulated with lipofectamine 2000. HPRT expression levels were evaluated 48 hours following transfection. A control experiment was also performed in which vehicle (phosphate-buffered saline) was delivered to Hepa 1-6 cells in culture and the cells were maintained for 48 hours. As shown in FIG. 1, it was found that the HPRT siRNA reduced HPRT expression levels by ~90% compared with controls.

Example 2: Targeting HPRT with a Muscle-Targeting Complex

A muscle-targeting complex was generated comprising the HPRT siRNA used in Example 1 (siHPRT) covalently linked, via a non-cleavable N-gamma-maleimidobutyryl-oxysuccinimide ester (GMBS) linker, to DTX-A-002, an anti-transferrin receptor antibody.

Briefly, the GMBS linker was dissolved in dry DMSO and coupled to the 3' end of the sense strand of siHPRT through amide bond formation under aqueous conditions. Completion of the reaction was verified by Kaiser test. Excess linker and organic solvents were removed by gel permeation chromatography. The purified, maleimide functionalized sense strand of siHPRT was then coupled to DTX-A-002 antibody using a Michael addition reaction.

The product of the antibody coupling reaction was then subjected to hydrophobic interaction chromatography (HIC-HPLC). antiTfR-siHPRT complexes comprising one or two siHPRT molecules covalently attached to DTX-A-002 antibody were purified. Densitometry confirmed that the purified sample of complexes had an average siHPRT to antibody ratio of 1.46. SDS-PAGE analysis demonstrated that >90% of the purified sample of complexes comprised DTX-A-002 linked to either one or two siHPRT molecules.

Using the same methods as described above, a control IgG2a-siHPRT complex was generated comprising the HPRT siRNA used in Example 1 (siHPRT) covalently linked via the GMBS linker to an IgG2a (Fab) antibody (DTX-A-003). Densitometry confirmed that DTX-C-001 had an average siHPRT to antibody ratio of 1.46 and SDS-PAGE demonstrated that >90% of the purified sample of control complexes comprised DTX-A-003 linked to either one or two siHPRT molecules.

The antiTfR-siHPRT complex was then tested for cellular internalization and inhibition of HPRT in cellulo. Hepa 1-6 cells, which have relatively high expression levels of transferrin receptor, were incubated in the presence of vehicle (phosphate-buffered saline), IgG2a-siHPRT (100 nM), antiTfR-siCTRL (100 nM), or antiTfR-siHPRT (100 nM), for 72 hours. After the 72 hour incubation, the cells were isolated and assayed for expression levels of HPRT (FIG. 2). Cells treated with the antiTfR-siHPRT demonstrated a reduction in HPRT expression by ~50% relative to the cells treated with the vehicle control. Meanwhile, cells treated with either of the IgG2a-siHPRT or antiTfR-siCTRL had HPRT expression levels comparable to the vehicle control (no reduction in HPRT expression). These data indicate that the antitransferrin receptor antibody of the antiTfR-siHPRT enabled cellular internalization of the complex, thereby allowing the siHPRT to inhibit expression of HPRT.

TABLE 2

Sequences of siHPRT and siCTRL

| | Sequence | SEQ ID NO: |
|---|---|---|
| siHPRT sense strand | 5'-UcCuAuGaCuGuAgAuUuUaU-$(CH_2)_6NH_2$-3' | 48 |
| siHPRT antisense strand | 5'-paUaAaAuCuAcAgUcAuAgGasAsu-3' | 49 |
| siCTRL sense strand | 5'-UgUaAuAaCcAuAuCuAcCuU-$(CH_2)_6NH_2$-3' | 50 |
| siCTRL antisense strand | 5'-aAgGuAgAuAuGgUuAuUaCasAsa-3' | 51 |

*Lower case—2'Ome ribose;
Capital letter—2'Fluoro ribose;
p—phosphate linkage; s—phosphorothioate linkage

Example 3: Targeting HPRT in Mouse Muscle Tissues with a Muscle-Targeting Complex The muscle-targeting complex described in Example 2, antiTfR-siHPRT, was tested for inhibition of HPRT in mouse tissues. C57BL/6 wild-type mice were intravenously injected with a single dose of a vehicle control (phosphate-buffered saline); siHPRT (2 mg/kg of RNA); IgG2a-siHPRT (2 mg/kg of RNA, corresponding to 9 mg/kg antibody complex); or antiTfR-siHPRT (2 mg/kg of RNA, corresponding to 9 mg/kg antibody complex. Each experimental condition was replicated in four individual C57BL/6 wild-type mice. Following a three-day period after injection, the mice were euthanized and segmented into isolated tissue types. Individual tissue samples were subsequently assayed for expression levels of HPRT (FIGS. 3A-3B and 4A-4E).

Figure 3A:
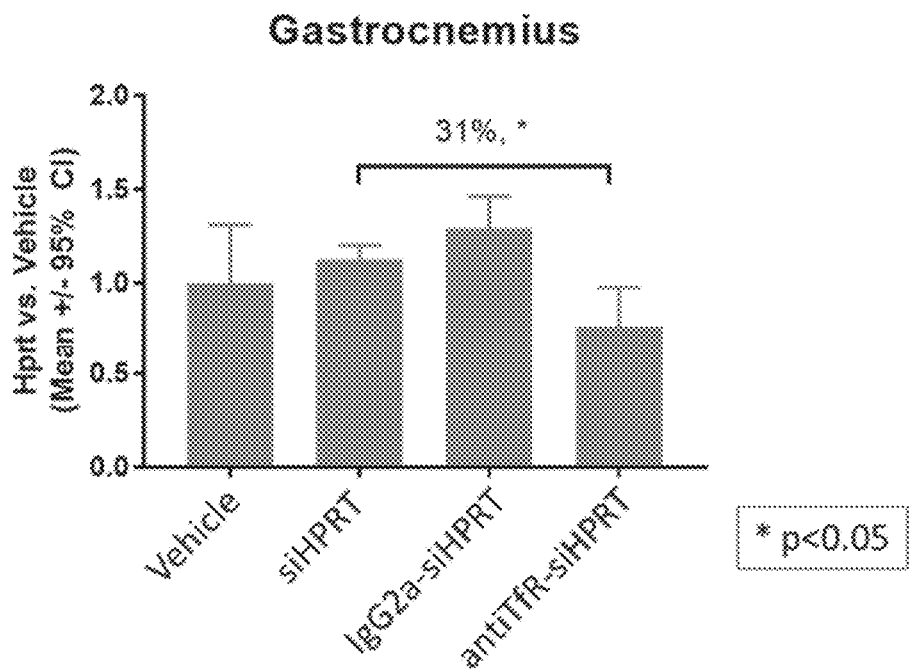
FIGS. 3A-3B depict non-limiting schematics showing the activity of a muscle targeting complex comprising an siRNA in mouse muscle tissues (gastrocnemius and heart) in vivo, relative to control experiments. (N=4 C57BL/6 WT mice)
Figure 3B:
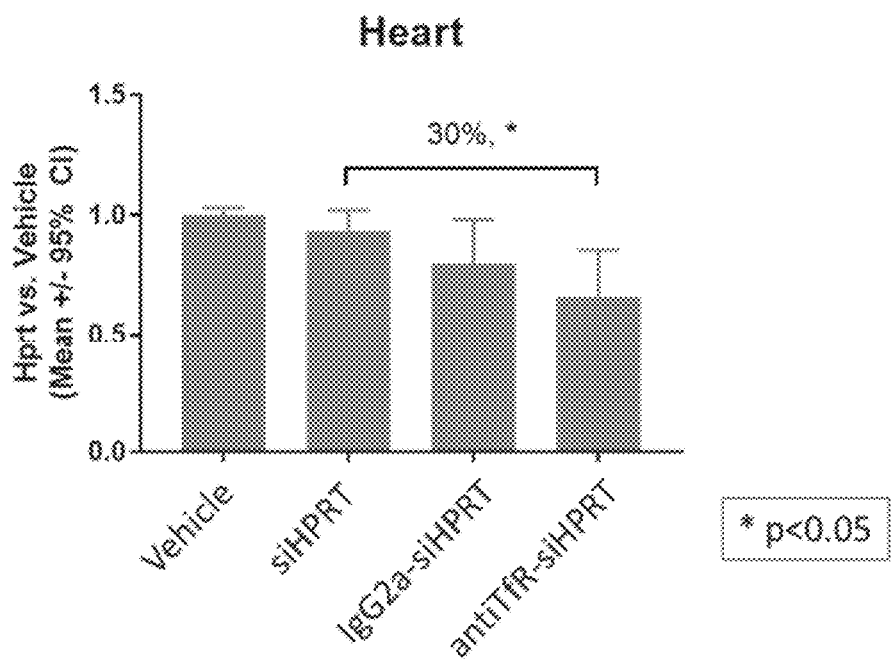
Figure 4A:
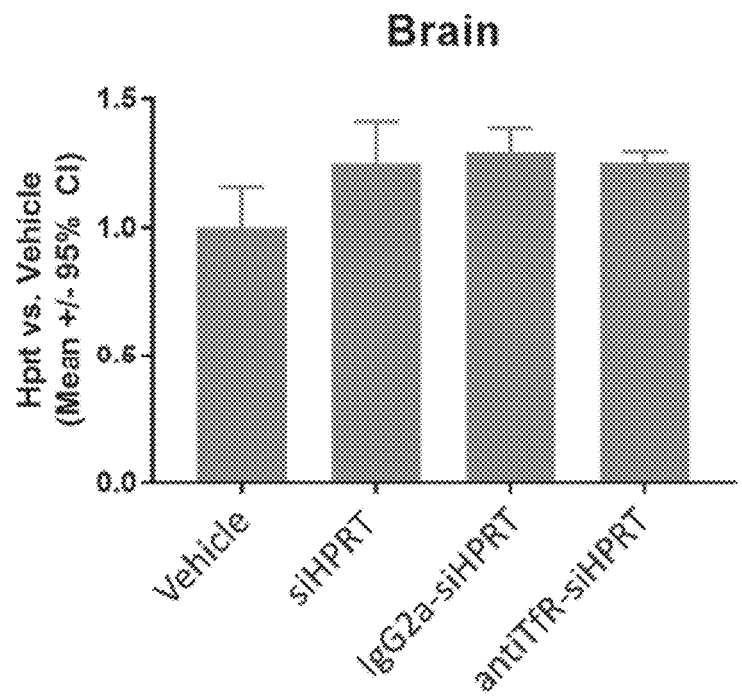
FIGS. 4A-4E depict non-limiting schematics showing the tissue selectivity of a muscle targeting complex comprising an siRNA.
Figure 4B:
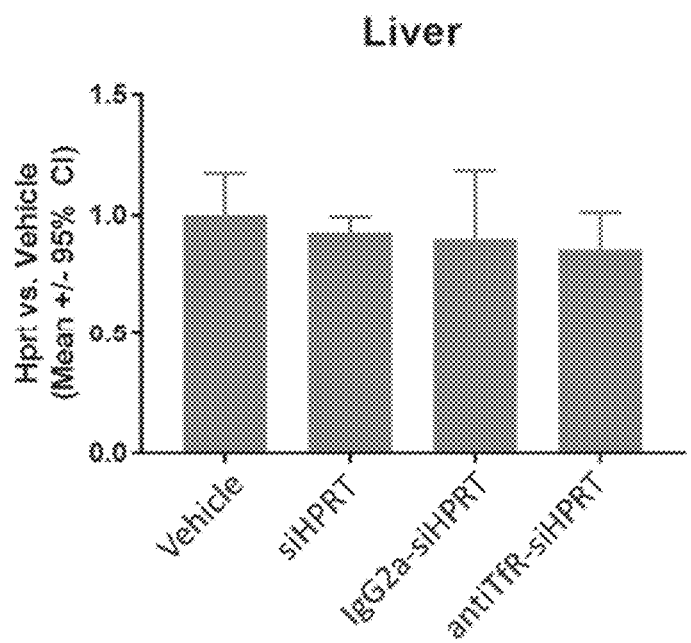
Figure 4C:
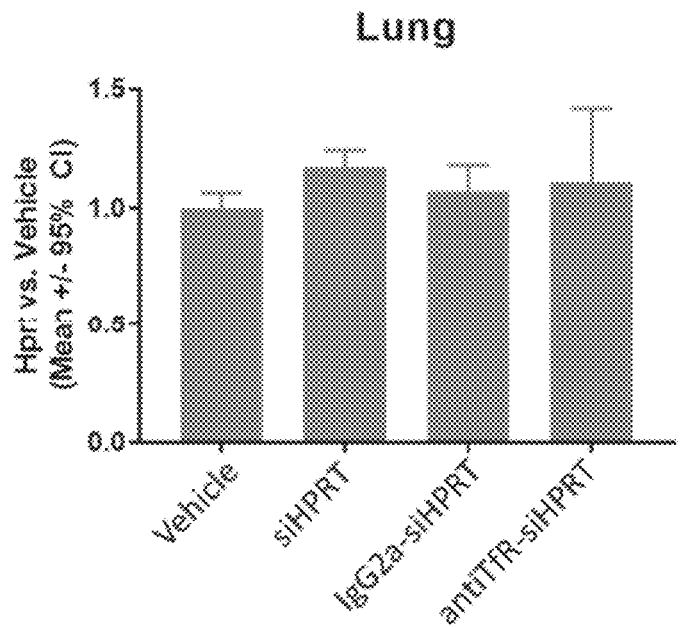
Figure 4D:
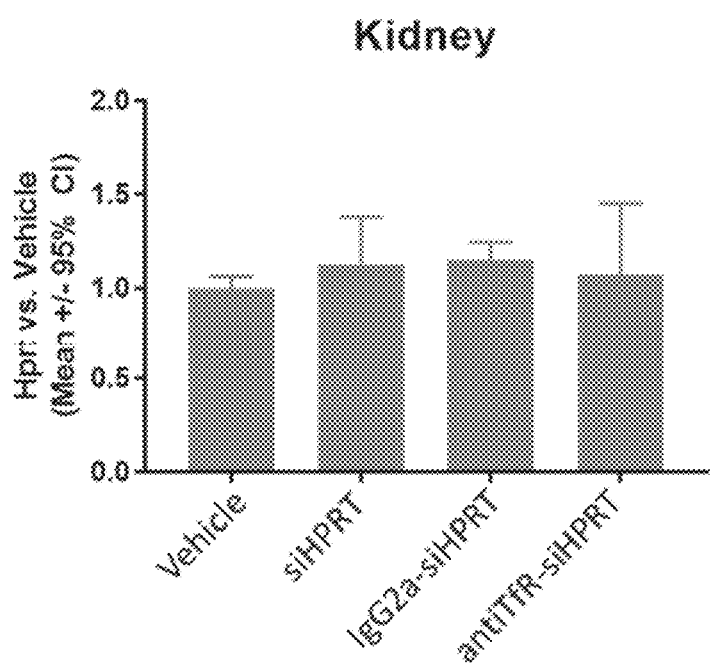
Figure 4E:
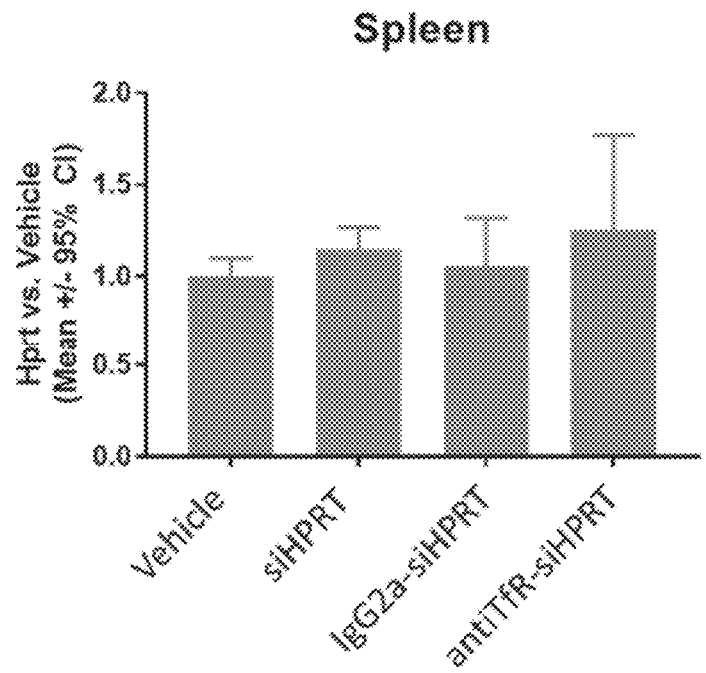

Mice treated with the antiTfR-siHPRT complex demonstrated a reduction in HPRT expression in gastrocnemius (31% reduction; $p<0.05$) and heart (30% reduction; $p<0.05$), relative to the mice treated with the siHPRT control (FIGS. 3A-3B). Meanwhile, mice treated with the IgG2a-siHPRT complex had HPRT expression levels comparable to the siHPRT control (little or no reduction in HPRT expression) for all assayed muscle tissue types.

Mice treated with the antiTfR-siHPRT complex demonstrated no change in HPRT expression in non-muscle tissues such as brain, liver, lung, kidney, and spleen tissues (FIGS. 4A-4E).

These data indicate that the anti-transferrin receptor antibody of the antiTfR-siHPRT complex enabled cellular internalization of the complex into muscle-specific tissues in an in vivo mouse model, thereby allowing the siHPRT to inhibit expression of HPRT. These data further demonstrate that the antiTfR-oligonucleotide complexes of the current disclosure are capable of specifically targeting muscle tissues.

Example 4: Targeting DUX4 with Transfected Antisense Oligonucleotides

Figure 5:
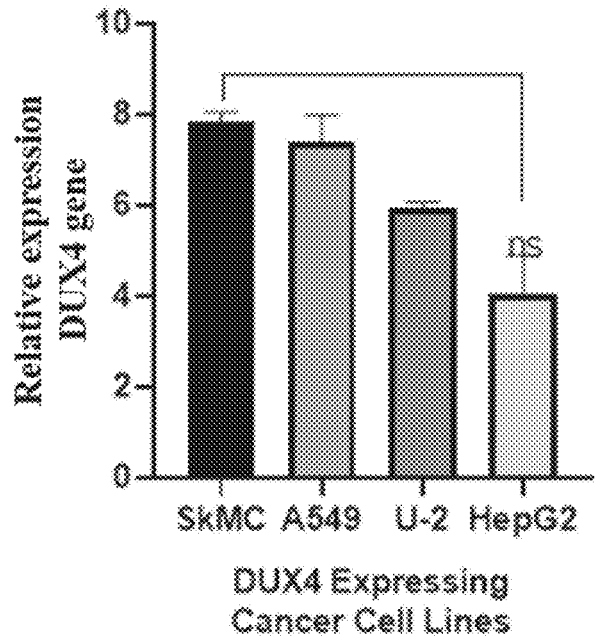
FIG. 5 depicts a non-limiting schematic showing the expression levels of DUX4 in three DUX4-expressing cell lines (A549, U-2 OS, and HepG2 cell lines) and immortalized skeletal muscle myoblasts (SkMC).

Three DUX4-expressing cell lines (A549, U-2 OS, and HepG2 cell lines) and immortalized skeletal muscle myoblasts (SkMC) were screened for expression of DUX4 mRNA (FIG. 5). Cells were seeded at a density of 10,000 cells/well and harvested for total RNA. cDNA was synthesized from the total RNA extracts and qPCR was performed to determine concentration of DUX4 relative to a control gene (PPIB) in technical quadruplicate. These data were used to aid in the selection of the U-2 OS cell line for downstream development of DUX4-targeting oligonucleotides.

Following selection of U-2 OS cells for development of DUX4-targeting oligonucleotides, a phosphorodiamidate morpholino oligomer (PMO) version of an antisense oligonucleotide that targets DUX4 (FM10 PMO) was evaluated for its ability to target DUX4 in vitro. FM10 PMO comprises the sequence GGGCATTTTAATATATCTCTGAACT (SEQ ID NO: 45). A control phosphorodiamidate morpholino oligomer (PMO), that comprises the sequence CCTCTTACCTCAGTTACAATTTATA (SEQ ID NO: 47), was utilized as a negative control.

Briefly, U-2 OS cells were seeded at a density of 10 k cells/well before being allowed to recover overnight. Cells were then treated with either a control PMO (100 nM) or with the FM10 PMO (10 μM). Cells were incubated for 72 hours before being harvested for total RNA. cDNA was then synthesized from the total RNA extracts and qPCR was performed to determine expression of downstream DUX4 genes (ZSCAN1, MBDL3L2, TRIM43) in technical quadruplicate. All qPCR data were analyzed using a standard ΔΔCT method and were normalized to a plate-based negative control comprised of untreated cells (i.e., without any oligonucleotide). Results were then converted to fold change to evaluate efficacy.

Figure 6:
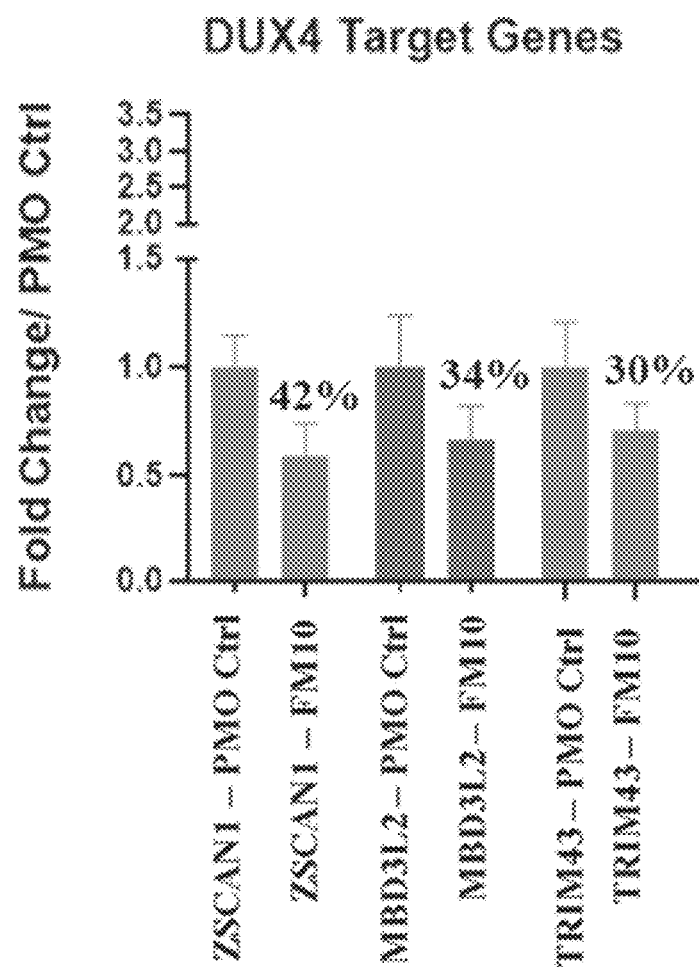
FIG. 6 depicts non-limiting schematics showing the ability of a phosphorodiamidate morpholino oligomer (PMO) version of an antisense oligonucleotide that targets DUX4 (FM10 PMO) to reduce expression levels of downstream DUX4 genes (ZSCAN1, MBDL3L2, TRIM43).

As shown in FIG. 6, all of ZSCAN1, MBDL3L2, and TRIM43 showed decreased expression in the presence of the FM10 PMO compared to the control PMO (42%, 34%, and 32%; respectively). These data demonstrate that the FM10 PMO is capable of targeting DUX4 in vitro.

Example 5: Targeting DUX4 with a Muscle-Targeting Complex

A muscle-targeting complex is generated comprising an antisense oligonucleotide that targets a mutant allele of DUX4 (DUX4 ASO) covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule is coupled to $NH_2$-$C_6$-DUX4 ASO using an amide coupling reaction. Excess linker and organic solvents are removed by gel permeation chromatography. The purified Val-Cit-linker-DUX4 ASO is then coupled to a thiol-reactive anti-transferrin receptor antibody (DTX-A-002).

The product of the antibody coupling reaction is then subjected to hydrophobic interaction chromatography (HIC-HPLC) to purify the muscle-targeting complex. Densitometry and SDS-PAGE analysis of the purified complex allow for determination of the average ratio of ASO-to-antibody and total purity, respectively.

Using the same methods as described above, a control complex is generated comprising DUX4 ASO covalently linked via a Val-Cit linker to an IgG2a (Fab) antibody.

The purified muscle-targeting complex comprising DTX-A-002 covalently linked to DUX4 ASO is then tested for cellular internalization and inhibition of DUX4. Disease-relevant muscle cells that have relatively high expression levels of transferrin receptor, are incubated in the presence of vehicle control (saline), muscle-targeting complex (100 nM), or control complex (100 nM) for 72 hours. After the 72 hour incubation, the cells are isolated and assayed for expression levels of DUX4.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising an anti-transferrin receptor antibody covalently linked to a 5' end or a 3' end of an oligonucleotide,
wherein the anti-transferrin receptor antibody binds in the range of C89 to F760 of human transferrin receptor protein 1 (TfR1) having an amino acid sequence as set forth in SEQ ID NO: 1 and wherein the anti-transferrin receptor antibody does not specifically bind to the transferrin binding site of TfR1;
wherein the oligonucleotide comprises one or more modifications and comprises a region of complementarity of at least 15 nucleotides in length to the nucleotide sequence as set forth in SEQ ID NO: 199, wherein the oligonucleotide is in the range of 15-30 nucleotides in length;
wherein the one or more modifications comprise a 2'-modified nucleoside selected from the group consisting of: a 2'-O-methyl nucleoside, a 2'-fluoro nucleoside, a 2'-O-methoxyethyl nucleoside, 2',4'-bridged nucleosides, and combinations thereof, and/or comprise a modified backbone comprising one or more phosphorothioate linkages.

2. The complex of claim 1, wherein the oligonucleotide is 15-23 nucleotides in length.

3. The complex of claim 1, wherein the region of complementarity is at least 16 nucleotides in length.

4. The complex of claim 1, wherein the region of complementarity is at least 17 nucleotides in length.

5. The complex of claim 1, wherein the region of complementarity is at least 18 nucleotides in length.

6. The complex of claim 1, wherein the region of complementarity is at least 19 nucleotides in length.

7. The complex of claim 1, wherein the oligonucleotide comprises a modified backbone comprising one or more phosphorothioate linkages.

8. The complex of claim 1, wherein the oligonucleotide comprises a gap region flanked both 5' and 3' by flanking regions, wherein the flanking regions comprises one or more 2'-modified nucleosides selected from the group consisting of: 2'-O-methyl, 2'-fluoro, 2'-O-methoxyethyl, 2',4'-bridged nucleosides, and combinations thereof, and wherein each nucleoside of the gap region is a 2'-deoxyribonucleoside.

9. The complex of claim 8, wherein each nucleotide of the flanking regions is a 2'-modified nucleoside.

10. The complex of claim 9, wherein each internucleoside linkage in the oligonucleotide is a phosphorothioate linkage.

11. The complex of claim 1, wherein the oligonucleotide is a double-stranded molecule comprising the single strand hybridized to a complementary strand.

12. The complex of claim 1, wherein the anti-transferrin receptor antibody further comprises one or more sugar or carbohydrate molecules.

13. The complex of claim 12, wherein the one or more sugar or carbohydrate molecules comprise a mannose unit, a glucose unit, an N-acetylglucosamine unit, an N-acetylgalactosamine unit, a galactose unit, a fucose unit, a phospholipid unit, or combinations thereof.

14. The complex of claim 1, wherein the oligonucleotide is covalently linked to a lysine in the anti-transferrin receptor antibody via a cleavable linker.

15. The complex of claim 14, wherein the cleavable linker comprises a valine-citrulline sequence.

16. The complex of claim 15, wherein the complex is obtained by a cycloaddition reaction between an azide and an alkyne to form a triazole.

17. The complex of claim 16, wherein, prior to the cycloaddition reaction, the azide is covalently linked to the valine-citrulline sequence of the cleavable linker that is covalently linked to the oligonucleotide and the alkyne is provided in a bicyclononyne moiety that further covalently links to the anti-transferrin receptor antibody.

18. The complex of claim 14, wherein the cleavable linker further comprises one or more polyethylene glycol units.

19. The complex of claim 1, wherein the anti-transferrin receptor antibody is in the form of a ScFv, Fab fragment, Fab' fragment, F(ab')2 fragment, or Fv fragment.

20. The complex of claim 1, wherein the anti-transferrin receptor antibody is in the form of a Fab fragment.

21. A method of delivering an oligonucleotide to a subject, the method comprising intravenously administering to the subject the complex of claim 1.

22. The method of claim 21, wherein the subject has a muscular dystrophy.

23. The method of claim 21, wherein the subject has myotonic dystrophy type I.

24. The method of claim 21, wherein the oligonucleotide is delivered to a muscle of the subject.

25. The method of claim 24, wherein the muscle cell is a skeletal muscle cell, a cardiac muscle cell, or a smooth muscle cell.

26. The method of claim 21, wherein the subject is human.

27. The method of claim 21, wherein the subject is cynomolgus.

* * * * *

```
                        SEQUENCE LISTING

Sequence total quantity: 929
SEQ ID NO: 1            moltype = AA  length = 760
FEATURE                 Location/Qualifiers
source                  1..760
                        mol_type = protein
                        organism = Homo sapiens
SEQUENCE: 1
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR 120
RLYWDDLKRK LSEKLDSTDF TGTIKLLNEN SYVPREAGSQ KDENLALYVE NQFREFKLSK 180
VWRDQHFVKI QVKDSAQNSV IIVDKNGRLV YLVENPGGYV AYSKAATVTG KLVHANFGTK 240
KDFEDLYTPV NGSIVIVRAG KITFAEKVAN AESLNAIGVL IYMDQTKFPI VNAELSFFGH 300
AHLGTGDPYT PGFPSFNHTQ FPPSRSSGLP NIPVQTISRA AAEKLFGNME GDCPSDWKTD 360
STCRMVTSES KNVKLTVSNV LKEIKILNIF GVIKGFVEPD HYVVVGAQRD AWGPGAAKSG 420
VGTALLLKLA QMFSDMVLKD GFQPSRSIIF ASWSAGDFGS VGATEWLEGY LSSLHLKAFT 480
YINLDKAVLG TSNFKVSASP LLYTLIEKTM QNVKHPVTGQ FLYQDSNWAS KVEKLTLDNA 540
AFPFLAYSGI PAVSFCFCED TDYPYLGTTM DTYKELIERI PELNKVARAA AEVAGQFVIK 600
LTHDVELNLD YERYNSQLLS FVRDLNQYRA DIKEMGLSLQ WLYSARGDFF RATSRLTTDF 660
GNAEKTDRFV MKKLNDRVMR VEYHFLSPYV SPKESPFRHV FWGSGSHTLP ALLENLKLRK 720
QNNGAFNETL FRNQLALATW TIQGAANALS GDVWDIDNEF                      760

SEQ ID NO: 2            moltype = AA  length = 760
FEATURE                 Location/Qualifiers
source                  1..760
                        mol_type = protein
                        organism = Macaca mulatta
SEQUENCE: 2
MMDQARSAFS NLFGGEPLSY TRFSLARQVD GDNSHVEMKL GVDEEENTDN NTKPNGTKPK  60
RCGGNICYGT IAVIIFFLIG FMIGYLGYCK GVEPKTECER LAGTESPARE EPEEDFPAAP 120
RLYWDDLKRK LSEKLDTTDF TSTIKLLNEN LYVPREAGSQ KDENLALYIE NQFREFKLSK 180
VWRDQHFVKI QVKDSAQNSV IIVDKNGGLV YLVENPGGYV AYSKAATVTG KLVHANFGTK 240
KDFEDLDSPV NGSIVIVRAG KITFAEKVAN AESLNAIGVL IYMDQTKFPI VKADLSFFGH 300
AHLGTGDPYT PGFPSFNHTQ FPPSQSSGLP NIPVQTISRA AAEKLFGNME GDCPSDWKTD 360
STCKMVTSEN KSVKLTVSNV LKETKILNIF GVIKGFVEPD HYVVVGAQRD AWGPGAAKSS 420
VGTALLLKLA QMFSDMVLKD GFQPSRSIIF ASWSAGDFGS VGATEWLEGY LSSLHLKAFT 480
YINLDKAVLG TSNFKVSASP LLYTLIEKTM QDVKHPVTGR SLYQDSNWAS KVEKLTLDNA 540
AFPFLAYSGI PAVSFCFCED TDYPYLGTTM DTYKELVERI PELNKVARAA AEVAGQFVIK 600
LTHDTELNLD YERYNSQLLL FLRDLNQYRA DVKEMGLSLQ WLYSARGDFF RATSLTTDF  660
RNAEKRDKFV MKKLNDRVMR VEYYFLSPYV SPKESPFRHV FWGSGSHTLS ALLESLKLRR 720
```

```
QNNSAFNETL FRNQLALATW TIQGAANALS GDVWDIDNEF                              760

SEQ ID NO: 3              moltype = AA  length = 760
FEATURE                   Location/Qualifiers
source                    1..760
                          mol_type = protein
                          organism = Macaca fascicularis
SEQUENCE: 3
MMDQARSAFS NLFGGEPLSY TRFSLARQVD GDNSHVEMKL GVDEEENTDN NTKANGTKPK         60
RCGGNICYGT IAVIIFFLIG FMIGYLGYCK GVEPKTECER LAGTESPARE EPEEDFPAAP        120
RLYWDDLKRK LSEKLDTTDF TSTIKLLNEN LYVPREAGSQ KDENLALYIE NQFREFKLSK        180
VWRDQHFVKI QVKDSAQNSV IIVDKNGGLV YLVENPGGYV AYSKAATVTG KLVHANFGTK        240
KDFEDLDSPV NGSIVIVRAG KITFAEKVAN AESLNAIGVL IYMDQTKFPI VKADLSFFGH        300
AHLGTGDPYT PGFPSFNHTQ FPPSQSSGLP NIPVQTISRA AAEKLFGNME GDCPSDWKTD        360
STCKMVTSEN KSVKLTVSNV LKETKILNIF GVIKGFVEPD HYVVVGAQRD AWGPGAAKSS        420
VGTALLLKLA QMFSDMVLKD GFQPSRSIIF ASWSAGDFGS VGATEWLEGY LSSLHLKAFT        480
YINLDKAVLG TSNFKVSASP LLYTLIEKTM QDVKHPVTGR SLYQDSNWAS KVEKLTLDNA        540
APPFLAYSGI PAVSFCFCED TDYPYLGTTM DTYKELVERI PELNKVARAA AEVAGQFVIK        600
LTHDTELNLD YERYNSQLLL FLRDLNQYRA DVKEMGLSLQ WLYSARGDFF RATSRLTTDF        660
RNAEKRDKFV MKKLNDRVMR VEYYFLSPYV SPKESPFRHV FWGSGSHTLS ALLESLKLRR        720
QNNSAFNETL FRNQLALATW TIQGAANALS GDVWDIDNEF                              760

SEQ ID NO: 4              moltype = AA  length = 763
FEATURE                   Location/Qualifiers
source                    1..763
                          mol_type = protein
                          organism = Mus musculus
SEQUENCE: 4
MMDQARSAFS NLFGGEPLSY TRFSLARQVD GDNSHVEMKL AADEEENADN NMKASVRKPK         60
RFNGRLCFAA IALVIFFLIG FMSGYLGYCK RVEQKEECVK LAETEETDKS ETMETEDVPT        120
SSRLYWADLK TLLSEKLNSI EFADTIKQLS QNTYTPREAG SQKDESLAYY IENQPHEFKF        180
SKVWRDEHYV KIQVKSSIGQ NMVTIVQSNG NLDPVESPEG YVAFSKPTEV SGKLVHANFG        240
TKKDFEELSY SVNGSLVIVR AGEITFAEKV ANAQSFNAIG VLIYMDKNKF PVVEADLALF        300
GHAHLGTGDP YTPGFPSFNH TQFPPSQSSG LPNIPVQTIS RAAAEKLFGK MEGSCPARWN        360
IDSSCKLELS QNQNVKLIVK NVLKERRILN IFGVIKGYEE PDRYVVVGAQ RDALGAGVAA        420
KSSVGTGLLL KLAQVFSDMI SKDGFRPSRS IIFASWTAGD FGAVGATEWL EGYLSSLHLK        480
AFTYINLDKV VLGTSNFKVS ASPLLYTLMG KIMQDVKHPV DGKSLYRDSN WISKVEKLSF        540
DNAAYPPLAY SGIPAVSFCF CEDADYPYLG TRLDTYEALT QKVPQLNQMV RTAAEVAGQL        600
IIKLTHDVEL NLDYEMYNSK LLSFMKDLNQ FKTDIRDMGL SLQWLYSARG DYFRATSRLT        660
TDFHNAEKTN RFVMREINDR IMKVEYHFLS PYVSPRESPF RHIFWGSGSH TLSALVENLK        720
LRQKNITAFN ETLFRNQLAL ATWTIQGVAN ALSGDIWNID NEF                          763

SEQ ID NO: 5              moltype = AA  length = 197
FEATURE                   Location/Qualifiers
REGION                    1..197
                          note = Synthetic polypeptide
source                    1..197
                          mol_type = protein
                          organism = synthetic construct
SEQUENCE: 5
FVKIQVKDSA QNSVIIVDKN GRLVYLVENP GGYVAYSKAA TVTGKLVHAN FGTKKDFEDL         60
YTPVNGSIVI VRAGKITFAE KVANAESLNA IGVLIYMDQT KFPIVNAELS FFGHAHLGTG        120
DPYTPGFPSF NHTQFPPSRS SGLPNIPVQT ISRAAAEKLF GNMEGDCPSD WKTDSTCRMV        180
TSESKNVKLT VSNVLKE                                                      197

SEQ ID NO: 6              moltype = AA  length = 7
FEATURE                   Location/Qualifiers
REGION                    1..7
                          note = Synthetic polypeptide
source                    1..7
                          mol_type = protein
                          organism = synthetic construct
SEQUENCE: 6
ASSLNIA                                                                    7

SEQ ID NO: 7              moltype = AA  length = 12
FEATURE                   Location/Qualifiers
REGION                    1..12
                          note = Synthetic polypeptide
source                    1..12
                          mol_type = protein
                          organism = synthetic construct
SEQUENCE: 7
SKTFNTHPQS TP                                                             12

SEQ ID NO: 8              moltype = AA  length = 12
FEATURE                   Location/Qualifiers
REGION                    1..12
                          note = Synthetic polypeptide
```

```
source                    1..12
                          mol_type = protein
                          organism = synthetic construct
SEQUENCE: 8
TARGEHKEEE LI                                                              12

SEQ ID NO: 9              moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 9
CQAQGQLVC                                                                   9

SEQ ID NO: 10             moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 10
CSERSMNFC                                                                   9

SEQ ID NO: 11             moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 11
CPKTRRVPC                                                                   9

SEQ ID NO: 12             moltype = AA   length = 20
FEATURE                   Location/Qualifiers
REGION                    1..20
                          note = Synthetic polypeptide
source                    1..20
                          mol_type = protein
                          organism = synthetic construct
SEQUENCE: 12
WLSEAGPVVT VRALRGTGSW                                                      20

SEQ ID NO: 13             moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 13
CMQHSMRVC                                                                   9

SEQ ID NO: 14             moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 14
DDTRHWG                                                                     7

SEQ ID NO: 15             moltype = DNA   length = 1275
FEATURE                   Location/Qualifiers
source                    1..1275
                          mol_type = genomic DNA
                          organism = Homo sapiens
SEQUENCE: 15
atggccctcc cgacaccctc ggacagcacc ctccccgcgg aagccccggg acgaggacgg    60
cgacggagac tcgtttggac cccgagccaa agcgaggccc tgcgagcctg ctttgagcgg   120
aacccgtacc cgggcatcgc caccagagaa cggctggccc aggccatcgg cattccggag   180
cccagggtcc agatttggtt tcagaatgag aggtcacgcc agctgaggca gcaccggcgg   240
gaatctcggc cctggcccgg agacgcggc ccgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc cggagtccag gattcagatc   420
```

```
tggtttcaga atcgaagggc caggcaccog ggacagggtg gcagggcgcc cgcgcaggca    480
ggcggcctgt gcagcgcggc ccccggcggg ggtcaccctg ctccctcgtg ggtcgccttc    540
gcccacaccg gcgcgtgggg aacgggggctt cccgcacccc acgtgccctg cgcgcctggg    600
gctctcccac agggggcttt cgtgagccag gcagcgaggg ccgcccccgc gctgcagccc    660
agccaggccg cgccggcaga ggggatctcc caacctgccg ggcgcggg ggatttcgcc    720
tacgccgccc cggctcctcc ggacggggcg ctctcccacc ctcaggctcc tcggtggcct    780
ccgcacccgg gcaaaagccg ggaggaccgg gaccccgcagc gcgacggcct gccgggcccc    840
tgcgcggtgg cacagcctgg gcccgctcaa gcggggccgc agggccaagg ggtgcttgcg    900
ccacccacgt cccaggggag tccgtggtgg ggctggggcc ggggtcccca ggtcgccggg    960
gcggcgtggg aaccccaagc cggggcagct ccactccccc agcccgcgcc cccgacgcc   1020
tccgcctccg cgcggcaggg gcagatgcaa ggcatcccgg cgccctccca ggcgctccag   1080
gagccggcgc cctggtctgc actcccctgc ggcctgctgc tggatgagct cctggcgagc   1140
ccggagtttc tgcagcaggc gcaacctctc ctagaaacgg aggccccggg ggagctggag   1200
gcctcggaag aggccgcctc gctggaagca ccctcagcc aggaagaata ccgggctctg   1260
ctggaggagc tttag                                                   1275

SEQ ID NO: 16              moltype = DNA  length = 2024
FEATURE                    Location/Qualifiers
source                     1..2024
                           mol_type = genomic DNA
                           organism = Mus musculus
SEQUENCE: 16
atggcagaag ctggcagccc tgttggtggc agtggtgtgg cacgggaatc ccggcggcgc     60
aggaagacgg tttggcaggc ctggcaagag caggccctgc tatcaacttt caagaagaag    120
agatacctga gcttcaagga gaggaaggag ctggccaagc gaatgggggt ctcagattgc    180
cgcatccgcg tgtggtttca gaaccgcagg aatcgcagtg gagaggaggg gcatgcctca    240
aagaggtcca tcagaggctc aggcggcta gcctcgccac agctccagga gagcttgga    300
tccaggccac agggtagagg catgcgctca tctggcagaa ggcctcgcac tcgactcacc    360
tcgctacagc tcaggatcct agggcaagcc tttgagagga acccacgacc aggctttgct    420
accagggagg agctggcgcg tgacacaggg ttgcccgagg acacgatcca catatggtta    480
caaaaccgaa gagctcggcg gcgccacagg aggggcaggc ccacagctca agatcaagac    540
ttgctggcgt cacaagggtc ggatggggcc cctgcaggtc cggaaggcag agagcgtgaa    600
ggtgcccagg agaacttgtt gccacaggaa gaagcaggaa gtacgggcat ggatacctcg    660
agcctagcg acttgccctc cttctgcgga gagtcccaac ctttccaagt ggcacagcca    720
cgtggagcag gccaacaaga ggcccccact cgagcaggca acgcaggctc tctgaaccc    780
ctccttgatc agctgctgga tgaagtccaa gtagaagagc ctgctccagc ccctctgaat    840
ttggatggaa ccctggtgg cagggtgcat gaaggttccc aggagagctt ttggccacag    900
gaagaagcag gaagtacagg catggatact tctagcccca gcgactcaaa ctccttctgc    960
agagagtccc agccttccca agtgcacag ccctgtgagg cggccaaga agatgcccgc   1020
actcaagcag acagcacagg ccctctggaa ctcctcctcc ttgatcaact gctggacgaa   1080
gtccaaaagg aagagcatgt gccagtccca ctggattggg gtagaaatcc tggcagcagg   1140
gagcatgaag gttcccagga cagcttactg ccctgagg aagcagtaaa ttcgggcatg   1200
gatacctcga tccctagcat ctggccaacc ttctgcagaa aatcccagcc tccccaagtg   1260
gcacagccct ctggaccagg ccaagcacag gccccactc aaggtgggaa cacggacccc   1320
ctggagctct tcctctatca actgttggat gaagtcaag tagaagagca tgctccagcc   1380
cctctgaatt gggatgtaga tcctggtggc agggtgcatg aaggttcgtg ggagagcttt   1440
tggccacagg aagaagcagg aagtacaggc ctggatactt caagccccag cgactcaaac   1500
tccttcttca gagagtccaa gccttccaa gtgcacacag gccgtggagc gggccaagaa   1560
gatgcccgca ctcaagcaga cagcacaggc cctctggaac tcctcctctt tgatcaactg   1620
ctggacgaag tccaaaagga agagcatgtg ccagccccac tggattgggg tagaaatcct   1680
ggcagcatgg agcatgaagg ttcccaggac agcttactgc ccctggagga agcagcaaat   1740
tcgggcaggg atacctcgat ccctagcatc tggccagcct tctgcagaaa atcccagcct   1800
ccccaagtgg cacagccctc tggaccaggc caagcacagg ccccattca aggtgggaac   1860
acggaccccc tggagctctt ccttgatcaa ctgctgaccg aagtccaact tgaggagcag   1920
gggcctgccc ctgtgaatgt ggaggaaaca tgggagcaaa tggacacaac acctatctgc   1980
ctctcacttc agaagaatat cagactcttc tagatatgct ctga                   2024

SEQ ID NO: 17              moltype = AA  length = 5
FEATURE                    Location/Qualifiers
REGION                     1..5
                           note = Synthetic polypeptide
source                     1..5
                           mol_type = protein
                           organism = synthetic construct
SEQUENCE: 17
SYWMH                                                                  5

SEQ ID NO: 18              moltype = AA  length = 17
FEATURE                    Location/Qualifiers
REGION                     1..17
                           note = Synthetic polypeptide
source                     1..17
                           mol_type = protein
                           organism = synthetic construct
SEQUENCE: 18
EINPTNGRTN YIEKFKS                                                    17

SEQ ID NO: 19              moltype = AA  length = 7
FEATURE                    Location/Qualifiers
```

```
REGION                  1..7
                        note = Synthetic polypeptide
source                  1..7
                        mol_type = protein
                        organism = synthetic construct
SEQUENCE: 19
GTRAYHY                                                                    7

SEQ ID NO: 20           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 20
RASDNLYSNL A                                                              11

SEQ ID NO: 21           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 21
DATNLAD                                                                    7

SEQ ID NO: 22           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 22
QHFWGTPLT                                                                  9

SEQ ID NO: 23           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 23
GYTFTSY                                                                    7

SEQ ID NO: 24           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 24
NPTNGR                                                                     6

SEQ ID NO: 25           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 25
TSYWMH                                                                     6

SEQ ID NO: 26           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 26
WIGEINPTNG RTN                                                            13

SEQ ID NO: 27           moltype = AA   length = 6
```

```
FEATURE                 Location/Qualifiers
REGION                  1..6
                        note = Synthetic polypeptide
source                  1..6
                        mol_type = protein
                        organism = synthetic construct
SEQUENCE: 27
ARGTRA                                                                      6

SEQ ID NO: 28           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 28
YSNLAWY                                                                     7

SEQ ID NO: 29           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 29
LLVYDATNLA                                                                  10

SEQ ID NO: 30           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 30
QHFWGTPL                                                                    8

SEQ ID NO: 31           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 31
QHFAGTPLT                                                                   9

SEQ ID NO: 32           moltype = AA  length = 8
FEATURE                 Location/Qualifiers
REGION                  1..8
                        note = Synthetic polypeptide
source                  1..8
                        mol_type = protein
                        organism = synthetic construct
SEQUENCE: 32
QHFAGTPL                                                                    8

SEQ ID NO: 33           moltype = AA  length = 116
FEATURE                 Location/Qualifiers
REGION                  1..116
                        note = Synthetic polypeptide
source                  1..116
                        mol_type = protein
                        organism = synthetic construct
SEQUENCE: 33
QVQLQQPGAE LVKPGASVKL SCKASGYTFT SYWMHWVKQR PGQGLEWIGE INPTNGRTNY            60
IEKFKSKATL TVDKSSSTAY MQLSSLTSED SAVYYCARGT RAYHYWGQGT SVTVSS               116

SEQ ID NO: 34           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 34
DIQMTQSPAS LSVSVGETVT ITCRASDNLY SNLAWYQQKQ GKSPQLLVYD ATNLADGVPS           60
```

```
RFSGSGSGTQ YSLKINSLQS EDFGTYYCQH FWGTPLTFGA GTKLELK                        107

SEQ ID NO: 35           moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 35
EVQLVQSGAE VKKPGASVKV SCKASGYTFT SYWMHWVRQA PGQRLEWIGE INPTNGRTNY           60
IEKFKSRATL TVDKSASTAY MELSSLRSED TAVYYCARGT RAYHYWGQGT MVTVSS              116

SEQ ID NO: 36           moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 36
DIQMTQSPSS LSASVGDRVT ITCRASDNLY SNLAWYQQKP GKSPKLLVYD ATNLADGVPS           60
RFSGSGSGTD YSLKINSLQS EDFGTYYCQH FWGTPLTFGA GTKLELK                        107

SEQ ID NO: 37           moltype = AA   length = 330
FEATURE                 Location/Qualifiers
REGION                  1..330
                        note = Synthetic polypeptide
source                  1..330
                        mol_type = protein
                        organism = synthetic construct
SEQUENCE: 37
ASTKGPSVFP LAPSSKSTSG GTAALGCLVK DYFPEPVTVS WNSGALTSGV HTFPAVLQSS           60
GLYSLSSVVT VPSSSLGTQT YICNVNHKPS NTKVDKKVEP KSCDKTHTCP PCPAPELLGG          120
PSVFLFPPKP KDTLMISRTP EVTCVVVDVS HEDPEVKFNW YVDGVEVHNA KTKPREEQYN          180
STYRVVSVLT VLHQDWLNGK EYKCKVSNKA LPAPIEKTIS KAKGQPREPQ VYTLPPSRDE          240
LTKNQVSLTC LVKGFYPSDI AVEWESNGQP ENNYKTTPPV LDSDGSFFLY SKLTVDKSRW          300
QQGNVFSCSV MHEALHNHYT QKSLSLSPGK                                          330

SEQ ID NO: 38           moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 38
ASTKGPSVFP LAPSSKSTSG GTAALGCLVK DYFPEPVTVS WNSGALTSGV HTFPAVLQSS           60
GLYSLSSVVT VPSSSLGTQT YICNVNHKPS NTKVDKKVEP KSCDKTHTCP                    110

SEQ ID NO: 39           moltype = AA   length = 446
FEATURE                 Location/Qualifiers
REGION                  1..446
                        note = Synthetic polypeptide
source                  1..446
                        mol_type = protein
                        organism = synthetic construct
SEQUENCE: 39
QVQLQQPGAE LVKPGASVKL SCKASGYTFT SYWMHWVKQR PGQGLEWIGE INPTNGRTNY           60
IEKFKSKATL TVDKSSSTAY MQLSSLTSED SAVYYCARGT RAYHYWGQGT SVTVSSASTK          120
GPSVFPLAPS SKSTSGGTAA LGCLVKDYFP EPVTVSWNSG ALTSGVHTFP AVLQSSGLYS          180
LSSVVTVPSS SLGTQTYICN VNHKPSNTKV DKKVEPKSCD KTHTCPPCPA PELLGGPSVF          240
LFPPKPKDTL MISRTPEVTC VVVDVSHEDP EVKFNWYVDG VEVHNAKTKP REEQYNSTYR          300
VVSVLTVLHQ DWLNGKEYKC KVSNKALPAP IEKTISKAKG QPREPQVYTL PPSRDELTKN          360
QVSLTCLVKG FYPSDIAVEW ESNGQPENNY KTTPPVLDSD GSFFLYSKLT VDKSRWQQGN          420
VFSCSVMHEA LHNHYTQKSL SLSPGK                                              446

SEQ ID NO: 40           moltype = AA   length = 226
FEATURE                 Location/Qualifiers
REGION                  1..226
                        note = Synthetic polypeptide
source                  1..226
                        mol_type = protein
                        organism = synthetic construct
SEQUENCE: 40
QVQLQQPGAE LVKPGASVKL SCKASGYTFT SYWMHWVKQR PGQGLEWIGE INPTNGRTNY           60
IEKFKSKATL TVDKSSSTAY MQLSSLTSED SAVYYCARGT RAYHYWGQGT SVTVSSASTK          120
GPSVFPLAPS SKSTSGGTAA LGCLVKDYFP EPVTVSWNSG ALTSGVHTFP AVLQSSGLYS          180
LSSVVTVPSS SLGTQTYICN VNHKPSNTKV DKKVEPKSCD KTHTCP                        226
```

-continued

```
SEQ ID NO: 41           moltype = AA  length = 446
FEATURE                 Location/Qualifiers
REGION                  1..446
                        note = Synthetic polypeptide
source                  1..446
                        mol_type = protein
                        organism = synthetic construct
SEQUENCE: 41
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 42           moltype = AA  length = 217
FEATURE                 Location/Qualifiers
REGION                  1..217
                        note = Synthetic polypeptide
source                  1..217
                        mol_type = protein
                        organism = synthetic construct
SEQUENCE: 42
DIQMTQSPSS LSASVGDRVT ITCRASDNLY SNLAWYQQKP GKSPKLLVYD ATNLADGVPS    60
RFSGSGSGTD YSLKINSLQS EDFGTYYCQH FWGTPLTFGA GTKLELKAST KGPSVFPLAP   120
SSKSTSGGTA ALGCLVKDYF PEPVTVSWNS GALTSGVHTF PAVLQSSGLY SLSSVVTVPS   180
SSLGTQTYIC NVNHKPSNTK VDKKVEPKSC DKTHTCP                            217

SEQ ID NO: 43           moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 43
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                  226

SEQ ID NO: 44           moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 44
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                  226

SEQ ID NO: 45           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 45
gggcatttta atatatctct gaact                                          25

SEQ ID NO: 46           moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 46
agttcagaga tatattaaaa tgccc                                          25

SEQ ID NO: 47           moltype = DNA  length = 25
FEATURE                 Location/Qualifiers
```

```
misc_feature            1..25
                        note = Synthetic
source                  1..25
                        mol_type = other DNA
                        organism = synthetic construct
SEQUENCE: 47
cctcttacct cagttacaat ttata                                              25

SEQ ID NO: 48           moltype = RNA   length = 21
FEATURE                 Location/Qualifiers
misc_feature            1..21
                        note = Synthetic
source                  1..21
                        mol_type = other RNA
                        organism = synthetic construct
modified_base           1
                        mod_base = OTHER
                        note = modified by 2prime Fluoro
modified_base           2
                        mod_base = cm
modified_base           3
                        mod_base = OTHER
                        note = modified by 2prime Fluoro
modified_base           4
                        mod_base = um
modified_base           5
                        mod_base = OTHER
                        note = modified by 2prime Fluoro
modified_base           6
                        mod_base = um
modified_base           7
                        mod_base = OTHER
                        note = modified by 2prime Fluoro
modified_base           8
                        mod_base = OTHER
                        note = modified by 2prime OMe
modified_base           9
                        mod_base = OTHER
                        note = modified by 2prime Fluoro
modified_base           10
                        mod_base = um
modified_base           11
                        mod_base = OTHER
                        note = modified by 2prime Fluoro
modified_base           12
                        mod_base = um
modified_base           13
                        mod_base = OTHER
                        note = modified by 2prime Fluoro
modified_base           14
                        mod_base = gm
modified_base           15
                        mod_base = OTHER
                        note = modified by 2prime Fluoro
modified_base           16
                        mod_base = um
modified_base           17
                        mod_base = OTHER
                        note = modified by 2prime Fluoro
modified_base           18
                        mod_base = um
modified_base           19
                        mod_base = OTHER
                        note = modified by 2prime Fluoro
modified_base           20
                        mod_base = OTHER
                        note = modified by 2prime OMe
modified_base           21
                        mod_base = OTHER
                        note = modified by 2prime Fluoro
SEQUENCE: 48
tcctatgact gtagatttta t                                                  21

SEQ ID NO: 49           moltype = RNA   length = 23
FEATURE                 Location/Qualifiers
misc_feature            1..23
                        note = Synthetic
source                  1..23
                        mol_type = other RNA
```

```
                        organism = synthetic construct
modified_base           1
                        mod_base = OTHER
                        note = modified by 2prime OMe
modified_base           2
                        mod_base = OTHER
                        note = modified by 2prime Fluoro
modified_base           3
                        mod_base = OTHER
                        note = modified by 2prime OMe
modified_base           4
                        mod_base = OTHER
                        note = modified by 2prime Fluoro
modified_base           5
                        mod_base = OTHER
                        note = modified by 2prime OMe
modified_base           6
                        mod_base = OTHER
                        note = modified by 2prime Fluoro
modified_base           7
                        mod_base = um
modified_base           8
                        mod_base = OTHER
                        note = modified by 2prime Fluoro
modified_base           9
                        mod_base = um
modified_base           10
                        mod_base = OTHER
                        note = modified by 2prime Fluoro
modified_base           11
                        mod_base = cm
modified_base           12
                        mod_base = OTHER
                        note = modified by 2prime Fluoro
modified_base           13
                        mod_base = gm
modified_base           14
                        mod_base = OTHER
                        note = modified by 2prime Fluoro
modified_base           15
                        mod_base = cm
modified_base           16
                        mod_base = OTHER
                        note = modified by 2prime Fluoro
modified_base           17
                        mod_base = um
modified_base           18
                        mod_base = OTHER
                        note = modified by 2prime Fluoro
modified_base           19
                        mod_base = gm
modified_base           20
                        mod_base = OTHER
                        note = modified by 2prime Fluoro
modified_base           21
                        mod_base = OTHER
                        note = modified by 2prime OMe
modified_base           21..23
                        mod_base = OTHER
                        note = phosphorothioate linkage
modified_base           22
                        mod_base = OTHER
                        note = modified by 2prime Fluoro
modified_base           23
                        mod_base = um
SEQUENCE: 49
ataaatcta cagtcatagg aat                                                 23

SEQ ID NO: 50           moltype = RNA   length = 21
FEATURE                 Location/Qualifiers
misc_feature            1..21
                        note = Synthetic
source                  1..21
                        mol_type = other RNA
                        organism = synthetic construct
modified_base           1
                        mod_base = OTHER
                        note = modified by 2prime Fluoro
modified_base           2
```

|                 |                                      |
|-----------------|--------------------------------------|
| modified_base   | mod_base = gm<br>3<br>mod_base = OTHER<br>note = modified by 2prime Fluoro |
| modified_base   | 4<br>mod_base = OTHER<br>note = modified by 2prime OMe |
| modified_base   | 5<br>mod_base = OTHER<br>note = modified by 2prime Fluoro |
| modified_base   | 6<br>mod_base = um |
| modified_base   | 7<br>mod_base = OTHER<br>note = modified by 2prime Fluoro |
| modified_base   | 8<br>mod_base = OTHER<br>note = modified by 2prime OMe |
| modified_base   | 9<br>mod_base = OTHER<br>note = modified by 2prime Fluoro |
| modified_base   | 10<br>mod_base = cm |
| modified_base   | 11<br>mod_base = OTHER<br>note = modified by 2prime Fluoro |
| modified_base   | 12<br>mod_base = um |
| modified_base   | 13<br>mod_base = OTHER<br>note = modified by 2prime Fluoro |
| modified_base   | 14<br>mod_base = um |
| modified_base   | 15<br>mod_base = OTHER<br>note = modified by 2prime Fluoro |
| modified_base   | 16<br>mod_base = um |
| modified_base   | 17<br>mod_base = OTHER<br>note = modified by 2prime Fluoro |
| modified_base   | 18<br>mod_base = cm |
| modified_base   | 19<br>mod_base = OTHER<br>note = modified by 2prime Fluoro |
| modified_base   | 20<br>mod_base = um |
| modified_base   | 21<br>mod_base = OTHER<br>note = modified by 2prime Fluoro |
| SEQUENCE: 50    |                                      |
| tgtaataacc atatctacct t |                          21  |
| SEQ ID NO: 51   | moltype = RNA  length = 23           |
| FEATURE         | Location/Qualifiers                  |
| misc_feature    | 1..23<br>note = Synthetic            |
| source          | 1..23<br>mol_type = other RNA<br>organism = synthetic construct |
| modified_base   | 1<br>mod_base = OTHER<br>note = modified by 2prime OMe |
| modified_base   | 2<br>mod_base = OTHER<br>note = modified by 2prime Fluoro |
| modified_base   | 3<br>mod_base = gm |
| modified_base   | 4<br>mod_base = OTHER<br>note = modified by 2prime Fluoro |
| modified_base   | 5<br>mod_base = um |
| modified_base   | 6<br>mod_base = OTHER<br>note = modified by 2prime Fluoro |
| modified_base   | 7<br>mod_base = gm |

| | | |
|---|---|---|
| modified_base | 8 | |
| | mod_base = OTHER | |
| | note = modified by 2prime Fluoro | |
| modified_base | 9 | |
| | mod_base = um | |
| modified_base | 10 | |
| | mod_base = OTHER | |
| | note = modified by 2prime Fluoro | |
| modified_base | 11 | |
| | mod_base = um | |
| modified_base | 12 | |
| | mod_base = OTHER | |
| | note = modified by 2prime Fluoro | |
| modified_base | 13 | |
| | mod_base = gm | |
| modified_base | 14 | |
| | mod_base = OTHER | |
| | note = modified by 2prime Fluoro | |
| modified_base | 15 | |
| | mod_base = um | |
| modified_base | 16 | |
| | mod_base = OTHER | |
| | note = modified by 2prime Fluoro | |
| modified_base | 17 | |
| | mod_base = um | |
| modified_base | 18 | |
| | mod_base = OTHER | |
| | note = modified by 2prime Fluoro | |
| modified_base | 19 | |
| | mod_base = OTHER | |
| | note = modified by 2prime OMe | |
| modified_base | 20 | |
| | mod_base = OTHER | |
| | note = modified by 2prime Fluoro | |
| modified_base | 21 | |
| | mod_base = OTHER | |
| | note = modified by 2prime OMe | |
| modified_base | 21..23 | |
| | mod_base = OTHER | |
| | note = phosphorothioate linkage | |
| modified_base | 22 | |
| | mod_base = OTHER | |
| | note = modified by 2prime Fluoro | |
| modified_base | 23 | |
| | mod_base = OTHER | |
| | note = modified by 2prime OMe | |

SEQUENCE: 51
aaggtagata tggttattac aaa                                              23

| | | |
|---|---|---|
| SEQ ID NO: 52 | moltype = DNA   length = 1710 | |
| FEATURE | Location/Qualifiers | |
| source | 1..1710 | |
| | mol_type = genomic DNA | |
| | organism = Homo sapiens | |

SEQUENCE: 52
```
atggccctcc cgacaccctc ggacagcacc ctccccgcgg aagcccgggg acgaggacgg    60
cgacggagac tcgtttggac cccgagccaa agcgaggccc tgcgagcctg ctttgagcgg   120
aacccgtacc cgggcatcgc caccagagaa cggctggccc aggccatcgg cattccggag   180
cccagggtcc agatttggtt tcagaatgag aggtcacgcc agctgaggcg gcaccggcgg   240
gaatctcggc cctggcccgg gagacgcggc ccgccagaag gccggcgaaa gcggaccgcc   300
gtcaccggat cccagaccgc cctgctcctc cgagcctttg agaaggatcg ctttccaggc   360
atcgccgccc gggaggagct ggccagagag acgggcctcc cggagtccag gattcagatc   420
tggtttcaga atcgaagggc caggcacccg ggacagggtg gcaggcgcc cgcgcaggca   480
ggcggcctgt gcagcgcggc ccccggcggg ggtcaccctg ctccctcgtg ggtcgccttc   540
gcccacaccg gcgcgtgggg aacgggcctt cccgcacccc acgtgccctg cgcgcctggg   600
gctctcccac agggggcttt cgtgagccag gcagcgaggg ccgcccccgc gctgcagccc   660
agccaggccg cgccggcaga ggggatctcc caacctgccc cggcgcgcgg ggatttcgcc   720
tacgccgccc cggctcctcc ggacggggcg ctctcccacc ctcaggctcc tcgctggcct   780
ccgcacccgg gcaaaagccg ggaggaccgg gacccgcagc gcgacggcct gccgggcccc   840
tgcgcggtgg cacagcctgg gcccgctcaa gcggggccgc agggccaagg ggtgcttgcg   900
ccacccacgt cccaggggag tccgtggtgg ggctggggcc ggggtcccca ggtcgccggg   960
gcggcgtggg aacccaagc cggggcagct ccacctcccc agcccgcgcc ccggacgcc   1020
tccgcctccg cgcggcaggg gcagatgcaa ggcatcccgg cgccctccca ggcgctccag   1080
gagccggcgg cctggtctgc actcccctgc ggcctgctgc tggatgagct cctgcgcagc   1140
ccggagtttc tgcagcaggc gcaacctctc ctagaaacgg aggccccggg ggagctggag   1200
gcctcggaag aggccgcctc gctgaagca cccctcagcg aggaagaata ccgggctctg   1260
ctggaggagc tttaggacgc ggggttggga cgggtcgggg tggttcgggg cagggcggtg   1320
gcctctcttt cgcggggaac acctggctgg ctacggaggg gcgtgtctcc gccccgcccc   1380
ctccaccggg ctgaccggcc tgggattcct gccttctagg tctaggcccg gtgagagact   1440
```

```
ccacaccgcg gagaactgcc attctttcct gggcatcccg gggatcccag agccggccca   1500
ggtaccagca gacctgcgcg cagtgcgcac cccggctgac gtgcaaggga gctcgctggc   1560
ctctctgtgc ccttgttctt ccgtgaaatt ctggctgaat gtctccccec accttccgac   1620
gctgtctagg caaacctgga ttagagttac atctcctgga tgattagttc agagatatat   1680
taaaatgccc cctccctgtg gatcctatag                                     1710
```

```
SEQ ID NO: 53           moltype = AA   length = 248
FEATURE                 Location/Qualifiers
source                  1..248
                        mol_type = protein
                        organism = synthetic construct
SEQUENCE: 53
DYKDIVMTQS HKFMSTSVGD RVSITCKASQ DVGTAVAWYQ QKPGQSPKLL IYWASTRHTG   60
VPDRFTGSGS GTDFTLTISN VQSEDLADYF CQQYSSYLTF GAGTKLELKR GGGGSGGGGS   120
GGGGSGGGGS EVMLVESGGD LVKPGGSLKL SCAASGFTFS SYGMSWVRQT PDKRLEWVAT   180
ISSGGSYTYY PDSVKGRFTI SRDNAKNTLY LQMSSLKSED TAMYYCALLR SDWYFDVWGA   240
GTTVTVSS                                                             248

SEQ ID NO: 54           moltype = AA   length = 245
FEATURE                 Location/Qualifiers
source                  1..245
                        mol_type = protein
                        organism = synthetic construct
SEQUENCE: 54
DYKDIVITQS HKFMSTSVGD RVSITCKASQ DVSTAVAWYQ QKPGQSPKLL IYSASYRYTG   60
VPDRFTGSGS GTDFTFTISS VQAEDLAVYY CQQHYSTPYT FGGGTKLEIK RGGGGSGGGS   120
SGGGGSGGGG SQVQLQQSGA ELVRPGASVT LSCKASGYTF TDYEMHWVKQ TPVHGLEWIG   180
AIDPETGGTA YNQKFKGKAT LTADKSSSTA YMELRSLTSE DSAVYYCTGW GFDYWGQGTT   240
LTVSS                                                                245

SEQ ID NO: 55           moltype = AA   length = 247
FEATURE                 Location/Qualifiers
source                  1..247
                        mol_type = protein
                        organism = synthetic construct
SEQUENCE: 55
DYKDIVMTQS HKFMSTSVGD RVSITCKASQ DVGTAVAWYQ QKPGQSPKLL IYWASTRHTG   60
VPDRFTGSGS GTDFTLTISN VQSEDLADYF CQQYSSYPYT FGGGTKLEIK RGGGGSGGGG   120
SGGGGSGGGG SQVQLQQPGS ELVRPGASVK LSCKASGYTF TSYWMHWVKQ RPGQGLEWIG   180
NIYPGSGSTN YDEKFKSKAT LTVDTSSSTA YMQLSSLTSE DSAVYYCTRG ATALDYWGQG   240
TTLTVSS                                                              247

SEQ ID NO: 56           moltype = AA   length = 131
FEATURE                 Location/Qualifiers
source                  1..131
                        mol_type = protein
                        organism = synthetic construct
SEQUENCE: 56
QVQLQESGPG LVKPSETLSL TCTVSAGSIS STSTSYYWGW IRQSPGKGLE WIGSIYYSGR   60
TYYNPSLKSR VTISVDRPNN QFSLKVSSVT AADSAVYYCA RHRRVLLWIG ELLDDYDRDV   120
WGQGTMVTVS S                                                         131

SEQ ID NO: 57           moltype = AA   length = 5
FEATURE                 Location/Qualifiers
source                  1..5
                        mol_type = protein
                        organism = synthetic construct
SEQUENCE: 57
DYAMH                                                                5

SEQ ID NO: 58           moltype = AA   length = 17
FEATURE                 Location/Qualifiers
source                  1..17
                        mol_type = protein
                        organism = synthetic construct
SEQUENCE: 58
GISTYFGRTN YNQKFKG                                                   17

SEQ ID NO: 59           moltype = AA   length = 10
FEATURE                 Location/Qualifiers
source                  1..10
                        mol_type = protein
                        organism = synthetic construct
SEQUENCE: 59
GLSGNYVMDY                                                           10

SEQ ID NO: 60           moltype = AA   length = 15
FEATURE                 Location/Qualifiers
source                  1..15
```

```
                           mol_type = protein
                           organism = synthetic construct
SEQUENCE: 60
RASESWDSYG NSFMH                                                        15

SEQ ID NO: 61              moltype = AA   length = 7
FEATURE                    Location/Qualifiers
source                     1..7
                           mol_type = protein
                           organism = synthetic construct
SEQUENCE: 61
RASNLES                                                                  7

SEQ ID NO: 62              moltype = AA   length = 9
FEATURE                    Location/Qualifiers
source                     1..9
                           mol_type = protein
                           organism = synthetic construct
SEQUENCE: 62
QQSNEAPPT                                                                9

SEQ ID NO: 63              moltype = AA   length = 60
FEATURE                    Location/Qualifiers
source                     1..60
                           mol_type = protein
                           organism = synthetic construct
SEQUENCE: 63
QVQLQQSGPE LVRPGVSVKI SCKGSGYTFT DYAMHWVKQS HAKSLEWIGG ISTYFGRTNY        60

SEQ ID NO: 64              moltype = AA   length = 111
FEATURE                    Location/Qualifiers
source                     1..111
                           mol_type = protein
                           organism = synthetic construct
SEQUENCE: 64
DIVLTQSPAS LAVSLGQRAT ISCRASESVD DYGNSFMHWY QQKPGQPPKL LIYRASNLES        60
GIPARFSGSG SRTDFTLTIN PVEADDVATY YCQQSNEAPP TFGGGTKLEI R                111

SEQ ID NO: 65              moltype = AA   length = 5
FEATURE                    Location/Qualifiers
source                     1..5
                           mol_type = protein
                           organism = synthetic construct
SEQUENCE: 65
DYGMH                                                                    5

SEQ ID NO: 66              moltype = AA   length = 17
FEATURE                    Location/Qualifiers
source                     1..17
                           mol_type = protein
                           organism = synthetic construct
SEQUENCE: 66
VISPYSGRTN YNQNFKG                                                      17

SEQ ID NO: 67              moltype = AA   length = 10
FEATURE                    Location/Qualifiers
source                     1..10
                           mol_type = protein
                           organism = synthetic construct
SEQUENCE: 67
GLSGNYVVDY                                                              10

SEQ ID NO: 68              moltype = AA   length = 15
FEATURE                    Location/Qualifiers
source                     1..15
                           mol_type = protein
                           organism = synthetic construct
SEQUENCE: 68
RASESWDSYG NSFMH                                                        15

SEQ ID NO: 69              moltype = AA   length = 7
FEATURE                    Location/Qualifiers
source                     1..7
                           mol_type = protein
                           organism = synthetic construct
SEQUENCE: 69
RASNLES                                                                  7

SEQ ID NO: 70              moltype = AA   length = 9
```

```
FEATURE              Location/Qualifiers
source               1..9
                     mol_type = protein
                     organism = synthetic construct
SEQUENCE: 70
QQSNEGPPT                                                                9

SEQ ID NO: 71        moltype = AA  length = 119
FEATURE              Location/Qualifiers
source               1..119
                     mol_type = protein
                     organism = synthetic construct
SEQUENCE: 71
QVQLQQSGPE LVRPGVSVKI SCKGSGYTFT DYGMHWVKQS HAKSLEWIGV ISPYSGRTNY          60
NQNFKGKATM TVDKSSSTAY LELARLTSED SAIYYCARGL SGNYVVDYWG QGTSVTVSS          119

SEQ ID NO: 72        moltype = AA  length = 111
FEATURE              Location/Qualifiers
source               1..111
                     mol_type = protein
                     organism = synthetic construct
SEQUENCE: 72
DIVLTQSPAS LAVSLGQRAT ISCRASESVD SYGNSFMHWY QQKPGQPPKL LIYRASNLES          60
GIPARFSGSG SRTDFTLTIN PVEADDVATY YCQQSNEGPP TFGGGTKLEI K                  111

SEQ ID NO: 73        moltype = AA  length = 5
FEATURE              Location/Qualifiers
source               1..5
                     mol_type = protein
                     organism = synthetic construct
SEQUENCE: 73
DYAMH                                                                    5

SEQ ID NO: 74        moltype = AA  length = 17
FEATURE              Location/Qualifiers
source               1..17
                     mol_type = protein
                     organism = synthetic construct
SEQUENCE: 74
VISFYSGKTN YNQKFMG                                                       17

SEQ ID NO: 75        moltype = AA  length = 10
FEATURE              Location/Qualifiers
source               1..10
                     mol_type = protein
                     organism = synthetic construct
SEQUENCE: 75
GLSGNYVMDY                                                               10

SEQ ID NO: 76        moltype = AA  length = 15
FEATURE              Location/Qualifiers
source               1..15
                     mol_type = protein
                     organism = synthetic construct
SEQUENCE: 76
RASESWDSYG NSFMH                                                         15

SEQ ID NO: 77        moltype = AA  length = 7
FEATURE              Location/Qualifiers
source               1..7
                     mol_type = protein
                     organism = synthetic construct
SEQUENCE: 77
RASNLES                                                                  7

SEQ ID NO: 78        moltype = AA  length = 9
FEATURE              Location/Qualifiers
source               1..9
                     mol_type = protein
                     organism = synthetic construct
SEQUENCE: 78
QQSNEGPPT                                                                9

SEQ ID NO: 79        moltype = AA  length = 119
FEATURE              Location/Qualifiers
source               1..119
                     mol_type = protein
                     organism = synthetic construct
SEQUENCE: 79
```

```
QVQLQQSGPE LVRPGVSVKI SCKGSGYTVT DYAMHWVKQS HAKSLEWIGV ISFYSGKTNY    60
NQKFMGKATM TVDKSSSTAY MELARLTSED SAIYYCARGL SGNYVMDYWG QGTSVTVSS    119

SEQ ID NO: 80           moltype = AA  length = 111
FEATURE                 Location/Qualifiers
source                  1..111
                        mol_type = protein
                        organism = synthetic construct
SEQUENCE: 80
DIVLTQSPAS LAVSLGQRAT ISCRASESVD SYGNSFMHWY QQKPGQPPKL LIYRASNLES    60
GIPARFSGSG SRTDFTLTIN PVEADDVATY YCQQSNEGPP TFGGGTKLEI K             111

SEQ ID NO: 81           moltype = AA  length = 5
FEATURE                 Location/Qualifiers
source                  1..5
                        mol_type = protein
                        organism = synthetic construct
SEQUENCE: 81
DYGMH                                                                5

SEQ ID NO: 82           moltype = AA  length = 17
FEATURE                 Location/Qualifiers
source                  1..17
                        mol_type = protein
                        organism = synthetic construct
SEQUENCE: 82
VISPYSGKTN YSQKFKG                                                   17

SEQ ID NO: 83           moltype = AA  length = 10
FEATURE                 Location/Qualifiers
source                  1..10
                        mol_type = protein
                        organism = synthetic construct
SEQUENCE: 83
GLSGNFVMDF                                                           10

SEQ ID NO: 84           moltype = AA  length = 15
FEATURE                 Location/Qualifiers
source                  1..15
                        mol_type = protein
                        organism = synthetic construct
SEQUENCE: 84
RASESWDSYG NSFMH                                                     15

SEQ ID NO: 85           moltype = AA  length = 7
FEATURE                 Location/Qualifiers
source                  1..7
                        mol_type = protein
                        organism = synthetic construct
SEQUENCE: 85
RASNLES                                                              7

SEQ ID NO: 86           moltype = AA  length = 9
FEATURE                 Location/Qualifiers
source                  1..9
                        mol_type = protein
                        organism = synthetic construct
SEQUENCE: 86
QHSNEDPPT                                                            9

SEQ ID NO: 87           moltype = AA  length = 119
FEATURE                 Location/Qualifiers
source                  1..119
                        mol_type = protein
                        organism = synthetic construct
SEQUENCE: 87
QVQLQQSGPE LVRPGVAVKI SCKGSGYKFI DYGMHWVKQS HTKSLQWIGV ISPYSGKTNY    60
SQKFKGKATM TVDKSSSTAY MELARLTSED SAIYYCARGL SGNFVMDFWG QGTSVTVSS     119

SEQ ID NO: 88           moltype = AA  length = 111
FEATURE                 Location/Qualifiers
source                  1..111
                        mol_type = protein
                        organism = synthetic construct
SEQUENCE: 88
DIVLTQSPAS LAVSLGQRAT ISCRASESVD SYGPSFMHWY QQKPGQPPKL LIYRASNLES    60
GIPARFSGSG SRTDFTLTIN PVEADDVATY YCQHSNEDPP TFGGGTRLEI K             111

SEQ ID NO: 89           moltype = AA  length = 5
```

| FEATURE | Location/Qualifiers |
| --- | --- |
| source | 1..5<br>mol_type = protein<br>organism = synthetic construct |

SEQUENCE: 89
DYAMH                                                                5

| SEQ ID NO: 90 | moltype = AA  length = 17 |
| --- | --- |
| FEATURE | Location/Qualifiers |
| source | 1..17<br>mol_type = protein<br>organism = synthetic construct |

SEQUENCE: 90
GISTYFGRTN YNQKFKG                                                  17

| SEQ ID NO: 91 | moltype = AA  length = 10 |
| --- | --- |
| FEATURE | Location/Qualifiers |
| source | 1..10<br>mol_type = protein<br>organism = synthetic construct |

SEQUENCE: 91
GLSGNYVMDY                                                          10

| SEQ ID NO: 92 | moltype = AA  length = 15 |
| --- | --- |
| FEATURE | Location/Qualifiers |
| source | 1..15<br>mol_type = protein<br>organism = synthetic construct |

SEQUENCE: 92
RASESWDSYG NSFMH                                                    15

| SEQ ID NO: 93 | moltype = AA  length = 7 |
| --- | --- |
| FEATURE | Location/Qualifiers |
| source | 1..7<br>mol_type = protein<br>organism = synthetic construct |

SEQUENCE: 93
RASNLES                                                              7

| SEQ ID NO: 94 | moltype = AA  length = 9 |
| --- | --- |
| FEATURE | Location/Qualifiers |
| source | 1..9<br>mol_type = protein<br>organism = synthetic construct |

SEQUENCE: 94
QQSNEAPPT                                                            9

| SEQ ID NO: 95 | moltype = AA  length = 119 |
| --- | --- |
| FEATURE | Location/Qualifiers |
| source | 1..119<br>mol_type = protein<br>organism = synthetic construct |

SEQUENCE: 95
QVQLQQSGPE LVRPGVSVKI SCKGSGYTFT DYAMHWVKQS HAKSLEWIGG ISTYFGRTNY    60
NQKFKGRATM TVDKSSSTAY MELARLTSED SALYYCARGL SGNYVMDYWG QGTSVTVSS    119

| SEQ ID NO: 96 | moltype = AA  length = 111 |
| --- | --- |
| FEATURE | Location/Qualifiers |
| source | 1..111<br>mol_type = protein<br>organism = synthetic construct |

SEQUENCE: 96
DIVLTQSPAS LAVSLGQRAT ISCRASESVD DYGNSFMHWY QQKPGQPPKL LIYRASNLES    60
GIPARFSGSG SRTDFTLTIN PVEADDVATY YCQQSNEAPP TFGGGTKLEI R            111

| SEQ ID NO: 97 | moltype = AA  length = 5 |
| --- | --- |
| FEATURE | Location/Qualifiers |
| source | 1..5<br>mol_type = protein<br>organism = synthetic construct |

SEQUENCE: 97
SYWMH                                                                5

| SEQ ID NO: 98 | moltype = AA  length = 17 |
| --- | --- |
| FEATURE | Location/Qualifiers |
| source | 1..17<br>mol_type = protein<br>organism = synthetic construct |

SEQUENCE: 98

```
EINPTNGRTN YNENFKS                                                        17

SEQ ID NO: 99              moltype = AA   length = 7
FEATURE                    Location/Qualifiers
source                     1..7
                           mol_type = protein
                           organism = synthetic construct
SEQUENCE: 99
GTRAYHF                                                                    7

SEQ ID NO: 100             moltype = AA   length = 11
FEATURE                    Location/Qualifiers
source                     1..11
                           mol_type = protein
                           organism = synthetic construct
SEQUENCE: 100
RASENIYSNL A                                                              11

SEQ ID NO: 101             moltype = AA   length = 7
FEATURE                    Location/Qualifiers
source                     1..7
                           mol_type = protein
                           organism = synthetic construct
SEQUENCE: 101
AATDLAD                                                                    7

SEQ ID NO: 102             moltype = AA   length = 9
FEATURE                    Location/Qualifiers
source                     1..9
                           mol_type = protein
                           organism = synthetic construct
SEQUENCE: 102
QHFWGTPLT                                                                  9

SEQ ID NO: 103             moltype = AA   length = 116
FEATURE                    Location/Qualifiers
source                     1..116
                           mol_type = protein
                           organism = synthetic construct
SEQUENCE: 103
QVQLQQPGAE LVRPGAAVKL SCKASGYTFT SYWMHWVKQR PGQGLEWIGE INPTNGRTNY          60
NENFKSKATL TVDKSSSTAY MQLSSLTSED SAVYYCARGT RAYHFWGQGT SVTVSS             116

SEQ ID NO: 104             moltype = AA   length = 107
FEATURE                    Location/Qualifiers
source                     1..107
                           mol_type = protein
                           organism = synthetic construct
SEQUENCE: 104
DIQLTQTPAS LSVSVGETVT ITCRASENIY SNLAWYQQKQ GKSPQLLVYA ATDLADGVPS          60
RFRGSGSGTQ YSLKINSLQS EDFGSYYCQH FWGTPLTFGA GTKLELI                       107

SEQ ID NO: 105             moltype = AA   length = 5
FEATURE                    Location/Qualifiers
source                     1..5
                           mol_type = protein
                           organism = synthetic construct
SEQUENCE: 105
SYWMH                                                                      5

SEQ ID NO: 106             moltype = AA   length = 17
FEATURE                    Location/Qualifiers
source                     1..17
                           mol_type = protein
                           organism = synthetic construct
SEQUENCE: 106
EINPINGRTN YSEKFKK                                                        17

SEQ ID NO: 107             moltype = AA   length = 7
FEATURE                    Location/Qualifiers
source                     1..7
                           mol_type = protein
                           organism = synthetic construct
SEQUENCE: 107
GTRAYHY                                                                    7

SEQ ID NO: 108             moltype = AA   length = 11
FEATURE                    Location/Qualifiers
source                     1..11
```

```
                        mol_type = protein
                        organism = synthetic construct
SEQUENCE: 108
RASDNIYSNL A                                                                11

SEQ ID NO: 109          moltype = AA   length = 7
FEATURE                 Location/Qualifiers
source                  1..7
                        mol_type = protein
                        organism = synthetic construct
SEQUENCE: 109
AATNLAD                                                                      7

SEQ ID NO: 110          moltype = AA   length = 9
FEATURE                 Location/Qualifiers
source                  1..9
                        mol_type = protein
                        organism = synthetic construct
SEQUENCE: 110
QHFWGTPLM                                                                    9

SEQ ID NO: 111          moltype = AA   length = 116
FEATURE                 Location/Qualifiers
source                  1..116
                        mol_type = protein
                        organism = synthetic construct
SEQUENCE: 111
QVQLQQPGAE LVKPGASVKL SCKASGYTFA SYWMHWVKQR PGQGLEWIGE INPINGRTNY            60
SEKFKKKATL TVDKSSSTAY MQLSSLTSED SAVYYCARGT RAYHYWGQGT SVTVSS               116

SEQ ID NO: 112          moltype = AA   length = 107
FEATURE                 Location/Qualifiers
source                  1..107
                        mol_type = protein
                        organism = synthetic construct
SEQUENCE: 112
DIQMTQSPAS LSVSVGETVT ITCRASDNIY SNLAWYQQKQ GKSPQLLVYA ATNLADGVPS            60
RFSGSGSGTQ YSLKINSLQS EDFGSYYCQH FWGTPLMFGS GTKLELK                        107

SEQ ID NO: 113          moltype = AA   length = 5
FEATURE                 Location/Qualifiers
source                  1..5
                        mol_type = protein
                        organism = synthetic construct
SEQUENCE: 113
SYWMH                                                                        5

SEQ ID NO: 114          moltype = AA   length = 17
FEATURE                 Location/Qualifiers
source                  1..17
                        mol_type = protein
                        organism = synthetic construct
SEQUENCE: 114
EINPSNGRTN YNETFKS                                                          17

SEQ ID NO: 115          moltype = AA   length = 7
FEATURE                 Location/Qualifiers
source                  1..7
                        mol_type = protein
                        organism = synthetic construct
SEQUENCE: 115
GTRAYHY                                                                      7

SEQ ID NO: 116          moltype = AA   length = 11
FEATURE                 Location/Qualifiers
source                  1..11
                        mol_type = protein
                        organism = synthetic construct
SEQUENCE: 116
RASDNIYSNL A                                                                11

SEQ ID NO: 117          moltype = AA   length = 7
FEATURE                 Location/Qualifiers
source                  1..7
                        mol_type = protein
                        organism = synthetic construct
SEQUENCE: 117
AVTNLAD                                                                      7
```

-continued

```
SEQ ID NO: 118           moltype = AA   length = 9
FEATURE                  Location/Qualifiers
source                   1..9
                         mol_type = protein
                         organism = synthetic construct
SEQUENCE: 118
QHFWGTPLT                                                                 9

SEQ ID NO: 119           moltype = AA   length = 116
FEATURE                  Location/Qualifiers
source                   1..116
                         mol_type = protein
                         organism = synthetic construct
SEQUENCE: 119
QVQLQQPGAE LVKPGASVKL SCKASGYTFT SYWMHWVKQR PGQGLEWIGE INPSNGRTNY   60
NETFKSKATL TVDKSSSTAY MQLSSLTSED SAVYYCARGT RAYHYWGQGT SVTVSS      116

SEQ ID NO: 120           moltype = AA   length = 107
FEATURE                  Location/Qualifiers
source                   1..107
                         mol_type = protein
                         organism = synthetic construct
SEQUENCE: 120
DIQMTQSPAS LSVSVGETVT ITCRASDNIY SNLAWYQQKQ GKSPQLLVYA VTNLADGVPS   60
RFSGSGSGTQ YSLKINSLQS EDFGSYYCQH FWGTPLTFGA GTKLELK                107

SEQ ID NO: 121           moltype = AA   length = 6
FEATURE                  Location/Qualifiers
source                   1..6
                         mol_type = protein
                         organism = synthetic construct
SEQUENCE: 121
SEYAWN                                                                    6

SEQ ID NO: 122           moltype = AA   length = 16
FEATURE                  Location/Qualifiers
source                   1..16
                         mol_type = protein
                         organism = synthetic construct
SEQUENCE: 122
YISYSGTTSY NPSLKS                                                        16

SEQ ID NO: 123           moltype = AA   length = 13
FEATURE                  Location/Qualifiers
source                   1..13
                         mol_type = protein
                         organism = synthetic construct
SEQUENCE: 123
YGYGNPATRY FDV                                                           13

SEQ ID NO: 124           moltype = AA   length = 11
FEATURE                  Location/Qualifiers
source                   1..11
                         mol_type = protein
                         organism = synthetic construct
SEQUENCE: 124
RASKSISKYL A                                                             11

SEQ ID NO: 125           moltype = AA   length = 7
FEATURE                  Location/Qualifiers
source                   1..7
                         mol_type = protein
                         organism = synthetic construct
SEQUENCE: 125
SGSTLQS                                                                   7

SEQ ID NO: 126           moltype = AA   length = 9
FEATURE                  Location/Qualifiers
source                   1..9
                         mol_type = protein
                         organism = synthetic construct
SEQUENCE: 126
QQHNEYPWT                                                                 9

SEQ ID NO: 127           moltype = AA   length = 124
FEATURE                  Location/Qualifiers
source                   1..124
                         mol_type = protein
                         organism = synthetic construct
```

```
SEQUENCE: 127
VHDVQLQESG PGLVKPSQSL SLTCTVTGNS ITSEYAWNWI RQFPGNKLEW MGYISYSGTT    60
SYNPSLKSRI SITRDTSKNQ LFLQLNSVTT EDTATYFCAR YGYGNPATRY FDVWGAGTTV   120
TVSS                                                                124

SEQ ID NO: 128              moltype = AA   length = 107
FEATURE                     Location/Qualifiers
source                      1..107
                            mol_type = protein
                            organism = synthetic construct
SEQUENCE: 128
DVQITQSPSY LTASPGETIT INCRASKSIS KYLAWYQEKP GKTNKLLIYS GSTLQSGIPS    60
RFSGSGSGTD FTLTISNLEP EDFAMYYCQQ HNEYPWTFGG GTKLEIK                 107

SEQ ID NO: 129              moltype = AA   length = 5
FEATURE                     Location/Qualifiers
source                      1..5
                            mol_type = protein
                            organism = synthetic construct
SEQUENCE: 129
SYWMH                                                                 5

SEQ ID NO: 130              moltype = AA   length = 17
FEATURE                     Location/Qualifiers
source                      1..17
                            mol_type = protein
                            organism = synthetic construct
SEQUENCE: 130
NIYPGSGSTK YDERFKS                                                   17

SEQ ID NO: 131              moltype = AA   length = 11
FEATURE                     Location/Qualifiers
source                      1..11
                            mol_type = protein
                            organism = synthetic construct
SEQUENCE: 131
GGYDSRAWFA Y                                                         11

SEQ ID NO: 132              moltype = AA   length = 15
FEATURE                     Location/Qualifiers
source                      1..15
                            mol_type = protein
                            organism = synthetic construct
SEQUENCE: 132
RARQSVSTSS YSFMH                                                     15

SEQ ID NO: 133              moltype = AA   length = 7
FEATURE                     Location/Qualifiers
source                      1..7
                            mol_type = protein
                            organism = synthetic construct
SEQUENCE: 133
YASIQES                                                               7

SEQ ID NO: 134              moltype = AA   length = 9
FEATURE                     Location/Qualifiers
source                      1..9
                            mol_type = protein
                            organism = synthetic construct
SEQUENCE: 134
QHTWEIPFT                                                             9

SEQ ID NO: 135              moltype = AA   length = 120
FEATURE                     Location/Qualifiers
source                      1..120
                            mol_type = protein
                            organism = synthetic construct
SEQUENCE: 135
QVQLQQPGSE LVRPGASVKL SCKASGYTFT SYWMHWVKQR HGQGLEWIGN IYPGSGSTKY     60
DERFKSKGTL TVDTSSSTAY MHLSSLTSED SAVYYCTRGG YDSRAWFAYW GQGTLVTVSA    120

SEQ ID NO: 136              moltype = AA   length = 111
FEATURE                     Location/Qualifiers
source                      1..111
                            mol_type = protein
                            organism = synthetic construct
SEQUENCE: 136
DIVLTQSPAS LAVSLGQRAT ISCRARQSVS TSSYSFMHWY RQKAGQPPKL LIKYASIQES     60
GVPARFSGSG SGTDFTLNIL PVEEEDTATY YCQHTWEIPF TFGSGTKLEI K             111
```

```
SEQ ID NO: 137            moltype = AA  length = 5
FEATURE                   Location/Qualifiers
source                    1..5
                          mol_type = protein
                          organism = synthetic construct
SEQUENCE: 137
SYWMH                                                                    5

SEQ ID NO: 138            moltype = AA  length = 17
FEATURE                   Location/Qualifiers
source                    1..17
                          mol_type = protein
                          organism = synthetic construct
SEQUENCE: 138
NIYPGSGSTK YDEKRKS                                                      17

SEQ ID NO: 139            moltype = AA  length = 11
FEATURE                   Location/Qualifiers
source                    1..11
                          mol_type = protein
                          organism = synthetic construct
SEQUENCE: 139
GGYDSRAWFA H                                                            11

SEQ ID NO: 140            moltype = AA  length = 15
FEATURE                   Location/Qualifiers
source                    1..15
                          mol_type = protein
                          organism = synthetic construct
SEQUENCE: 140
RARQSVSTSS YSFMH                                                        15

SEQ ID NO: 141            moltype = AA  length = 7
FEATURE                   Location/Qualifiers
source                    1..7
                          mol_type = protein
                          organism = synthetic construct
SEQUENCE: 141
YASIQES                                                                  7

SEQ ID NO: 142            moltype = AA  length = 9
FEATURE                   Location/Qualifiers
source                    1..9
                          mol_type = protein
                          organism = synthetic construct
SEQUENCE: 142
QHTWEIPFT                                                                9

SEQ ID NO: 143            moltype = AA  length = 120
FEATURE                   Location/Qualifiers
source                    1..120
                          mol_type = protein
                          organism = synthetic construct
SEQUENCE: 143
QVQLQQPGSE LVRPGASVKL SCKASGYTFT SYWMHWVKQR HGQGLEWIGN IYPGSGSTKY        60
DEKFKSKGTL TVDTSSSTAY MHLSSLTSED SAVYYCTRGG YDSRAWFAHW GQGTLVTVSA       120

SEQ ID NO: 144            moltype = AA  length = 111
FEATURE                   Location/Qualifiers
source                    1..111
                          mol_type = protein
                          organism = synthetic construct
SEQUENCE: 144
DIVLTQSPAS LAVSLGQRAT ISCRARQSVS TSSYSFMHWY QQKPGQPPKL LIKYASIQES        60
GVPARFSGSG SGTDFTLNIL PVEEEDTATY YCQHTWEIPF TFGSGTNLEI K                111

SEQ ID NO: 145            moltype = AA  length = 5
FEATURE                   Location/Qualifiers
source                    1..5
                          mol_type = protein
                          organism = synthetic construct
SEQUENCE: 145
DYYMY                                                                    5

SEQ ID NO: 146            moltype = AA  length = 17
FEATURE                   Location/Qualifiers
source                    1..17
                          mol_type = protein
```

```
                                    -continued
                              organism = synthetic construct
SEQUENCE: 146
SISNGGDNTY YPDTVKG                                                         17

SEQ ID NO: 147              moltype = AA   length = 15
FEATURE                     Location/Qualifiers
source                      1..15
                            mol_type = protein
                            organism = synthetic construct
SEQUENCE: 147
QGALYDGYYR GAMDY                                                           15

SEQ ID NO: 148              moltype = AA   length = 12
FEATURE                     Location/Qualifiers
source                      1..12
                            mol_type = protein
                            organism = synthetic construct
SEQUENCE: 148
TTSSSWPSSY FH                                                              12

SEQ ID NO: 149              moltype = AA   length = 7
FEATURE                     Location/Qualifiers
source                      1..7
                            mol_type = protein
                            organism = synthetic construct
SEQUENCE: 149
STSNLAS                                                                     7

SEQ ID NO: 150              moltype = AA   length = 9
FEATURE                     Location/Qualifiers
source                      1..9
                            mol_type = protein
                            organism = synthetic construct
SEQUENCE: 150
HQYHRSPFT                                                                   9

SEQ ID NO: 151              moltype = AA   length = 124
FEATURE                     Location/Qualifiers
source                      1..124
                            mol_type = protein
                            organism = synthetic construct
SEQUENCE: 151
EVKLVESGGG LVQPGGFLKL SCATSGFTFS DYYMYWVRQT PEKRLEWVAS ISNGGDNTYY           60
PDTVKGRFTI SRDNAKNTLY LQMSRLKSED TAMYYCARQG ALYDGYYRGA MDYWGQGTSV          120
TVSS                                                                      124

SEQ ID NO: 152              moltype = AA   length = 108
FEATURE                     Location/Qualifiers
source                      1..108
                            mol_type = protein
                            organism = synthetic construct
SEQUENCE: 152
QIVLTQSPAI MSASLGGRVT MTCTTSSSVP SSYFHWYQQK PGSSPKLWIY STSNLASGVP           60
ARFSGSGSGT SYSLTISSME AEDAATYYCH QYHRSPFTFG SGTKLEIK                       108

SEQ ID NO: 153              moltype = AA   length = 5
FEATURE                     Location/Qualifiers
source                      1..5
                            mol_type = protein
                            organism = synthetic construct
SEQUENCE: 153
NYWIE                                                                       5

SEQ ID NO: 154              moltype = AA   length = 17
FEATURE                     Location/Qualifiers
source                      1..17
                            mol_type = protein
                            organism = synthetic construct
SEQUENCE: 154
EILPGSGSTK YNEKFKG                                                         17

SEQ ID NO: 155              moltype = AA   length = 12
FEATURE                     Location/Qualifiers
source                      1..12
                            mol_type = protein
                            organism = synthetic construct
SEQUENCE: 155
RGGYGYDGEF AY                                                              12
```

| SEQ ID NO: 156 | moltype = AA length = 11 | |
|---|---|---|
| FEATURE | Location/Qualifiers | |
| source | 1..11 | |
| | mol_type = protein | |
| | organism = synthetic construct | |
| SEQUENCE: 156 | | |
| RAGQDITNYL N | | 11 |

| SEQ ID NO: 157 | moltype = AA length = 7 | |
|---|---|---|
| FEATURE | Location/Qualifiers | |
| source | 1..7 | |
| | mol_type = protein | |
| | organism = synthetic construct | |
| SEQUENCE: 157 | | |
| YTSRLHS | | 7 |

| SEQ ID NO: 158 | moltype = AA length = 9 | |
|---|---|---|
| FEATURE | Location/Qualifiers | |
| source | 1..9 | |
| | mol_type = protein | |
| | organism = synthetic construct | |
| SEQUENCE: 158 | | |
| QQANTLPYT | | 9 |

| SEQ ID NO: 159 | moltype = AA length = 121 | |
|---|---|---|
| FEATURE | Location/Qualifiers | |
| source | 1..121 | |
| | mol_type = protein | |
| | organism = synthetic construct | |
| SEQUENCE: 159 | | |
| QVQLQQSGAE LMKPGASVKI SCKAAGYTFS NYWIEWVKQR PGHGLEWIGE ILPGSGSTKY | | 60 |
| NEKFKGKATF TADTSSNTAY MQLSSLTSED SAVYYCARRG GYGYDGEFAY WGQGTLVTVS | | 120 |
| A | | 121 |

| SEQ ID NO: 160 | moltype = AA length = 107 | |
|---|---|---|
| FEATURE | Location/Qualifiers | |
| source | 1..107 | |
| | mol_type = protein | |
| | organism = synthetic construct | |
| SEQUENCE: 160 | | |
| DIQMTQTTSS LSASLGDRVT INCRAGQDIT NYLNWFQQKP DGTVKLLIYY TSRLHSGVPS | | 60 |
| RFSGSGSGTD YSLTITNLEQ EDIATYFCQQ ANTLPYTFGG GTKLEIK | | 107 |

| SEQ ID NO: 161 | moltype = AA length = 8 | |
|---|---|---|
| FEATURE | Location/Qualifiers | |
| source | 1..8 | |
| | mol_type = protein | |
| | organism = synthetic construct | |
| SEQUENCE: 161 | | |
| GYTFTNYW | | 8 |

| SEQ ID NO: 162 | moltype = AA length = 8 | |
|---|---|---|
| FEATURE | Location/Qualifiers | |
| source | 1..8 | |
| | mol_type = protein | |
| | organism = synthetic construct | |
| SEQUENCE: 162 | | |
| INPINGRS | | 8 |

| SEQ ID NO: 163 | moltype = AA length = 9 | |
|---|---|---|
| FEATURE | Location/Qualifiers | |
| source | 1..9 | |
| | mol_type = protein | |
| | organism = synthetic construct | |
| SEQUENCE: 163 | | |
| ARGTRAMHY | | 9 |

| SEQ ID NO: 164 | moltype = AA length = 6 | |
|---|---|---|
| FEATURE | Location/Qualifiers | |
| source | 1..6 | |
| | mol_type = protein | |
| | organism = synthetic construct | |
| SEQUENCE: 164 | | |
| ENIYNN | | 6 |

| SEQ ID NO: 165 | moltype = AA length = 9 |
|---|---|
| FEATURE | Location/Qualifiers |
| source | 1..9 |
| | mol_type = protein |

```
SEQUENCE: 165
QHFWGTPLT                                                                   9

SEQ ID NO: 166          moltype = AA   length = 5
FEATURE                 Location/Qualifiers
source                  1..5
                        mol_type = protein
                        organism = synthetic construct
SEQUENCE: 166
NYWMH                                                                       5

SEQ ID NO: 167          moltype = AA   length = 17
FEATURE                 Location/Qualifiers
source                  1..17
                        mol_type = protein
                        organism = synthetic construct
SEQUENCE: 167
EINPINGRSN YGERFKT                                                         17

SEQ ID NO: 168          moltype = AA   length = 7
FEATURE                 Location/Qualifiers
source                  1..7
                        mol_type = protein
                        organism = synthetic construct
SEQUENCE: 168
GTRAMHY                                                                     7

SEQ ID NO: 169          moltype = AA   length = 11
FEATURE                 Location/Qualifiers
source                  1..11
                        mol_type = protein
                        organism = synthetic construct
SEQUENCE: 169
RTSENIYNNL A                                                               11

SEQ ID NO: 170          moltype = AA   length = 7
FEATURE                 Location/Qualifiers
source                  1..7
                        mol_type = protein
                        organism = synthetic construct
SEQUENCE: 170
AATNLAD                                                                     7

SEQ ID NO: 171          moltype = AA   length = 9
FEATURE                 Location/Qualifiers
source                  1..9
                        mol_type = protein
                        organism = synthetic construct
SEQUENCE: 171
QHFWGTPLT                                                                   9

SEQ ID NO: 172          moltype = AA   length = 7
FEATURE                 Location/Qualifiers
source                  1..7
                        mol_type = protein
                        organism = synthetic construct
SEQUENCE: 172
GYTFTNY                                                                     7

SEQ ID NO: 173          moltype = AA   length = 5
FEATURE                 Location/Qualifiers
source                  1..5
                        mol_type = protein
                        organism = synthetic construct
SEQUENCE: 173
TRAMH                                                                       5

SEQ ID NO: 174          moltype = AA   length = 7
FEATURE                 Location/Qualifiers
source                  1..7
                        mol_type = protein
                        organism = synthetic construct
SEQUENCE: 174
SENIYNN                                                                     7

SEQ ID NO: 175          moltype = AA   length = 6
FEATURE                 Location/Qualifiers
source                  1..6
```

```
                    mol_type = protein
                    organism = synthetic construct
SEQUENCE: 175
FWGTPL                                                                    6

SEQ ID NO: 176      moltype = AA   length = 116
FEATURE             Location/Qualifiers
source              1..116
                    mol_type = protein
                    organism = synthetic construct
SEQUENCE: 176
QVQLQQPGAE LVKPGASVKL SCKASGYTFT NYWMHWVKQR PGQGLEWIGE INPINGRSNY        60
GERFKTKATL TVDKSSSTAY MQLSSLTSED SAVYYCARGT RAMHYWGQGT SVTVSS            116

SEQ ID NO: 177      moltype = AA   length = 107
FEATURE             Location/Qualifiers
source              1..107
                    mol_type = protein
                    organism = synthetic construct
SEQUENCE: 177
DIQMTQSPAS LSVSVGETVT ITCRTSENIY NNLAWYQQKQ GKSPQLLVYA ATNLADGVPS        60
RFSGSGSGTQ YSLKINSLQS EDFGNYYCQH FWGTPLTFGA GTKLELK                      107

SEQ ID NO: 178      moltype = AA   length = 10
FEATURE             Location/Qualifiers
source              1..10
                    mol_type = protein
                    organism = synthetic construct
SEQUENCE: 178
GFTFSNYGMH                                                                10

SEQ ID NO: 179      moltype = AA   length = 17
FEATURE             Location/Qualifiers
source              1..17
                    mol_type = protein
                    organism = synthetic construct
SEQUENCE: 179
MIYYDSSKMN YADTVKG                                                        17

SEQ ID NO: 180      moltype = AA   length = 9
FEATURE             Location/Qualifiers
source              1..9
                    mol_type = protein
                    organism = synthetic construct
SEQUENCE: 180
PTSHYVVDV                                                                 9

SEQ ID NO: 181      moltype = AA   length = 11
FEATURE             Location/Qualifiers
source              1..11
                    mol_type = protein
                    organism = synthetic construct
SEQUENCE: 181
QASQDIGNWL A                                                              11

SEQ ID NO: 182      moltype = AA   length = 7
FEATURE             Location/Qualifiers
source              1..7
                    mol_type = protein
                    organism = synthetic construct
SEQUENCE: 182
GATSLAD                                                                   7

SEQ ID NO: 183      moltype = AA   length = 9
FEATURE             Location/Qualifiers
source              1..9
                    mol_type = protein
                    organism = synthetic construct
SEQUENCE: 183
LQAYNTPWT                                                                 9

SEQ ID NO: 184      moltype = AA   length = 117
FEATURE             Location/Qualifiers
source              1..117
                    mol_type = protein
                    organism = synthetic construct
SEQUENCE: 184
EVQLVWSGGG LVQPQNSLTL SCVASGFTFS NYGMHWRQAP KKGLEWIAMI YYDSSKMNYA        60
DTVKGRFTIS RDNSKNTLYL EMNSLRSEDT AMYYCAVPTS HYVVDWGQG VSVTVSS            117
```

```
SEQ ID NO: 185         moltype = AA  length = 108
FEATURE                Location/Qualifiers
source                 1..108
                       mol_type = protein
                       organism = synthetic construct
SEQUENCE: 185
DIQMTQSPAS LSASLEEIVT ITCQASQDIG NWLAWYQQKP GKSPQLLIYG ATSLADGVPS      60
RFSGSRSGTQ FSLKISRVQV EDIGIYYCLQ AYNTPWTFGG GTKLELKR                 108

SEQ ID NO: 186         moltype = AA  length = 60
FEATURE                Location/Qualifiers
source                 1..60
                       mol_type = protein
                       organism = Mus musculus
SEQUENCE: 186
MEFGLSWLFL VAILKGVQCE VQLQQSGTVL ARPGASVKMS CKASGYSFTI YWIHWVKQRP      60

SEQ ID NO: 187         moltype = AA  length = 130
FEATURE                Location/Qualifiers
source                 1..130
                       mol_type = protein
                       organism = Mus musculus
SEQUENCE: 187
MDMRVPAQLL GLLLLWLPGA RCDVQITQSP SYLAASPGET IIINCRASKS ISKYLAWYQE      60
KPGKTNKLLI YSGSTLQSGI PSRFSGSGSG TDFTLTISSL EPQDFAMYYC QQHNEYPWTF     120
GGGTKLEIKR                                                           130

SEQ ID NO: 188         moltype = RNA  length = 19
FEATURE                Location/Qualifiers
source                 1..19
                       mol_type = other RNA
                       organism = synthetic construct
modified_base          3
                       mod_base = OTHER
                       note = may be thymine
modified_base          5
                       mod_base = OTHER
                       note = may be thymine
modified_base          14
                       mod_base = OTHER
                       note = may be thymine
SEQUENCE: 188
ggtctaggcc cggtgagag                                                   19

SEQ ID NO: 189         moltype = RNA  length = 19
FEATURE                Location/Qualifiers
source                 1..19
                       mol_type = other RNA
                       organism = synthetic construct
modified_base          3
                       mod_base = OTHER
                       note = may be thymine
modified_base          7..8
                       mod_base = OTHER
                       note = may be thymine
modified_base          13..14
                       mod_base = OTHER
                       note = may be thymine
modified_base          18
                       mod_base = OTHER
                       note = may be thymine
SEQUENCE: 189
cctggattag agttacatc                                                   19

SEQ ID NO: 190         moltype = DNA  length = 25
FEATURE                Location/Qualifiers
source                 1..25
                       mol_type = other DNA
                       organism = synthetic construct
SEQUENCE: 190
cttctaggtc taggcccggt gagag                                            25

SEQ ID NO: 191         moltype = RNA  length = 25
FEATURE                Location/Qualifiers
source                 1..25
                       mol_type = other RNA
                       organism = synthetic construct
modified_base          2
```

```
                        mod_base = OTHER
                        note = may be thymine
modified_base           4
                        mod_base = OTHER
                        note = may be thymine
modified_base           14
                        mod_base = OTHER
                        note = may be thymine
modified_base           20
                        mod_base = OTHER
                        note = may be thymine
SEQUENCE: 191
ctctcaccgg gcctagacct agaag                                             25

SEQ ID NO: 192          moltype = RNA   length = 35
FEATURE                 Location/Qualifiers
source                  1..35
                        mol_type = other RNA
                        organism = synthetic construct
modified_base           14
                        mod_base = OTHER
                        note = may be thymine
modified_base           18
                        mod_base = OTHER
                        note = may be thymine
modified_base           22
                        mod_base = OTHER
                        note = may be thymine
modified_base           34
                        mod_base = OTHER
                        note = may be thymine
SEQUENCE: 192
cgcggggaac acctggctgg ctacggaggg gcgtg                                  35

SEQ ID NO: 193          moltype = RNA   length = 35
FEATURE                 Location/Qualifiers
source                  1..35
                        mol_type = other RNA
                        organism = synthetic construct
modified_base           4..5
                        mod_base = OTHER
                        note = may be thymine
modified_base           7
                        mod_base = OTHER
                        note = may be thymine
modified_base           11
                        mod_base = OTHER
                        note = may be thymine
modified_base           13
                        mod_base = OTHER
                        note = may be thymine
modified_base           22
                        mod_base = OTHER
                        note = may be thymine
modified_base           30
                        mod_base = OTHER
                        note = may be thymine
SEQUENCE: 193
gccttctagg tctaggcccg gtgagagact ccaca                                  35

SEQ ID NO: 194          moltype = DNA   length = 38
FEATURE                 Location/Qualifiers
source                  1..38
                        mol_type = other DNA
                        organism = synthetic construct
SEQUENCE: 194
gctccacgcc ctctgcaagg gacctgttgc tcgcgtgt                               38

SEQ ID NO: 195          moltype = DNA   length = 40
FEATURE                 Location/Qualifiers
source                  1..40
                        mol_type = other DNA
                        organism = synthetic construct
SEQUENCE: 195
ctgggattcc tgccttctag gtctaggccc ggtgagagac                             40

SEQ ID NO: 196          moltype = DNA   length = 60
FEATURE                 Location/Qualifiers
source                  1..60
```

```
                        mol_type = other DNA
                        organism = synthetic construct
SEQUENCE: 196
cgggttccac gctccttcgc cctctgcaag gggacctgtt gctcgcgtgt ctcccgcccc    60

SEQ ID NO: 197          moltype = DNA   length = 60
FEATURE                 Location/Qualifiers
source                  1..60
                        mol_type = other DNA
                        organism = synthetic construct
SEQUENCE: 197
agtcaagaca gcggcttcca gtttccatag aattactgga gaacctcaga gagccagccc    60

SEQ ID NO: 198          moltype = DNA   length = 59
FEATURE                 Location/Qualifiers
source                  1..59
                        mol_type = other DNA
                        organism = synthetic construct
SEQUENCE: 198
gctgaccggc ctgggattcc tgccactagg tctaggcccg gtgagagact ccacaccgc     59

SEQ ID NO: 199          moltype = DNA   length = 2859
FEATURE                 Location/Qualifiers
source                  1..2859
                        mol_type = genomic DNA
                        organism = Homo sapiens
SEQUENCE: 199
agggggggctg gaccaagggg tgggagaaag gggaggaggc ctcggccggc cgcagagaga    60
agtggccaga gaggcccagg ggacagccag ggacaggcag acatgcagcc agggctccag   120
ggcctggaca ggggctgcca ggccctgtga caggaggacc ccgagccccc ggcccgggga   180
ggggccatgg tgctgcctgt ccaacatgtc agccgaggtg cggctgaggc ggctccagca   240
gctggtgttg gacccgggct tcctggggct ggagcccctg ctcgaccttc tcctgggcgt   300
ccaccaggag ctgggcgcct ccgaactggc ccaggacaag tacgtggccg acttcttgca   360
gtgggcggag cccatcgtgg tgaggcttaa ggaggtccga ctgcagaggg acgacttcga   420
gattctgaag gtgatcggac gcggggcgtt cagcgaggta ggctagtga agataagcga   480
gacgggccag gtgtatgcca tgaagatcat gaacaagtgg gacatgctga agaggggcga   540
ggtgtcgtgc ttccgtgagg agagggacgt gttggtgaat ggggaccggc ggtggatcac   600
gcagctgcac ttcgccttcc aggatgagaa ctacctgtac ctggtcatgg agtattacgt   660
gggcgggac ctgctgacac tgctgagcaa gtttgggaag cggattccgg ccgagatgcg   720
gcgcttctac ctggcggaga ttgtcatggc catagactcg gtgcaccggc ttggctacgt   780
gcacagggac atcaaacccg acaacatcct gctggaccgc tgtggccaca tccgcctggc   840
cgacttcggc tcttgcctca agctgcgggc agatggaacg gtgcggtcgc tggtggctgt   900
gggcaccca gactacctgt ccccccgagat cctgcaggct gtgggcggtg ggcctggcac   960
aggcagctac gggcccgagt gtgactggtg ggcgctgggc gtattcgcct atgaaatgtt  1020
ctatgggcag acgcccttct acgcggattc cacggcggag acctatggca agatcgtcca  1080
ctacaaggag cacctctctc tgccgctggt ggacgaaggg gtccctgagg aggctcgaga  1140
cttcattcag cggttgctgt gtccccccgga gacacggctg ggcgggggtg gagcaggcga  1200
cttccggaca catcccttct tctttgcct cgactgggat ggtctccggg acagcgtgcc  1260
ccccttaca ccggatttcg aaggtgccac cgacacatgc aacttcgact ggtggaggga  1320
cgggctcact gccatggaga cactgtcgga cattcgggaa ggtgcgccgc taggggtcca  1380
cctgcctttt gtgggctact cctactcctg catggccctc agggacagtg aggtcccagg  1440
ccccacaccc atgaactgg aggccgagca gctgcttgag ccacacgtgc aagcgcccag  1500
cctggagccc tcggtgtccc cacaggatga aacagctgaa gtggcagttc cagcggctgt  1560
ccctgcggca gaggctgagg ccgaggtgac gctgcggagg ctccaggaag ccctggagga  1620
ggaggtgctc acccggcaga gcctgagccg ggagatggag gccatccgga cggacaacca  1680
gaacttcgcc agtcaactac gcaggcagag ggctcgaac cgggacctag aggcacacgt  1740
ccggcagttg caggagcgga tggagttgct gcaggcagag ggagcacag ctgtcacggg  1800
ggtccccagt ccccgggcca cggatccacc ttcccatcta gatggccccc cggccgtggc  1860
tgtgggccag tgcccgctgg tggggccagg cccatgcac cgcgcccaac tgctgctccc  1920
tgccagggtc cctaggcctg gcctatcgga ggcgcttcc ctgctcctgt tcgccgttgt  1980
tctgtctcgt gccgccgccc tgggctgcat tgggttggtg gccacgccg gccaactcac  2040
cgcagtctgg cgccgcccag gagccgcccg cgctccctga accctagaac tgtcttcgac  2100
tccggggccc cgttggaaga ctgagtgccc ggggcacggc acagaagccg cgcccaccgc  2160
ctgccagttc acaaccgctc cgagcgtggg tctccgccca gctccagtcc tgtgatccgg  2220
gcccgccccc tagcggccgg ggagggaggg gccgggtccg cggccggcga acggggctcg  2280
aagggtcctt gtagccggga atgctgctgc tgctgctgct gctgctgctg ctgctgctgc  2340
tgctgctgct gctgctgctg ctgggggggat cacagaccat ttctttcttt cggccaggct  2400
gaggccctga cgttggatggg caaactgcag gcctgggaag gcagcaagcc gggccgttcg  2460
tgttccatcc tccacgcacc cccacctatc gttggttcga aaagtgcaaa gctttctttgt  2520
gcatgacgcc ctgctctggg gagcgtctgg cgcgatctct gcctgcttac tcggaaatt  2580
tgcttttgcc aaacccgctt tttcggggat cccgcgcccc cctcctcact tgcgctgctc  2640
tcggagcccc agccggctcc gccgcttcg cggtttgga tatttattga cctcgtcctc  2700
cgactcgctg acaggctaca ggaccccaa caaccccaat ccacgttttg gatgcactga  2760
gaccccgaca ttcctcggta tttattgtct gtcccacct aggaccccca ccccgaccc    2820
tcgcgaataa aaggccctcc atctgcccaa agctctgga                          2859

SEQ ID NO: 200          moltype = DNA   length = 2683
FEATURE                 Location/Qualifiers
source                  1..2683
```

```
                        mol_type = genomic DNA
                        organism = Mus musculus
SEQUENCE: 200
gaactggcca gagagaccca agggatagtc agggacgggc agacatgcag ctagggttct   60
ggggcctgga caggggcagc caggccctgt gacgggaaga ccccgagctc cggcccgggg  120
aggggccatg gtgttgcctg cccaacatgt cagccgaagt gcggctgagg cagctccagc  180
agctggtgct ggaccaggcc ttcctgggac tggagcccct gctcgacctt ctcctgggcg  240
tccaccagga gctgggtgcc tctcacctag cccaggacaa gtatgtggcc gacttcttgc  300
agtgggtgga gcccattgca gcaaggctta aggaggtccg actgcagagg gatgattttg  360
agattttgaa ggtgatcggg cgtgggcgt tcagcgaggt agcggtggtg aagatgaaac  420
agacgggcca agtgtatgcc atgaagatta tgaataagtg ggacatgctg aagagaggcg  480
aggtgtcgtg cttccgggaa gaagggatg tattagtgaa aggggaccgg cgctggatca  540
cacagctgca ctttgccttc caggatgaga actacctgta cctggtcatg gaatactacg  600
tgggcgggga cctgctaacg ctgctgagca gtttgcaggt gggatcccc gccgagatgg  660
ctcgcttcta cctggccgag attgtcatgg ccatagactc cgtgcaccgg ctgggctacg  720
tgcacaggga catcaaacca gataacattc tgctggaccg atgtgggcac attcgcctgg  780
cagacttcgg ctcctgcctc aaactgcagc ctgatggaat ggtgaggtcg ctggtggctg  840
tgggcacccc ggactacctg tctcctgaga ttctgcaggc cgttggtgga gggcctgggg  900
caggcagcta cgggcagag tgtgactggt gggcactggg cgtgttcgcc tatgagatgt  960
tctatgggca gaccccttc tacgcggact ccacagccga gacatatgcc aagattgtgc 1020
actcagggga acacttgtcg ctgccgctgg cagacacagt tgtccccgag gaagctcagg 1080
acctcattcg tgggctgctg tgtcctgctg agataaggct aggtcgaggt gggcagact 1140
tcgagggtgc cacggacaca tgcaatttcg atgtggtgga ggaccggctc actgccatgg 1200
tgagcggggg cggggagacg ctgtcagaca tgcaggaaga catgcccctt ggggtgcgcc 1260
tgcccttcgt gggctactcc tactgctgca tggcctcag agacaatcag gtcccggacc 1320
ccaccccttat ggaactagag gccctgcagt tgcctgtgtc agacttgcaa gggcttgact 1380
tgcagccccc agtgtcccca ccggatcaag tggctgaaga ggctgaccta gtggctgtcc 1440
ctgcccctgt ggctgaggca gagaccacgg taacgctgca gcagctccag gaagccctgg 1500
aagaagaggt tctcacccgg cagagcctga gccgcgagct ggaggccatc cggaccgcca 1560
accagaactt ctccagccaa ctacaggagg ccgaggtccg aaaccgagac ctggaggcgc 1620
atgttcggca gctacaggaa cggatggaga tgctgcaggc cccaggagcc gcagccatca 1680
cgggggtccc cagtccccgg gccacggatc caccttccca tctagatggc ccccggccg 1740
tggctgtggg ccagtgcccg ctggtggggc caggccccat gcaccgcgt cacctgctgc 1800
tccctgccag gatccctagg cctggcctat ccgaggcgcg ttgcctgctc ctgttcgccg 1860
ctgctctggc tgctgccgcc acactgggct gcactgggtt ggtggcctat accggcggtc 1920
tcacccccagt ctggtgtttc ccgggagcca ccttcgcccc ctgaaccta agactccaag 1980
ccatctttca tttaggcctc ctaggaaggt cgagcgacca gggagcgacc caaagcgtct 2040
ctgtgccat cgcgcccccc ccccccccc accgctccgc tccacacttc tgtgagcctg 2100
ggtccccacc cagctccgct cctgtgatcc aggcctgcca cctggccgcc gggagggag 2160
gaacagggct cgtgccagc acccctggtt cctgcagagc tggtagccac cgctgctgca 2220
gcagctgggc attcgccgac cttgctttac tcagccccga cgtggatggg caaactgctc 2280
agctcatccg atttcacttt ttcactctcc cagccatcag ttacaagcca taagcatgag 2340
cccctatttt ccagggacat cccattccca tagtgatgga tcagcaagac ctctgccagc 2400
acacacggag tctttggctt cggacagcct cactcctggg ggttgctgca actccttccc 2460
cgtgtacacg tctgcactct aacaacggag ccacagctgc actccccct cccccaaagc 2520
agtgtgggta tttattgatc ttgttatctg actcactgac agactccggg acccacgttt 2580
tagatgcatt gagactcgac attcctcggt atttattgtc tgtccccacc tacgacctcc 2640
actcccgacc cttgcgaata aaatacttct ggtctgccct aaa                   2683

SEQ ID NO: 201          moltype = RNA    length = 20
FEATURE                 Location/Qualifiers
source                  1..20
                        mol_type = other RNA
                        organism = synthetic construct
SEQUENCE: 201
ggacggcccg gcttgctgcc                                                20

SEQ ID NO: 202          moltype = RNA    length = 20
FEATURE                 Location/Qualifiers
source                  1..20
                        mol_type = other RNA
                        organism = synthetic construct
SEQUENCE: 202
gggcccggat cacaggactg                                                20

SEQ ID NO: 203          moltype = RNA    length = 20
FEATURE                 Location/Qualifiers
source                  1..20
                        mol_type = other RNA
                        organism = synthetic construct
SEQUENCE: 203
caaacttgct cagcagtgtc                                                20

SEQ ID NO: 204          moltype = RNA    length = 20
FEATURE                 Location/Qualifiers
source                  1..20
                        mol_type = other RNA
                        organism = synthetic construct
SEQUENCE: 204
```

-continued

```
aaacttgctc agcagtgtca                                              20

SEQ ID NO: 205         moltype = RNA   length = 20
FEATURE                Location/Qualifiers
source                 1..20
                       mol_type = other RNA
                       organism = synthetic construct SEQUENCE: 205
cggatggcct ccatctcccg                                              20

SEQ ID NO: 206         moltype = RNA   length = 20
FEATURE                Location/Qualifiers
source                 1..20
                       mol_type = other RNA
                       organism = synthetic construct SEQUENCE: 206
ctcggccgga atccgctccc                                              20

SEQ ID NO: 207         moltype = RNA   length = 20
FEATURE                Location/Qualifiers
source                 1..20
                       mol_type = other RNA
                       organism = synthetic construct SEQUENCE: 207
tctcggccgg aatccgctcc                                              20

SEQ ID NO: 208         moltype = RNA   length = 20
FEATURE                Location/Qualifiers
source                 1..20
                       mol_type = other RNA
                       organism = synthetic construct SEQUENCE: 208
tgctcagcag tgtcagcagg                                              20

SEQ ID NO: 209         moltype = RNA   length = 20
FEATURE                Location/Qualifiers
source                 1..20
                       mol_type = other RNA
                       organism = synthetic construct SEQUENCE: 209
ttgtcgggtt tgatgtccct                                              20

SEQ ID NO: 210         moltype = RNA   length = 20
FEATURE                Location/Qualifiers
source                 1..20
                       mol_type = other RNA
                       organism = synthetic construct SEQUENCE: 210
gttgtcgggt ttgatgtccc                                              20

SEQ ID NO: 211         moltype = RNA   length = 20
FEATURE                Location/Qualifiers
source                 1..20
                       mol_type = other RNA
                       organism = synthetic construct SEQUENCE: 211
tccgccaggt agaagcgcgc                                              20

SEQ ID NO: 212         moltype = RNA   length = 20
FEATURE                Location/Qualifiers
source                 1..20
                       mol_type = other RNA
                       organism = synthetic construct SEQUENCE: 212
catggcatac acctggcccg                                              20

SEQ ID NO: 213         moltype = RNA   length = 20
FEATURE                Location/Qualifiers
source                 1..20
                       mol_type = other RNA
                       organism = synthetic construct SEQUENCE: 213
aacttgctca gcagtgtcag                                              20

SEQ ID NO: 214         moltype = RNA   length = 20
FEATURE                Location/Qualifiers
source                 1..20
                       mol_type = other RNA
                       organism = synthetic construct
```

| | | |
|---|---|---|
| SEQUENCE: 214 cagctgcgtg atccaccgcc | | 20 |
| SEQ ID NO: 215 FEATURE source | moltype = RNA length = 20 Location/Qualifiers 1..20 mol_type = other RNA organism = synthetic construct | |
| SEQUENCE: 215 cgaatgtccg acagtgtctc | | 20 |
| SEQ ID NO: 216 FEATURE source | moltype = RNA length = 20 Location/Qualifiers 1..20 mol_type = other RNA organism = synthetic construct | |
| SEQUENCE: 216 gaagtcggcc aggcggatgt | | 20 |
| SEQ ID NO: 217 FEATURE source | moltype = RNA length = 20 Location/Qualifiers 1..20 mol_type = other RNA organism = synthetic construct | |
| SEQUENCE: 217 tgtcgggttt gatgtccctg | | 20 |
| SEQ ID NO: 218 FEATURE source | moltype = RNA length = 20 Location/Qualifiers 1..20 mol_type = other RNA organism = synthetic construct | |
| SEQUENCE: 218 ggatggcctc catctcccgg | | 20 |
| SEQ ID NO: 219 FEATURE source | moltype = RNA length = 20 Location/Qualifiers 1..20 mol_type = other RNA organism = synthetic construct | |
| SEQUENCE: 219 aggatgttgt cgggtttgat | | 20 |
| SEQ ID NO: 220 FEATURE source | moltype = RNA length = 20 Location/Qualifiers 1..20 mol_type = other RNA organism = synthetic construct | |
| SEQUENCE: 220 gtcgggtttg atgtccctgt | | 20 |
| SEQ ID NO: 221 FEATURE source | moltype = RNA length = 20 Location/Qualifiers 1..20 mol_type = other RNA organism = synthetic construct | |
| SEQUENCE: 221 aatactccat gaccaggtac | | 20 |
| SEQ ID NO: 222 FEATURE source | moltype = RNA length = 20 Location/Qualifiers 1..20 mol_type = other RNA organism = synthetic construct | |
| SEQUENCE: 222 cttgttcatg atcttcatgg | | 20 |
| SEQ ID NO: 223 FEATURE source | moltype = RNA length = 20 Location/Qualifiers 1..20 mol_type = other RNA organism = synthetic construct | |
| SEQUENCE: 223 tcagtgcatc caaaacgtgg | | 20 |
| SEQ ID NO: 224 FEATURE source | moltype = RNA length = 20 Location/Qualifiers 1..20 mol_type = other RNA | |

-continued

```
                          organism = synthetic construct
SEQUENCE: 224
ctgtcccgga gaccatccca                                                    20

SEQ ID NO: 225            moltype = RNA   length = 20
FEATURE                   Location/Qualifiers
source                    1..20
                          mol_type = other RNA
                          organism = synthetic construct
SEQUENCE: 225
gggcctggga cctcactgtc                                                    20

SEQ ID NO: 226            moltype = RNA   length = 20
FEATURE                   Location/Qualifiers
source                    1..20
                          mol_type = other RNA
                          organism = synthetic construct
SEQUENCE: 226
cccacgtaat actccatgac                                                    20

SEQ ID NO: 227            moltype = RNA   length = 20
FEATURE                   Location/Qualifiers
source                    1..20
                          mol_type = other RNA
                          organism = synthetic construct
SEQUENCE: 227
ctctgccgca gggacagccg                                                    20

SEQ ID NO: 228            moltype = RNA   length = 20
FEATURE                   Location/Qualifiers
source                    1..20
                          mol_type = other RNA
                          organism = synthetic construct
SEQUENCE: 228
ctgtgcacgt agccaagccg                                                    20

SEQ ID NO: 229            moltype = RNA   length = 20
FEATURE                   Location/Qualifiers
source                    1..20
                          mol_type = other RNA
                          organism = synthetic construct
SEQUENCE: 229
tgcccatcca cgtcagggcc                                                    20

SEQ ID NO: 230            moltype = RNA   length = 20
FEATURE                   Location/Qualifiers
source                    1..20
                          mol_type = other RNA
                          organism = synthetic construct
SEQUENCE: 230
agcgcctccg ataggccagg                                                    20

SEQ ID NO: 231            moltype = RNA   length = 20
FEATURE                   Location/Qualifiers
source                    1..20
                          mol_type = other RNA
                          organism = synthetic construct
SEQUENCE: 231
tgtgcacgta gccaagccgg                                                    20

SEQ ID NO: 232            moltype = RNA   length = 20
FEATURE                   Location/Qualifiers
source                    1..20
                          mol_type = other RNA
                          organism = synthetic construct
SEQUENCE: 232
gaccaggtac aggtagttct                                                    20

SEQ ID NO: 233            moltype = RNA   length = 20
FEATURE                   Location/Qualifiers
source                    1..20
                          mol_type = other RNA
                          organism = synthetic construct
SEQUENCE: 233
ccatctcggc cggaatccgc                                                    20

SEQ ID NO: 234            moltype = RNA   length = 20
FEATURE                   Location/Qualifiers
source                    1..20
```

```
                              mol_type = other RNA
                              organism = synthetic construct
SEQUENCE: 234
catctcggcc ggaatccgct                                                    20

SEQ ID NO: 235                moltype = RNA  length = 20
FEATURE                       Location/Qualifiers
source                        1..20
                              mol_type = other RNA
                              organism = synthetic construct
SEQUENCE: 235
ttgccatagg tctccgccgt                                                    20

SEQ ID NO: 236                moltype = RNA  length = 20
FEATURE                       Location/Qualifiers
source                        1..20
                              mol_type = other RNA
                              organism = synthetic construct
SEQUENCE: 236
acagcggtcc agcaggatgt                                                    20

SEQ ID NO: 237                moltype = RNA  length = 20
FEATURE                       Location/Qualifiers
source                        1..20
                              mol_type = other RNA
                              organism = synthetic construct
SEQUENCE: 237
aaagcgcctc cgataggcca                                                    20

SEQ ID NO: 238                moltype = RNA  length = 20
FEATURE                       Location/Qualifiers
source                        1..20
                              mol_type = other RNA
                              organism = synthetic construct
SEQUENCE: 238
gccaaagaag aagggatgtg                                                    20

SEQ ID NO: 239                moltype = RNA  length = 20
FEATURE                       Location/Qualifiers
source                        1..20
                              mol_type = other RNA
                              organism = synthetic construct
SEQUENCE: 239
cacgtaatac tccatgacca                                                    20

SEQ ID NO: 240                moltype = RNA  length = 20
FEATURE                       Location/Qualifiers
source                        1..20
                              mol_type = other RNA
                              organism = synthetic construct
SEQUENCE: 240
atctcggccg gaatccgctc                                                    20

SEQ ID NO: 241                moltype = RNA  length = 20
FEATURE                       Location/Qualifiers
source                        1..20
                              mol_type = other RNA
                              organism = synthetic construct
SEQUENCE: 241
gcttcatctt cactaccgct                                                    20

SEQ ID NO: 242                moltype = RNA  length = 20
FEATURE                       Location/Qualifiers
source                        1..20
                              mol_type = other RNA
                              organism = synthetic construct
SEQUENCE: 242
gccatctcgg ccggaatccg                                                    20

SEQ ID NO: 243                moltype = RNA  length = 20
FEATURE                       Location/Qualifiers
source                        1..20
                              mol_type = other RNA
                              organism = synthetic construct
SEQUENCE: 243
cagggacagc cgctggaact                                                    20

SEQ ID NO: 244                moltype = RNA  length = 20
FEATURE                       Location/Qualifiers
```

```
source                          1..20
                                mol_type = other RNA
                                organism = synthetic construct
SEQUENCE: 244
atgacaatct ccgccaggta                                                        20

SEQ ID NO: 245                  moltype = RNA   length = 20
FEATURE                         Location/Qualifiers
source                          1..20
                                mol_type = other RNA
                                organism = synthetic construct
SEQUENCE: 245
ggccatgaca atctccgcca                                                        20

SEQ ID NO: 246                  moltype = RNA   length = 20
FEATURE                         Location/Qualifiers
source                          1..20
                                mol_type = other RNA
                                organism = synthetic construct
SEQUENCE: 246
atactccatg accaggtaca                                                        20

SEQ ID NO: 247                  moltype = RNA   length = 20
FEATURE                         Location/Qualifiers
source                          1..20
                                mol_type = other RNA
                                organism = synthetic construct
SEQUENCE: 247
gcctctgcct cgcgtagttg                                                        20

SEQ ID NO: 248                  moltype = RNA   length = 20
FEATURE                         Location/Qualifiers
source                          1..20
                                mol_type = other RNA
                                organism = synthetic construct
SEQUENCE: 248
gaatgtccga cagtgtctcc                                                        20

SEQ ID NO: 249                  moltype = RNA   length = 20
FEATURE                         Location/Qualifiers
source                          1..20
                                mol_type = other RNA
                                organism = synthetic construct
SEQUENCE: 249
cgttccatct gcccgcagct                                                        20

SEQ ID NO: 250                  moltype = RNA   length = 20
FEATURE                         Location/Qualifiers
source                          1..20
                                mol_type = other RNA
                                organism = synthetic construct
SEQUENCE: 250
ccttgtagtg gacgatcttg                                                        20

SEQ ID NO: 251                  moltype = RNA   length = 20
FEATURE                         Location/Qualifiers
source                          1..20
                                mol_type = other RNA
                                organism = synthetic construct
SEQUENCE: 251
atctccgcca ggtagaagcg                                                        20

SEQ ID NO: 252                  moltype = RNA   length = 20
FEATURE                         Location/Qualifiers
source                          1..20
                                mol_type = other RNA
                                organism = synthetic construct
SEQUENCE: 252
ctcaggctct gccgggtgag                                                        20

SEQ ID NO: 253                  moltype = RNA   length = 20
FEATURE                         Location/Qualifiers
source                          1..20
                                mol_type = other RNA
                                organism = synthetic construct
SEQUENCE: 253
tgcttcatct tcactaccgc                                                        20

SEQ ID NO: 254                  moltype = RNA   length = 20
```

-continued

```
FEATURE                 Location/Qualifiers
source                  1..20
                        mol_type = other RNA
                        organism = synthetic construct
SEQUENCE: 254
gcaggatgtt gtcgggtttg                                                    20

SEQ ID NO: 255          moltype = RNA   length = 20
FEATURE                 Location/Qualifiers
source                  1..20
                        mol_type = other RNA
                        organism = synthetic construct
SEQUENCE: 255
ggcctcagcc tctgccgcag                                                    20

SEQ ID NO: 256          moltype = RNA   length = 20
FEATURE                 Location/Qualifiers
source                  1..20
                        mol_type = other RNA
                        organism = synthetic construct
SEQUENCE: 256
tgttgtcggg tttgatgtcc                                                    20

SEQ ID NO: 257          moltype = RNA   length = 20
FEATURE                 Location/Qualifiers
source                  1..20
                        mol_type = other RNA
                        organism = synthetic construct
SEQUENCE: 257
ccacgtaata ctccatgacc                                                    20

SEQ ID NO: 258          moltype = RNA   length = 20
FEATURE                 Location/Qualifiers
source                  1..20
                        mol_type = other RNA
                        organism = synthetic construct
SEQUENCE: 258
ccgttccatc tgcccgcagc                                                    20

SEQ ID NO: 259          moltype = RNA   length = 20
FEATURE                 Location/Qualifiers
source                  1..20
                        mol_type = other RNA
                        organism = synthetic construct
SEQUENCE: 259
ttcccgagta agcaggcaga                                                    20

SEQ ID NO: 260          moltype = RNA   length = 20
FEATURE                 Location/Qualifiers
source                  1..20
                        mol_type = other RNA
                        organism = synthetic construct
SEQUENCE: 260
tgatcttcat ggcatacacc                                                    20

SEQ ID NO: 261          moltype = RNA   length = 20
FEATURE                 Location/Qualifiers
source                  1..20
                        mol_type = other RNA
                        organism = synthetic construct
SEQUENCE: 261
agggacagcc gctggaactg                                                    20

SEQ ID NO: 262          moltype = RNA   length = 20
FEATURE                 Location/Qualifiers
source                  1..20
                        mol_type = other RNA
                        organism = synthetic construct
SEQUENCE: 262
gggtttgatg tccctgtgca                                                    20

SEQ ID NO: 263          moltype = RNA   length = 20
FEATURE                 Location/Qualifiers
source                  1..20
                        mol_type = other RNA
                        organism = synthetic construct
SEQUENCE: 263
tgacaatctc cgccaggtag                                                    20
```

| | | |
|---|---|---|
| SEQ ID NO: 264<br>FEATURE<br>source | moltype = RNA length = 20<br>Location/Qualifiers<br>1..20<br>mol_type = other RNA<br>organism = synthetic construct | |
| SEQUENCE: 264<br>cacagcggtc cagcaggatg | | 20 |
| SEQ ID NO: 265<br>FEATURE<br>source | moltype = RNA length = 20<br>Location/Qualifiers<br>1..20<br>mol_type = other RNA<br>organism = synthetic construct | |
| SEQUENCE: 265<br>gcgtagaagg gcgtctgccc | | 20 |
| SEQ ID NO: 266<br>FEATURE<br>source | moltype = RNA length = 20<br>Location/Qualifiers<br>1..20<br>mol_type = other RNA<br>organism = synthetic construct | |
| SEQUENCE: 266<br>ctcagcctct gccgcaggga | | 20 |
| SEQ ID NO: 267<br>FEATURE<br>source | moltype = RNA length = 20<br>Location/Qualifiers<br>1..20<br>mol_type = other RNA<br>organism = synthetic construct | |
| SEQUENCE: 267<br>gtctcagtgc atccaaaacg | | 20 |
| SEQ ID NO: 268<br>FEATURE<br>source | moltype = RNA length = 20<br>Location/Qualifiers<br>1..20<br>mol_type = other RNA<br>organism = synthetic construct | |
| SEQUENCE: 268<br>ggacgatctt gccataggtc | | 20 |
| SEQ ID NO: 269<br>FEATURE<br>source | moltype = RNA length = 20<br>Location/Qualifiers<br>1..20<br>mol_type = other RNA<br>organism = synthetic construct | |
| SEQUENCE: 269<br>tcagcagtgt cagcaggtcc | | 20 |
| SEQ ID NO: 270<br>FEATURE<br>source | moltype = RNA length = 20<br>Location/Qualifiers<br>1..20<br>mol_type = other RNA<br>organism = synthetic construct | |
| SEQUENCE: 270<br>gctcctgggc ggcgccagac | | 20 |
| SEQ ID NO: 271<br>FEATURE<br>source | moltype = RNA length = 20<br>Location/Qualifiers<br>1..20<br>mol_type = other RNA<br>organism = synthetic construct | |
| SEQUENCE: 271<br>agcaggatgt tgtcgggttt | | 20 |
| SEQ ID NO: 272<br>FEATURE<br>source | moltype = RNA length = 20<br>Location/Qualifiers<br>1..20<br>mol_type = other RNA<br>organism = synthetic construct | |
| SEQUENCE: 272<br>atccgctcct gcaactgccg | | 20 |
| SEQ ID NO: 273<br>FEATURE<br>source | moltype = RNA length = 20<br>Location/Qualifiers<br>1..20<br>mol_type = other RNA<br>organism = synthetic construct | |
| SEQUENCE: 273<br>aggagcaggg aaagcgcctc | | 20 |

| | | |
|---|---|---|
| SEQ ID NO: 274<br>FEATURE<br>source | moltype = RNA length = 20<br>Location/Qualifiers<br>1..20<br>mol_type = other RNA<br>organism = synthetic construct | |
| SEQUENCE: 274<br>acacctggcc cgtctgcttc | | 20 |
| SEQ ID NO: 275<br>FEATURE<br>source | moltype = RNA length = 20<br>Location/Qualifiers<br>1..20<br>mol_type = other RNA<br>organism = synthetic construct | |
| SEQUENCE: 275<br>cccagcgccc accagtcaca | | 20 |
| SEQ ID NO: 276<br>FEATURE<br>source | moltype = RNA length = 20<br>Location/Qualifiers<br>1..20<br>mol_type = other RNA<br>organism = synthetic construct | |
| SEQUENCE: 276<br>gctccctctg cctgcagcaa | | 20 |
| SEQ ID NO: 277<br>FEATURE<br>source | moltype = RNA length = 20<br>Location/Qualifiers<br>1..20<br>mol_type = other RNA<br>organism = synthetic construct | |
| SEQUENCE: 277<br>gctcaggctc tgccgggtga | | 20 |
| SEQ ID NO: 278<br>FEATURE<br>source | moltype = RNA length = 20<br>Location/Qualifiers<br>1..20<br>mol_type = other RNA<br>organism = synthetic construct | |
| SEQUENCE: 278<br>ttgatgtccc tgtgcacgta | | 20 |
| SEQ ID NO: 279<br>FEATURE<br>source | moltype = RNA length = 20<br>Location/Qualifiers<br>1..20<br>mol_type = other RNA<br>organism = synthetic construct | |
| SEQUENCE: 279<br>gcctcagcct ctgccgcagg | | 20 |
| SEQ ID NO: 280<br>FEATURE<br>source | moltype = RNA length = 20<br>Location/Qualifiers<br>1..20<br>mol_type = other RNA<br>organism = synthetic construct | |
| SEQUENCE: 280<br>ggtagttctc atcctggaag | | 20 |
| SEQ ID NO: 281<br>FEATURE<br>source | moltype = RNA length = 20<br>Location/Qualifiers<br>1..20<br>mol_type = other RNA<br>organism = synthetic construct | |
| SEQUENCE: 281<br>cagcgcccac cagtcacact | | 20 |
| SEQ ID NO: 282<br>FEATURE<br>source | moltype = RNA length = 20<br>Location/Qualifiers<br>1..20<br>mol_type = other RNA<br>organism = synthetic construct | |
| SEQUENCE: 282<br>cccaaacttg ctcagcagtg | | 20 |
| SEQ ID NO: 283<br>FEATURE<br>source | moltype = RNA length = 20<br>Location/Qualifiers<br>1..20<br>mol_type = other RNA<br>organism = synthetic construct | |
| SEQUENCE: 283 | | |

```
cttgccatag gtctccgccg                                                  20

SEQ ID NO: 284         moltype = RNA   length = 20
FEATURE                Location/Qualifiers
source                 1..20
                       mol_type = other RNA
                       organism = synthetic construct SEQUENCE: 284
tacacctggc ccgtctgctt                                                  20

SEQ ID NO: 285         moltype = RNA   length = 20
FEATURE                Location/Qualifiers
source                 1..20
                       mol_type = other RNA
                       organism = synthetic construct SEQUENCE: 285
ccagcgccca ccagtcacac                                                  20

SEQ ID NO: 286         moltype = RNA   length = 20
FEATURE                Location/Qualifiers
source                 1..20
                       mol_type = other RNA
                       organism = synthetic construct SEQUENCE: 286
ggcctcagcc tggccgaaag                                                  20

SEQ ID NO: 287         moltype = RNA   length = 20
FEATURE                Location/Qualifiers
source                 1..20
                       mol_type = other RNA
                       organism = synthetic construct SEQUENCE: 287
aatctccgcc aggtagaagc                                                  20

SEQ ID NO: 288         moltype = RNA   length = 20
FEATURE                Location/Qualifiers
source                 1..20
                       mol_type = other RNA
                       organism = synthetic construct SEQUENCE: 288
atggcataca cctggcccgt                                                  20

SEQ ID NO: 289         moltype = RNA   length = 20
FEATURE                Location/Qualifiers
source                 1..20
                       mol_type = other RNA
                       organism = synthetic construct SEQUENCE: 289
ccatgacaat ctccgccagg                                                  20

SEQ ID NO: 290         moltype = RNA   length = 20
FEATURE                Location/Qualifiers
source                 1..20
                       mol_type = other RNA
                       organism = synthetic construct SEQUENCE: 290
tccccaaact tgctcagcag                                                  20

SEQ ID NO: 291         moltype = RNA   length = 20
FEATURE                Location/Qualifiers
source                 1..20
                       mol_type = other RNA
                       organism = synthetic construct SEQUENCE: 291
gatgttgtcg ggtttgatgt                                                  20

SEQ ID NO: 292         moltype = RNA   length = 20
FEATURE                Location/Qualifiers
source                 1..20
                       mol_type = other RNA
                       organism = synthetic construct SEQUENCE: 292
gtttgcccat ccacgtcagg                                                  20

SEQ ID NO: 293         moltype = RNA   length = 20
FEATURE                Location/Qualifiers
source                 1..20
                       mol_type = other RNA
                       organism = synthetic construct
```

| | | |
|---|---|---|
| SEQUENCE: 293 cggacggccc ggcttgctgc | | 20 |
| SEQ ID NO: 294 FEATURE source | moltype = RNA   length = 20 Location/Qualifiers 1..20 mol_type = other RNA organism = synthetic construct | |
| SEQUENCE: 294 ctccgccagg tagaagcgcg | | 20 |
| SEQ ID NO: 295 FEATURE source | moltype = RNA   length = 20 Location/Qualifiers 1..20 mol_type = other RNA organism = synthetic construct | |
| SEQUENCE: 295 gtacaggtag ttctcatcct | | 20 |
| SEQ ID NO: 296 FEATURE source | moltype = RNA   length = 20 Location/Qualifiers 1..20 mol_type = other RNA organism = synthetic construct | |
| SEQUENCE: 296 agggcgtctg cccatagaac | | 20 |
| SEQ ID NO: 297 FEATURE source | moltype = RNA   length = 20 Location/Qualifiers 1..20 mol_type = other RNA organism = synthetic construct | |
| SEQUENCE: 297 tggccacagc ggtccagcag | | 20 |
| SEQ ID NO: 298 FEATURE source | moltype = RNA   length = 20 Location/Qualifiers 1..20 mol_type = other RNA organism = synthetic construct | |
| SEQUENCE: 298 cgtagttgac tggcgaagtt | | 20 |
| SEQ ID NO: 299 FEATURE source | moltype = RNA   length = 20 Location/Qualifiers 1..20 mol_type = other RNA organism = synthetic construct | |
| SEQUENCE: 299 tctgccgcag ggacagccgc | | 20 |
| SEQ ID NO: 300 FEATURE source | moltype = RNA   length = 20 Location/Qualifiers 1..20 mol_type = other RNA organism = synthetic construct | |
| SEQUENCE: 300 aagcgcctcc gataggccag | | 20 |
| SEQ ID NO: 301 FEATURE source | moltype = RNA   length = 20 Location/Qualifiers 1..20 mol_type = other RNA organism = synthetic construct | |
| SEQUENCE: 301 gacagaacaa cggcgaacag | | 20 |
| SEQ ID NO: 302 FEATURE source | moltype = RNA   length = 20 Location/Qualifiers 1..20 mol_type = other RNA organism = synthetic construct | |
| SEQUENCE: 302 gctcagcagt gtcagcaggt | | 20 |
| SEQ ID NO: 303 FEATURE source | moltype = RNA   length = 20 Location/Qualifiers 1..20 mol_type = other RNA | |

-continued

```
                     organism = synthetic construct
SEQUENCE: 303
atgatcttca tggcatacac                                                 20

SEQ ID NO: 304       moltype = RNA  length = 20
FEATURE              Location/Qualifiers
source               1..20
                     mol_type = other RNA
                     organism = synthetic construct
SEQUENCE: 304
tttgcccatc cacgtcaggg                                                 20

SEQ ID NO: 305       moltype = RNA  length = 20
FEATURE              Location/Qualifiers
source               1..20
                     mol_type = other RNA
                     organism = synthetic construct
SEQUENCE: 305
acttgctcag cagtgtcagc                                                 20

SEQ ID NO: 306       moltype = RNA  length = 20
FEATURE              Location/Qualifiers
source               1..20
                     mol_type = other RNA
                     organism = synthetic construct
SEQUENCE: 306
tgatgtccct gtgcacgtag                                                 20

SEQ ID NO: 307       moltype = RNA  length = 20
FEATURE              Location/Qualifiers
source               1..20
                     mol_type = other RNA
                     organism = synthetic construct
SEQUENCE: 307
aaataccgag gaatgtcggg                                                 20

SEQ ID NO: 308       moltype = RNA  length = 20
FEATURE              Location/Qualifiers
source               1..20
                     mol_type = other RNA
                     organism = synthetic construct
SEQUENCE: 308
ggcgaataca cccagcgccc                                                 20

SEQ ID NO: 309       moltype = RNA  length = 20
FEATURE              Location/Qualifiers
source               1..20
                     mol_type = other RNA
                     organism = synthetic construct
SEQUENCE: 309
agacaataaa taccgaggaa                                                 20

SEQ ID NO: 310       moltype = RNA  length = 20
FEATURE              Location/Qualifiers
source               1..20
                     mol_type = other RNA
                     organism = synthetic construct
SEQUENCE: 310
cccgtctgct tcatcttcac                                                 20

SEQ ID NO: 311       moltype = RNA  length = 20
FEATURE              Location/Qualifiers
source               1..20
                     mol_type = other RNA
                     organism = synthetic construct
SEQUENCE: 311
ctgcctgcag caactccatc                                                 20

SEQ ID NO: 312       moltype = RNA  length = 20
FEATURE              Location/Qualifiers
source               1..20
                     mol_type = other RNA
                     organism = synthetic construct
SEQUENCE: 312
cctcagcctc tgccgcaggg                                                 20

SEQ ID NO: 313       moltype = RNA  length = 20
FEATURE              Location/Qualifiers
source               1..20
```

```
                        mol_type = other RNA
                        organism = synthetic construct
SEQUENCE: 313
gtgtccggaa gtcgcctgct                                                   20

SEQ ID NO: 314          moltype = RNA   length = 20
FEATURE                 Location/Qualifiers
source                  1..20
                        mol_type = other RNA
                        organism = synthetic construct
SEQUENCE: 314
tgcacgtgtg gctcaagcag                                                   20

SEQ ID NO: 315          moltype = RNA   length = 20
FEATURE                 Location/Qualifiers
source                  1..20
                        mol_type = other RNA
                        organism = synthetic construct
SEQUENCE: 315
gacaataaat accgaggaat                                                   20

SEQ ID NO: 316          moltype = RNA   length = 20
FEATURE                 Location/Qualifiers
source                  1..20
                        mol_type = other RNA
                        organism = synthetic construct
SEQUENCE: 316
gccatgacaa tctccgccag                                                   20

SEQ ID NO: 317          moltype = RNA   length = 20
FEATURE                 Location/Qualifiers
source                  1..20
                        mol_type = other RNA
                        organism = synthetic construct
SEQUENCE: 317
gctgtcccgg agaccatccc                                                   20

SEQ ID NO: 318          moltype = RNA   length = 20
FEATURE                 Location/Qualifiers
source                  1..20
                        mol_type = other RNA
                        organism = synthetic construct
SEQUENCE: 318
catgaccagg tacaggtagt                                                   20

SEQ ID NO: 319          moltype = RNA   length = 20
FEATURE                 Location/Qualifiers
source                  1..20
                        mol_type = other RNA
                        organism = synthetic construct
SEQUENCE: 319
agcgcccacc agtcacactc                                                   20

SEQ ID NO: 320          moltype = RNA   length = 20
FEATURE                 Location/Qualifiers
source                  1..20
                        mol_type = other RNA
                        organism = synthetic construct
SEQUENCE: 320
tctcagtgca tccaaaacgt                                                   20

SEQ ID NO: 321          moltype = RNA   length = 20
FEATURE                 Location/Qualifiers
source                  1..20
                        mol_type = other RNA
                        organism = synthetic construct
SEQUENCE: 321
tttgggcaga tggagggcct                                                   20

SEQ ID NO: 322          moltype = RNA   length = 20
FEATURE                 Location/Qualifiers
source                  1..20
                        mol_type = other RNA
                        organism = synthetic construct
SEQUENCE: 322
gatgtccctg tgcacgtagc                                                   20

SEQ ID NO: 323          moltype = RNA   length = 20
FEATURE                 Location/Qualifiers
```

```
                                      -continued source                   1..20
                         mol_type = other RNA
                         organism = synthetic construct
SEQUENCE: 323
cagcagtgtc agcaggtccc                                                   20

SEQ ID NO: 324           moltype = RNA   length = 20
FEATURE                  Location/Qualifiers
source                   1..20
                         mol_type = other RNA
                         organism = synthetic construct
SEQUENCE: 324
catgacaatc tccgccaggt                                                   20

SEQ ID NO: 325           moltype = RNA   length = 20
FEATURE                  Location/Qualifiers
source                   1..20
                         mol_type = other RNA
                         organism = synthetic construct
SEQUENCE: 325
acttgttcat gatcttcatg                                                   20

SEQ ID NO: 326           moltype = RNA   length = 20
FEATURE                  Location/Qualifiers
source                   1..20
                         mol_type = other RNA
                         organism = synthetic construct
SEQUENCE: 326
gtggaatccg cgtagaaggg                                                   20

SEQ ID NO: 327           moltype = RNA   length = 20
FEATURE                  Location/Qualifiers
source                   1..20
                         mol_type = other RNA
                         organism = synthetic construct
SEQUENCE: 327
tggccatgac aatctccgcc                                                   20

SEQ ID NO: 328           moltype = RNA   length = 20
FEATURE                  Location/Qualifiers
source                   1..20
                         mol_type = other RNA
                         organism = synthetic construct
SEQUENCE: 328
gggacagaca ataaataccg                                                   20

SEQ ID NO: 329           moltype = RNA   length = 20
FEATURE                  Location/Qualifiers
source                   1..20
                         mol_type = other RNA
                         organism = synthetic construct
SEQUENCE: 329
ccgctcccca aacttgctca                                                   20

SEQ ID NO: 330           moltype = RNA   length = 20
FEATURE                  Location/Qualifiers
source                   1..20
                         mol_type = other RNA
                         organism = synthetic construct
SEQUENCE: 330
cggctcaggc tctgccgggt                                                   20

SEQ ID NO: 331           moltype = RNA   length = 20
FEATURE                  Location/Qualifiers
source                   1..20
                         mol_type = other RNA
                         organism = synthetic construct
SEQUENCE: 331
ggctcctggg cggcgccaga                                                   20

SEQ ID NO: 332           moltype = RNA   length = 20
FEATURE                  Location/Qualifiers
source                   1..20
                         mol_type = other RNA
                         organism = synthetic construct
SEQUENCE: 332
tttcccgagt aagcaggcag                                                   20

SEQ ID NO: 333           moltype = RNA   length = 20
```

```
FEATURE           Location/Qualifiers
source            1..20
                  mol_type = other RNA
                  organism = synthetic construct
SEQUENCE: 333
ggatgttgtc gggtttgatg                                              20

SEQ ID NO: 334    moltype = RNA   length = 20
FEATURE           Location/Qualifiers
source            1..20
                  mol_type = other RNA
                  organism = synthetic construct
SEQUENCE: 334
caggtagttc tcatcctgga                                              20

SEQ ID NO: 335    moltype = RNA   length = 20
FEATURE           Location/Qualifiers
source            1..20
                  mol_type = other RNA
                  organism = synthetic construct
SEQUENCE: 335
tgcccataga acatttcata                                              20

SEQ ID NO: 336    moltype = RNA   length = 20
FEATURE           Location/Qualifiers
source            1..20
                  mol_type = other RNA
                  organism = synthetic construct
SEQUENCE: 336
tagttctcat cctggaaggc                                              20

SEQ ID NO: 337    moltype = RNA   length = 20
FEATURE           Location/Qualifiers
source            1..20
                  mol_type = other RNA
                  organism = synthetic construct
SEQUENCE: 337
atgtccctgt gcacgtagcc                                              20

SEQ ID NO: 338    moltype = RNA   length = 20
FEATURE           Location/Qualifiers
source            1..20
                  mol_type = other RNA
                  organism = synthetic construct
SEQUENCE: 338
cgggcccgga tcacaggact                                              20

SEQ ID NO: 339    moltype = RNA   length = 20
FEATURE           Location/Qualifiers
source            1..20
                  mol_type = other RNA
                  organism = synthetic construct
SEQUENCE: 339
tggacgatct tgccataggt                                              20

SEQ ID NO: 340    moltype = RNA   length = 20
FEATURE           Location/Qualifiers
source            1..20
                  mol_type = other RNA
                  organism = synthetic construct
SEQUENCE: 340
gttggccggc gtgggccacc                                              20

SEQ ID NO: 341    moltype = RNA   length = 20
FEATURE           Location/Qualifiers
source            1..20
                  mol_type = other RNA
                  organism = synthetic construct
SEQUENCE: 341
ctcagtgcat ccaaaacgtg                                              20

SEQ ID NO: 342    moltype = RNA   length = 20
FEATURE           Location/Qualifiers
source            1..20
                  mol_type = other RNA
                  organism = synthetic construct
SEQUENCE: 342
tcgaagttgc atgtgtcggt                                              20
```

| | | |
|---|---|---|
| SEQ ID NO: 343<br>FEATURE<br>source | moltype = RNA length = 20<br>Location/Qualifiers<br>1..20<br>mol_type = other RNA<br>organism = synthetic construct | |
| SEQUENCE: 343<br>tggaacacgg acggcccggc | | 20 |
| SEQ ID NO: 344<br>FEATURE<br>source | moltype = RNA length = 20<br>Location/Qualifiers<br>1..20<br>mol_type = other RNA<br>organism = synthetic construct | |
| SEQUENCE: 344<br>ccgagagcag cgcaagtgag | | 20 |
| SEQ ID NO: 345<br>FEATURE<br>source | moltype = RNA length = 20<br>Location/Qualifiers<br>1..20<br>mol_type = other RNA<br>organism = synthetic construct | |
| SEQUENCE: 345<br>tcctgcaact gccggacgtg | | 20 |
| SEQ ID NO: 346<br>FEATURE<br>source | moltype = RNA length = 20<br>Location/Qualifiers<br>1..20<br>mol_type = other RNA<br>organism = synthetic construct | |
| SEQUENCE: 346<br>tcaccaacac gtccctctcc | | 20 |
| SEQ ID NO: 347<br>FEATURE<br>source | moltype = RNA length = 20<br>Location/Qualifiers<br>1..20<br>mol_type = other RNA<br>organism = synthetic construct | |
| SEQUENCE: 347<br>tgcctgcagc aactccatcc | | 20 |
| SEQ ID NO: 348<br>FEATURE<br>source | moltype = RNA length = 20<br>Location/Qualifiers<br>1..20<br>mol_type = other RNA<br>organism = synthetic construct | |
| SEQUENCE: 348<br>ttggccggcg tgggccacca | | 20 |
| SEQ ID NO: 349<br>FEATURE<br>source | moltype = RNA length = 20<br>Location/Qualifiers<br>1..20<br>mol_type = other RNA<br>organism = synthetic construct | |
| SEQUENCE: 349<br>gagcctctgc ctcgcgtagt | | 20 |
| SEQ ID NO: 350<br>FEATURE<br>source | moltype = RNA length = 20<br>Location/Qualifiers<br>1..20<br>mol_type = other RNA<br>organism = synthetic construct | |
| SEQUENCE: 350<br>aagggcgtct gcccatagaa | | 20 |
| SEQ ID NO: 351<br>FEATURE<br>source | moltype = RNA length = 20<br>Location/Qualifiers<br>1..20<br>mol_type = other RNA<br>organism = synthetic construct | |
| SEQUENCE: 351<br>acagacaata aataccgagg | | 20 |
| SEQ ID NO: 352<br>FEATURE<br>source | moltype = RNA length = 20<br>Location/Qualifiers<br>1..20<br>mol_type = other RNA<br>organism = synthetic construct | |
| SEQUENCE: 352<br>ggacagacaa taaataccga | | 20 |

```
SEQ ID NO: 353              moltype = RNA   length = 20
FEATURE                     Location/Qualifiers
source                      1..20
                            mol_type = other RNA
                            organism = synthetic construct
SEQUENCE: 353
acgtgtgcct ctaggtcccg                                                       20

SEQ ID NO: 354              moltype = RNA   length = 20
FEATURE                     Location/Qualifiers
source                      1..20
                            mol_type = other RNA
                            organism = synthetic construct
SEQUENCE: 354
ggcacgagac agaacaacgg                                                       20

SEQ ID NO: 355              moltype = RNA   length = 20
FEATURE                     Location/Qualifiers
source                      1..20
                            mol_type = other RNA
                            organism = synthetic construct
SEQUENCE: 355
tgaccaggta caggtagttc                                                       20

SEQ ID NO: 356              moltype = RNA   length = 20
FEATURE                     Location/Qualifiers
source                      1..20
                            mol_type = other RNA
                            organism = synthetic construct
SEQUENCE: 356
ctctgccggg tgagcacctc                                                       20

SEQ ID NO: 357              moltype = RNA   length = 20
FEATURE                     Location/Qualifiers
source                      1..20
                            mol_type = other RNA
                            organism = synthetic construct
SEQUENCE: 357
gacaatctcc gccaggtaga                                                       20

SEQ ID NO: 358              moltype = RNA   length = 20
FEATURE                     Location/Qualifiers
source                      1..20
                            mol_type = other RNA
                            organism = synthetic construct
SEQUENCE: 358
tctccgccag gtagaagcgc                                                       20

SEQ ID NO: 359              moltype = RNA   length = 20
FEATURE                     Location/Qualifiers
source                      1..20
                            mol_type = other RNA
                            organism = synthetic construct
SEQUENCE: 359
ctctgcctcg cgtagttgac                                                       20

SEQ ID NO: 360              moltype = RNA   length = 20
FEATURE                     Location/Qualifiers
source                      1..20
                            mol_type = other RNA
                            organism = synthetic construct
SEQUENCE: 360
ctttgggcag atggagggcc                                                       20

SEQ ID NO: 361              moltype = RNA   length = 20
FEATURE                     Location/Qualifiers
source                      1..20
                            mol_type = other RNA
                            organism = synthetic construct
SEQUENCE: 361
acaggtagtt ctcatcctgg                                                       20

SEQ ID NO: 362              moltype = RNA   length = 20
FEATURE                     Location/Qualifiers
source                      1..20
                            mol_type = other RNA
                            organism = synthetic construct
SEQUENCE: 362
```

```
ccaaacttgc tcagcagtgt                                              20

SEQ ID NO: 363          moltype = RNA   length = 20
FEATURE                 Location/Qualifiers
source                  1..20
                        mol_type = other RNA
                        organism = synthetic construct
SEQUENCE: 363
tcgggtttga tgtccctgtg                                              20

SEQ ID NO: 364          moltype = RNA   length = 20
FEATURE                 Location/Qualifiers
source                  1..20
                        mol_type = other RNA
                        organism = synthetic construct
SEQUENCE: 364
ggcttgctgc cttcccaggc                                              20

SEQ ID NO: 365          moltype = RNA   length = 20
FEATURE                 Location/Qualifiers
source                  1..20
                        mol_type = other RNA
                        organism = synthetic construct
SEQUENCE: 365
tacaggtagt tctcatcctg                                              20

SEQ ID NO: 366          moltype = RNA   length = 20
FEATURE                 Location/Qualifiers
source                  1..20
                        mol_type = other RNA
                        organism = synthetic construct
SEQUENCE: 366
ttgcccatcc acgtcagggc                                              20

SEQ ID NO: 367          moltype = RNA   length = 20
FEATURE                 Location/Qualifiers
source                  1..20
                        mol_type = other RNA
                        organism = synthetic construct
SEQUENCE: 367
aggtacaggt agttctcatc                                              20

SEQ ID NO: 368          moltype = RNA   length = 20
FEATURE                 Location/Qualifiers
source                  1..20
                        mol_type = other RNA
                        organism = synthetic construct
SEQUENCE: 368
gacagacaat aaataccgag                                              20

SEQ ID NO: 369          moltype = RNA   length = 20
FEATURE                 Location/Qualifiers
source                  1..20
                        mol_type = other RNA
                        organism = synthetic construct
SEQUENCE: 369
tagaacattt cataggcgaa                                              20

SEQ ID NO: 370          moltype = RNA   length = 20
FEATURE                 Location/Qualifiers
source                  1..20
                        mol_type = other RNA
                        organism = synthetic construct
SEQUENCE: 370
agggcctttt attcgcgagg                                              20

SEQ ID NO: 371          moltype = RNA   length = 20
FEATURE                 Location/Qualifiers
source                  1..20
                        mol_type = other RNA
                        organism = synthetic construct
SEQUENCE: 371
gcctcgcgta gttgactggc                                              20

SEQ ID NO: 372          moltype = RNA   length = 20
FEATURE                 Location/Qualifiers
source                  1..20
                        mol_type = other RNA
                        organism = synthetic construct
```

| | | |
|---|---|---|
| SEQUENCE: 372 ccagcaggat gttgtcgggt | | 20 |
| SEQ ID NO: 373<br>FEATURE<br>source | moltype = RNA  length = 20<br>Location/Qualifiers<br>1..20<br>mol_type = other RNA<br>organism = synthetic construct | |
| SEQUENCE: 373 gtagttgact ggcgaagttc | | 20 |
| SEQ ID NO: 374<br>FEATURE<br>source | moltype = RNA  length = 20<br>Location/Qualifiers<br>1..20<br>mol_type = other RNA<br>organism = synthetic construct | |
| SEQUENCE: 374 tgcggatggc ctccatctcc | | 20 |
| SEQ ID NO: 375<br>FEATURE<br>source | moltype = RNA  length = 20<br>Location/Qualifiers<br>1..20<br>mol_type = other RNA<br>organism = synthetic construct | |
| SEQUENCE: 375 acaatctccg ccaggtagaa | | 20 |
| SEQ ID NO: 376<br>FEATURE<br>source | moltype = RNA  length = 20<br>Location/Qualifiers<br>1..20<br>mol_type = other RNA<br>organism = synthetic construct | |
| SEQUENCE: 376 gcgaatacac ccagcgccca | | 20 |
| SEQ ID NO: 377<br>FEATURE<br>source | moltype = RNA  length = 20<br>Location/Qualifiers<br>1..20<br>mol_type = other RNA<br>organism = synthetic construct | |
| SEQUENCE: 377 gtagttctca tcctggaagg | | 20 |
| SEQ ID NO: 378<br>FEATURE<br>source | moltype = RNA  length = 20<br>Location/Qualifiers<br>1..20<br>mol_type = other RNA<br>organism = synthetic construct | |
| SEQUENCE: 378 ggctcaggct ctgccgggtg | | 20 |
| SEQ ID NO: 379<br>FEATURE<br>source | moltype = RNA  length = 20<br>Location/Qualifiers<br>1..20<br>mol_type = other RNA<br>organism = synthetic construct | |
| SEQUENCE: 379 ccattcacca acacgtccct | | 20 |
| SEQ ID NO: 380<br>FEATURE<br>source | moltype = RNA  length = 20<br>Location/Qualifiers<br>1..20<br>mol_type = other RNA<br>organism = synthetic construct | |
| SEQUENCE: 380 accaggtaca ggtagttctc | | 20 |
| SEQ ID NO: 381<br>FEATURE<br>source | moltype = RNA  length = 20<br>Location/Qualifiers<br>1..20<br>mol_type = other RNA<br>organism = synthetic construct | |
| SEQUENCE: 381 ctgcagtttg cccatccacg | | 20 |
| SEQ ID NO: 382<br>FEATURE<br>source | moltype = RNA  length = 20<br>Location/Qualifiers<br>1..20<br>mol_type = other RNA | |

-continued

```
SEQUENCE: 382
ttgttcatga tcttcatggc                                              20

SEQ ID NO: 383           moltype = RNA   length = 20
FEATURE                  Location/Qualifiers
source                   1..20
                         mol_type = other RNA
                         organism = synthetic construct
SEQUENCE: 383
tttgatgtcc ctgtgcacgt                                              20

SEQ ID NO: 384           moltype = RNA   length = 20
FEATURE                  Location/Qualifiers
source                   1..20
                         mol_type = other RNA
                         organism = synthetic construct
SEQUENCE: 384
gcggtccagc aggatgttgt                                              20

SEQ ID NO: 385           moltype = RNA   length = 20
FEATURE                  Location/Qualifiers
source                   1..20
                         mol_type = other RNA
                         organism = synthetic construct
SEQUENCE: 385
gtctatggcc atgacaatct                                              20

SEQ ID NO: 386           moltype = RNA   length = 20
FEATURE                  Location/Qualifiers
source                   1..20
                         mol_type = other RNA
                         organism = synthetic construct
SEQUENCE: 386
ggagcaggga aagcgcctcc                                              20

SEQ ID NO: 387           moltype = RNA   length = 20
FEATURE                  Location/Qualifiers
source                   1..20
                         mol_type = other RNA
                         organism = synthetic construct
SEQUENCE: 387
tgcctcgcgt agttgactgg                                              20

SEQ ID NO: 388           moltype = RNA   length = 20
FEATURE                  Location/Qualifiers
source                   1..20
                         mol_type = other RNA
                         organism = synthetic construct
SEQUENCE: 388
gcggatggcc tccatctccc                                              20

SEQ ID NO: 389           moltype = RNA   length = 20
FEATURE                  Location/Qualifiers
source                   1..20
                         mol_type = other RNA
                         organism = synthetic construct
SEQUENCE: 389
tttcataggc gaatacaccc                                              20

SEQ ID NO: 390           moltype = RNA   length = 20
FEATURE                  Location/Qualifiers
source                   1..20
                         mol_type = other RNA
                         organism = synthetic construct
SEQUENCE: 390
gcctgtcagc gagtcggagg                                              20

SEQ ID NO: 391           moltype = RNA   length = 20
FEATURE                  Location/Qualifiers
source                   1..20
                         mol_type = other RNA
                         organism = synthetic construct
SEQUENCE: 391
ccacttcagc tgtttcatcc                                              20

SEQ ID NO: 392           moltype = RNA   length = 20
FEATURE                  Location/Qualifiers
source                   1..20
```

```
                        mol_type = other RNA
                        organism = synthetic construct
SEQUENCE: 392
catccgctcc tgcaactgcc                                               20

SEQ ID NO: 393          moltype = RNA  length = 20
FEATURE                 Location/Qualifiers
source                  1..20
                        mol_type = other RNA
                        organism = synthetic construct
SEQUENCE: 393
tctagggttc agggagcgcg                                               20

SEQ ID NO: 394          moltype = RNA  length = 20
FEATURE                 Location/Qualifiers
source                  1..20
                        mol_type = other RNA
                        organism = synthetic construct
SEQUENCE: 394
caccaacacg tccctctcct                                               20

SEQ ID NO: 395          moltype = RNA  length = 20
FEATURE                 Location/Qualifiers
source                  1..20
                        mol_type = other RNA
                        organism = synthetic construct
SEQUENCE: 395
caggagcagg gaaagcgcct                                               20

SEQ ID NO: 396          moltype = RNA  length = 20
FEATURE                 Location/Qualifiers
source                  1..20
                        mol_type = other RNA
                        organism = synthetic construct
SEQUENCE: 396
caatctccgc caggtagaag                                               20

SEQ ID NO: 397          moltype = RNA  length = 20
FEATURE                 Location/Qualifiers
source                  1..20
                        mol_type = other RNA
                        organism = synthetic construct
SEQUENCE: 397
atgttgtcgg gtttgatgtc                                               20

SEQ ID NO: 398          moltype = RNA  length = 20
FEATURE                 Location/Qualifiers
source                  1..20
                        mol_type = other RNA
                        organism = synthetic construct
SEQUENCE: 398
ccatccgctc ctgcaactgc                                               20

SEQ ID NO: 399          moltype = RNA  length = 20
FEATURE                 Location/Qualifiers
source                  1..20
                        mol_type = other RNA
                        organism = synthetic construct
SEQUENCE: 399
gcgtcacctc ggcctcagcc                                               20

SEQ ID NO: 400          moltype = RNA  length = 20
FEATURE                 Location/Qualifiers
source                  1..20
                        mol_type = other RNA
                        organism = synthetic construct
SEQUENCE: 400
gagggccttt tattcgcgag                                               20

SEQ ID NO: 401          moltype = RNA  length = 20
FEATURE                 Location/Qualifiers
source                  1..20
                        mol_type = other RNA
                        organism = synthetic construct
SEQUENCE: 401
agcggcagag agaggtgctc                                               20

SEQ ID NO: 402          moltype = RNA  length = 20
FEATURE                 Location/Qualifiers
```

```
source                  1..20
                        mol_type = other RNA
                        organism = synthetic construct
SEQUENCE: 402
catccaaaac gtggattggg                                                      20

SEQ ID NO: 403          moltype = RNA   length = 20
FEATURE                 Location/Qualifiers
source                  1..20
                        mol_type = other RNA
                        organism = synthetic construct
SEQUENCE: 403
ttgggcagat ggagggcctt                                                      20

SEQ ID NO: 404          moltype = RNA   length = 20
FEATURE                 Location/Qualifiers
source                  1..20
                        mol_type = other RNA
                        organism = synthetic construct
SEQUENCE: 404
cctctgcctc gcgtagttga                                                      20

SEQ ID NO: 405          moltype = RNA   length = 20
FEATURE                 Location/Qualifiers
source                  1..20
                        mol_type = other RNA
                        organism = synthetic construct
SEQUENCE: 405
acagaacaac ggcgaacagg                                                      20

SEQ ID NO: 406          moltype = RNA   length = 20
FEATURE                 Location/Qualifiers
source                  1..20
                        mol_type = other RNA
                        organism = synthetic construct
SEQUENCE: 406
caggatgttg tcgggtttga                                                      20

SEQ ID NO: 407          moltype = RNA   length = 20
FEATURE                 Location/Qualifiers
source                  1..20
                        mol_type = other RNA
                        organism = synthetic construct
SEQUENCE: 407
cggcctcagc ctctgccgca                                                      20

SEQ ID NO: 408          moltype = RNA   length = 20
FEATURE                 Location/Qualifiers
source                  1..20
                        mol_type = other RNA
                        organism = synthetic construct
SEQUENCE: 408
cagcaggatg ttgtcgggtt                                                      20

SEQ ID NO: 409          moltype = RNA   length = 20
FEATURE                 Location/Qualifiers
source                  1..20
                        mol_type = other RNA
                        organism = synthetic construct
SEQUENCE: 409
gcagagagag gtgctccttg                                                      20

SEQ ID NO: 410          moltype = RNA   length = 20
FEATURE                 Location/Qualifiers
source                  1..20
                        mol_type = other RNA
                        organism = synthetic construct
SEQUENCE: 410
tccagttcca tgggtgtggg                                                      20

SEQ ID NO: 411          moltype = RNA   length = 20
FEATURE                 Location/Qualifiers
source                  1..20
                        mol_type = other RNA
                        organism = synthetic construct
SEQUENCE: 411
cctcagcctg gccgaaagaa                                                      20

SEQ ID NO: 412          moltype = RNA   length = 20
```

```
                                -continued

FEATURE              Location/Qualifiers
source               1..20
                     mol_type = other RNA
                     organism = synthetic construct
SEQUENCE: 412
gggccttttattcgcgaggg                                                        20

SEQ ID NO: 413       moltype = RNA   length = 20
FEATURE              Location/Qualifiers
source               1..20
                     mol_type = other RNA
                     organism = synthetic construct
SEQUENCE: 413
gtcggccagg cggatgtggc                                                       20

SEQ ID NO: 414       moltype = RNA   length = 20
FEATURE              Location/Qualifiers
source               1..20
                     mol_type = other RNA
                     organism = synthetic construct
SEQUENCE: 414
gcttgctgcc ttcccaggcc                                                       20

SEQ ID NO: 415       moltype = RNA   length = 20
FEATURE              Location/Qualifiers
source               1..20
                     mol_type = other RNA
                     organism = synthetic construct
SEQUENCE: 415
ggtccagcag gatgttgtcg                                                       20

SEQ ID NO: 416       moltype = RNA   length = 20
FEATURE              Location/Qualifiers
source               1..20
                     mol_type = other RNA
                     organism = synthetic construct
SEQUENCE: 416
cggagaccat cccagtcgag                                                       20

SEQ ID NO: 417       moltype = RNA   length = 20
FEATURE              Location/Qualifiers
source               1..20
                     mol_type = other RNA
                     organism = synthetic construct
SEQUENCE: 417
tctgcctcgc gtagttgact                                                       20

SEQ ID NO: 418       moltype = RNA   length = 20
FEATURE              Location/Qualifiers
source               1..20
                     mol_type = other RNA
                     organism = synthetic construct
SEQUENCE: 418
aggtagttct catcctggaa                                                       20

SEQ ID NO: 419       moltype = RNA   length = 20
FEATURE              Location/Qualifiers
source               1..20
                     mol_type = other RNA
                     organism = synthetic construct
SEQUENCE: 419
tccttgtagt ggacgatctt                                                       20

SEQ ID NO: 420       moltype = RNA   length = 20
FEATURE              Location/Qualifiers
source               1..20
                     mol_type = other RNA
                     organism = synthetic construct
SEQUENCE: 420
gcatccaaaa cgtggattgg                                                       20

SEQ ID NO: 421       moltype = RNA   length = 20
FEATURE              Location/Qualifiers
source               1..20
                     mol_type = other RNA
                     organism = synthetic construct
SEQUENCE: 421
gtccagcagg atgttgtcgg                                                       20
```

```
SEQ ID NO: 422          moltype = RNA   length = 20
FEATURE                 Location/Qualifiers
source                  1..20
                        mol_type = other RNA
                        organism = synthetic construct
SEQUENCE: 422
agctcccgca gcgtcacctc                                                    20

SEQ ID NO: 423          moltype = RNA   length = 20
FEATURE                 Location/Qualifiers
source                  1..20
                        mol_type = other RNA
                        organism = synthetic construct
SEQUENCE: 423
cgagagcagc gcaagtgagg                                                    20

SEQ ID NO: 424          moltype = RNA   length = 20
FEATURE                 Location/Qualifiers
source                  1..20
                        mol_type = other RNA
                        organism = synthetic construct
SEQUENCE: 424
cagggaaagc gcctccgata                                                    20

SEQ ID NO: 425          moltype = RNA   length = 20
FEATURE                 Location/Qualifiers
source                  1..20
                        mol_type = other RNA
                        organism = synthetic construct
SEQUENCE: 425
atttcatagg cgaatacacc                                                    20

SEQ ID NO: 426          moltype = RNA   length = 20
FEATURE                 Location/Qualifiers
source                  1..20
                        mol_type = other RNA
                        organism = synthetic construct
SEQUENCE: 426
tcggccaggc ggatgtggcc                                                    20

SEQ ID NO: 427          moltype = RNA   length = 20
FEATURE                 Location/Qualifiers
source                  1..20
                        mol_type = other RNA
                        organism = synthetic construct
SEQUENCE: 427
aagggatgtg tccggaagtc                                                    20

SEQ ID NO: 428          moltype = RNA   length = 20
FEATURE                 Location/Qualifiers
source                  1..20
                        mol_type = other RNA
                        organism = synthetic construct
SEQUENCE: 428
cttgtagtgg acgatcttgc                                                    20

SEQ ID NO: 429          moltype = RNA   length = 20
FEATURE                 Location/Qualifiers
source                  1..20
                        mol_type = other RNA
                        organism = synthetic construct
SEQUENCE: 429
agtcggccag gcggatgtgg                                                    20

SEQ ID NO: 430          moltype = RNA   length = 20
FEATURE                 Location/Qualifiers
source                  1..20
                        mol_type = other RNA
                        organism = synthetic construct
SEQUENCE: 430
gcctcagcct ggccgaaaga                                                    20

SEQ ID NO: 431          moltype = RNA   length = 20
FEATURE                 Location/Qualifiers
source                  1..20
                        mol_type = other RNA
                        organism = synthetic construct
SEQUENCE: 431
agcgtcacct cggcctcagc                                                    20
```

-continued

```
SEQ ID NO: 432            moltype = RNA   length = 20
FEATURE                   Location/Qualifiers
source                    1..20
                          mol_type = other RNA
                          organism = synthetic construct
SEQUENCE: 432
cagcggcaga gagaggtgct                                                     20

SEQ ID NO: 433            moltype = RNA   length = 20
FEATURE                   Location/Qualifiers
source                    1..20
                          mol_type = other RNA
                          organism = synthetic construct
SEQUENCE: 433
ccagcggcag agagaggtgc                                                     20

SEQ ID NO: 434            moltype = RNA   length = 20
FEATURE                   Location/Qualifiers
source                    1..20
                          mol_type = other RNA
                          organism = synthetic construct
SEQUENCE: 434
ttgtagtgga cgatcttgcc                                                     20

SEQ ID NO: 435            moltype = RNA   length = 20
FEATURE                   Location/Qualifiers
source                    1..20
                          mol_type = other RNA
                          organism = synthetic construct
SEQUENCE: 435
agggaaagcg cctccgatag                                                     20

SEQ ID NO: 436            moltype = RNA   length = 20
FEATURE                   Location/Qualifiers
source                    1..20
                          mol_type = other RNA
                          organism = synthetic construct
SEQUENCE: 436
gggaaagcgc ctccgatagg                                                     20

SEQ ID NO: 437            moltype = DNA   length = 20
FEATURE                   Location/Qualifiers
source                    1..20
                          mol_type = other DNA
                          organism = synthetic construct
SEQUENCE: 437
ggcagcaagc cgggccgtcc                                                     20

SEQ ID NO: 438            moltype = DNA   length = 20
FEATURE                   Location/Qualifiers
source                    1..20
                          mol_type = other DNA
                          organism = synthetic construct
SEQUENCE: 438
cagtcctgtg atccgggccc                                                     20

SEQ ID NO: 439            moltype = DNA   length = 20
FEATURE                   Location/Qualifiers
source                    1..20
                          mol_type = other DNA
                          organism = synthetic construct
SEQUENCE: 439
gacactgctg agcaagtttg                                                     20

SEQ ID NO: 440            moltype = DNA   length = 20
FEATURE                   Location/Qualifiers
source                    1..20
                          mol_type = other DNA
                          organism = synthetic construct
SEQUENCE: 440
tgacactgct gagcaagttt                                                     20

SEQ ID NO: 441            moltype = DNA   length = 20
FEATURE                   Location/Qualifiers
source                    1..20
                          mol_type = other DNA
                          organism = synthetic construct
SEQUENCE: 441
```

```
cgggagatgg aggccatccg                                                 20

SEQ ID NO: 442         moltype = DNA   length = 20
FEATURE                Location/Qualifiers
source                 1..20
                       mol_type = other DNA
                       organism = synthetic construct SEQUENCE: 442
gggagcggat tccggccgag                                                 20

SEQ ID NO: 443         moltype = DNA   length = 20
FEATURE                Location/Qualifiers
source                 1..20
                       mol_type = other DNA
                       organism = synthetic construct SEQUENCE: 443
ggagcggatt ccggccgaga                                                 20

SEQ ID NO: 444         moltype = DNA   length = 20
FEATURE                Location/Qualifiers
source                 1..20
                       mol_type = other DNA
                       organism = synthetic construct SEQUENCE: 444
cctgctgaca ctgctgagca                                                 20

SEQ ID NO: 445         moltype = DNA   length = 20
FEATURE                Location/Qualifiers
source                 1..20
                       mol_type = other DNA
                       organism = synthetic construct SEQUENCE: 445
agggacatca aacccgacaa                                                 20

SEQ ID NO: 446         moltype = DNA   length = 20
FEATURE                Location/Qualifiers
source                 1..20
                       mol_type = other DNA
                       organism = synthetic construct SEQUENCE: 446
gggacatcaa acccgacaac                                                 20

SEQ ID NO: 447         moltype = DNA   length = 20
FEATURE                Location/Qualifiers
source                 1..20
                       mol_type = other DNA
                       organism = synthetic construct SEQUENCE: 447
gcgcgcttct acctggcgga                                                 20

SEQ ID NO: 448         moltype = DNA   length = 20
FEATURE                Location/Qualifiers
source                 1..20
                       mol_type = other DNA
                       organism = synthetic construct SEQUENCE: 448
cgggccaggt gtatgccatg                                                 20

SEQ ID NO: 449         moltype = DNA   length = 20
FEATURE                Location/Qualifiers
source                 1..20
                       mol_type = other DNA
                       organism = synthetic construct SEQUENCE: 449
ctgacactgc tgagcaagtt                                                 20

SEQ ID NO: 450         moltype = DNA   length = 20
FEATURE                Location/Qualifiers
source                 1..20
                       mol_type = other DNA
                       organism = synthetic construct SEQUENCE: 450
ggcggtggat cacgcagctg                                                 20

SEQ ID NO: 451         moltype = DNA   length = 20
FEATURE                Location/Qualifiers
source                 1..20
                       mol_type = other DNA
                       organism = synthetic construct
```

```
SEQUENCE: 451
gagacactgt cggacattcg                                             20

SEQ ID NO: 452          moltype = DNA  length = 20
FEATURE                 Location/Qualifiers
source                  1..20
                        mol_type = other DNA
                        organism = synthetic construct
SEQUENCE: 452
acatccgcct ggccgacttc                                             20

SEQ ID NO: 453          moltype = DNA  length = 20
FEATURE                 Location/Qualifiers
source                  1..20
                        mol_type = other DNA
                        organism = synthetic construct
SEQUENCE: 453
cagggacatc aaacccgaca                                             20

SEQ ID NO: 454          moltype = DNA  length = 20
FEATURE                 Location/Qualifiers
source                  1..20
                        mol_type = other DNA
                        organism = synthetic construct
SEQUENCE: 454
ccgggagatg gaggccatcc                                             20

SEQ ID NO: 455          moltype = DNA  length = 20
FEATURE                 Location/Qualifiers
source                  1..20
                        mol_type = other DNA
                        organism = synthetic construct
SEQUENCE: 455
atcaaacccg acaacatcct                                             20

SEQ ID NO: 456          moltype = DNA  length = 20
FEATURE                 Location/Qualifiers
source                  1..20
                        mol_type = other DNA
                        organism = synthetic construct
SEQUENCE: 456
acagggacat caaacccgac                                             20

SEQ ID NO: 457          moltype = DNA  length = 20
FEATURE                 Location/Qualifiers
source                  1..20
                        mol_type = other DNA
                        organism = synthetic construct
SEQUENCE: 457
gtacctggtc atggagtatt                                             20

SEQ ID NO: 458          moltype = DNA  length = 20
FEATURE                 Location/Qualifiers
source                  1..20
                        mol_type = other DNA
                        organism = synthetic construct
SEQUENCE: 458
ccatgaagat catgaacaag                                             20

SEQ ID NO: 459          moltype = DNA  length = 20
FEATURE                 Location/Qualifiers
source                  1..20
                        mol_type = other DNA
                        organism = synthetic construct
SEQUENCE: 459
ccacgttttg gatgcactga                                             20

SEQ ID NO: 460          moltype = DNA  length = 20
FEATURE                 Location/Qualifiers
source                  1..20
                        mol_type = other DNA
                        organism = synthetic construct
SEQUENCE: 460
tgggatggtc tccgggacag                                             20

SEQ ID NO: 461          moltype = DNA  length = 20
FEATURE                 Location/Qualifiers
source                  1..20
                        mol_type = other DNA
```

```
                        organism = synthetic construct
SEQUENCE: 461
gacagtgagg tcccaggccc                                               20

SEQ ID NO: 462          moltype = DNA   length = 20
FEATURE                 Location/Qualifiers
source                  1..20
                        mol_type = other DNA
                        organism = synthetic construct
SEQUENCE: 462
gtcatggagt attacgtggg                                               20

SEQ ID NO: 463          moltype = DNA   length = 20
FEATURE                 Location/Qualifiers
source                  1..20
                        mol_type = other DNA
                        organism = synthetic construct
SEQUENCE: 463
cggctgtccc tgcggcagag                                               20

SEQ ID NO: 464          moltype = DNA   length = 20
FEATURE                 Location/Qualifiers
source                  1..20
                        mol_type = other DNA
                        organism = synthetic construct
SEQUENCE: 464
cggcttggct acgtgcacag                                               20

SEQ ID NO: 465          moltype = DNA   length = 20
FEATURE                 Location/Qualifiers
source                  1..20
                        mol_type = other DNA
                        organism = synthetic construct
SEQUENCE: 465
ggccctgacg tggatgggca                                               20

SEQ ID NO: 466          moltype = DNA   length = 20
FEATURE                 Location/Qualifiers
source                  1..20
                        mol_type = other DNA
                        organism = synthetic construct
SEQUENCE: 466
cctggcctat cggaggcgct                                               20

SEQ ID NO: 467          moltype = DNA   length = 20
FEATURE                 Location/Qualifiers
source                  1..20
                        mol_type = other DNA
                        organism = synthetic construct
SEQUENCE: 467
ccggcttggc tacgtgcaca                                               20

SEQ ID NO: 468          moltype = DNA   length = 20
FEATURE                 Location/Qualifiers
source                  1..20
                        mol_type = other DNA
                        organism = synthetic construct
SEQUENCE: 468
agaactacct gtacctggtc                                               20

SEQ ID NO: 469          moltype = DNA   length = 20
FEATURE                 Location/Qualifiers
source                  1..20
                        mol_type = other DNA
                        organism = synthetic construct
SEQUENCE: 469
gcggattccg gccgagatgg                                               20

SEQ ID NO: 470          moltype = DNA   length = 20
FEATURE                 Location/Qualifiers
source                  1..20
                        mol_type = other DNA
                        organism = synthetic construct
SEQUENCE: 470
agcggattcc ggccgagatg                                               20

SEQ ID NO: 471          moltype = DNA   length = 20
FEATURE                 Location/Qualifiers
source                  1..20
```

-continued

```
                        mol_type = other DNA
                        organism = synthetic construct
SEQUENCE: 471
acggcggaga cctatggcaa                                                        20

SEQ ID NO: 472          moltype = DNA   length = 20
FEATURE                 Location/Qualifiers
source                  1..20
                        mol_type = other DNA
                        organism = synthetic construct
SEQUENCE: 472
acatcctgct ggaccgctgt                                                        20

SEQ ID NO: 473          moltype = DNA   length = 20
FEATURE                 Location/Qualifiers
source                  1..20
                        mol_type = other DNA
                        organism = synthetic construct
SEQUENCE: 473
tggcctatcg gaggcgcttt                                                        20

SEQ ID NO: 474          moltype = DNA   length = 20
FEATURE                 Location/Qualifiers
source                  1..20
                        mol_type = other DNA
                        organism = synthetic construct
SEQUENCE: 474
cacatccctt cttctttggc                                                        20

SEQ ID NO: 475          moltype = DNA   length = 20
FEATURE                 Location/Qualifiers
source                  1..20
                        mol_type = other DNA
                        organism = synthetic construct
SEQUENCE: 475
tggtcatgga gtattacgtg                                                        20

SEQ ID NO: 476          moltype = DNA   length = 20
FEATURE                 Location/Qualifiers
source                  1..20
                        mol_type = other DNA
                        organism = synthetic construct
SEQUENCE: 476
gagcggattc cggccgagat                                                        20

SEQ ID NO: 477          moltype = DNA   length = 20
FEATURE                 Location/Qualifiers
source                  1..20
                        mol_type = other DNA
                        organism = synthetic construct
SEQUENCE: 477
agcggtagtg aagatgaagc                                                        20

SEQ ID NO: 478          moltype = DNA   length = 20
FEATURE                 Location/Qualifiers
source                  1..20
                        mol_type = other DNA
                        organism = synthetic construct
SEQUENCE: 478
cggattccgg ccgagatggc                                                        20

SEQ ID NO: 479          moltype = DNA   length = 20
FEATURE                 Location/Qualifiers
source                  1..20
                        mol_type = other DNA
                        organism = synthetic construct
SEQUENCE: 479
agttccagcg gctgtccctg                                                        20

SEQ ID NO: 480          moltype = DNA   length = 20
FEATURE                 Location/Qualifiers
source                  1..20
                        mol_type = other DNA
                        organism = synthetic construct
SEQUENCE: 480
tacctggcgg agattgtcat                                                        20

SEQ ID NO: 481          moltype = DNA   length = 20
FEATURE                 Location/Qualifiers
```

```
source                  1..20
                        mol_type = other DNA
                        organism = synthetic construct
SEQUENCE: 481
tggcggagat tgtcatggcc                                                     20

SEQ ID NO: 482          moltype = DNA  length = 20
FEATURE                 Location/Qualifiers
source                  1..20
                        mol_type = other DNA
                        organism = synthetic construct
SEQUENCE: 482
tgtacctggt catggagtat                                                     20

SEQ ID NO: 483          moltype = DNA  length = 20
FEATURE                 Location/Qualifiers
source                  1..20
                        mol_type = other DNA
                        organism = synthetic construct
SEQUENCE: 483
caactacgcg aggcagaggc                                                     20

SEQ ID NO: 484          moltype = DNA  length = 20
FEATURE                 Location/Qualifiers
source                  1..20
                        mol_type = other DNA
                        organism = synthetic construct
SEQUENCE: 484
ggagacactg tcggacattc                                                     20

SEQ ID NO: 485          moltype = DNA  length = 20
FEATURE                 Location/Qualifiers
source                  1..20
                        mol_type = other DNA
                        organism = synthetic construct
SEQUENCE: 485
agctgcgggc agatggaacg                                                     20

SEQ ID NO: 486          moltype = DNA  length = 20
FEATURE                 Location/Qualifiers
source                  1..20
                        mol_type = other DNA
                        organism = synthetic construct
SEQUENCE: 486
caagatcgtc cactacaagg                                                     20

SEQ ID NO: 487          moltype = DNA  length = 20
FEATURE                 Location/Qualifiers
source                  1..20
                        mol_type = other DNA
                        organism = synthetic construct
SEQUENCE: 487
cgcttctacc tggcggagat                                                     20

SEQ ID NO: 488          moltype = DNA  length = 20
FEATURE                 Location/Qualifiers
source                  1..20
                        mol_type = other DNA
                        organism = synthetic construct
SEQUENCE: 488
ctcacccggc agagcctgag                                                     20

SEQ ID NO: 489          moltype = DNA  length = 20
FEATURE                 Location/Qualifiers
source                  1..20
                        mol_type = other DNA
                        organism = synthetic construct
SEQUENCE: 489
gcggtagtga agatgaagca                                                     20

SEQ ID NO: 490          moltype = DNA  length = 20
FEATURE                 Location/Qualifiers
source                  1..20
                        mol_type = other DNA
                        organism = synthetic construct
SEQUENCE: 490
caaacccgac aacatcctgc                                                     20

SEQ ID NO: 491          moltype = DNA  length = 20
```

```
FEATURE                Location/Qualifiers
source                 1..20
                       mol_type = other DNA
                       organism = synthetic construct
SEQUENCE: 491
ctgcggcaga ggctgaggcc                                                   20

SEQ ID NO: 492         moltype = DNA   length = 20
FEATURE                Location/Qualifiers
source                 1..20
                       mol_type = other DNA
                       organism = synthetic construct
SEQUENCE: 492
ggacatcaaa cccgacaaca                                                   20

SEQ ID NO: 493         moltype = DNA   length = 20
FEATURE                Location/Qualifiers
source                 1..20
                       mol_type = other DNA
                       organism = synthetic construct
SEQUENCE: 493
ggtcatggag tattacgtgg                                                   20

SEQ ID NO: 494         moltype = DNA   length = 20
FEATURE                Location/Qualifiers
source                 1..20
                       mol_type = other DNA
                       organism = synthetic construct
SEQUENCE: 494
gctgcgggca gatggaacgg                                                   20

SEQ ID NO: 495         moltype = DNA   length = 20
FEATURE                Location/Qualifiers
source                 1..20
                       mol_type = other DNA
                       organism = synthetic construct
SEQUENCE: 495
tctgcctgct tactcgggaa                                                   20

SEQ ID NO: 496         moltype = DNA   length = 20
FEATURE                Location/Qualifiers
source                 1..20
                       mol_type = other DNA
                       organism = synthetic construct
SEQUENCE: 496
ggtgtatgcc atgaagatca                                                   20

SEQ ID NO: 497         moltype = DNA   length = 20
FEATURE                Location/Qualifiers
source                 1..20
                       mol_type = other DNA
                       organism = synthetic construct
SEQUENCE: 497
cagttccagc ggctgtccct                                                   20

SEQ ID NO: 498         moltype = DNA   length = 20
FEATURE                Location/Qualifiers
source                 1..20
                       mol_type = other DNA
                       organism = synthetic construct
SEQUENCE: 498
tgcacaggga catcaaaccc                                                   20

SEQ ID NO: 499         moltype = DNA   length = 20
FEATURE                Location/Qualifiers
source                 1..20
                       mol_type = other DNA
                       organism = synthetic construct
SEQUENCE: 499
ctacctggcg gagattgtca                                                   20

SEQ ID NO: 500         moltype = DNA   length = 20
FEATURE                Location/Qualifiers
source                 1..20
                       mol_type = other DNA
                       organism = synthetic construct
SEQUENCE: 500
catcctgctg gaccgctgtg                                                   20
```

| | | |
|---|---|---|
| SEQ ID NO: 501<br>FEATURE<br>source | moltype = DNA  length = 20<br>Location/Qualifiers<br>1..20<br>mol_type = other DNA<br>organism = synthetic construct | |
| SEQUENCE: 501<br>gggcagacgc ccttctacgc | | 20 |
| SEQ ID NO: 502<br>FEATURE<br>source | moltype = DNA  length = 20<br>Location/Qualifiers<br>1..20<br>mol_type = other DNA<br>organism = synthetic construct | |
| SEQUENCE: 502<br>tccctgcggc agaggctgag | | 20 |
| SEQ ID NO: 503<br>FEATURE<br>source | moltype = DNA  length = 20<br>Location/Qualifiers<br>1..20<br>mol_type = other DNA<br>organism = synthetic construct | |
| SEQUENCE: 503<br>cgttttggat gcactgagac | | 20 |
| SEQ ID NO: 504<br>FEATURE<br>source | moltype = DNA  length = 20<br>Location/Qualifiers<br>1..20<br>mol_type = other DNA<br>organism = synthetic construct | |
| SEQUENCE: 504<br>gacctatggc aagatcgtcc | | 20 |
| SEQ ID NO: 505<br>FEATURE<br>source | moltype = DNA  length = 20<br>Location/Qualifiers<br>1..20<br>mol_type = other DNA<br>organism = synthetic construct | |
| SEQUENCE: 505<br>ggacctgctg acactgctga | | 20 |
| SEQ ID NO: 506<br>FEATURE<br>source | moltype = DNA  length = 20<br>Location/Qualifiers<br>1..20<br>mol_type = other DNA<br>organism = synthetic construct | |
| SEQUENCE: 506<br>gtctggcgcc gcccaggagc | | 20 |
| SEQ ID NO: 507<br>FEATURE<br>source | moltype = DNA  length = 20<br>Location/Qualifiers<br>1..20<br>mol_type = other DNA<br>organism = synthetic construct | |
| SEQUENCE: 507<br>aaacccgaca acatcctgct | | 20 |
| SEQ ID NO: 508<br>FEATURE<br>source | moltype = DNA  length = 20<br>Location/Qualifiers<br>1..20<br>mol_type = other DNA<br>organism = synthetic construct | |
| SEQUENCE: 508<br>cggcagttgc aggagcggat | | 20 |
| SEQ ID NO: 509<br>FEATURE<br>source | moltype = DNA  length = 20<br>Location/Qualifiers<br>1..20<br>mol_type = other DNA<br>organism = synthetic construct | |
| SEQUENCE: 509<br>gaggcgcttt ccctgctcct | | 20 |
| SEQ ID NO: 510<br>FEATURE<br>source | moltype = DNA  length = 20<br>Location/Qualifiers<br>1..20<br>mol_type = other DNA<br>organism = synthetic construct | |
| SEQUENCE: 510<br>gaagcagacg ggccaggtgt | | 20 |

| | | |
|---|---|---|
| SEQ ID NO: 511<br>FEATURE<br>source | moltype = DNA length = 20<br>Location/Qualifiers<br>1..20<br>mol_type = other DNA<br>organism = synthetic construct | |
| SEQUENCE: 511<br>tgtgactggt gggcgctggg | | 20 |
| SEQ ID NO: 512<br>FEATURE<br>source | moltype = DNA length = 20<br>Location/Qualifiers<br>1..20<br>mol_type = other DNA<br>organism = synthetic construct | |
| SEQUENCE: 512<br>ttgctgcagg cagagggagc | | 20 |
| SEQ ID NO: 513<br>FEATURE<br>source | moltype = DNA length = 20<br>Location/Qualifiers<br>1..20<br>mol_type = other DNA<br>organism = synthetic construct | |
| SEQUENCE: 513<br>tcacccggca gagcctgagc | | 20 |
| SEQ ID NO: 514<br>FEATURE<br>source | moltype = DNA length = 20<br>Location/Qualifiers<br>1..20<br>mol_type = other DNA<br>organism = synthetic construct | |
| SEQUENCE: 514<br>tacgtgcaca gggacatcaa | | 20 |
| SEQ ID NO: 515<br>FEATURE<br>source | moltype = DNA length = 20<br>Location/Qualifiers<br>1..20<br>mol_type = other DNA<br>organism = synthetic construct | |
| SEQUENCE: 515<br>cctgcggcag aggctgaggc | | 20 |
| SEQ ID NO: 516<br>FEATURE<br>source | moltype = DNA length = 20<br>Location/Qualifiers<br>1..20<br>mol_type = other DNA<br>organism = synthetic construct | |
| SEQUENCE: 516<br>cttccaggat gagaactacc | | 20 |
| SEQ ID NO: 517<br>FEATURE<br>source | moltype = DNA length = 20<br>Location/Qualifiers<br>1..20<br>mol_type = other DNA<br>organism = synthetic construct | |
| SEQUENCE: 517<br>agtgtgactg gtgggcgctg | | 20 |
| SEQ ID NO: 518<br>FEATURE<br>source | moltype = DNA length = 20<br>Location/Qualifiers<br>1..20<br>mol_type = other DNA<br>organism = synthetic construct | |
| SEQUENCE: 518<br>cactgctgag caagtttggg | | 20 |
| SEQ ID NO: 519<br>FEATURE<br>source | moltype = DNA length = 20<br>Location/Qualifiers<br>1..20<br>mol_type = other DNA<br>organism = synthetic construct | |
| SEQUENCE: 519<br>cggcggagac ctatggcaag | | 20 |
| SEQ ID NO: 520<br>FEATURE<br>source | moltype = DNA length = 20<br>Location/Qualifiers<br>1..20<br>mol_type = other DNA<br>organism = synthetic construct | |
| SEQUENCE: 520 | | |

```
aagcagacgg gccaggtgta                                          20

SEQ ID NO: 521          moltype = DNA   length = 20
FEATURE                 Location/Qualifiers
source                  1..20
                        mol_type = other DNA
                        organism = synthetic construct SEQUENCE: 521
gtgtgactgg tgggcgctgg                                          20

SEQ ID NO: 522          moltype = DNA   length = 20
FEATURE                 Location/Qualifiers
source                  1..20
                        mol_type = other DNA
                        organism = synthetic construct SEQUENCE: 522
ctttcggcca ggctgaggcc                                          20

SEQ ID NO: 523          moltype = DNA   length = 20
FEATURE                 Location/Qualifiers
source                  1..20
                        mol_type = other DNA
                        organism = synthetic construct SEQUENCE: 523
gcttctacct ggcggagatt                                          20

SEQ ID NO: 524          moltype = DNA   length = 20
FEATURE                 Location/Qualifiers
source                  1..20
                        mol_type = other DNA
                        organism = synthetic construct SEQUENCE: 524
acgggccagg tgtatgccat                                          20

SEQ ID NO: 525          moltype = DNA   length = 20
FEATURE                 Location/Qualifiers
source                  1..20
                        mol_type = other DNA
                        organism = synthetic construct SEQUENCE: 525
cctggcggag attgtcatgg                                          20

SEQ ID NO: 526          moltype = DNA   length = 20
FEATURE                 Location/Qualifiers
source                  1..20
                        mol_type = other DNA
                        organism = synthetic construct SEQUENCE: 526
ctgctgagca agtttgggga                                          20

SEQ ID NO: 527          moltype = DNA   length = 20
FEATURE                 Location/Qualifiers
source                  1..20
                        mol_type = other DNA
                        organism = synthetic construct SEQUENCE: 527
acatcaaacc cgacaacatc                                          20

SEQ ID NO: 528          moltype = DNA   length = 20
FEATURE                 Location/Qualifiers
source                  1..20
                        mol_type = other DNA
                        organism = synthetic construct SEQUENCE: 528
cctgacgtgg atgggcaaac                                          20

SEQ ID NO: 529          moltype = DNA   length = 20
FEATURE                 Location/Qualifiers
source                  1..20
                        mol_type = other DNA
                        organism = synthetic construct SEQUENCE: 529
gcagcaagcc gggccgtccg                                          20

SEQ ID NO: 530          moltype = DNA   length = 20
FEATURE                 Location/Qualifiers
source                  1..20
                        mol_type = other DNA
                        organism = synthetic construct
```

| | | |
|---|---|---|
| SEQUENCE: 530 cgcgcttcta cctggcggag | | 20 |
| SEQ ID NO: 531 FEATURE source | moltype = DNA length = 20 Location/Qualifiers 1..20 mol_type = other DNA organism = synthetic construct | |
| SEQUENCE: 531 aggatgagaa ctacctgtac | | 20 |
| SEQ ID NO: 532 FEATURE source | moltype = DNA length = 20 Location/Qualifiers 1..20 mol_type = other DNA organism = synthetic construct | |
| SEQUENCE: 532 gttctatggg cagacgccct | | 20 |
| SEQ ID NO: 533 FEATURE source | moltype = DNA length = 20 Location/Qualifiers 1..20 mol_type = other DNA organism = synthetic construct | |
| SEQUENCE: 533 ctgctggacc gctgtggcca | | 20 |
| SEQ ID NO: 534 FEATURE source | moltype = DNA length = 20 Location/Qualifiers 1..20 mol_type = other DNA organism = synthetic construct | |
| SEQUENCE: 534 aacttcgcca gtcaactacg | | 20 |
| SEQ ID NO: 535 FEATURE source | moltype = DNA length = 20 Location/Qualifiers 1..20 mol_type = other DNA organism = synthetic construct | |
| SEQUENCE: 535 gcggctgtcc ctgcggcaga | | 20 |
| SEQ ID NO: 536 FEATURE source | moltype = DNA length = 20 Location/Qualifiers 1..20 mol_type = other DNA organism = synthetic construct | |
| SEQUENCE: 536 ctggcctatc ggaggcgctt | | 20 |
| SEQ ID NO: 537 FEATURE source | moltype = DNA length = 20 Location/Qualifiers 1..20 mol_type = other DNA organism = synthetic construct | |
| SEQUENCE: 537 ctgttcgccg ttgttctgtc | | 20 |
| SEQ ID NO: 538 FEATURE source | moltype = DNA length = 20 Location/Qualifiers 1..20 mol_type = other DNA organism = synthetic construct | |
| SEQUENCE: 538 acctgctgac actgctgagc | | 20 |
| SEQ ID NO: 539 FEATURE source | moltype = DNA length = 20 Location/Qualifiers 1..20 mol_type = other DNA organism = synthetic construct | |
| SEQUENCE: 539 gtgtatgcca tgaagatcat | | 20 |
| SEQ ID NO: 540 FEATURE source | moltype = DNA length = 20 Location/Qualifiers 1..20 mol_type = other DNA | |

```
                        organism = synthetic construct
SEQUENCE: 540
ccctgacgtg gatgggcaaa                                                    20

SEQ ID NO: 541          moltype = DNA  length = 20
FEATURE                 Location/Qualifiers
source                  1..20
                        mol_type = other DNA
                        organism = synthetic construct
SEQUENCE: 541
gctgacactg ctgagcaagt                                                    20

SEQ ID NO: 542          moltype = DNA  length = 20
FEATURE                 Location/Qualifiers
source                  1..20
                        mol_type = other DNA
                        organism = synthetic construct
SEQUENCE: 542
ctacgtgcac agggacatca                                                    20

SEQ ID NO: 543          moltype = DNA  length = 20
FEATURE                 Location/Qualifiers
source                  1..20
                        mol_type = other DNA
                        organism = synthetic construct
SEQUENCE: 543
cccgacattc ctcggtattt                                                    20

SEQ ID NO: 544          moltype = DNA  length = 20
FEATURE                 Location/Qualifiers
source                  1..20
                        mol_type = other DNA
                        organism = synthetic construct
SEQUENCE: 544
gggcgctggg tgtattcgcc                                                    20

SEQ ID NO: 545          moltype = DNA  length = 20
FEATURE                 Location/Qualifiers
source                  1..20
                        mol_type = other DNA
                        organism = synthetic construct
SEQUENCE: 545
ttcctcggta tttattgtct                                                    20

SEQ ID NO: 546          moltype = DNA  length = 20
FEATURE                 Location/Qualifiers
source                  1..20
                        mol_type = other DNA
                        organism = synthetic construct
SEQUENCE: 546
gtgaagatga agcagacggg                                                    20

SEQ ID NO: 547          moltype = DNA  length = 20
FEATURE                 Location/Qualifiers
source                  1..20
                        mol_type = other DNA
                        organism = synthetic construct
SEQUENCE: 547
gatggagttg ctgcaggcag                                                    20

SEQ ID NO: 548          moltype = DNA  length = 20
FEATURE                 Location/Qualifiers
source                  1..20
                        mol_type = other DNA
                        organism = synthetic construct
SEQUENCE: 548
ccctgcggca gaggctgagg                                                    20

SEQ ID NO: 549          moltype = DNA  length = 20
FEATURE                 Location/Qualifiers
source                  1..20
                        mol_type = other DNA
                        organism = synthetic construct
SEQUENCE: 549
agcaggcgac ttccggacac                                                    20

SEQ ID NO: 550          moltype = DNA  length = 20
FEATURE                 Location/Qualifiers
source                  1..20
```

-continued

```
                          mol_type = other DNA
                          organism = synthetic construct
SEQUENCE: 550
ctgcttgagc cacacgtgca                                                 20

SEQ ID NO: 551            moltype = DNA   length = 20
FEATURE                   Location/Qualifiers
source                    1..20
                          mol_type = other DNA
                          organism = synthetic construct
SEQUENCE: 551
attcctcggt atttattgtc                                                 20

SEQ ID NO: 552            moltype = DNA   length = 20
FEATURE                   Location/Qualifiers
source                    1..20
                          mol_type = other DNA
                          organism = synthetic construct
SEQUENCE: 552
ctggcggaga ttgtcatggc                                                 20

SEQ ID NO: 553            moltype = DNA   length = 20
FEATURE                   Location/Qualifiers
source                    1..20
                          mol_type = other DNA
                          organism = synthetic construct
SEQUENCE: 553
gggatggtct ccgggacagc                                                 20

SEQ ID NO: 554            moltype = DNA   length = 20
FEATURE                   Location/Qualifiers
source                    1..20
                          mol_type = other DNA
                          organism = synthetic construct
SEQUENCE: 554
actacctgta cctggtcatg                                                 20

SEQ ID NO: 555            moltype = DNA   length = 20
FEATURE                   Location/Qualifiers
source                    1..20
                          mol_type = other DNA
                          organism = synthetic construct
SEQUENCE: 555
gagtgtgact ggtgggcgct                                                 20

SEQ ID NO: 556            moltype = DNA   length = 20
FEATURE                   Location/Qualifiers
source                    1..20
                          mol_type = other DNA
                          organism = synthetic construct
SEQUENCE: 556
acgttttgga tgcactgaga                                                 20

SEQ ID NO: 557            moltype = DNA   length = 20
FEATURE                   Location/Qualifiers
source                    1..20
                          mol_type = other DNA
                          organism = synthetic construct
SEQUENCE: 557
aggccctcca tctgcccaaa                                                 20

SEQ ID NO: 558            moltype = DNA   length = 20
FEATURE                   Location/Qualifiers
source                    1..20
                          mol_type = other DNA
                          organism = synthetic construct
SEQUENCE: 558
gctacgtgca cagggacatc                                                 20

SEQ ID NO: 559            moltype = DNA   length = 20
FEATURE                   Location/Qualifiers
source                    1..20
                          mol_type = other DNA
                          organism = synthetic construct
SEQUENCE: 559
gggacctgct gacactgctg                                                 20

SEQ ID NO: 560            moltype = DNA   length = 20
FEATURE                   Location/Qualifiers
```

```
source                       1..20
                             mol_type = other DNA
                             organism = synthetic construct
SEQUENCE: 560
acctggcgga gattgtcatg                                              20

SEQ ID NO: 561               moltype = DNA   length = 20
FEATURE                      Location/Qualifiers
source                       1..20
                             mol_type = other DNA
                             organism = synthetic construct
SEQUENCE: 561
catgaagatc atgaacaagt                                              20

SEQ ID NO: 562               moltype = DNA   length = 20
FEATURE                      Location/Qualifiers
source                       1..20
                             mol_type = other DNA
                             organism = synthetic construct
SEQUENCE: 562
cccttctacg cggattccac                                              20

SEQ ID NO: 563               moltype = DNA   length = 20
FEATURE                      Location/Qualifiers
source                       1..20
                             mol_type = other DNA
                             organism = synthetic construct
SEQUENCE: 563
ggcggagatt gtcatggcca                                              20

SEQ ID NO: 564               moltype = DNA   length = 20
FEATURE                      Location/Qualifiers
source                       1..20
                             mol_type = other DNA
                             organism = synthetic construct
SEQUENCE: 564
cggtatttat tgtctgtccc                                              20

SEQ ID NO: 565               moltype = DNA   length = 20
FEATURE                      Location/Qualifiers
source                       1..20
                             mol_type = other DNA
                             organism = synthetic construct
SEQUENCE: 565
tgagcaagtt tggggagcgg                                              20

SEQ ID NO: 566               moltype = DNA   length = 20
FEATURE                      Location/Qualifiers
source                       1..20
                             mol_type = other DNA
                             organism = synthetic construct
SEQUENCE: 566
acccggcaga gcctgagccg                                              20

SEQ ID NO: 567               moltype = DNA   length = 20
FEATURE                      Location/Qualifiers
source                       1..20
                             mol_type = other DNA
                             organism = synthetic construct
SEQUENCE: 567
tctggcgccg cccaggagcc                                              20

SEQ ID NO: 568               moltype = DNA   length = 20
FEATURE                      Location/Qualifiers
source                       1..20
                             mol_type = other DNA
                             organism = synthetic construct
SEQUENCE: 568
ctgcctgctt actcgggaaa                                              20

SEQ ID NO: 569               moltype = DNA   length = 20
FEATURE                      Location/Qualifiers
source                       1..20
                             mol_type = other DNA
                             organism = synthetic construct
SEQUENCE: 569
catcaaaccc gacaacatcc                                              20

SEQ ID NO: 570               moltype = DNA   length = 20
```

```
FEATURE              Location/Qualifiers
source               1..20
                     mol_type = other DNA
                     organism = synthetic construct
SEQUENCE: 570
tccaggatga gaactacctg                                               20

SEQ ID NO: 571       moltype = DNA  length = 20
FEATURE              Location/Qualifiers
source               1..20
                     mol_type = other DNA
                     organism = synthetic construct
SEQUENCE: 571
tatgaaatgt tctatgggca                                               20

SEQ ID NO: 572       moltype = DNA  length = 20
FEATURE              Location/Qualifiers
source               1..20
                     mol_type = other DNA
                     organism = synthetic construct
SEQUENCE: 572
gccttccagg atgagaacta                                               20

SEQ ID NO: 573       moltype = DNA  length = 20
FEATURE              Location/Qualifiers
source               1..20
                     mol_type = other DNA
                     organism = synthetic construct
SEQUENCE: 573
ggctacgtgc acagggacat                                               20

SEQ ID NO: 574       moltype = DNA  length = 20
FEATURE              Location/Qualifiers
source               1..20
                     mol_type = other DNA
                     organism = synthetic construct
SEQUENCE: 574
agtcctgtga tccgggcccg                                               20

SEQ ID NO: 575       moltype = DNA  length = 20
FEATURE              Location/Qualifiers
source               1..20
                     mol_type = other DNA
                     organism = synthetic construct
SEQUENCE: 575
acctatggca agatcgtcca                                               20

SEQ ID NO: 576       moltype = DNA  length = 20
FEATURE              Location/Qualifiers
source               1..20
                     mol_type = other DNA
                     organism = synthetic construct
SEQUENCE: 576
ggtggcccac gccggccaac                                               20

SEQ ID NO: 577       moltype = DNA  length = 20
FEATURE              Location/Qualifiers
source               1..20
                     mol_type = other DNA
                     organism = synthetic construct
SEQUENCE: 577
cacgttttgg atgcactgag                                               20

SEQ ID NO: 578       moltype = DNA  length = 20
FEATURE              Location/Qualifiers
source               1..20
                     mol_type = other DNA
                     organism = synthetic construct
SEQUENCE: 578
accgacacat gcaacttcga                                               20

SEQ ID NO: 579       moltype = DNA  length = 20
FEATURE              Location/Qualifiers
source               1..20
                     mol_type = other DNA
                     organism = synthetic construct
SEQUENCE: 579
gccgggccgt ccgtgttcca                                               20
```

-continued

| | | |
|---|---|---|
| SEQ ID NO: 580<br>FEATURE<br>source | moltype = DNA   length = 20<br>Location/Qualifiers<br>1..20<br>mol_type = other DNA<br>organism = synthetic construct | |
| SEQUENCE: 580<br>ctcacttgcg ctgctctcgg | | 20 |
| SEQ ID NO: 581<br>FEATURE<br>source | moltype = DNA   length = 20<br>Location/Qualifiers<br>1..20<br>mol_type = other DNA<br>organism = synthetic construct | |
| SEQUENCE: 581<br>cacgtccggc agttgcagga | | 20 |
| SEQ ID NO: 582<br>FEATURE<br>source | moltype = DNA   length = 20<br>Location/Qualifiers<br>1..20<br>mol_type = other DNA<br>organism = synthetic construct | |
| SEQUENCE: 582<br>ggagagggac gtgttggtga | | 20 |
| SEQ ID NO: 583<br>FEATURE<br>source | moltype = DNA   length = 20<br>Location/Qualifiers<br>1..20<br>mol_type = other DNA<br>organism = synthetic construct | |
| SEQUENCE: 583<br>ggatggagtt gctgcaggca | | 20 |
| SEQ ID NO: 584<br>FEATURE<br>source | moltype = DNA   length = 20<br>Location/Qualifiers<br>1..20<br>mol_type = other DNA<br>organism = synthetic construct | |
| SEQUENCE: 584<br>tggtggccca cgccggccaa | | 20 |
| SEQ ID NO: 585<br>FEATURE<br>source | moltype = DNA   length = 20<br>Location/Qualifiers<br>1..20<br>mol_type = other DNA<br>organism = synthetic construct | |
| SEQUENCE: 585<br>actacgcgag gcagaggctc | | 20 |
| SEQ ID NO: 586<br>FEATURE<br>source | moltype = DNA   length = 20<br>Location/Qualifiers<br>1..20<br>mol_type = other DNA<br>organism = synthetic construct | |
| SEQUENCE: 586<br>ttctatgggc agacgccctt | | 20 |
| SEQ ID NO: 587<br>FEATURE<br>source | moltype = DNA   length = 20<br>Location/Qualifiers<br>1..20<br>mol_type = other DNA<br>organism = synthetic construct | |
| SEQUENCE: 587<br>cctcggtatt tattgtctgt | | 20 |
| SEQ ID NO: 588<br>FEATURE<br>source | moltype = DNA   length = 20<br>Location/Qualifiers<br>1..20<br>mol_type = other DNA<br>organism = synthetic construct | |
| SEQUENCE: 588<br>tcggtattta ttgtctgtcc | | 20 |
| SEQ ID NO: 589<br>FEATURE<br>source | moltype = DNA   length = 20<br>Location/Qualifiers<br>1..20<br>mol_type = other DNA<br>organism = synthetic construct | |
| SEQUENCE: 589<br>cgggacctag aggcacacgt | | 20 |

```
SEQ ID NO: 590          moltype = DNA  length = 20
FEATURE                 Location/Qualifiers
source                  1..20
                        mol_type = other DNA
                        organism = synthetic construct
SEQUENCE: 590
ccgttgttct gtctcgtgcc                                                    20

SEQ ID NO: 591          moltype = DNA  length = 20
FEATURE                 Location/Qualifiers
source                  1..20
                        mol_type = other DNA
                        organism = synthetic construct
SEQUENCE: 591
gaactacctg tacctggtca                                                    20

SEQ ID NO: 592          moltype = DNA  length = 20
FEATURE                 Location/Qualifiers
source                  1..20
                        mol_type = other DNA
                        organism = synthetic construct
SEQUENCE: 592
gaggtgctca cccggcagag                                                    20

SEQ ID NO: 593          moltype = DNA  length = 20
FEATURE                 Location/Qualifiers
source                  1..20
                        mol_type = other DNA
                        organism = synthetic construct
SEQUENCE: 593
tctacctggc ggagattgtc                                                    20

SEQ ID NO: 594          moltype = DNA  length = 20
FEATURE                 Location/Qualifiers
source                  1..20
                        mol_type = other DNA
                        organism = synthetic construct
SEQUENCE: 594
gcgcttctac ctggcggaga                                                    20

SEQ ID NO: 595          moltype = DNA  length = 20
FEATURE                 Location/Qualifiers
source                  1..20
                        mol_type = other DNA
                        organism = synthetic construct
SEQUENCE: 595
gtcaactacg cgaggcagag                                                    20

SEQ ID NO: 596          moltype = DNA  length = 20
FEATURE                 Location/Qualifiers
source                  1..20
                        mol_type = other DNA
                        organism = synthetic construct
SEQUENCE: 596
ggccctccat ctgcccaaag                                                    20

SEQ ID NO: 597          moltype = DNA  length = 20
FEATURE                 Location/Qualifiers
source                  1..20
                        mol_type = other DNA
                        organism = synthetic construct
SEQUENCE: 597
ccaggatgag aactacctgt                                                    20

SEQ ID NO: 598          moltype = DNA  length = 20
FEATURE                 Location/Qualifiers
source                  1..20
                        mol_type = other DNA
                        organism = synthetic construct
SEQUENCE: 598
acactgctga gcaagtttgg                                                    20

SEQ ID NO: 599          moltype = DNA  length = 20
FEATURE                 Location/Qualifiers
source                  1..20
                        mol_type = other DNA
                        organism = synthetic construct
SEQUENCE: 599
```

```
cacagggaca tcaaacccga                                              20

SEQ ID NO: 600         moltype = DNA   length = 20
FEATURE                Location/Qualifiers
source                 1..20
                       mol_type = other DNA
                       organism = synthetic construct
SEQUENCE: 600
gcctgggaag gcagcaagcc                                              20

SEQ ID NO: 601         moltype = DNA   length = 20
FEATURE                Location/Qualifiers
source                 1..20
                       mol_type = other DNA
                       organism = synthetic construct
SEQUENCE: 601
caggatgaga actacctgta                                              20

SEQ ID NO: 602         moltype = DNA   length = 20
FEATURE                Location/Qualifiers
source                 1..20
                       mol_type = other DNA
                       organism = synthetic construct
SEQUENCE: 602
gccctgacgt ggatgggcaa                                              20

SEQ ID NO: 603         moltype = DNA   length = 20
FEATURE                Location/Qualifiers
source                 1..20
                       mol_type = other DNA
                       organism = synthetic construct
SEQUENCE: 603
gatgagaact acctgtacct                                              20

SEQ ID NO: 604         moltype = DNA   length = 20
FEATURE                Location/Qualifiers
source                 1..20
                       mol_type = other DNA
                       organism = synthetic construct
SEQUENCE: 604
ctcggtattt attgtctgtc                                              20

SEQ ID NO: 605         moltype = DNA   length = 20
FEATURE                Location/Qualifiers
source                 1..20
                       mol_type = other DNA
                       organism = synthetic construct
SEQUENCE: 605
ttcgcctatg aaatgttcta                                              20

SEQ ID NO: 606         moltype = DNA   length = 20
FEATURE                Location/Qualifiers
source                 1..20
                       mol_type = other DNA
                       organism = synthetic construct
SEQUENCE: 606
cctcgcgaat aaaaggccct                                              20

SEQ ID NO: 607         moltype = DNA   length = 20
FEATURE                Location/Qualifiers
source                 1..20
                       mol_type = other DNA
                       organism = synthetic construct
SEQUENCE: 607
gccagtcaac tacgcgaggc                                              20

SEQ ID NO: 608         moltype = DNA   length = 20
FEATURE                Location/Qualifiers
source                 1..20
                       mol_type = other DNA
                       organism = synthetic construct
SEQUENCE: 608
acccgacaac atcctgctgg                                              20

SEQ ID NO: 609         moltype = DNA   length = 20
FEATURE                Location/Qualifiers
source                 1..20
                       mol_type = other DNA
                       organism = synthetic construct
```

```
SEQUENCE: 609
gaacttcgcc agtcaactac                                                    20

SEQ ID NO: 610          moltype = DNA  length = 20
FEATURE                 Location/Qualifiers
source                  1..20
                        mol_type = other DNA
                        organism = synthetic construct SEQUENCE: 610
ggagatggag gccatccgca                                                    20

SEQ ID NO: 611          moltype = DNA  length = 20
FEATURE                 Location/Qualifiers
source                  1..20
                        mol_type = other DNA
                        organism = synthetic construct SEQUENCE: 611
ttctacctgg cggagattgt                                                    20

SEQ ID NO: 612          moltype = DNA  length = 20
FEATURE                 Location/Qualifiers
source                  1..20
                        mol_type = other DNA
                        organism = synthetic construct SEQUENCE: 612
tgggcgctgg gtgtattcgc                                                    20

SEQ ID NO: 613          moltype = DNA  length = 20
FEATURE                 Location/Qualifiers
source                  1..20
                        mol_type = other DNA
                        organism = synthetic construct SEQUENCE: 613
ccttccagga tgagaactac                                                    20

SEQ ID NO: 614          moltype = DNA  length = 20
FEATURE                 Location/Qualifiers
source                  1..20
                        mol_type = other DNA
                        organism = synthetic construct SEQUENCE: 614
cacccggcag agcctgagcc                                                    20

SEQ ID NO: 615          moltype = DNA  length = 20
FEATURE                 Location/Qualifiers
source                  1..20
                        mol_type = other DNA
                        organism = synthetic construct SEQUENCE: 615
agggacgtgt tggtgaatgg                                                    20

SEQ ID NO: 616          moltype = DNA  length = 20
FEATURE                 Location/Qualifiers
source                  1..20
                        mol_type = other DNA
                        organism = synthetic construct SEQUENCE: 616
gagaactacc tgtacctggt                                                    20

SEQ ID NO: 617          moltype = DNA  length = 20
FEATURE                 Location/Qualifiers
source                  1..20
                        mol_type = other DNA
                        organism = synthetic construct SEQUENCE: 617
cgtggatggg caaactgcag                                                    20

SEQ ID NO: 618          moltype = DNA  length = 20
FEATURE                 Location/Qualifiers
source                  1..20
                        mol_type = other DNA
                        organism = synthetic construct SEQUENCE: 618
gccatgaaga tcatgaacaa                                                    20

SEQ ID NO: 619          moltype = DNA  length = 20
FEATURE                 Location/Qualifiers
source                  1..20
                        mol_type = other DNA
```

```
                            organism = synthetic construct
SEQUENCE: 619
acgtgcacag ggacatcaaa                                                       20

SEQ ID NO: 620          moltype = DNA  length = 20
FEATURE                 Location/Qualifiers
source                  1..20
                        mol_type = other DNA
                        organism = synthetic construct
SEQUENCE: 620
acaacatcct gctggaccgc                                                       20

SEQ ID NO: 621          moltype = DNA  length = 20
FEATURE                 Location/Qualifiers
source                  1..20
                        mol_type = other DNA
                        organism = synthetic construct
SEQUENCE: 621
agattgtcat ggccatagac                                                       20

SEQ ID NO: 622          moltype = DNA  length = 20
FEATURE                 Location/Qualifiers
source                  1..20
                        mol_type = other DNA
                        organism = synthetic construct
SEQUENCE: 622
ggaggcgctt tccctgctcc                                                       20

SEQ ID NO: 623          moltype = DNA  length = 20
FEATURE                 Location/Qualifiers
source                  1..20
                        mol_type = other DNA
                        organism = synthetic construct
SEQUENCE: 623
ccagtcaact acgcgaggca                                                       20

SEQ ID NO: 624          moltype = DNA  length = 20
FEATURE                 Location/Qualifiers
source                  1..20
                        mol_type = other DNA
                        organism = synthetic construct
SEQUENCE: 624
gggagatgga ggccatccgc                                                       20

SEQ ID NO: 625          moltype = DNA  length = 20
FEATURE                 Location/Qualifiers
source                  1..20
                        mol_type = other DNA
                        organism = synthetic construct
SEQUENCE: 625
gggtgtattc gcctatgaaa                                                       20

SEQ ID NO: 626          moltype = DNA  length = 20
FEATURE                 Location/Qualifiers
source                  1..20
                        mol_type = other DNA
                        organism = synthetic construct
SEQUENCE: 626
cctccgactc gctgacaggc                                                       20

SEQ ID NO: 627          moltype = DNA  length = 20
FEATURE                 Location/Qualifiers
source                  1..20
                        mol_type = other DNA
                        organism = synthetic construct
SEQUENCE: 627
ggatgaaaca gctgaagtgg                                                       20

SEQ ID NO: 628          moltype = DNA  length = 20
FEATURE                 Location/Qualifiers
source                  1..20
                        mol_type = other DNA
                        organism = synthetic construct
SEQUENCE: 628
ggcagttgca ggagcggatg                                                       20

SEQ ID NO: 629          moltype = DNA  length = 20
FEATURE                 Location/Qualifiers
source                  1..20
```

-continued

```
                        mol_type = other DNA
                        organism = synthetic construct
SEQUENCE: 629
cgcgctccct gaaccctaga                                               20

SEQ ID NO: 630          moltype = DNA   length = 20
FEATURE                 Location/Qualifiers
source                  1..20
                        mol_type = other DNA
                        organism = synthetic construct
SEQUENCE: 630
aggagaggga cgtgttggtg                                               20

SEQ ID NO: 631          moltype = DNA   length = 20
FEATURE                 Location/Qualifiers
source                  1..20
                        mol_type = other DNA
                        organism = synthetic construct
SEQUENCE: 631
aggcgctttc cctgctcctg                                               20

SEQ ID NO: 632          moltype = DNA   length = 20
FEATURE                 Location/Qualifiers
source                  1..20
                        mol_type = other DNA
                        organism = synthetic construct
SEQUENCE: 632
cttctacctg gcggagattg                                               20

SEQ ID NO: 633          moltype = DNA   length = 20
FEATURE                 Location/Qualifiers
source                  1..20
                        mol_type = other DNA
                        organism = synthetic construct
SEQUENCE: 633
gacatcaaac ccgacaacat                                               20

SEQ ID NO: 634          moltype = DNA   length = 20
FEATURE                 Location/Qualifiers
source                  1..20
                        mol_type = other DNA
                        organism = synthetic construct
SEQUENCE: 634
gcagttgcag gagcggatgg                                               20

SEQ ID NO: 635          moltype = DNA   length = 20
FEATURE                 Location/Qualifiers
source                  1..20
                        mol_type = other DNA
                        organism = synthetic construct
SEQUENCE: 635
ggctgaggcc gaggtgacgc                                               20

SEQ ID NO: 636          moltype = DNA   length = 20
FEATURE                 Location/Qualifiers
source                  1..20
                        mol_type = other DNA
                        organism = synthetic construct
SEQUENCE: 636
ctcgcgaata aaaggccctc                                               20

SEQ ID NO: 637          moltype = DNA   length = 20
FEATURE                 Location/Qualifiers
source                  1..20
                        mol_type = other DNA
                        organism = synthetic construct
SEQUENCE: 637
gagcacctct ctctgccgct                                               20

SEQ ID NO: 638          moltype = DNA   length = 20
FEATURE                 Location/Qualifiers
source                  1..20
                        mol_type = other DNA
                        organism = synthetic construct
SEQUENCE: 638
cccaatccac gttttggatg                                               20

SEQ ID NO: 639          moltype = DNA   length = 20
FEATURE                 Location/Qualifiers
```

```
source                      1..20
                            mol_type = other DNA
                            organism = synthetic construct
SEQUENCE: 639
aaggccctcc atctgcccaa                                                     20

SEQ ID NO: 640              moltype = DNA   length = 20
FEATURE                     Location/Qualifiers
source                      1..20
                            mol_type = other DNA
                            organism = synthetic construct
SEQUENCE: 640
tcaactacgc gaggcagagg                                                     20

SEQ ID NO: 641              moltype = DNA   length = 20
FEATURE                     Location/Qualifiers
source                      1..20
                            mol_type = other DNA
                            organism = synthetic construct
SEQUENCE: 641
cctgttcgcc gttgttctgt                                                     20

SEQ ID NO: 642              moltype = DNA   length = 20
FEATURE                     Location/Qualifiers
source                      1..20
                            mol_type = other DNA
                            organism = synthetic construct
SEQUENCE: 642
tcaacccga caacatcctg                                                      20

SEQ ID NO: 643              moltype = DNA   length = 20
FEATURE                     Location/Qualifiers
source                      1..20
                            mol_type = other DNA
                            organism = synthetic construct
SEQUENCE: 643
tgcggcagag gctgaggccg                                                     20

SEQ ID NO: 644              moltype = DNA   length = 20
FEATURE                     Location/Qualifiers
source                      1..20
                            mol_type = other DNA
                            organism = synthetic construct
SEQUENCE: 644
aacccgacaa catcctgctg                                                     20

SEQ ID NO: 645              moltype = DNA   length = 20
FEATURE                     Location/Qualifiers
source                      1..20
                            mol_type = other DNA
                            organism = synthetic construct
SEQUENCE: 645
caaggagcac ctctctctgc                                                     20

SEQ ID NO: 646              moltype = DNA   length = 20
FEATURE                     Location/Qualifiers
source                      1..20
                            mol_type = other DNA
                            organism = synthetic construct
SEQUENCE: 646
cccacaccca tggaactgga                                                     20

SEQ ID NO: 647              moltype = DNA   length = 20
FEATURE                     Location/Qualifiers
source                      1..20
                            mol_type = other DNA
                            organism = synthetic construct
SEQUENCE: 647
ttctttcggc caggctgagg                                                     20

SEQ ID NO: 648              moltype = DNA   length = 20
FEATURE                     Location/Qualifiers
source                      1..20
                            mol_type = other DNA
                            organism = synthetic construct
SEQUENCE: 648
ccctcgcgaa taaaaggccc                                                     20

SEQ ID NO: 649              moltype = DNA   length = 20
```

```
FEATURE                 Location/Qualifiers
source                  1..20
                        mol_type = other DNA
                        organism = synthetic construct
SEQUENCE: 649
gccacatccg cctggccgac                                                    20

SEQ ID NO: 650          moltype = DNA   length = 20
FEATURE                 Location/Qualifiers
source                  1..20
                        mol_type = other DNA
                        organism = synthetic construct
SEQUENCE: 650
ggcctgggaa ggcagcaagc                                                    20

SEQ ID NO: 651          moltype = DNA   length = 20
FEATURE                 Location/Qualifiers
source                  1..20
                        mol_type = other DNA
                        organism = synthetic construct
SEQUENCE: 651
cgacaacatc ctgctggacc                                                    20

SEQ ID NO: 652          moltype = DNA   length = 20
FEATURE                 Location/Qualifiers
source                  1..20
                        mol_type = other DNA
                        organism = synthetic construct
SEQUENCE: 652
ctcgactggg atggtctccg                                                    20

SEQ ID NO: 653          moltype = DNA   length = 20
FEATURE                 Location/Qualifiers
source                  1..20
                        mol_type = other DNA
                        organism = synthetic construct
SEQUENCE: 653
agtcaactac gcgaggcaga                                                    20

SEQ ID NO: 654          moltype = DNA   length = 20
FEATURE                 Location/Qualifiers
source                  1..20
                        mol_type = other DNA
                        organism = synthetic construct
SEQUENCE: 654
ttccaggatg agaactacct                                                    20

SEQ ID NO: 655          moltype = DNA   length = 20
FEATURE                 Location/Qualifiers
source                  1..20
                        mol_type = other DNA
                        organism = synthetic construct
SEQUENCE: 655
aagatcgtcc actacaagga                                                    20

SEQ ID NO: 656          moltype = DNA   length = 20
FEATURE                 Location/Qualifiers
source                  1..20
                        mol_type = other DNA
                        organism = synthetic construct
SEQUENCE: 656
ccaatccacg ttttggatgc                                                    20

SEQ ID NO: 657          moltype = DNA   length = 20
FEATURE                 Location/Qualifiers
source                  1..20
                        mol_type = other DNA
                        organism = synthetic construct
SEQUENCE: 657
ccgacaacat cctgctggac                                                    20

SEQ ID NO: 658          moltype = DNA   length = 20
FEATURE                 Location/Qualifiers
source                  1..20
                        mol_type = other DNA
                        organism = synthetic construct
SEQUENCE: 658
gaggtgacgc tgcgggagct                                                    20
```

-continued

| | | |
|---|---|---|
| SEQ ID NO: 659<br>FEATURE<br>source | moltype = DNA   length = 20<br>Location/Qualifiers<br>1..20<br>mol_type = other DNA<br>organism = synthetic construct | |
| SEQUENCE: 659<br>cctcacttgc gctgctctcg | | 20 |
| SEQ ID NO: 660<br>FEATURE<br>source | moltype = DNA   length = 20<br>Location/Qualifiers<br>1..20<br>mol_type = other DNA<br>organism = synthetic construct | |
| SEQUENCE: 660<br>tatcggaggc gctttccctg | | 20 |
| SEQ ID NO: 661<br>FEATURE<br>source | moltype = DNA   length = 20<br>Location/Qualifiers<br>1..20<br>mol_type = other DNA<br>organism = synthetic construct | |
| SEQUENCE: 661<br>ggtgtattcg cctatgaaat | | 20 |
| SEQ ID NO: 662<br>FEATURE<br>source | moltype = DNA   length = 20<br>Location/Qualifiers<br>1..20<br>mol_type = other DNA<br>organism = synthetic construct | |
| SEQUENCE: 662<br>ggccacatcc gcctggccga | | 20 |
| SEQ ID NO: 663<br>FEATURE<br>source | moltype = DNA   length = 20<br>Location/Qualifiers<br>1..20<br>mol_type = other DNA<br>organism = synthetic construct | |
| SEQUENCE: 663<br>gacttccgga cacatccctt | | 20 |
| SEQ ID NO: 664<br>FEATURE<br>source | moltype = DNA   length = 20<br>Location/Qualifiers<br>1..20<br>mol_type = other DNA<br>organism = synthetic construct | |
| SEQUENCE: 664<br>gcaagatcgt ccactacaag | | 20 |
| SEQ ID NO: 665<br>FEATURE<br>source | moltype = DNA   length = 20<br>Location/Qualifiers<br>1..20<br>mol_type = other DNA<br>organism = synthetic construct | |
| SEQUENCE: 665<br>ccacatccgc ctggccgact | | 20 |
| SEQ ID NO: 666<br>FEATURE<br>source | moltype = DNA   length = 20<br>Location/Qualifiers<br>1..20<br>mol_type = other DNA<br>organism = synthetic construct | |
| SEQUENCE: 666<br>tctttcggcc aggctgaggc | | 20 |
| SEQ ID NO: 667<br>FEATURE<br>source | moltype = DNA   length = 20<br>Location/Qualifiers<br>1..20<br>mol_type = other DNA<br>organism = synthetic construct | |
| SEQUENCE: 667<br>gctgaggccg aggtgacgct | | 20 |
| SEQ ID NO: 668<br>FEATURE<br>source | moltype = DNA   length = 20<br>Location/Qualifiers<br>1..20<br>mol_type = other DNA<br>organism = synthetic construct | |
| SEQUENCE: 668<br>agcacctctc tctgccgctg | | 20 |

```
SEQ ID NO: 669          moltype = DNA  length = 20
FEATURE                 Location/Qualifiers
source                  1..20
                        mol_type = other DNA
                        organism = synthetic construct
SEQUENCE: 669
gcacctctct ctgccgctgg                                                  20

SEQ ID NO: 670          moltype = DNA  length = 20
FEATURE                 Location/Qualifiers
source                  1..20
                        mol_type = other DNA
                        organism = synthetic construct
SEQUENCE: 670
ggcaagatcg tccactacaa                                                  20

SEQ ID NO: 671          moltype = DNA  length = 20
FEATURE                 Location/Qualifiers
source                  1..20
                        mol_type = other DNA
                        organism = synthetic construct
SEQUENCE: 671
ctatcggagg cgctttccct                                                  20

SEQ ID NO: 672          moltype = DNA  length = 20
FEATURE                 Location/Qualifiers
source                  1..20
                        mol_type = other DNA
                        organism = synthetic construct
SEQUENCE: 672
cctatcggag gcgctttccc                                                  20

SEQ ID NO: 673          moltype = DNA  length = 3635
FEATURE                 Location/Qualifiers
source                  1..3635
                        mol_type = genomic DNA
                        organism = Homo sapiens
SEQUENCE: 673
tcctggcggc tgcgaggttt cactgcaggg gcgccagtgg gctcagtgac gctgcggcct      60
ccttctgcct aggtcccaac gcttcggggc aggggtgcgg tcttgcaata ggaagccgag     120
cgtcttgcaa gcttcccgtc gggcaccagc tactcggccc cgcaccctac ctggtgcatt     180
ccctagacac ctccggggtc cctacctgga gatccccgga gccccccttc ctgcgccagc     240
catgcctttt aaccgcactt tgtccatgtc ctcactgcca ggactggagg actgggagga     300
tgaattcgac ctggagaacg cagtgctctt cgaagtggcc tgggaggtgg ctaacaaggt     360
gggtggcatc tacacggtgc tgcagacgaa ggcgaaggtg acaggggacg aatgggcga     420
caactacttc ctggtgggc cgtacacgga gcagggcgtg aggacccagg tggaactgct     480
ggaggccccc acccggccc tgaagaggac actggattcc atgaacagca agggctgcaa     540
ggtgtatttc gggcgctggc tgatcgaggg aggccctg gtggtgctcc tggacgtggg     600
tgcctcagct tgggccctgg agcgctgaa gggagagctc tgggatacct gcaacatcgg     660
agtgccgtgg tacgaccgcg aggccaacga cgctgtcctc tttggctttc tgaccacctg     720
gttcctgggt gagttcctgg cacagagtga ggagaagcca catgtggttg ctcacttcca     780
tgagtggttg gcaggcgttg gactctgcct gtgtcgtgcc cggcgactgc ctgtagcaac     840
catcttcacc acccatgcca cgctgctggg gcgctacctg tgtgccggtg ccgtggactt     900
ctacaacaac ctgagagaact tcaacgtgga caaggaagca ggggagaggc agatctacca     960
ccgatactgc atggaaaggg cggcagccca ctgcgctcac gtcttcacta ctgtgtccca    1020
gatcaccgcc atcgaggcac agcacttgct caagaggaaa ccagatattg taccccaa     1080
tgggctgaat gtgaagaagt tttctgccat gcatgagttc cagaacctcc atgctcgag     1140
caaggctcga atccaggagt ttgtgcgggg ccattttttat gggcatctgg acttcaactt    1200
ggacaagacc ttatacttct ttatcgccgg ccgctatgag ttctccaaca agggtgctga    1260
cgtcttcctg gaggcattgg ctcggctcaa ctatctgctc agagtgaacg gcagcgagca    1320
gacagtggtt gccttcttca tcatgccagc gcggaccaac aatttcaacg tggaaaccct    1380
caaaggccaa gctgtgcgca aacagctttg ggacacggcc aacacggtga aggaaaagtt    1440
cggggaggaag ctttatgaat ccttactggt tgggagcctt cccgacatga caagatgct    1500
ggataaggaa gacttcacta tgatgaagag agccatcttt gcaacgcagc ggcagtcttt    1560
ccccctgtg tgcacccaca atatgctgga tgactcctca gaccccatcc tgaccaccat    1620
ccgccgaatc ggcctcttca atagcagtgc cgacagggtg aaggtgattt ccacccgga    1680
gttcctctcc tccacaagcc ccctgctccc tgtggactgg gaggagtttg tccgtggctg    1740
tcaccttgga gtcttcccct cctactatga gccttggtgc tacacaccgg ctgagtgcac    1800
ggttatggga atccccagta tctccaccaa tctctccggc ttcggctgct catggaggga    1860
acacatcgca gaccctcag cttacggtat ctacattctt gaccggcggt tccgcagcct    1920
ggatgattcc tgctcgcagc tcacctcctt cctctacagt ttctgtcagc agagccggcg    1980
gcagcgtatc atccagcgga accgcacgga gcgcctctcc gaccttctgg actggaaata    2040
cctaggccgg tactatatgt ctgcgcgcca catgcgctg tccaaggcct ttcaagacac    2100
cttcacctac gagcccaacg aggcggatgc ggcccagggg taccgctacc cacgccagc    2160
ctcggtgcca ccgtcgccct cgctgtcacg acactccagc ccgcaccaga gtgaggacga    2220
ggaggatccc cggaacgggc cgctggagga agcggcgag cgctacgatg aggacgagga    2280
ggccgccaag gaccggcgca acatccgtgc accagagtgg ccgcgccgag cgtcctgcac    2340
ctcctccacc agcggcagca agcgcaactc tgtggacacg gccacctcca gctcactcag    2400
```

```
caccccgagc gagcccctca gccccaccag ctccctgggc gaggagcgta actaagtccg   2460
ccccaccaca ctcccgcct gtcctgcctc tctgctccag agagaggatg cagaggggtg    2520
ctgctcctaa accccgctc cagatctgca ctgggtgtgg cccgcagtg cccccaccca     2580
gtccgccaaa cactccaccc cctccagctc cagtttccaa gttcctgcac tccagaatcc   2640
acaaagccgt gcctttctct ggctccagaa tatgcataat cagcgcctg gagtccctg     2700
ggcctggacc gcttcccaga ggccaggaat ctgccattac tctgcggtgg tgccagaggt   2760
tttaggaaac ctggcatggt gctttcaggt ctggggcttt tagagccccc cgtgtggctt   2820
acaaattcta cagcatacag agcaggccac gctcaggccc ggcatgcggg ccaccaagtt   2880
ctggaaacca cgtggtgtcc ctgcgaatgg ggcgatcaag tccagagccg gggcactttg   2940
agagtttgaa ggtaactgag agcagatggt cctccatttc aactccagaa gtggggctct   3000
gggagggatg ttctagccct ccctggcatg tcagagccag gctctgcctg gaggatccct   3060
ccatccggct cctgtcatcc cctacacttt ggccaagcaa gaggtggtag aaccacttgg   3120
ctgctcattc cttctggagg acacacagtc tcagtccaga tgccttcctg tctttctggc   3180
cctttctgga ccagatccta ctcttccttt ctaaatctga gatctccctc cagggaatcc   3240
gcctgcagag gacagagctg gctgtcttcc cccaccccta acctggctta ttcccaactg   3300
ctctgcccac tgtgaaacca ctaggttcta ggtcctggct tctagatctg gaaccttacc   3360
acgttactgc atactgatcc cttttcccatg atccagaact gaggtcactg ggttctagaa   3420
ccccacatt tacctcgagg ctcttccatc cccaaactgt gccgcctt cagctttggt      3480
gaaaggagg gcccctcatg tgtgctgtgc tgtgtctgca ccgcttggtt tgcagttgag    3540
aggggaggc aggagggtg tgattggagt gtgtccggag atgagatgaa aaaaatacat     3600
ctatatttaa gaatcccaaa aaaaaaaaaa aaaaa                              3635
```

SEQ ID NO: 674          moltype = DNA   length = 3681
FEATURE                 Location/Qualifiers
source                  1..3681
                        mol_type = genomic DNA
                        organism = Mus musculus
SEQUENCE: 674

```
actgcagctg cccgcccgat tcagtgtctc agctcaccct acctgagtcg gagcgctctg   60
gggcggggt gcgtcgtgc aataggaagc ggagcgcctt gcaagcttcc cctgggacac     120
ccgctaactc taccggtcac caagtctgct gcgttcccag ccgatctctc tggtttccag   180
ttttggtgct cgaagtcccc tgccgcagt agccatgcct ctcagccgca gtctctctgt    240
gtcctcgctt ccaggattgg aagactggga ggatgaattc gaccccgaga acgcagtgct   300
tttcgaggtg gcctgggagg tggccaacaa ggtgggtggc atctacactg tgctgcagac   360
gaaggcgaag gtgacagggg atgaatgggg tgacaactac tatctggtgg gaccatacac   420
ggagcagggt gtgaggacgc aggtagagct cctggagccc ccaactccgg aactgaagag   480
gactttggat tccatgaaca gcaagggttg taaggtgtat tttgggcgtt ggctgatcga   540
gggggaccc ctagtggtgc tcctggatgt aggagcctca gcttgggccc tggagcgctg    600
gaaggtgag cttttgggaca cctgcaacat cggggtaccc tggtacgacc gcgaggccaa   660
tgacgctgtc ctgttcggct tcctcaccac ctggttcctg ggtgagttcc tggcccagaa   720
cgaagagaag ccgtatgtgg ttgccactt ccacgaatgg ttggctggcg ttggtctgtg    780
tctgtgccgt gccggcgct tgccggtggc aaccatcttc accactcatg ccacgctgct    840
gggggctac ctgtgtgctg gcgctgtgga cttctacaac aacctggaga atttcaatgt    900
agacaaggaa gcaggagaga ggcagatcta tcaccggtac tgcatggagc gtgcagcagc   960
tcactgtgcc catgtcttca ctaccgtatc ccagatcacc gcaatcgagg ctcaacacct   1020
ccttaagaga aaaccagata ttgtgacccc caacgggctg aatgtgaaga agttctctgc   1080
tatgcacgaa ttccagaacc ttcatgctca gagcaaagca cgaatccagg aatttgtgcg   1140
tggccatttt tatgggcacc tggacttcaa cctagacaag acttttgtatt tctttatcgc   1200
tggccgctat gagttttcca acaagggagc tgatgtgttc ctgaggcat tggcccggct    1260
caactatctg ctcagagtga atggcagtga gcaaacagtt gtcgcattct tcatcatgcc   1320
ggcccggacc aataatttca acgtggaaac cctgaaggcc caagccgtgc gcaaacaact   1380
atgggacaca gccaatacag tcaaggagaa atttgggagg aagctctacg aatcccttt    1440
agtggggagc ctcccggaca tgaacaagat gctggacaag gaggacttca ctatgatgaa   1500
gagagccatc tttgccactc agcggcagtc tttcccacca gtgtgcaccc acaacatgct   1560
ggacactcc tcagacccca tcttgaccac catccgccga attggccttt tcaacagcag    1620
tgccgaccgt gtgaaggtga tttttcaccc agaattcctt tcttccacaa gccctctcct   1680
ccccgtggat tatgaggaat ttgtccgcgg ctgtcacctt ggggtcttcc cctcctacta   1740
tgagccctgg ggctacacac cagcggagtg cactgtcatg gcatcccca gcatctccac   1800
caacctctcc ggctttggct gctttatgga ggaacacatc gcagatccct cagcttacgg   1860
catttacatt ctggatcgga ggttccgcag cctggatgat tcatgctcac agctcacctc   1920
cttcctgtac agcttctgcc agcagagccg gcgacagcgc atcatccagc ggaaccgcac   1980
agaacggttc tcggacttgc tagattgaa gtacctgggc cggtactaca tgtctgcgcg   2040
ccacatggct ctggccaagg cctttccaga ccacttcacc tatgaacccc atgaggtaga   2100
tgcgacccag gggtaccggt acccacgacc agcctccgtc ccgcccgtcc cctcactgtc   2160
tcgacactcc agcccacacc agagtgagga tgaggaagac ccacgggatg gacccctggg   2220
ggaagacagt gagcgttatg atgaggaaga ggaggctgcc aaggaccgcc gcaacatccg   2280
ggcacctgag tggccacgca gggcctcctg ttcctcctcc acaggtggca gcaagagaag   2340
caactcggtg gacactgggc cctccagctc actcagcaca cccactgagc ccctgagtcg   2400
taccagttcc ctgggtgagg agcgcaacta agctcccacc cccatccat tccctgcctg     2460
tccagtgctc ctctcgcaga gggcctatgc agatgggagg gtgcctgaac cccactccag   2520
actcttgagt gggacccta cccagtgtgg tccatagcct aacctctgtt tcagacactc    2580
cagcccttga gctccaatct tggagttccc gcactcacg ccgccgtgcc tttcttggat    2640
tgcaggatgc attctttgtg cactgatctg gagtctccag gcttagactg ggtcccagag   2700
gccaggcctg tgccattgtt tttcaatgcc agaggtttta gcacctggt tttattggct    2760
tccaggctgt ggcttcttcg tttgatccta taatcataca gagtatgctt tgctcaggcc   2820
tgcctctggg accacctcat gttggattct gtgtggcttc ccgaatcagc caagttcaga   2880
gttaggacat ttcaggggatt aacataattg aaaatcagcc tgcaaggtag ctcagtagct   2940
ctgtcgacac attgcttgtc tagcatgccc gaagccctgg gatctaactc tagaacctca   3000
taaacctggt gcggtgatac acatctgtaa tcccagcact cggtaggtag aggtagacgg   3060
```

```
atcaagagtt aaaggccatc atcctctgct acatagggag ttcaaggcca aactgggcaa      3120
catgagacac tgtctcaaaa gcaaagtaaa ggtggtggaa tgctcacggt cctccatttc      3180
aacccacgac tgcgatgctg ggacatgctg caaggttggc ctccctgggt gtgttcttca      3240
aaggagcatg cggagttgga ccagacacct ttctgccttt tttctggacc agaccttctt      3300
ttccttggtc cagtgtcccc tctagggaat gcctccattg agggcagaat gtctgtcaac      3360
cccacaagtg ctcagcccac tgtgaaacca ctgggttctg ggtcccagtg gctgaatcag      3420
gagtcttttg tcactgtgct gcaccccggt cccctttcct gatacaaaac cgagcccacc      3480
ggcttcttga agcccacat gtacctcgag gcctttctgc ctgcaagctt cagtgaatgg       3540
gcgggcccct cctcacgtgt gctgtgtctg gcccagtgcc tttggtttgc atttgggagg      3600
gggagggcag aaggtgtgtg attggagtgt gtctagagat gaaaaaaaaa aaagaaaat      3660
acacctgtat ttaagaatgc c                                                3681

SEQ ID NO: 675          moltype = AA  length = 5
FEATURE                 Location/Qualifiers
source                  1..5
                        mol_type = protein
                        organism = synthetic construct
VARIANT                 3
                        note = X can be any naturally occurring amino acid
SEQUENCE: 675
LPXTG                                                                  5

SEQ ID NO: 676          moltype = RNA  length = 19
FEATURE                 Location/Qualifiers
source                  1..19
                        mol_type = other RNA
                        organism = synthetic construct
SEQUENCE: 676
cttcctggat ggcttcaat                                                   19

SEQ ID NO: 677          moltype = RNA  length = 19
FEATURE                 Location/Qualifiers
source                  1..19
                        mol_type = other RNA
                        organism = synthetic construct
SEQUENCE: 677
gtacattaag atggacttc                                                   19

SEQ ID NO: 678          moltype = RNA  length = 30
FEATURE                 Location/Qualifiers
source                  1..30
                        mol_type = other RNA
                        organism = synthetic construct
SEQUENCE: 678
tatctggata ggtggtatca agatctgtaa                                       30

SEQ ID NO: 679          moltype = RNA  length = 25
FEATURE                 Location/Qualifiers
source                  1..25
                        mol_type = other RNA
                        organism = synthetic construct
SEQUENCE: 679
atgtaactga aaatgttctt cttta                                            25

SEQ ID NO: 680          moltype = RNA  length = 30
FEATURE                 Location/Qualifiers
source                  1..30
                        mol_type = other RNA
                        organism = synthetic construct
SEQUENCE: 680
tggataggtg gtatcaacat ctgtaagcac                                       30

SEQ ID NO: 681          moltype = RNA  length = 22
FEATURE                 Location/Qualifiers
source                  1..22
                        mol_type = other RNA
                        organism = synthetic construct
SEQUENCE: 681
gataggtggt atcaacatct gt                                               22

SEQ ID NO: 682          moltype = RNA  length = 30
FEATURE                 Location/Qualifiers
source                  1..30
                        mol_type = other RNA
                        organism = synthetic construct
SEQUENCE: 682
tatctggata ggtggtatca acatctgtaa                                       30

SEQ ID NO: 683          moltype = RNA  length = 25
```

```
FEATURE                 Location/Qualifiers
source                  1..25
                        mol_type = other RNA
                        organism = synthetic construct
SEQUENCE: 683
aaacttggaa gagtgatgtg atgta                                           25

SEQ ID NO: 684          moltype = RNA   length = 27
FEATURE                 Location/Qualifiers
source                  1..27
                        mol_type = other RNA
                        organism = synthetic construct
SEQUENCE: 684
gctcacttgt tgaggcaaaa cttggaa                                         27

SEQ ID NO: 685          moltype = RNA   length = 25
FEATURE                 Location/Qualifiers
source                  1..25
                        mol_type = other RNA
                        organism = synthetic construct
SEQUENCE: 685
gccttggcaa catttccact tcctg                                           25

SEQ ID NO: 686          moltype = RNA   length = 25
FEATURE                 Location/Qualifiers
source                  1..25
                        mol_type = other RNA
                        organism = synthetic construct
SEQUENCE: 686
tacacacttt acctgttgag aatag                                           25

SEQ ID NO: 687          moltype = RNA   length = 24
FEATURE                 Location/Qualifiers
source                  1..24
                        mol_type = other RNA
                        organism = synthetic construct
SEQUENCE: 687
gataggtggt atcaacatct gtaa                                            24

SEQ ID NO: 688          moltype = RNA   length = 21
FEATURE                 Location/Qualifiers
source                  1..21
                        mol_type = other RNA
                        organism = synthetic construct
SEQUENCE: 688
gataggtggt atcaacatct g                                               21

SEQ ID NO: 689          moltype = RNA   length = 25
FEATURE                 Location/Qualifiers
source                  1..25
                        mol_type = other RNA
                        organism = synthetic construct
SEQUENCE: 689
gataggtggt atcaacatct gtaag                                           25

SEQ ID NO: 690          moltype = RNA   length = 20
FEATURE                 Location/Qualifiers
source                  1..20
                        mol_type = other RNA
                        organism = synthetic construct
SEQUENCE: 690
ggtggtatca acatctgtaa                                                 20

SEQ ID NO: 691          moltype = RNA   length = 20
FEATURE                 Location/Qualifiers
source                  1..20
                        mol_type = other RNA
                        organism = synthetic construct
SEQUENCE: 691
gtatcaacat ctgtaagcac                                                 20

SEQ ID NO: 692          moltype = RNA   length = 30
FEATURE                 Location/Qualifiers
source                  1..30
                        mol_type = other RNA
                        organism = synthetic construct
misc_difference         27
                        note = n can be any nucleotide
SEQUENCE: 692
```

```
cggctaattt cagagggcgc tttcttngac                                             30

SEQ ID NO: 693          moltype = RNA   length = 26
FEATURE                 Location/Qualifiers
source                  1..26
                        mol_type = other RNA
                        organism = synthetic construct
SEQUENCE: 693
acagtggtgc tgagatagta taggcc                                                 26

SEQ ID NO: 694          moltype = RNA   length = 22
FEATURE                 Location/Qualifiers
source                  1..22
                        mol_type = other RNA
                        organism = synthetic construct
SEQUENCE: 694
taggccactt tgttgctctt gc                                                     22

SEQ ID NO: 695          moltype = RNA   length = 19
FEATURE                 Location/Qualifiers
source                  1..19
                        mol_type = other RNA
                        organism = synthetic construct
SEQUENCE: 695
ttcagagggc gctttcttc                                                         19

SEQ ID NO: 696          moltype = RNA   length = 30
FEATURE                 Location/Qualifiers
source                  1..30
                        mol_type = other RNA
                        organism = synthetic construct
SEQUENCE: 696
tcttcaggtg caccttctgt ttctcaatct                                             30

SEQ ID NO: 697          moltype = RNA   length = 30
FEATURE                 Location/Qualifiers
source                  1..30
                        mol_type = other RNA
                        organism = synthetic construct
SEQUENCE: 697
tctgtgatac tcttcaggtg caccttctgt                                             30

SEQ ID NO: 698          moltype = RNA   length = 21
FEATURE                 Location/Qualifiers
source                  1..21
                        mol_type = other RNA
                        organism = synthetic construct
SEQUENCE: 698
tcttctgctc gggaggtgac a                                                      21

SEQ ID NO: 699          moltype = RNA   length = 20
FEATURE                 Location/Qualifiers
source                  1..20
                        mol_type = other RNA
                        organism = synthetic construct
SEQUENCE: 699
ccagttacta ttcagaagac                                                        20

SEQ ID NO: 700          moltype = RNA   length = 20
FEATURE                 Location/Qualifiers
source                  1..20
                        mol_type = other RNA
                        organism = synthetic construct
SEQUENCE: 700
tcttcaggtg caccttctgt                                                        20

SEQ ID NO: 701          moltype = RNA   length = 18
FEATURE                 Location/Qualifiers
source                  1..18
                        mol_type = other RNA
                        organism = synthetic construct
SEQUENCE: 701
tgctgctgtc ttcttgct                                                          18

SEQ ID NO: 702          moltype = RNA   length = 19
FEATURE                 Location/Qualifiers
source                  1..19
                        mol_type = other RNA
                        organism = synthetic construct
```

-continued

| | | |
|---|---|---|
| SEQUENCE: 702 | | |
| ttgttaactt tttcccatt | | 19 |
| SEQ ID NO: 703 | moltype = RNA   length = 20 | |
| FEATURE | Location/Qualifiers | |
| source | 1..20 | |
| | mol_type = other RNA | |
| | organism = synthetic construct | |
| SEQUENCE: 703 | | |
| tgttaacttt ttcccattgg | | 20 |
| SEQ ID NO: 704 | moltype = RNA   length = 20 | |
| FEATURE | Location/Qualifiers | |
| source | 1..20 | |
| | mol_type = other RNA | |
| | organism = synthetic construct | |
| SEQUENCE: 704 | | |
| cattttgtta acttttccc | | 20 |
| SEQ ID NO: 705 | moltype = RNA   length = 19 | |
| FEATURE | Location/Qualifiers | |
| source | 1..19 | |
| | mol_type = other RNA | |
| | organism = synthetic construct | |
| SEQUENCE: 705 | | |
| ctgtagcttc acccttttcc | | 19 |
| SEQ ID NO: 706 | moltype = RNA   length = 26 | |
| FEATURE | Location/Qualifiers | |
| source | 1..26 | |
| | mol_type = other RNA | |
| | organism = synthetic construct | |
| SEQUENCE: 706 | | |
| gagagcttcc tgtagcttca ccctttt | | 26 |
| SEQ ID NO: 707 | moltype = RNA   length = 28 | |
| FEATURE | Location/Qualifiers | |
| source | 1..28 | |
| | mol_type = other RNA | |
| | organism = synthetic construct | |
| SEQUENCE: 707 | | |
| tcctgtagct tcacccttc cacaggcg | | 28 |
| SEQ ID NO: 708 | moltype = RNA   length = 20 | |
| FEATURE | Location/Qualifiers | |
| source | 1..20 | |
| | mol_type = other RNA | |
| | organism = synthetic construct | |
| SEQUENCE: 708 | | |
| tgtgttacct accctttgtcg | | 20 |
| SEQ ID NO: 709 | moltype = RNA   length = 27 | |
| FEATURE | Location/Qualifiers | |
| source | 1..27 | |
| | mol_type = other RNA | |
| | organism = synthetic construct | |
| SEQUENCE: 709 | | |
| tagactatct tttatattct gtaatat | | 27 |
| SEQ ID NO: 710 | moltype = RNA   length = 29 | |
| FEATURE | Location/Qualifiers | |
| source | 1..29 | |
| | mol_type = other RNA | |
| | organism = synthetic construct | |
| SEQUENCE: 710 | | |
| gagagcttcc tgtagcttca ccctttcca | | 29 |
| SEQ ID NO: 711 | moltype = RNA   length = 31 | |
| FEATURE | Location/Qualifiers | |
| source | 1..31 | |
| | mol_type = other RNA | |
| | organism = synthetic construct | |
| SEQUENCE: 711 | | |
| ttcctgtagc ttcacccttt ccacaggcgt t | | 31 |
| SEQ ID NO: 712 | moltype = RNA   length = 23 | |
| FEATURE | Location/Qualifiers | |
| source | 1..23 | |
| | mol_type = other RNA | |

-continued

```
                        organism = synthetic construct
SEQUENCE: 712
agcttcctgt agcttcaccc ttt                                              23

SEQ ID NO: 713          moltype = RNA   length = 29
FEATURE                 Location/Qualifiers
source                  1..29
                        mol_type = other RNA
                        organism = synthetic construct
SEQUENCE: 713
ggagagagct tcctgtagct tcacccttt                                        29

SEQ ID NO: 714          moltype = RNA   length = 23
FEATURE                 Location/Qualifiers
source                  1..23
                        mol_type = other RNA
                        organism = synthetic construct
SEQUENCE: 714
gagagcttcc tgtagcttca ccc                                              23

SEQ ID NO: 715          moltype = RNA   length = 25
FEATURE                 Location/Qualifiers
source                  1..25
                        mol_type = other RNA
                        organism = synthetic construct
SEQUENCE: 715
tatgtgttac ctaccttgt cggtc                                             25

SEQ ID NO: 716          moltype = RNA   length = 20
FEATURE                 Location/Qualifiers
source                  1..20
                        mol_type = other RNA
                        organism = synthetic construct
SEQUENCE: 716
ggagagagct tcctgtagct                                                  20

SEQ ID NO: 717          moltype = RNA   length = 23
FEATURE                 Location/Qualifiers
source                  1..23
                        mol_type = other RNA
                        organism = synthetic construct
SEQUENCE: 717
tcacccttc cacaggcgtt gca                                               23

SEQ ID NO: 718          moltype = RNA   length = 28
FEATURE                 Location/Qualifiers
source                  1..28
                        mol_type = other RNA
                        organism = synthetic construct
SEQUENCE: 718
gctgggagag agcttcctgt agcttcac                                         28

SEQ ID NO: 719          moltype = RNA   length = 28
FEATURE                 Location/Qualifiers
source                  1..28
                        mol_type = other RNA
                        organism = synthetic construct
SEQUENCE: 719
tgttacctac ccttgtcggt ccttgtac                                         28

SEQ ID NO: 720          moltype = RNA   length = 28
FEATURE                 Location/Qualifiers
source                  1..28
                        mol_type = other RNA
                        organism = synthetic construct
SEQUENCE: 720
ctgctgtctt cttgctatga ataatgtc                                         28

SEQ ID NO: 721          moltype = RNA   length = 28
FEATURE                 Location/Qualifiers
source                  1..28
                        mol_type = other RNA
                        organism = synthetic construct
SEQUENCE: 721
ggcgttgcac tttgcaatgc tgctgtct                                         28

SEQ ID NO: 722          moltype = RNA   length = 28
FEATURE                 Location/Qualifiers
source                  1..28
```

```
                              mol_type = other RNA
                              organism = synthetic construct
SEQUENCE: 722
ttggaaatca agctgggaga gagcttcc                                          28

SEQ ID NO: 723                moltype = RNA   length = 28
FEATURE                       Location/Qualifiers
source                        1..28
                              mol_type = other RNA
                              organism = synthetic construct
SEQUENCE: 723
ctacccttgt cggtccttgt acattttg                                          28

SEQ ID NO: 724                moltype = RNA   length = 28
FEATURE                       Location/Qualifiers
source                        1..28
                              mol_type = other RNA
                              organism = synthetic construct
SEQUENCE: 724
gtcaatccga cctgagcttt gttgtaga                                          28

SEQ ID NO: 725                moltype = RNA   length = 27
FEATURE                       Location/Qualifiers
source                        1..27
                              mol_type = other RNA
                              organism = synthetic construct
SEQUENCE: 725
cttgctatga ataatgtcaa tccgacc                                           27

SEQ ID NO: 726                moltype = RNA   length = 28
FEATURE                       Location/Qualifiers
source                        1..28
                              mol_type = other RNA
                              organism = synthetic construct
SEQUENCE: 726
tatatgtgtt acctaccctt gtcggtcc                                          28

SEQ ID NO: 727                moltype = RNA   length = 20
FEATURE                       Location/Qualifiers
source                        1..20
                              mol_type = other RNA
                              organism = synthetic construct
SEQUENCE: 727
tttgtgtctt tctgagaaac                                                   20

SEQ ID NO: 728                moltype = RNA   length = 20
FEATURE                       Location/Qualifiers
source                        1..20
                              mol_type = other RNA
                              organism = synthetic construct
SEQUENCE: 728
aaagacttac cttaagatac                                                   20

SEQ ID NO: 729                moltype = RNA   length = 20
FEATURE                       Location/Qualifiers
source                        1..20
                              mol_type = other RNA
                              organism = synthetic construct
SEQUENCE: 729
atctgtcaaa tcgcctgcag                                                   20

SEQ ID NO: 730                moltype = RNA   length = 19
FEATURE                       Location/Qualifiers
source                        1..19
                              mol_type = other RNA
                              organism = synthetic construct
SEQUENCE: 730
cgccgccatt tctcaacag                                                    19

SEQ ID NO: 731                moltype = RNA   length = 20
FEATURE                       Location/Qualifiers
source                        1..20
                              mol_type = other RNA
                              organism = synthetic construct
SEQUENCE: 731
tttgtattta gcatgttccc                                                   20

SEQ ID NO: 732                moltype = RNA   length = 17
FEATURE                       Location/Qualifiers
```

```
source                  1..17
                        mol_type = other RNA
                        organism = synthetic construct
SEQUENCE: 732
ccgccatttc tcaacag                                                        17

SEQ ID NO: 733          moltype = RNA   length = 21
FEATURE                 Location/Qualifiers
source                  1..21
                        mol_type = other RNA
                        organism = synthetic construct
SEQUENCE: 733
ttctcaggaa tttgtgtctt t                                                   21

SEQ ID NO: 734          moltype = RNA   length = 11
FEATURE                 Location/Qualifiers
source                  1..11
                        mol_type = other RNA
                        organism = synthetic construct
SEQUENCE: 734
gacaactctt t                                                              11

SEQ ID NO: 735          moltype = RNA   length = 20
FEATURE                 Location/Qualifiers
source                  1..20
                        mol_type = other RNA
                        organism = synthetic construct
SEQUENCE: 735
tcagcttctg ttagccactg                                                     20

SEQ ID NO: 736          moltype = RNA   length = 24
FEATURE                 Location/Qualifiers
source                  1..24
                        mol_type = other RNA
                        organism = synthetic construct
SEQUENCE: 736
tgttcagctt ctgttagcca ctga                                                24

SEQ ID NO: 737          moltype = RNA   length = 27
FEATURE                 Location/Qualifiers
source                  1..27
                        mol_type = other RNA
                        organism = synthetic construct
SEQUENCE: 737
ctgttcagct tctgttagcc actgatt                                             27

SEQ ID NO: 738          moltype = RNA   length = 30
FEATURE                 Location/Qualifiers
source                  1..30
                        mol_type = other RNA
                        organism = synthetic construct
SEQUENCE: 738
ttctcaacag atctgtcaaa tcgcctgcag                                          30

SEQ ID NO: 739          moltype = RNA   length = 25
FEATURE                 Location/Qualifiers
source                  1..25
                        mol_type = other RNA
                        organism = synthetic construct
SEQUENCE: 739
gccactgatt aaatatcttt atatc                                               25

SEQ ID NO: 740          moltype = RNA   length = 30
FEATURE                 Location/Qualifiers
source                  1..30
                        mol_type = other RNA
                        organism = synthetic construct
SEQUENCE: 740
tctgttagcc actgattaaa tatctttata                                          30

SEQ ID NO: 741          moltype = RNA   length = 31
FEATURE                 Location/Qualifiers
source                  1..31
                        mol_type = other RNA
                        organism = synthetic construct
SEQUENCE: 741
gagaaactgt tcagcttctg ttagccactg a                                        31

SEQ ID NO: 742          moltype = RNA   length = 31
```

```
FEATURE                 Location/Qualifiers
source                  1..31
                        mol_type = other RNA
                        organism = synthetic construct
SEQUENCE: 742
tctttctgag aaactgttca gcttctgtta g                                      31

SEQ ID NO: 743          moltype = RNA   length = 26
FEATURE                 Location/Qualifiers
source                  1..26
                        mol_type = other RNA
                        organism = synthetic construct
SEQUENCE: 743
cagatctgtc aaatcgcctg caggta                                            26

SEQ ID NO: 744          moltype = RNA   length = 26
FEATURE                 Location/Qualifiers
source                  1..26
                        mol_type = other RNA
                        organism = synthetic construct
SEQUENCE: 744
caacagatct gtcaaatcgc ctgcag                                            26

SEQ ID NO: 745          moltype = RNA   length = 33
FEATURE                 Location/Qualifiers
source                  1..33
                        mol_type = other RNA
                        organism = synthetic construct
SEQUENCE: 745
aaactgttca gcttctgtta gccactgatt aaa                                    33

SEQ ID NO: 746          moltype = RNA   length = 31
FEATURE                 Location/Qualifiers
source                  1..31
                        mol_type = other RNA
                        organism = synthetic construct
SEQUENCE: 746
gaaactgttc agcttctgtt agccactgat t                                      31

SEQ ID NO: 747          moltype = RNA   length = 28
FEATURE                 Location/Qualifiers
source                  1..28
                        mol_type = other RNA
                        organism = synthetic construct
SEQUENCE: 747
aaactgttca gcttctgtta gccactga                                          28

SEQ ID NO: 748          moltype = RNA   length = 28
FEATURE                 Location/Qualifiers
source                  1..28
                        mol_type = other RNA
                        organism = synthetic construct
SEQUENCE: 748
tgagaaactg ttcagcttct gttagcca                                          28

SEQ ID NO: 749          moltype = RNA   length = 32
FEATURE                 Location/Qualifiers
source                  1..32
                        mol_type = other RNA
                        organism = synthetic construct
SEQUENCE: 749
ttctgagaaa ctgttcagct tctgttagcc ac                                     32

SEQ ID NO: 750          moltype = RNA   length = 26
FEATURE                 Location/Qualifiers
source                  1..26
                        mol_type = other RNA
                        organism = synthetic construct
SEQUENCE: 750
ttctgagaaa ctgttcagct tctgtt                                            26

SEQ ID NO: 751          moltype = RNA   length = 25
FEATURE                 Location/Qualifiers
source                  1..25
                        mol_type = other RNA
                        organism = synthetic construct
SEQUENCE: 751
gatctgtcaa atcgcctgca ggtaa                                             25
```

-continued

```
SEQ ID NO: 752         moltype = RNA   length = 25
FEATURE                Location/Qualifiers
source                 1..25
                       mol_type = other RNA
                       organism = synthetic construct
SEQUENCE: 752
ataatgaaaa cgccgccatt tctca                                              25

SEQ ID NO: 753         moltype = RNA   length = 25
FEATURE                Location/Qualifiers
source                 1..25
                       mol_type = other RNA
                       organism = synthetic construct
SEQUENCE: 753
aaactgttca gcttctgtta gccac                                              25

SEQ ID NO: 754         moltype = RNA   length = 25
FEATURE                Location/Qualifiers
source                 1..25
                       mol_type = other RNA
                       organism = synthetic construct
SEQUENCE: 754
ttgtgtcttt ctgagaaact gttca                                              25

SEQ ID NO: 755         moltype = RNA   length = 25
FEATURE                Location/Qualifiers
source                 1..25
                       mol_type = other RNA
                       organism = synthetic construct
SEQUENCE: 755
ccaattctca ggaatttgtg tcttt                                              25

SEQ ID NO: 756         moltype = RNA   length = 25
FEATURE                Location/Qualifiers
source                 1..25
                       mol_type = other RNA
                       organism = synthetic construct
SEQUENCE: 756
atcgcctgca ggtaaaagca tatgg                                              25

SEQ ID NO: 757         moltype = RNA   length = 30
FEATURE                Location/Qualifiers
source                 1..30
                       mol_type = other RNA
                       organism = synthetic construct
SEQUENCE: 757
tgaaaacgcc gccatttctc aacagatctg                                         30

SEQ ID NO: 758         moltype = RNA   length = 30
FEATURE                Location/Qualifiers
source                 1..30
                       mol_type = other RNA
                       organism = synthetic construct
SEQUENCE: 758
cataatgaaa acgccgccat ttctcaacag                                         30

SEQ ID NO: 759         moltype = RNA   length = 30
FEATURE                Location/Qualifiers
source                 1..30
                       mol_type = other RNA
                       organism = synthetic construct
SEQUENCE: 759
tgttcagctt ctgttagcca ctgattaaat                                         30

SEQ ID NO: 760         moltype = RNA   length = 24
FEATURE                Location/Qualifiers
source                 1..24
                       mol_type = other RNA
                       organism = synthetic construct
SEQUENCE: 760
cagatctgtc aaatcgcctg cagg                                               24

SEQ ID NO: 761         moltype = RNA   length = 27
FEATURE                Location/Qualifiers
source                 1..27
                       mol_type = other RNA
                       organism = synthetic construct
SEQUENCE: 761
caacagatct gtcaaatcgc ctgcagg                                            27
```

-continued

```
SEQ ID NO: 762          moltype = RNA   length = 29
FEATURE                 Location/Qualifiers
source                  1..29
                        mol_type = other RNA
                        organism = synthetic construct
SEQUENCE: 762
ctcaacagat ctgtcaaatc gcctgcagg                                              29

SEQ ID NO: 763          moltype = RNA   length = 23
FEATURE                 Location/Qualifiers
source                  1..23
                        mol_type = other RNA
                        organism = synthetic construct
SEQUENCE: 763
gatctgtcaa atcgcctgca ggt                                                    23

SEQ ID NO: 764          moltype = RNA   length = 22
FEATURE                 Location/Qualifiers
source                  1..22
                        mol_type = other RNA
                        organism = synthetic construct
SEQUENCE: 764
gatctgtcaa atcgcctgca gg                                                     22

SEQ ID NO: 765          moltype = RNA   length = 21
FEATURE                 Location/Qualifiers
source                  1..21
                        mol_type = other RNA
                        organism = synthetic construct
SEQUENCE: 765
gatctgtcaa atcgcctgca g                                                      21

SEQ ID NO: 766          moltype = RNA   length = 25
FEATURE                 Location/Qualifiers
source                  1..25
                        mol_type = other RNA
                        organism = synthetic construct
SEQUENCE: 766
cagatctgtc aaatcgcctg caggt                                                  25

SEQ ID NO: 767          moltype = RNA   length = 23
FEATURE                 Location/Qualifiers
source                  1..23
                        mol_type = other RNA
                        organism = synthetic construct
SEQUENCE: 767
cagatctgtc aaatcgcctg cag                                                    23

SEQ ID NO: 768          moltype = RNA   length = 25
FEATURE                 Location/Qualifiers
source                  1..25
                        mol_type = other RNA
                        organism = synthetic construct
SEQUENCE: 768
gtgtctttct gagaaactgt tcagc                                                  25

SEQ ID NO: 769          moltype = RNA   length = 28
FEATURE                 Location/Qualifiers
source                  1..28
                        mol_type = other RNA
                        organism = synthetic construct
SEQUENCE: 769
gagaaactgt tcagcttctg ttagccac                                               28

SEQ ID NO: 770          moltype = RNA   length = 28
FEATURE                 Location/Qualifiers
source                  1..28
                        mol_type = other RNA
                        organism = synthetic construct
SEQUENCE: 770
gaaactgttc agcttctgtt agccactg                                               28

SEQ ID NO: 771          moltype = RNA   length = 24
FEATURE                 Location/Qualifiers
source                  1..24
                        mol_type = other RNA
                        organism = synthetic construct
SEQUENCE: 771
```
ctgttcagct tctgttagcc actg                                          24

SEQ ID NO: 772         moltype = RNA   length = 27
FEATURE                Location/Qualifiers
source                 1..27
                       mol_type = other RNA
                       organism = synthetic construct SEQUENCE: 772
atctgtcaaa tcgcctgcag gtaaaag                                       27

SEQ ID NO: 773         moltype = RNA   length = 29
FEATURE                Location/Qualifiers
source                 1..29
                       mol_type = other RNA
                       organism = synthetic construct SEQUENCE: 773
gatctgtcaa atcgcctgca ggtaaaagc                                     29

SEQ ID NO: 774         moltype = RNA   length = 19
FEATURE                Location/Qualifiers
source                 1..19
                       mol_type = other RNA
                       organism = synthetic construct SEQUENCE: 774
gctgaattat ttcttcccc                                                19

SEQ ID NO: 775         moltype = RNA   length = 19
FEATURE                Location/Qualifiers
source                 1..19
                       mol_type = other RNA
                       organism = synthetic construct SEQUENCE: 775
tttttctgtc tgacagctg                                                19

SEQ ID NO: 776         moltype = RNA   length = 18
FEATURE                Location/Qualifiers
source                 1..18
                       mol_type = other RNA
                       organism = synthetic construct SEQUENCE: 776
tctgttttg aggattgc                                                  18

SEQ ID NO: 777         moltype = RNA   length = 17
FEATURE                Location/Qualifiers
source                 1..17
                       mol_type = other RNA
                       organism = synthetic construct SEQUENCE: 777
ccaccgcaga ttcaggc                                                  17

SEQ ID NO: 778         moltype = RNA   length = 17
FEATURE                Location/Qualifiers
source                 1..17
                       mol_type = other RNA
                       organism = synthetic construct SEQUENCE: 778
gcccaatgcc atcctgg                                                  17

SEQ ID NO: 779         moltype = RNA   length = 17
FEATURE                Location/Qualifiers
source                 1..17
                       mol_type = other RNA
                       organism = synthetic construct SEQUENCE: 779
tttgcagacc tcctgcc                                                  17

SEQ ID NO: 780         moltype = RNA   length = 17
FEATURE                Location/Qualifiers
source                 1..17
                       mol_type = other RNA
                       organism = synthetic construct SEQUENCE: 780
cagtttgccg ctgccca                                                  17

SEQ ID NO: 781         moltype = RNA   length = 20
FEATURE                Location/Qualifiers
source                 1..20
                       mol_type = other RNA
                       organism = synthetic construct -continued

```
SEQUENCE: 781
gttgcattca atgttctgac                                              20

SEQ ID NO: 782          moltype = RNA   length = 21
FEATURE                 Location/Qualifiers
source                  1..21
                        mol_type = other RNA
                        organism = synthetic construct
SEQUENCE: 782
atttttcctg tagaatactg g                                            21

SEQ ID NO: 783          moltype = RNA   length = 34
FEATURE                 Location/Qualifiers
source                  1..34
                        mol_type = other RNA
                        organism = synthetic construct
SEQUENCE: 783
gctgcccaat gcgatcctgg agttcctgta agat                              34

SEQ ID NO: 784          moltype = RNA   length = 28
FEATURE                 Location/Qualifiers
source                  1..28
                        mol_type = other RNA
                        organism = synthetic construct
SEQUENCE: 784
gctgcccaat gccatcctgg agttcctg                                     28

SEQ ID NO: 785          moltype = RNA   length = 31
FEATURE                 Location/Qualifiers
source                  1..31
                        mol_type = other RNA
                        organism = synthetic construct
SEQUENCE: 785
gctgcccaat gccatcctgg agttcctgta a                                 31

SEQ ID NO: 786          moltype = RNA   length = 31
FEATURE                 Location/Qualifiers
source                  1..31
                        mol_type = other RNA
                        organism = synthetic construct
SEQUENCE: 786
caatgccatc ctggagttcc tgtaagatac c                                 31

SEQ ID NO: 787          moltype = RNA   length = 32
FEATURE                 Location/Qualifiers
source                  1..32
                        mol_type = other RNA
                        organism = synthetic construct
SEQUENCE: 787
gctgcccaat gccatcctgg agttcctgta ag                                32

SEQ ID NO: 788          moltype = RNA   length = 30
FEATURE                 Location/Qualifiers
source                  1..30
                        mol_type = other RNA
                        organism = synthetic construct
SEQUENCE: 788
ccaatgccat cctggagttc ctgtaagata                                   30

SEQ ID NO: 789          moltype = RNA   length = 39
FEATURE                 Location/Qualifiers
source                  1..39
                        mol_type = other RNA
                        organism = synthetic construct
SEQUENCE: 789
ttgccgctgc ccaatgccat cctggagttc ctgtaagat                         39

SEQ ID NO: 790          moltype = RNA   length = 34
FEATURE                 Location/Qualifiers
source                  1..34
                        mol_type = other RNA
                        organism = synthetic construct
SEQUENCE: 790
gctgcccaat gccatcctgg agttcctgta agat                              34

SEQ ID NO: 791          moltype = RNA   length = 27
FEATURE                 Location/Qualifiers
source                  1..27
                        mol_type = other RNA
```

```
                         organism = synthetic construct
SEQUENCE: 791
caatgccatc ctggagttcc tgtaaga                                            27

SEQ ID NO: 792           moltype = RNA  length = 26
FEATURE                  Location/Qualifiers
source                   1..26
                         mol_type = other RNA
                         organism = synthetic construct
SEQUENCE: 792
cagtttgccg ctgcccaatg ccatcc                                             26

SEQ ID NO: 793           moltype = RNA  length = 24
FEATURE                  Location/Qualifiers
source                   1..24
                         mol_type = other RNA
                         organism = synthetic construct
SEQUENCE: 793
cttccccagt tgcattcaat gttc                                               24

SEQ ID NO: 794           moltype = RNA  length = 23
FEATURE                  Location/Qualifiers
source                   1..23
                         mol_type = other RNA
                         organism = synthetic construct
SEQUENCE: 794
ctggcatctg tttttgagga ttg                                                23

SEQ ID NO: 795           moltype = RNA  length = 20
FEATURE                  Location/Qualifiers
source                   1..20
                         mol_type = other RNA
                         organism = synthetic construct
SEQUENCE: 795
ttagatctgt cgccctacct                                                    20

SEQ ID NO: 796           moltype = RNA  length = 39
FEATURE                  Location/Qualifiers
source                   1..39
                         mol_type = other RNA
                         organism = synthetic construct
SEQUENCE: 796
gctgcccaat gccatcctgg agttcctgta agataccaa                               39

SEQ ID NO: 797           moltype = RNA  length = 34
FEATURE                  Location/Qualifiers
source                   1..34
                         mol_type = other RNA
                         organism = synthetic construct
SEQUENCE: 797
gcccaatgcc atcctggagt tcctgtaaga tacc                                    34

SEQ ID NO: 798           moltype = RNA  length = 25
FEATURE                  Location/Qualifiers
source                   1..25
                         mol_type = other RNA
                         organism = synthetic construct
SEQUENCE: 798
catcctggag ttcctgtaag atacc                                              25

SEQ ID NO: 799           moltype = RNA  length = 28
FEATURE                  Location/Qualifiers
source                   1..28
                         mol_type = other RNA
                         organism = synthetic construct
SEQUENCE: 799
tgccatcctg gagttcctgt aagatacc                                           28

SEQ ID NO: 800           moltype = RNA  length = 25
FEATURE                  Location/Qualifiers
source                   1..25
                         mol_type = other RNA
                         organism = synthetic construct
SEQUENCE: 800
tgccatcctg gagttcctgt aagat                                              25

SEQ ID NO: 801           moltype = RNA  length = 28
FEATURE                  Location/Qualifiers
source                   1..28
```

```
SEQUENCE: 801
caatgccatc ctggagttcc tgtaagat                                              28

SEQ ID NO: 802           moltype = RNA   length = 31
FEATURE                  Location/Qualifiers
source                   1..31
                         mol_type = other RNA
                         organism = synthetic construct
SEQUENCE: 802
gcccaatgcc atcctggagt tcctgtaaga t                                          31

SEQ ID NO: 803           moltype = RNA   length = 28
FEATURE                  Location/Qualifiers
source                   1..28
                         mol_type = other RNA
                         organism = synthetic construct
SEQUENCE: 803
gcccaatgcc atcctggagt tcctgtaa                                              28

SEQ ID NO: 804           moltype = RNA   length = 34
FEATURE                  Location/Qualifiers
source                   1..34
                         mol_type = other RNA
                         organism = synthetic construct
SEQUENCE: 804
gccgctgccc aatgcacatcc tggagttcct gtaa                                      34

SEQ ID NO: 805           moltype = RNA   length = 25
FEATURE                  Location/Qualifiers
source                   1..25
                         mol_type = other RNA
                         organism = synthetic construct
SEQUENCE: 805
gccatcctgg agttcctgta agata                                                 25

SEQ ID NO: 806           moltype = RNA   length = 25
FEATURE                  Location/Qualifiers
source                   1..25
                         mol_type = other RNA
                         organism = synthetic construct
SEQUENCE: 806
ccaatgccat cctggagttc ctgta                                                 25

SEQ ID NO: 807           moltype = RNA   length = 25
FEATURE                  Location/Qualifiers
source                   1..25
                         mol_type = other RNA
                         organism = synthetic construct
SEQUENCE: 807
ctgacaacag tttgccgctg cccaa                                                 25

SEQ ID NO: 808           moltype = RNA   length = 25
FEATURE                  Location/Qualifiers
source                   1..25
                         mol_type = other RNA
                         organism = synthetic construct
SEQUENCE: 808
tttgaggatt gctgaattat ttctt                                                 25

SEQ ID NO: 809           moltype = RNA   length = 30
FEATURE                  Location/Qualifiers
source                   1..30
                         mol_type = other RNA
                         organism = synthetic construct
SEQUENCE: 809
cagtttgccg ctgcccaatg ccatcctgga                                            30

SEQ ID NO: 810           moltype = RNA   length = 30
FEATURE                  Location/Qualifiers
source                   1..30
                         mol_type = other RNA
                         organism = synthetic construct
SEQUENCE: 810
ttgccgctgc ccaatgccat cctggagttc                                            30

SEQ ID NO: 811           moltype = RNA   length = 25
FEATURE                  Location/Qualifiers
```

```
source                   1..25
                         mol_type = other RNA
                         organism = synthetic construct
SEQUENCE: 811
tttgccgctg cccaatgcca tcctg                                         25

SEQ ID NO: 812           moltype = RNA   length = 22
FEATURE                  Location/Qualifiers
source                   1..22
                         mol_type = other RNA
                         organism = synthetic construct
SEQUENCE: 812
ccaatgccat cctggagttc ct                                            22

SEQ ID NO: 813           moltype = RNA   length = 29
FEATURE                  Location/Qualifiers
source                   1..29
                         mol_type = other RNA
                         organism = synthetic construct
SEQUENCE: 813
cccaatgcca tcctggagtt cctgtaaga                                     29

SEQ ID NO: 814           moltype = RNA   length = 28
FEATURE                  Location/Qualifiers
source                   1..28
                         mol_type = other RNA
                         organism = synthetic construct
SEQUENCE: 814
ccgctgccca atgccatcct ggagttcc                                      28

SEQ ID NO: 815           moltype = RNA   length = 30
FEATURE                  Location/Qualifiers
source                   1..30
                         mol_type = other RNA
                         organism = synthetic construct
SEQUENCE: 815
cccaatgcca tcctggagtt cctgtaagat                                    30

SEQ ID NO: 816           moltype = RNA   length = 30
FEATURE                  Location/Qualifiers
source                   1..30
                         mol_type = other RNA
                         organism = synthetic construct
SEQUENCE: 816
ccgctgccca atgccatcct ggagttcctg                                    30

SEQ ID NO: 817           moltype = RNA   length = 30
FEATURE                  Location/Qualifiers
source                   1..30
                         mol_type = other RNA
                         organism = synthetic construct
SEQUENCE: 817
tgcccaatgc catcctggag ttcctgtaag                                    30

SEQ ID NO: 818           moltype = RNA   length = 28
FEATURE                  Location/Qualifiers
source                   1..28
                         mol_type = other RNA
                         organism = synthetic construct
SEQUENCE: 818
cccaatgcca tcctggagtt cctgtaag                                      28

SEQ ID NO: 819           moltype = RNA   length = 28
FEATURE                  Location/Qualifiers
source                   1..28
                         mol_type = other RNA
                         organism = synthetic construct
SEQUENCE: 819
tgcccaatgc catcctggag ttcctgta                                      28

SEQ ID NO: 820           moltype = RNA   length = 22
FEATURE                  Location/Qualifiers
source                   1..22
                         mol_type = other RNA
                         organism = synthetic construct
SEQUENCE: 820
caatgccatc ctggagttcc tg                                            22

SEQ ID NO: 821           moltype = RNA   length = 29
```

```
FEATURE              Location/Qualifiers
source               1..29
                     mol_type = other RNA
                     organism = synthetic construct
SEQUENCE: 821
agcctctcgc tcactcaccc tgcaaagga                                             29

SEQ ID NO: 822       moltype = RNA   length = 29
FEATURE              Location/Qualifiers
source               1..29
                     mol_type = other RNA
                     organism = synthetic construct
SEQUENCE: 822
ccactcagag ctcagatctt ctaacttcc                                             29

SEQ ID NO: 823       moltype = RNA   length = 27
FEATURE              Location/Qualifiers
source               1..27
                     mol_type = other RNA
                     organism = synthetic construct
SEQUENCE: 823
cttccactca gagctcagat cttctaa                                               27

SEQ ID NO: 824       moltype = RNA   length = 25
FEATURE              Location/Qualifiers
source               1..25
                     mol_type = other RNA
                     organism = synthetic construct
SEQUENCE: 824
gggatccagt atacttacag gctcc                                                 25

SEQ ID NO: 825       moltype = RNA   length = 17
FEATURE              Location/Qualifiers
source               1..17
                     mol_type = other RNA
                     organism = synthetic construct
SEQUENCE: 825
ctcagagctc agatctt                                                          17

SEQ ID NO: 826       moltype = RNA   length = 15
FEATURE              Location/Qualifiers
source               1..15
                     mol_type = other RNA
                     organism = synthetic construct
SEQUENCE: 826
ggctgctttg ccctc                                                            15

SEQ ID NO: 827       moltype = RNA   length = 27
FEATURE              Location/Qualifiers
source               1..27
                     mol_type = other RNA
                     organism = synthetic construct
SEQUENCE: 827
ctcagatctt ctaacttcct ctttaac                                               27

SEQ ID NO: 828       moltype = RNA   length = 29
FEATURE              Location/Qualifiers
source               1..29
                     mol_type = other RNA
                     organism = synthetic construct
SEQUENCE: 828
ctcagagctc agatcttcta acttcctct                                             29

SEQ ID NO: 829       moltype = RNA   length = 27
FEATURE              Location/Qualifiers
source               1..27
                     mol_type = other RNA
                     organism = synthetic construct
SEQUENCE: 829
cgccttccac tcagagctca gatcttc                                               27

SEQ ID NO: 830       moltype = RNA   length = 27
FEATURE              Location/Qualifiers
source               1..27
                     mol_type = other RNA
                     organism = synthetic construct
SEQUENCE: 830
tcagctcttg aagtaaacgg tttaccg                                               27
```

| | | |
|---|---|---|
| SEQ ID NO: 831 | moltype = RNA length = 27 | |
| FEATURE | Location/Qualifiers | |
| source | 1..27 mol_type = other RNA organism = synthetic construct | |
| SEQUENCE: 831 | | |
| tttgccctca gctcttgaag taaacgg | | 27 |
| | | |
| SEQ ID NO: 832 | moltype = RNA length = 27 | |
| FEATURE | Location/Qualifiers | |
| source | 1..27 mol_type = other RNA organism = synthetic construct | |
| SEQUENCE: 832 | | |
| ggctgctttg ccctcagctc ttgaagt | | 27 |
| | | |
| SEQ ID NO: 833 | moltype = RNA length = 26 | |
| FEATURE | Location/Qualifiers | |
| source | 1..26 mol_type = other RNA organism = synthetic construct | |
| SEQUENCE: 833 | | |
| caggagctag gtcaggctgc tttgcc | | 26 |
| | | |
| SEQ ID NO: 834 | moltype = RNA length = 25 | |
| FEATURE | Location/Qualifiers | |
| source | 1..25 mol_type = other RNA organism = synthetic construct | |
| SEQUENCE: 834 | | |
| tccaatagtg gtcagtccag gagct | | 25 |
| | | |
| SEQ ID NO: 835 | moltype = RNA length = 27 | |
| FEATURE | Location/Qualifiers | |
| source | 1..27 mol_type = other RNA organism = synthetic construct | |
| SEQUENCE: 835 | | |
| aaagagaatg ggatccagta tacttac | | 27 |
| | | |
| SEQ ID NO: 836 | moltype = RNA length = 27 | |
| FEATURE | Location/Qualifiers | |
| source | 1..27 mol_type = other RNA organism = synthetic construct | |
| SEQUENCE: 836 | | |
| aaatagctag agccaaagag aatggga | | 27 |
| | | |
| SEQ ID NO: 837 | moltype = RNA length = 33 | |
| FEATURE | Location/Qualifiers | |
| source | 1..33 mol_type = other RNA organism = synthetic construct | |
| SEQUENCE: 837 | | |
| ggctgctttg ccctcagctc ttgaagtaaa cgg | | 33 |
| | | |
| SEQ ID NO: 838 | moltype = RNA length = 30 | |
| FEATURE | Location/Qualifiers | |
| source | 1..30 mol_type = other RNA organism = synthetic construct | |
| SEQUENCE: 838 | | |
| aggctgcttt gccctcagct cttgaagtaa | | 30 |
| | | |
| SEQ ID NO: 839 | moltype = RNA length = 30 | |
| FEATURE | Location/Qualifiers | |
| source | 1..30 mol_type = other RNA organism = synthetic construct | |
| SEQUENCE: 839 | | |
| gtcaggctgc tttgccctca gctcttgaag | | 30 |
| | | |
| SEQ ID NO: 840 | moltype = RNA length = 30 | |
| FEATURE | Location/Qualifiers | |
| source | 1..30 mol_type = other RNA organism = synthetic construct | |
| SEQUENCE: 840 | | |
| aggtcaggct gctttgccct cagctcttga | | 30 |

```
SEQ ID NO: 841         moltype = RNA   length = 25
FEATURE                Location/Qualifiers
source                 1..25
                       mol_type = other RNA
                       organism = synthetic construct
SEQUENCE: 841
cagagctcag atcttctaac ttcct                                              25

SEQ ID NO: 842         moltype = RNA   length = 25
FEATURE                Location/Qualifiers
source                 1..25
                       mol_type = other RNA
                       organism = synthetic construct
SEQUENCE: 842
cttacaggct ccaatagtgg tcagt                                              25

SEQ ID NO: 843         moltype = RNA   length = 25
FEATURE                Location/Qualifiers
source                 1..25
                       mol_type = other RNA
                       organism = synthetic construct
SEQUENCE: 843
atgggatcca gtatacttac aggct                                              25

SEQ ID NO: 844         moltype = RNA   length = 25
FEATURE                Location/Qualifiers
source                 1..25
                       mol_type = other RNA
                       organism = synthetic construct
SEQUENCE: 844
agagaatggg atccagtata cttac                                              25

SEQ ID NO: 845         moltype = RNA   length = 27
FEATURE                Location/Qualifiers
source                 1..27
                       mol_type = other RNA
                       organism = synthetic construct
SEQUENCE: 845
aacttcctct ttaacagaaa agcatac                                            27

SEQ ID NO: 846         moltype = RNA   length = 23
FEATURE                Location/Qualifiers
source                 1..23
                       mol_type = other RNA
                       organism = synthetic construct
SEQUENCE: 846
ctcatacctt ctgcttgatg atc                                                23

SEQ ID NO: 847         moltype = RNA   length = 20
FEATURE                Location/Qualifiers
source                 1..20
                       mol_type = other RNA
                       organism = synthetic construct
SEQUENCE: 847
tcaaggaaga tggcatttct                                                    20

SEQ ID NO: 848         moltype = RNA   length = 20
FEATURE                Location/Qualifiers
source                 1..20
                       mol_type = other RNA
                       organism = synthetic construct
SEQUENCE: 848
gaaagccagt cggtaagttc                                                    20

SEQ ID NO: 849         moltype = RNA   length = 15
FEATURE                Location/Qualifiers
source                 1..15
                       mol_type = other RNA
                       organism = synthetic construct
SEQUENCE: 849
cacccaccat caccc                                                         15

SEQ ID NO: 850         moltype = RNA   length = 23
FEATURE                Location/Qualifiers
source                 1..23
                       mol_type = other RNA
                       organism = synthetic construct
SEQUENCE: 850
```

```
cctctgtgat tttataactt gat                                              23

SEQ ID NO: 851          moltype = RNA   length = 20
FEATURE                 Location/Qualifiers
source                  1..20
                        mol_type = other RNA
                        organism = synthetic construct
SEQUENCE: 851
tgatatcctc aaggtcaccc                                                  20

SEQ ID NO: 852          moltype = RNA   length = 30
FEATURE                 Location/Qualifiers
source                  1..30
                        mol_type = other RNA
                        organism = synthetic construct
SEQUENCE: 852
ggtacctcca acatcaagga agatggcatt                                       30

SEQ ID NO: 853          moltype = RNA   length = 26
FEATURE                 Location/Qualifiers
source                  1..26
                        mol_type = other RNA
                        organism = synthetic construct
SEQUENCE: 853
atttctagtt tggagatggc agtttc                                           26

SEQ ID NO: 854          moltype = RNA   length = 26
FEATURE                 Location/Qualifiers
source                  1..26
                        mol_type = other RNA
                        organism = synthetic construct
SEQUENCE: 854
catcaaggaa gatggcattt ctagtt                                           26

SEQ ID NO: 855          moltype = RNA   length = 26
FEATURE                 Location/Qualifiers
source                  1..26
                        mol_type = other RNA
                        organism = synthetic construct
SEQUENCE: 855
gagcaggtac ctccaacatc aaggaa                                           26

SEQ ID NO: 856          moltype = RNA   length = 30
FEATURE                 Location/Qualifiers
source                  1..30
                        mol_type = other RNA
                        organism = synthetic construct
SEQUENCE: 856
ctccaacatc aaggaagatg gcatttctag                                       30

SEQ ID NO: 857          moltype = RNA   length = 25
FEATURE                 Location/Qualifiers
source                  1..25
                        mol_type = other RNA
                        organism = synthetic construct
SEQUENCE: 857
accagagtaa cagtctgagt aggag                                            25

SEQ ID NO: 858          moltype = RNA   length = 25
FEATURE                 Location/Qualifiers
source                  1..25
                        mol_type = other RNA
                        organism = synthetic construct
SEQUENCE: 858
caccagagta acagtctgag tagga                                            25

SEQ ID NO: 859          moltype = RNA   length = 25
FEATURE                 Location/Qualifiers
source                  1..25
                        mol_type = other RNA
                        organism = synthetic construct
SEQUENCE: 859
tcaccagagt aacagtctga gtagg                                            25

SEQ ID NO: 860          moltype = RNA   length = 25
FEATURE                 Location/Qualifiers
source                  1..25
                        mol_type = other RNA
                        organism = synthetic construct
```

```
SEQUENCE: 860
gtcaccagag taacagtctg agtag                                          25

SEQ ID NO: 861         moltype = RNA   length = 26
FEATURE                Location/Qualifiers
source                 1..26
                       mol_type = other RNA
                       organism = synthetic construct
SEQUENCE: 861
accagagtaa cagtctgagt aggagc                                         26

SEQ ID NO: 862         moltype = RNA   length = 24
FEATURE                Location/Qualifiers
source                 1..24
                       mol_type = other RNA
                       organism = synthetic construct
SEQUENCE: 862
ttctgtccaa gcccggttga aatc                                           24

SEQ ID NO: 863         moltype = RNA   length = 30
FEATURE                Location/Qualifiers
source                 1..30
                       mol_type = other RNA
                       organism = synthetic construct
SEQUENCE: 863
acatcaagga agatggcatt tctagtttgg                                     30

SEQ ID NO: 864         moltype = RNA   length = 25
FEATURE                Location/Qualifiers
source                 1..25
                       mol_type = other RNA
                       organism = synthetic construct
SEQUENCE: 864
acatcaagga agatggcatt tctag                                          25

SEQ ID NO: 865         moltype = RNA   length = 25
FEATURE                Location/Qualifiers
source                 1..25
                       mol_type = other RNA
                       organism = synthetic construct
SEQUENCE: 865
atcatttttt ctcatacctt ctgct                                          25

SEQ ID NO: 866         moltype = RNA   length = 21
FEATURE                Location/Qualifiers
source                 1..21
                       mol_type = other RNA
                       organism = synthetic construct
SEQUENCE: 866
cacccaccat caccctctgt g                                              21

SEQ ID NO: 867         moltype = RNA   length = 22
FEATURE                Location/Qualifiers
source                 1..22
                       mol_type = other RNA
                       organism = synthetic construct
SEQUENCE: 867
atcatctcgt tgatatcctc aa                                             22

SEQ ID NO: 868         moltype = RNA   length = 28
FEATURE                Location/Qualifiers
source                 1..28
                       mol_type = other RNA
                       organism = synthetic construct
SEQUENCE: 868
ctccaacatc aaggaagatg gcatttct                                       28

SEQ ID NO: 869         moltype = RNA   length = 25
FEATURE                Location/Qualifiers
source                 1..25
                       mol_type = other RNA
                       organism = synthetic construct
SEQUENCE: 869
catcaaggaa gatggcattt ctagt                                          25

SEQ ID NO: 870         moltype = RNA   length = 18
FEATURE                Location/Qualifiers
source                 1..18
                       mol_type = other RNA
```

-continued

```
SEQUENCE: 870
ttgctggtct tgtttttc                                                       18

SEQ ID NO: 871         moltype = RNA   length = 16
FEATURE                Location/Qualifiers
source                 1..16
                       mol_type = other RNA
                       organism = synthetic construct
SEQUENCE: 871
ccgtaatgat tgttct                                                         16

SEQ ID NO: 872         moltype = RNA   length = 18
FEATURE                Location/Qualifiers
source                 1..18
                       mol_type = other RNA
                       organism = synthetic construct
SEQUENCE: 872
gctggtcttg tttttcaa                                                       18

SEQ ID NO: 873         moltype = RNA   length = 20
FEATURE                Location/Qualifiers
source                 1..20
                       mol_type = other RNA
                       organism = synthetic construct
SEQUENCE: 873
tggtcttgtt tttcaaattt                                                     20

SEQ ID NO: 874         moltype = RNA   length = 20
FEATURE                Location/Qualifiers
source                 1..20
                       mol_type = other RNA
                       organism = synthetic construct
SEQUENCE: 874
gtcttgtttt tcaaatttg                                                      20

SEQ ID NO: 875         moltype = RNA   length = 20
FEATURE                Location/Qualifiers
source                 1..20
                       mol_type = other RNA
                       organism = synthetic construct
SEQUENCE: 875
cttgtttttc aaattttggg                                                     20

SEQ ID NO: 876         moltype = RNA   length = 19
FEATURE                Location/Qualifiers
source                 1..19
                       mol_type = other RNA
                       organism = synthetic construct
SEQUENCE: 876
tgtttttcaa attttgggc                                                      19

SEQ ID NO: 877         moltype = RNA   length = 33
FEATURE                Location/Qualifiers
source                 1..33
                       mol_type = other RNA
                       organism = synthetic construct
SEQUENCE: 877
tccaactggg gacgcctctg ttccaaatcc tgc                                      33

SEQ ID NO: 878         moltype = RNA   length = 21
FEATURE                Location/Qualifiers
source                 1..21
                       mol_type = other RNA
                       organism = synthetic construct
SEQUENCE: 878
tcctgcattg ttgcctgtaa g                                                   21

SEQ ID NO: 879         moltype = RNA   length = 30
FEATURE                Location/Qualifiers
source                 1..30
                       mol_type = other RNA
                       organism = synthetic construct
SEQUENCE: 879
tccaactggg gacgcctctg ttccaaatcc                                          30

SEQ ID NO: 880         moltype = RNA   length = 21
FEATURE                Location/Qualifiers
source                 1..21
```

```
                            mol_type = other RNA
                            organism = synthetic construct
SEQUENCE: 880
actggggacg cctctgttcc a                                          21

SEQ ID NO: 881             moltype = RNA  length = 20
FEATURE                    Location/Qualifiers
source                     1..20
                           mol_type = other RNA
                           organism = synthetic construct
SEQUENCE: 881
ccgtaatgat tgttctagcc                                            20

SEQ ID NO: 882             moltype = RNA  length = 20
FEATURE                    Location/Qualifiers
source                     1..20
                           mol_type = other RNA
                           organism = synthetic construct
SEQUENCE: 882
tgttaaaaaa cttacttcga                                            20

SEQ ID NO: 883             moltype = RNA  length = 18
FEATURE                    Location/Qualifiers
source                     1..18
                           mol_type = other RNA
                           organism = synthetic construct
SEQUENCE: 883
ctgttgcctc cggttctg                                              18

SEQ ID NO: 884             moltype = RNA  length = 18
FEATURE                    Location/Qualifiers
source                     1..18
                           mol_type = other RNA
                           organism = synthetic construct
SEQUENCE: 884
ttggctctgg cctgtcct                                              18

SEQ ID NO: 885             moltype = RNA  length = 33
FEATURE                    Location/Qualifiers
source                     1..33
                           mol_type = other RNA
                           organism = synthetic construct
SEQUENCE: 885
ttcaactgtt gcctccggtt ctgaaggtgt tct                             33

SEQ ID NO: 886             moltype = RNA  length = 25
FEATURE                    Location/Qualifiers
source                     1..25
                           mol_type = other RNA
                           organism = synthetic construct
SEQUENCE: 886
tacttcatcc cactgattct gaatt                                      25

SEQ ID NO: 887             moltype = RNA  length = 25
FEATURE                    Location/Qualifiers
source                     1..25
                           mol_type = other RNA
                           organism = synthetic construct
SEQUENCE: 887
ctgaaggtgt tcttgtactt catcc                                      25

SEQ ID NO: 888             moltype = RNA  length = 25
FEATURE                    Location/Qualifiers
source                     1..25
                           mol_type = other RNA
                           organism = synthetic construct
SEQUENCE: 888
ctgttgcctc cggttctgaa ggtgt                                      25

SEQ ID NO: 889             moltype = RNA  length = 30
FEATURE                    Location/Qualifiers
source                     1..30
                           mol_type = other RNA
                           organism = synthetic construct
SEQUENCE: 889
ctgttgcctc cggttctgaa ggtgttcttg                                 30

SEQ ID NO: 890             moltype = RNA  length = 30
FEATURE                    Location/Qualifiers
```

| | | |
|---|---|---|
| source | 1..30<br>mol_type = other RNA<br>organism = synthetic construct | |
| SEQUENCE: 890<br>caactgttgc ctccggttct gaaggtgttc | | 30 |
| SEQ ID NO: 891<br>FEATURE<br>source | moltype = RNA   length = 30<br>Location/Qualifiers<br>1..30<br>mol_type = other RNA<br>organism = synthetic construct | |
| SEQUENCE: 891<br>ttgcctccgg ttctgaaggt gttcttgtac | | 30 |
| SEQ ID NO: 892<br>FEATURE<br>source | moltype = RNA   length = 25<br>Location/Qualifiers<br>1..25<br>mol_type = other RNA<br>organism = synthetic construct | |
| SEQUENCE: 892<br>gttgcctccg gttctgaagg tgttc | | 25 |
| SEQ ID NO: 893<br>FEATURE<br>source | moltype = RNA   length = 23<br>Location/Qualifiers<br>1..23<br>mol_type = other RNA<br>organism = synthetic construct | |
| SEQUENCE: 893<br>ctccggttct gaaggtgttc ttg | | 23 |
| SEQ ID NO: 894<br>FEATURE<br>source | moltype = RNA   length = 22<br>Location/Qualifiers<br>1..22<br>mol_type = other RNA<br>organism = synthetic construct | |
| SEQUENCE: 894<br>ctccggttct gaaggtgttc tt | | 22 |
| SEQ ID NO: 895<br>FEATURE<br>source | moltype = RNA   length = 21<br>Location/Qualifiers<br>1..21<br>mol_type = other RNA<br>organism = synthetic construct | |
| SEQUENCE: 895<br>ctccggttct gaaggtgttc t | | 21 |
| SEQ ID NO: 896<br>FEATURE<br>source | moltype = RNA   length = 20<br>Location/Qualifiers<br>1..20<br>mol_type = other RNA<br>organism = synthetic construct | |
| SEQUENCE: 896<br>ctccggttct gaaggtgttc | | 20 |
| SEQ ID NO: 897<br>FEATURE<br>source | moltype = RNA   length = 19<br>Location/Qualifiers<br>1..19<br>mol_type = other RNA<br>organism = synthetic construct | |
| SEQUENCE: 897<br>ctccggttct gaaggtgtt | | 19 |
| SEQ ID NO: 898<br>FEATURE<br>source | moltype = RNA   length = 25<br>Location/Qualifiers<br>1..25<br>mol_type = other RNA<br>organism = synthetic construct | |
| SEQUENCE: 898<br>cattcaactg ttgcctccgg ttctg | | 25 |
| SEQ ID NO: 899<br>FEATURE<br>source | moltype = RNA   length = 24<br>Location/Qualifiers<br>1..24<br>mol_type = other RNA<br>organism = synthetic construct | |
| SEQUENCE: 899<br>ctgttgcctc cggttctgaa ggtg | | 24 |
| SEQ ID NO: 900 | moltype = RNA   length = 31 | |

```
FEATURE              Location/Qualifiers
source               1..31
                     mol_type = other RNA
                     organism = synthetic construct
SEQUENCE: 900
cattcaactg ttgcctccgg ttctgaaggt g                              31

SEQ ID NO: 901       moltype = RNA   length = 21
FEATURE              Location/Qualifiers
source               1..21
                     mol_type = other RNA
                     organism = synthetic construct
SEQUENCE: 901
tactaacctt ggtttctgtg a                                         21

SEQ ID NO: 902       moltype = RNA   length = 27
FEATURE              Location/Qualifiers
source               1..27
                     mol_type = other RNA
                     organism = synthetic construct
SEQUENCE: 902
tgtataggga ccctccttcc atgactc                                   27

SEQ ID NO: 903       moltype = RNA   length = 25
FEATURE              Location/Qualifiers
source               1..25
                     mol_type = other RNA
                     organism = synthetic construct
SEQUENCE: 903
ctaaccttgg tttctgtgat tttct                                     25

SEQ ID NO: 904       moltype = RNA   length = 27
FEATURE              Location/Qualifiers
source               1..27
                     mol_type = other RNA
                     organism = synthetic construct
SEQUENCE: 904
ggtatctttg atactaacct tggtttc                                   27

SEQ ID NO: 905       moltype = RNA   length = 22
FEATURE              Location/Qualifiers
source               1..22
                     mol_type = other RNA
                     organism = synthetic construct
SEQUENCE: 905
attctttcaa ctagaataaa ag                                        22

SEQ ID NO: 906       moltype = RNA   length = 25
FEATURE              Location/Qualifiers
source               1..25
                     mol_type = other RNA
                     organism = synthetic construct
SEQUENCE: 906
gattctgaat tctttcaact agaat                                     25

SEQ ID NO: 907       moltype = RNA   length = 20
FEATURE              Location/Qualifiers
source               1..20
                     mol_type = other RNA
                     organism = synthetic construct
SEQUENCE: 907
atcccactga ttctgaattc                                           20

SEQ ID NO: 908       moltype = RNA   length = 22
FEATURE              Location/Qualifiers
source               1..22
                     mol_type = other RNA
                     organism = synthetic construct
SEQUENCE: 908
aaccgagacc ggacaggatt ct                                        22

SEQ ID NO: 909       moltype = RNA   length = 20
FEATURE              Location/Qualifiers
source               1..20
                     mol_type = other RNA
                     organism = synthetic construct
SEQUENCE: 909
ctgttgcagt aatctatgag                                           20
```

```
SEQ ID NO: 910          moltype = RNA   length = 23
FEATURE                 Location/Qualifiers
source                  1..23
                        mol_type = other RNA
                        organism = synthetic construct
SEQUENCE: 910
tgccattgtt tcatcagctc ttt                                            23

SEQ ID NO: 911          moltype = RNA   length = 20
FEATURE                 Location/Qualifiers
source                  1..20
                        mol_type = other RNA
                        organism = synthetic construct
SEQUENCE: 911
tgcagtaatc tatgagtttc                                                20

SEQ ID NO: 912          moltype = RNA   length = 20
FEATURE                 Location/Qualifiers
source                  1..20
                        mol_type = other RNA
                        organism = synthetic construct
SEQUENCE: 912
tcctgtagga cattggcagt                                                20

SEQ ID NO: 913          moltype = RNA   length = 18
FEATURE                 Location/Qualifiers
source                  1..18
                        mol_type = other RNA
                        organism = synthetic construct
SEQUENCE: 913
gagtcttcta ggagcctt                                                  18

SEQ ID NO: 914          moltype = RNA   length = 25
FEATURE                 Location/Qualifiers
source                  1..25
                        mol_type = other RNA
                        organism = synthetic construct
SEQUENCE: 914
ggccaaacct cggcttacct gaaat                                          25

SEQ ID NO: 915          moltype = RNA   length = 20
FEATURE                 Location/Qualifiers
source                  1..20
                        mol_type = other RNA
                        organism = synthetic construct
SEQUENCE: 915
ggccaaacct cggcttacct                                                20

SEQ ID NO: 916          moltype = RNA   length = 29
FEATURE                 Location/Qualifiers
source                  1..29
                        mol_type = other RNA
                        organism = synthetic construct
SEQUENCE: 916
aatcagctgg gagagagctt cctgtagct                                      29

SEQ ID NO: 917          moltype = RNA   length = 26
FEATURE                 Location/Qualifiers
source                  1..26
                        mol_type = other RNA
                        organism = synthetic construct
SEQUENCE: 917
tcgttcttct gtcgtcgtaa cgtttc                                         26

SEQ ID NO: 918          moltype = RNA   length = 16
FEATURE                 Location/Qualifiers
source                  1..16
                        mol_type = other RNA
                        organism = synthetic construct
SEQUENCE: 918
caccgattgt cttcga                                                    16

SEQ ID NO: 919          moltype = RNA   length = 17
FEATURE                 Location/Qualifiers
source                  1..17
                        mol_type = other RNA
                        organism = synthetic construct
SEQUENCE: 919
cccttgtacg atttatg                                                   17
```

-continued

```
SEQ ID NO: 920          moltype = RNA   length = 18
FEATURE                 Location/Qualifiers
source                  1..18
                        mol_type = other RNA
                        organism = synthetic construct
SEQUENCE: 920
tctgtgttta aggactct                                                 18

SEQ ID NO: 921          moltype = RNA   length = 31
FEATURE                 Location/Qualifiers
source                  1..31
                        mol_type = other RNA
                        organism = synthetic construct
SEQUENCE: 921
gccgctgccc aatgccatcc tggagttcct g                                  31

SEQ ID NO: 922          moltype = RNA   length = 29
FEATURE                 Location/Qualifiers
source                  1..29
                        mol_type = other RNA
                        organism = synthetic construct
SEQUENCE: 922
attagatctg tcgccctacc tcttttttc                                     29

SEQ ID NO: 923          moltype = RNA   length = 27
FEATURE                 Location/Qualifiers
source                  1..27
                        mol_type = other RNA
                        organism = synthetic construct
SEQUENCE: 923
tgtcgcccta cctctttttt ctgtctg                                       27

SEQ ID NO: 924          moltype = RNA   length = 25
FEATURE                 Location/Qualifiers
source                  1..25
                        mol_type = other RNA
                        organism = synthetic construct
SEQUENCE: 924
gcccaatgcc atcctggagt tcctg                                         25

SEQ ID NO: 925          moltype = RNA   length = 30
FEATURE                 Location/Qualifiers
source                  1..30
                        mol_type = other RNA
                        organism = synthetic construct
SEQUENCE: 925
gagcctctcg ctcactcacc ctgcaaagga                                    30

SEQ ID NO: 926          moltype = RNA   length = 36
FEATURE                 Location/Qualifiers
source                  1..36
                        mol_type = other RNA
                        organism = synthetic construct
SEQUENCE: 926
atcatttttt ctcatacctt ctgctaggag ctaaaa                             36

SEQ ID NO: 927          moltype = RNA   length = 26
FEATURE                 Location/Qualifiers
source                  1..26
                        mol_type = other RNA
                        organism = synthetic construct
SEQUENCE: 927
ggaagctaag gaagaagctg agcagg                                        26

SEQ ID NO: 928          moltype = DNA   length = 6054
FEATURE                 Location/Qualifiers
source                  1..6054
                        mol_type = genomic DNA
                        organism = Homo sapiens
SEQUENCE: 928
cagcccctga gaccaggtct ggctccacag ctctgtcctg ctctgtgtct ttccctgctg    60
ctctcaggtc ccctgcaggc cttggcccct ttcctcatct gtagacacac ttgagtagcc   120
caggcacagc catgggagat tcggagatgg cagtcttttg ggctgccgcc ccctacctgc   180
gcaagtcaga gaaggagcgg ctagaagcgc agaccaggcc ttttgacctc aagaaggatg   240
tcttcgtgcc tgatgacaaa caggagtttg tcaaggccaa gatcgtgtct cgagagggtg   300
gcaaagtcac tgccgagacc gagtatggca agacagtgac cgtgaaggag gaccaggtga   360
tgcagcagaa cccacccaag ttcgacaaaa tcgaggacat ggccatgctg accttcctgc   420
atgagcccgc ggtgctctac aacctcaagg atcgctacgc ctcctggatg atctacacct   480
```

```
actcgggcct cttctgtgtc accgtcaacc cttacaagtg gctgccggtg tacactcctg    540
aggtggtggc tgcctaccgg ggcaagaaga ggagcgaggc cccgcccac atctttctcca    600
tctccgacaa cgcctatcag tacatgctga cagacagaga aaaccagtcc atcctgatca    660
ccggagaatc cggagcaggg aagacagtca acaccaagag ggtcatccag tactttgctg    720
ttattgcagc cattggggac cgcagcaaga aggaccagag cccgggcaag ggcaccctgg    780
aggaccagat catccaggcc aaccctgctc tggaggcctt tggcaatgcc aagaccgtcc    840
ggaacgacaa ctcctcccgc ttcgggaaat tcattcgaat tcattttggg gcaacaggaa    900
agttggcatc tgcagacata gagacctatc ttctggaaaa atccagagtt attttccagc    960
tgaaagcaga gagagattat cacatttttct accaaatcct gtctaacaaa aagcctgagc   1020
tgctggacat gctgctgatc accaacaacc cctacgatta tgcattcatc tcccaaggag   1080
agaccaccgt ggcctccatt gatgacgctg aggagctcat ggccactgat aacgcttttg   1140
atgtgctggg cttcacttca gaggagaaaa actccatgta taagctgaca ggcgccatca   1200
tgcactttgg aaacatgaag ttcaagctga agcagcggga ggagcaggcg gagccagacg   1260
gcactgaaga ggctgacaag tctgcctacc tcatggatgc gaactcagcc gacctgctca   1320
aggggctgtg ccaccctcgg gtgaaagtgg gcaatgagta cgtcaccaag gggcagaatg   1380
tccagcaggt gatatatgcc actggggcac tggccaaggc agtgtatgag aggatgttca   1440
actggatggt gacgcgcatc aatgccaccc tggagaccaa gcagccacgc cagtacttca   1500
taggagtcct ggacatgctt ggcttcgaga tcttcgattt caacagcttt gagcagctct   1560
gcatcaactt caccaacgag aagctgcagc agttcttcaa ccaccacatg tttgtgctgg   1620
agcaggagga gtacaagaag gagggcatcg agtggacatt cattgacttt ggcatggacc   1680
tgcaggcctg cattgacctc atcgagaagc ccatgggcat catgtccatc ctggaagagg   1740
agtgcatgtt ccccaaggcc accgacatga ccttcaaggc caagctgtttt gacaaccacc   1800
tgggcaaatc cgccaacttc cagaagccac gcaatatcaa ggggaagcct gaagcccact   1860
tctccctgat ccactatgcc ggcatcgtgg actacaacat cattggctgg ctgcagaaga   1920
acaaggatcc tctcaatgag actgtcgtgg gcttgtatca gaagtcttcc ctcaagctgc   1980
tcagcaccct gtttgccaac tatgctgggg ctgatgcgcc tattgagaag ggcaaaggca   2040
aggccaagaa aggctcgtcc tttcagactg tgtcagctct gcacagggaa aatctgaaca   2100
agctgatgac caacttgcgc tccacccatc cccactttgt acgttgtatc atccctaatg   2160
agacaaagtc tccaggggtg atggacaacc ccctggtcat gcaccagctg cgctgcaatg   2220
gtgtgctgga gggcatccgc atctgcagga aggcttccc caaccgcatc ctctacgggg   2280
acttccggca gaggtatcgc atcctgaacc cagcggccat ccctgaggga cagttcattg   2340
atagcaggaa gggggcagag aagctgctca gctccctgga cattgatcac aaccagtaca   2400
agtttggcca caccaaggtg ttcttcaagg ccgggctgct ggggctgctg gaggaaatga   2460
gggacgagag gctgagccgc atcatcacgc gtatccaggc ccagtcccga ggtgtgctcg   2520
ccagaatgga gtacaaaaag ctgctggaac gtagagactc cctgctggta atccagtgga   2580
acattcgggc cttcatgggg gtcaagaatt ggcctggat gaagcctac ttcaagatca   2640
agccgctgct gaagagtgca gaaagagaga aggagatggc ctccatgaag gaggagttca   2700
cacgcctcaa gaggcgcta gagaagtccg aggctcgccg caaggagctg aggagaaga   2760
tggtgtccct gctgcaggag aagaatgacc tgcagctcca agtgcaggcg gaacaagaca   2820
acctggcaga tgctgaggag cgctgtgatc agctgatcaa aaacaagatt cagctggagg   2880
ccaaggtgaa ggagatgaac gagaggctgg aggatgagga ggagatgaat gctgagctca   2940
ctgccaagaa gcgcaagctg gaagatgagt gctcagagct caaaagggac atcgatgatc   3000
tggagctgac actggcaaa gtggaaggg agaaacacgc aacagaacaa aaggtgaaga   3060
acctgacaga ggagatggct gggctggatg agatcattgc caagctgacc aaggagaaga   3120
aagctctgca agaggcccac caacaggctc tggatgacct tcaggccgag gaggacaagg   3180
tcaacaccct gactaaggcc aaagtcaagc tggagcagca agtggatgat ctggaaggat   3240
ccctggagca agagaaagaag gtgcgcatgg acctggagcg agcgaagcgg aagctggagg   3300
gcgacctgaa gctgacccag gagagcatca tggaccttgga gaatgacaag cagcagctgg   3360
atgagcggct gaaaaaaaaa gactttgagc tgaatgctct caacgcaagg attgaggatg   3420
aacaggccct cggcagccag ctgcagaaga gctcaaggaa gcttcaggca cgcatcgagg   3480
agtcgaggca ggactggag gccgagcgca ccgccaagcg taaggtggaa aagctgcgct   3540
cagacctgtc tcgggagctg gaggagatca gcgagcggct ggaagaggcc ggcgggggca   3600
cgtccgtgca gatcgagatg aacaagaagc gcgaggccga gttccagaag atgcggcggg   3660
acctggagga ggccacgctg cagcacgagg ccactgccgc ggccctgcgc aagaagcacg   3720
ccgacagcgt ggccgagctg ggcgagcaga tcgacaacct gcagcgggtg aagcagaagc   3780
tggagaagga gaagagcgag ttcaagctgg agctggatga cgtcacctcc aacatggagc   3840
agatcatcaa ggccaaggct aacctggaga agatgtgccg gaccttggaa gaccagatga   3900
atgagcaccg gagcaaggcg gaggagaccc agcgttctgt caacgacctc accagcagc   3960
gggccaagtt gcaaaccgag aatggtgagc tgtcccggca gctgatgag aaggaggcac   4020
tgatctccca gctgacccga gcaagctca cctacacccca gcagctggga gacctcaaga   4080
ggcagctgga ggaggaggtt aaggcgaaga acgcccggc ccacgcactg cagtcggccc   4140
ggcatgactc gacctgctg cgggagcagt acgaggagga gacggaggcc aaggccgagc   4200
tgcagcgcgt cctttccaag gccaactcgg aggtggccca gtggaggacc aagtatgaga   4260
cggacgccat tcagcggact gaggagcgtcg aggaggccaa ggaggcgttc ccagccgac   4320
tgcaggaagc tgaggaggcc gtggaggctg ttaatgccaa gtgctcctcg ctggagaaga   4380
ccaagcaccg gctacagaat gagatcgagg acttgatggt ggacgtagag cgctccaatg   4440
ctgctgctgc agccctggac aagaagcaga ggaacttcga caagatcctg gccgagtgga   4500
agcagaagta tgaggagtcg cagtcgggagc tggagtcctg gcaaaggag gctgctctcc   4560
tcagcacaga gctcttcaaa ctcaagaacg cctatgagga gtccctggaa catctggaga   4620
ccttcaagcg ggagaacaaa aacctgcagg aggagatctc cgacttgact gagcagttgg   4680
gttcagcgcg aaagactatc catgagctgg agaaggtccg aaagcagctg gaggccgaga   4740
agatggagct gcagtcagcc ctggaggagg ccgaggcctc cctggagcac gaggaggggca   4800
agatcctccg ggcccagctg gagttcaacc agatcaaggc agagatcgag cggaagctgg   4860
cagagagcga cgaggaggat gaacaggcca gcgcaacc cctgctggtg actctg   4920
tgcagacctc cctggacgca gagacacgca gccgcaacga ggccctgagg gtgaagaaga   4980
agatggaagg agacctcaat gagatggaga tccagctcag ccacgccaac cgcatggccg   5040
ccgaggccca aagcaagtc aagagcctcc agagcttgtt gaaggacacc cagattcagc   5100
tggacgatgc agtccgtgcc aacgacgacc tgaaggagaa catcgccatc gtggagcggc   5160
gcaacaacct gctgcaggct gagctggagg agttgcgtgc cgtggtggag cagacagagc   5220
```

```
ggtcccggaa gctggcgag caggagctga ttgagactag tgagcggtg cagctgctgc    5280
attcccagaa caccagcctc atcaaccaga agaagaagat ggatgctgac ctgtcccagc    5340
tccagactga agtggaggag gcagtgcagg agtgcaggaa tgctgaggag aaggccaaga    5400
aggccatcac ggatgccgcc atgatggcag aggagctgaa gaaggagcag gacaccagcg    5460
cccacctgga gcgcatgaag aagaacatgg aacagacata taaggacctg cagcaccggc    5520
tggacgaagc cgagcagatc gccctcaagg gcggcaagaa gcagctgcag aagctggaag    5580
cgcgggtgcg ggagctggag aatgagctgg aggccgagca gaagcgcaac gcagagtcgg    5640
tgaagggcat gaggaagagc gagcggcgca tcaaggagct cacctaccag acggaggagg    5700
acaggaaaaa cctgctgcgg ctgcaggacc tggtagacaa gctgcagcta aaggtcaagg    5760
cctacaagcg ccaggccgag gaggcggagg agcaagccaa caccaacctg tccaagttcc    5820
gcaaggtgca gcacgagctg gatgaggcag aggagcgggc ggacatcgcc gagtcccagg    5880
tcaacaagct gcgggccaag agccgtgaca ttggcacgaa gggcttgaat gaggagtagc    5940
tttgccacat cttgatctgc tcagccctgg aggtgccagc aaagcccat gctggagcct    6000
gtgtaacagc tccttgggag gaagcagaat aaagcaattt tccttgaagc cgag           6054

SEQ ID NO: 929     moltype = DNA   length = 6313
FEATURE            Location/Qualifiers
source             1..6313
                   mol_type = genomic DNA
                   organism = Mus musculus
SEQUENCE: 929
gctagggact gggtgcaggt gggggatggg gcaccctgct gccccatata tacagcccct      60
gagaccaggt ctggctctga gcattctcct gctgtttcct tacttgctac cctcaggtag     120
gagtgggagc tggaggcttc cctctgggat aaggggctcc aggttcagga agtgattcct     180
ctagaacagc agcgggcttc tggcatgtag taccaggtta tcattgaaca ctcctgtgca     240
gatctaaata cgcatgcttg tgccgtagga atgtgggagc ccaagtgttc caaggtggct     300
ccgagaaagg aagcctcagc agaggagtac agctcttcta caggcctggg cttacctctc     360
tatcactaga cacgtttgag aatccaaggc tcagccatgg cggatgcaga gatggctgca     420
tttggggctg cagcccccctt cctgcggaag tctgagaagg agaggctgga ggcacagacc     480
aggccctttg acctcaagaa agatgttttt gtgcccgatg acaaagaaga gtttgtcaag     540
gccaagatcg tgtcccgaga gggtggcaaa gtcactgctg agacggagaa tggcaagacg     600
gtgactgtga aggaggacca ggtgatgcag cagaacccac ccaagttcga caagatcgag     660
gacatggcca tgctgacctt cctgcatgag ccggctgtgc tgtacaacct caaggagcgc     720
tacgcttcct ggatgatcta tacctactcg ggcctcttct gcgtcaccgt caacctcac      780
aagtggctgc ctgtgtacaa tgcggaagtg gtggctgcct accggggcaa gaagaggagc     840
gaggcccctc ctcacatctt ctccatctct gacaacgcct atcagtacat gctgacagat     900
cgggagaatc agtccatcct catcaccgga gaatccggag ctgggaagac tgtcaacact     960
aagagggtca tccaatattt tgctgttatt gccgccattg gggaccgcag caagaaggac    1020
cagaccccag gcaagggtac cctggaagat caaatcatcc aagccaaccc tgctctggag    1080
gcctttggca atgccaagac agttcggaat gacaactcct ctcgatttgg gaaattcatc    1140
cgaatccatt ttggggcaac aggaaagttg gcatctgcag acatagagac ctaccttctg    1200
gaaaaatcca gggttatttt ccagctgaaa gcagaaagag attatcacat tttctaccaa    1260
atcctgtcta ataaaaagcc tgagcttcta gacatcctgg tgatcaccaa caacccccta    1320
gattatgcgt tcatctccca aggagagacg actgtggcct ccattgatga ctctgaaagg    1380
ctcatggcca cggatagcgc cttttgacgtg ctgggcttca ctccagaaga gaagaactcc    1440
atttacaagc tgacaggcgc catcatgcac tttgaaaaca tgaagttcaa gcagaagcag    1500
cgggaggagc aggcggaacc agacggcact gaagaggctg acaaaatcgc ctacctcatg    1560
gggctgaact cagccgacct gcttaagggg ctgtgccatc ctagagtcaa agtgggcaac    1620
gagtacgtca ccaaggggca gaatgtccag caggtgtcat acgccatcgg ggcactggcc    1680
aagtcagtgt acgagaagat gttcaactgg atggtgacac gcatcaatgc aaccctggag    1740
accaagcgc cgcgccagta cttcataggt gtcctgacca ttgccggctt tgagatcttc    1800
gatttcaaca gctttgagca gctgtgcatc aacttcacca atgagaagct gcagcagttc    1860
ttcaaccacc acatgttcgt gctggagcag gaggagtaca agaaggaggg cattgagtgg    1920
accttcatag acttcggcat ggacttgcag gcctgcattg acctcatcga gaagcccatg    1980
ggcatcatgt ccatccttga ggaggtgc atgttcccca aggccacaga catgaccttc    2040
aaggccaagc tgtacgacaa ccacctgggc aagtccaaca cttccagaa gcctcgaaat    2100
gtcaagggga gcaggaagc ccacttctct ttggtccact atgctggcac tgtggactac    2160
aatatcctgg gctggctaca aagaacaag acccactca atgagacggt ggtgggtttg    2220
taccagaagt cttccctcaa gctgctcagc aatctatttg ccaactatgc tggagctgat    2280
gccccggcgg acaaaggcaa aggcaaggca aagaaaaggct catcctttca gaccgtgtct    2340
gctctgcaca gagaaaatct gaacaaactt atgacaaact tgcgctccac gcaccctcac    2400
tttgtacgct gcatcatccc caatgagaca agtctccag gggtgatgga caaccccctg    2460
gtcatgcacc agctgcgatg caatggcgtg ctggaggta ccgcatctg caggaaggc a    2520
ttcccaacc gcattctcta tggggacttc cggcagagat atcgcatcct gaaccccaga    2580
gccatccctg aggggcaatt cattgatagc aggaaagggg ctgagaaact gctgggctcc    2640
ctggacattg accacaacca atacaagttt ggtcacacac aggtgttctt caaggcgggc    2700
ctgctggggc tgctggagga gatgcgtgat gagaggctga gccgcatcat caccagaatc    2760
caggcccagt cccgaggtgt gctctccaga atggagttca gaagctgct ggagcgcaga    2820
gactccctgc tgattatcca gtggaacatt agggccttca tgggggtcaa gaattgggcc    2880
tggatgaagc tctacttcaa gatcaagccg ctgctgaaga gcgcggagac ggagaaggag    2940
atggccacca tgaaggagga gtttgggcga tcaaagatg cactagaaa gtctgaggct    3000
cgccgcaagg agctggagga gaagatggtg tccctgctgc aggagaagaa tgacctgcag    3060
ctccaagtgc aggcggaaca agacaacttg gcggatgcag aggagcgctg tgaccagctg    3120
atcaagaaca gatcggct gggaccggg gtgaaggaga tgcggaggac gtgtggag    3180
gaggaggaga tgaatgccga gctcactgcc aagaagcgca gctggaaga tgagtgctca    3240
gagctcaagc gggatatcga tgacctggag ctgacgctgg ccaaggtgga aaggaaaag    3300
catgcaacag agaacaaggt gaaaaacctg acagaggaga tggctggttt ggatgagatc    3360
attgtcaagc tgacaaagga gaagaaagct ctgcaagagg cccaccagca ggctctggat    3420
gacctgcagg ctgaggaaga caggtcaat actctgacca aggccaaggt caagctggag    3480
```

```
cagcaggtgg atgatctgga gggatccctg gagcaggaga agaaggtgcg catggaccta   3540
gagcgagcca agcggaagct ggagggagac ctgaagctga cgcaggagag catcatggac   3600
ctggagaatg acaagcagca gttggatgag cgactcaaaa agaaggactt tgagttaaat   3660
gcactcaatg ccaggattga ggatgagcaa gccctgggca gtcagctgca gaagaagctc   3720
aaggagcttc aggcacgcat caggagctg gaggaggagc tggaggccga gcgcacagcc    3780
cgggccaagg tggagaagct gcgctctgac ctgtcccggg agctggagga gatcagtgaa   3840
aggctggagg aggcaggcgg ggccacatcc gtgcagatag agatgaacaa gaagcgcgag   3900
gccgagttcc agaagatgcg gcgggacctg gaggaggcca cgctgcagca cgaggccacg   3960
gcggcggccc tgcgcaagaa gcatgccgac agcgtggcgg agctgggcga gcagatcgac   4020
aacctccagc gggtgaagca gaagctggag aaagagaaaa gcgagttcaa gctggagctg   4080
gatgacgtca cctccaacat ggagcagatc atcaaggcca aggctaacct ggagaagatg   4140
tgccggacct tggaagacca gatgaatgag caccggagca aggccgagga gacgcagcgt   4200
tctgtcaatg acctcaccag ccagcgggcc aagctgcaga cagagaatgg ggagctgtcc   4260
cggcagctgg acgagaagga ggctctgatc tctcagctaa cccgaggcaa gctcacatat   4320
acacagcagc tggaggacct caagaggcaa ctggaggagg aggtcaaggc caagaacgcg   4380
ctggccacg cactgcagtc agcacggcat gattgtgacc tgctgaggga acagtatgag    4440
gaggagacag aggccaaggc tgagctacag cgagtcctgt ccaaggccaa ttcagaggtg   4500
gcccagtgga ggaccaagta tgagacggat gccatacaga ggacagagga gctggaggaa   4560
gccaagaaga agctggctca gaggctgcag gatgcagagg aggcagtgga ggctgtcaat   4620
gccaagtgtt cctctctgga gaagaccaag cacaggctgc agaatgagat cgaggacctg   4680
atggtggacg tggagcgctc caatgccgcc gccgcagccc tggacaagaa gcagaggaac   4740
tttgacaaga tcctggctga gtggaagcag aagtatgagg agtcgcagtc agagctggag   4800
tcttcccaga aggaggcgcg ctccctgagc acagagctct tcaagctcaa gaacgcctat   4860
gaggagtctc tggagcacct agagaccttc aagcgggaga acaagaacct ccaggaggag   4920
atctcagacc tgactgagca gctgggctcc acggggaaga gcatccatga gctggagaag   4980
atccgaaagc aactggaggc cgagaagctg gagctgcagt cggccctgga ggaggctgag   5040
gcctccctgg agcacgagga gggcaagatc ctccgcgcc agctagagtt caaccagatc    5100
aaggcagaga ttgaaaggaa gctggagag aaggatgagg agatggagca ggccaagcgc    5160
aaccacctgc ggatggtgga ctccctgcag acctccctgg atgcggagac acgcagccgc   5220
aatgaggccc tgcgggtgaa gaagaagatg gagggcgacc tcaacgagat ggagatccag   5280
ctcagccatg ccaaccgtat ggctgctgag gcccagaaac aagtgaagag cctccagagt   5340
ctgctgaagg acactcaaat ccagctggat gatgctgtcc gtgccaatga cgacctgaaa   5400
gagaacatcg ccatcgtgga acggcgcaac aacctgctgc aggcggagct ggaggagctt   5460
cgggctgtgg tggagcagac ggagcggtct cggaagctgg cagagcagga gctgattgag   5520
accagccagc gggtgcagct gctgcactcg cagaacacca gcctcatcaa ccagaagaag   5580
aagatggatg cagacctatc ccagctccag acagaagtag aggaggcagt gcaggagtgt   5640
aggaacgcag aggagaaggc caagaaggct atcacagatg ccgccatgat ggctgaggag   5700
ctgaagaagg agcaggacac cagcgcccac ctggagcgca tgaagaagaa catggagcag   5760
accatcaagg acttgcagca ccgtctggac gaggcagagc agatcgccct caagggcggc   5820
aagaagcagc tgcagaagct ggaggcccgg gtccgggagc tggagaatga gctggaggct   5880
gagcaaaagc gcaatgcaga gtcagtgaag ggcatgagga agagtgagcg gcgcatcaag   5940
gagctcacct accagacaga ggaagacagg aagaacctac tgcggctgca ggacctggtg   6000
gacaagctgc agctgaaggt gaaggcctac aagcgccagg ctgaggaggc ggaggagcag   6060
gccaacacca acctgtccaa gttccgcaag gtgcagcacg agctggatga ggcggaggag   6120
agggcggaca tcgccgagtc ccaggtcaac aagctgcggg ccaagagccg ggacattggt   6180
gccaagggcc tgaatgagga gtagctcttg tgctacccag ctccaagggt gcccgtgaag   6240
ccctcagacc tggagccttt gcaacagccc tttaggtgga agcagaataa agcaattttc   6300
cttaaagcca aaa                                                      6313
```